United States Patent [19]

Wexler

[11] Patent Number: 4,671,817

[45] Date of Patent: Jun. 9, 1987

[54] HERBICIDAL PYRAZOLE SULFONAMIDES

[75] Inventor: Barry A. Wexler, Wilmington, Del.

[73] Assignee: E. I. Du Pont de Nemours and Company, Wilmington, Del.

[21] Appl. No.: 726,386

[22] Filed: Apr. 23, 1985

[51] Int. Cl.$^4$ .................... A01N 47/36; C07D 513/04
[52] U.S. Cl. ............................................ 71/91; 544/48
[58] Field of Search ..................... 544/320, 321, 48; 71/92, 91

[56] References Cited

U.S. PATENT DOCUMENTS 4,622,062 11/1986 Wexler .................................. 71/90

FOREIGN PATENT DOCUMENTS 87780 7/1983 European Pat. Off. .
107979 5/1984 European Pat. Off. .

Primary Examiner—Robert Gerstl

[57] ABSTRACT

Pyrazole sulfonamides are found to have utility as pre-emergent and/or postemergent herbicides or plant growth regulants.

24 Claims, No Drawings

HERBICIDAL PYRAZOLE SULFONAMIDES

BACKGROUND OF THE INVENTION

This invention relates to novel pyrazole sulfonamides. The compounds of this invention and their agriculturally suitable salts, are useful as agricultural chemicals, e.g. plant growth regulants and herbicides. As herbicides, the compounds of this invention have both preemergent and/or postemergent utility. The invention is also intended to cover the use of these chemicals in the form of compositions.

Herbicidal sulfonylureas are claimed in U.S. Pat. No. 4,127,405 and U.S. Pat. No. 4,167,719.

No. EP-A-79,683 discloses herbicidal sulfonylureas including those of formula

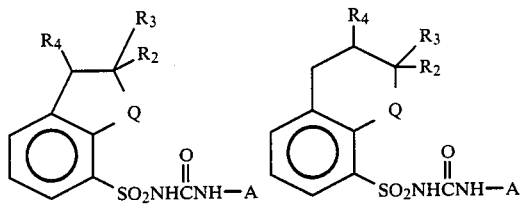

wherein
Q is O, S or $SO_2$;
$R_2$ is H or $C_1-C_3$ alkyl;
$R_3$ is H or $CH_3$; and
$R_4$ is H or $CH_3$.

No. EP-A-107,979 discloses, in part, herbicidal sulfonylureas of formula

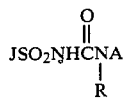

wherein
J is, among other values,

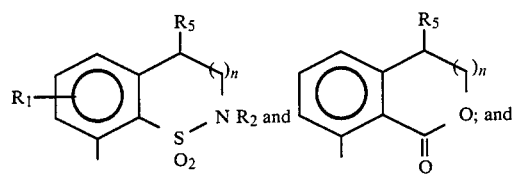

A is a heterocyclic pyrimidine, triazine, triazole or a derivative thereof.

South African Patent Appliction No. 83/5165 discloses herbicidal sulfonylureas of the formula

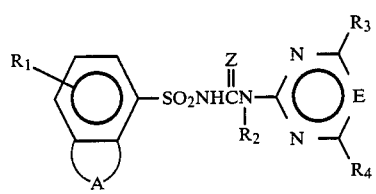

wherein
A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or $SO_2$— group.

No. EP-A-87,780 (published 9/7/83) claims pyrazole sulfonylureas of formula

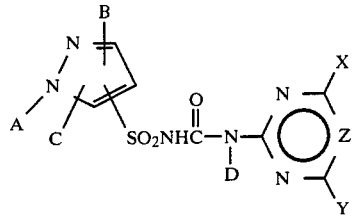

wherein
A is H, $C_1-C_8$ alkyl or optionally substituted phenyl;
B and C are independently H, halogen, $C_1-C_8$ alkyl, $CO_2R$, $SO_2NR_4R_5$, etc.
D is H or $C_1-C_8$ alkyl;
X and Y are independently H, halogen, $C_1-C_8$ alkyl, $C_1-C_8$ alkoxy, etc.; and
Z is $C-R_8$ or N.

The presence of undesired vegetation causes substantial damage to useful crops, especially agricultural products that satisfy man's basic food and fiber needs, such as cotton, rice, corn, wheat and the like. The current population explosion and concomitant world food and fiber shortage demand improvements in the efficiency of producing these crops. Preventing or minimizing loss of a portion of such valuable crops by killing or inhibiting the growth of undesired vegetation is one way of improving this efficiency.

A wide variety of materials useful for killing or inhibiting (controlling) the growth of undesired vegetation is available; such materials are commonly referred to as herbicides. The need still exists however, for more effective herbicides.

SUMMARY OF THE INVENTION

This invention relates to novel compounds of Formula I, agriculturally suitable compositions containing them and their method-of-use as preemergent and/or postemergent herbicides or plant growth regulants.

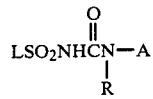

wherein
L is

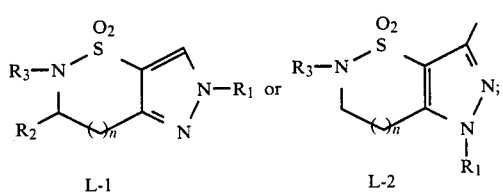

R is H or $CH_3$;
$R_1$ is H, $C_1-C_3$ alkyl, $CH_2CH=CH_2$, $CH_2C\equiv CH$, $CH_2CF_3$, $CHF_2$, $C(O)CH_3$, $SO_2CH_3$, SO$_2$N(CH$_3$)$_2$, CO$_2$CH$_3$, phenyl or phenyl substituted with NO$_2$, CH$_3$, OCH$_3$, Cl, Br or F;

R$_2$ is H or CH$_3$;

R$_3$ is R$_4$, SR$_4$, SO$_2$R$_4$, OR$_4$, C(O)R$_4$, C(O)OR$_4$, (C(O))$_2$OR$_4$, (CO)$_2$R$_4$, C(O)NR$_5$R$_6$, C(O)NRA, C(S)SR$_4$, NR$_5$R$_6$, OH, CN, P(O)R$_7$R$_8$, P(S)R$_7$R$_8$, Si(CH$_3$)$_2$R$_9$, J or C(O)J;

R$_4$ is C$_1$-C$_{10}$ alkyl, C$_2$-C$_{10}$ alkoxyalkyl, C$_2$-C$_{10}$ alkenyl, C$_2$-C$_{10}$ epoxyalkyl, C$_2$-C$_{10}$ alkynyl, C$_3$-C$_6$ cycloalkyl, C$_4$-C$_7$ cycloalkylalkyl or

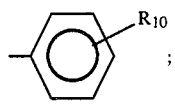

when R$_4$ is C$_3$-C$_6$ cycloalkyl or C$_4$-C$_7$ cycloalkylalkyl it may optionally be substituted by C$_1$-C$_4$ alkyl, 1 to 3 atoms of Cl or F or 1 Br; when R$_4$ is C$_1$-C$_{10}$ alkyl, C$_2$-C$_{10}$ alkenyl or C$_2$-C$_{10}$ alkynyl it may optionally be substituted by one or more halogens and/or by (R$_{11}$)$_p$, provided that when p is 2, the values of R$_{11}$ may be identical or different;

p is 1 or 2;

R$_5$ is H or C$_1$-C$_4$ alkyl;

R$_6$ is H, C$_1$-C$_{10}$ alkyl, C$_1$-C$_{10}$ haloalkyl, C$_2$-C$_{10}$ alkenyl, C$_2$-C$_{10}$ alkynyl, C$_3$-C$_6$ cycloalkyl or

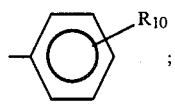

R$_7$ and R$_8$ are independently C$_1$-C$_4$ alkyl, C$_1$-C$_4$ alkoxy or C$_1$-C$_4$ alkylthio;

R$_9$ is C$_1$-C$_{10}$ alkyl, benzyl or

R$_{10}$ is H, F, Cl, Br, CH$_3$, OCH$_3$, NO$_2$, CN, SCH$_3$, SO$_2$CH$_3$ or CF$_3$;

R$_{11}$ is OR$_6$, OC(O)R$_6$, P+R$_9$R$_{13}$R$_{14}$, P+(C$_6$H$_5$)$_3$, OC(O)NR$_5$R$_6$, OSO$_2$R$_6$, OP(O)R$_7$R$_8$, P(O)R$_7$R$_8$ OP(S)R$_7$R$_8$, P(S)R$_7$R$_8$, OSi(CH$_3$)$_2$R$_9$, Si(CH$_3$)$_2$R$_9$, SR$_6$, SOR$_6$, SO$_2$R$_6$, SCN, CN, SP(O)R$_7$R$_8$, SP(S)R$_7$R$_8$, N+R$_5$R$_6$R$_9$, NR$_5$R$_6$, NR$_5$C(O)R$_6$, NR$_5$C(O)OR$_6$, NR$_5$C(O)NR$_5$R$_6$, NR$_5$SO$_2$R$_6$, NR$_5$P(O)R$_7$R$_8$, NR$_5$P(S)R$_7$R$_8$, NO$_2$, C(O)R$_6$, C(O)OR$_6$, C(O)NR$_5$R$_6$, SeR$_6$, naphthyl, J,

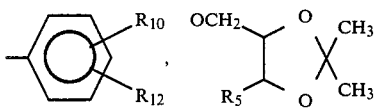

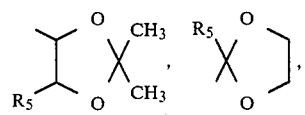

-continued

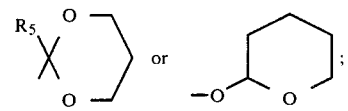

R$_{12}$ is H, F, Cl, Br, CH$_3$,

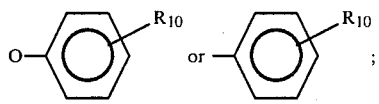

R$_{13}$ and R$_{14}$ are independently C$_1$-C$_3$ alkyl;

J is a 5- or 6-membered aromatic heterocycle, a 5- or 6-membered dihydroaromatic heterocycle or a 5- or 6-membered tetrahydroaromatic heterocycle which contains 1–4 heteroatoms selected from 0–1 oxygen atoms, 0–1 sulfur atoms and/or 0–4 nitrogen atoms and these heterocycles may optionally be substituted by 1–4 CH$_3$, 1–2 OCH$_3$, SCH$_3$, Cl, N(CH$_3$)$_2$ or CN groups or J is a 5- or 6-membered lactone, lactam or cycloalkanone which may optionally be substituted by 1–4 CH$_3$ groups;

A is

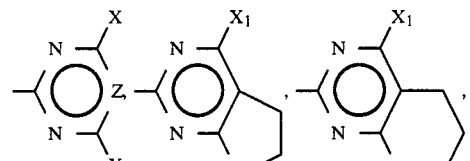

A-1    A-2    A-3

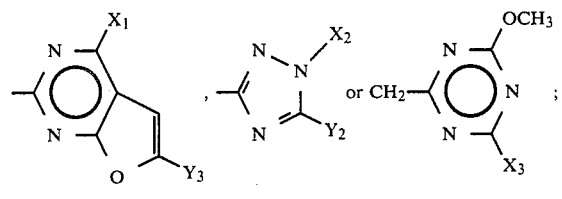

A-4    A-5    A-6

X is H, C$_1$-C$_4$ alkyl, C$_1$-C$_4$ alkoxy, C$_1$-C$_4$ haloalkoxy, C$_1$-C$_4$ haloalkyl, C$_1$-C$_4$ haloalkylthio, C$_1$-C$_4$ alkylthio, halogen, C$_2$-C$_5$ alkoxyalkyl, C$_2$-C$_5$ alkoxyalkoxy, amino, C$_1$-C$_3$ alkylamino, di(C$_1$-C$_3$ alkyl)amino or C$_3$-C$_5$ cycloalkyl;

Y is H, C$_1$-C$_4$ alkyl, C$_1$-C$_4$ alkoxy, C$_1$-C$_4$ haloalkoxy, C$_1$-C$_4$ haloalkylthio, C$_1$-C$_4$ alkylthio, halogen, C$_2$-C$_5$ alkoxyalkyl, C$_2$-C$_5$ alkoxyalkoxy, amino, C$_1$-C$_3$ alkylamino, di(C$_1$-C$_3$ alkyl)amino, C$_3$-C$_4$ alkenyloxy, C$_3$-C$_4$ alkynyloxy, C$_2$-C$_5$ alkylthioalkyl, C$_2$-C$_5$ alkylsulfinylalkyl, C$_2$-C$_5$ alkylsulfonylalkyl, C$_1$-C$_4$ haloalkyl, C$_2$-C$_4$ alkynyl, azido, cyano,

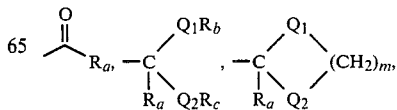

-continued

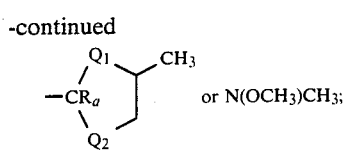 or N(OCH₃)CH₃;

m is 2 or 3;

$Q_1$ and $Q_2$ are independently O or S;

$R_a$ is H or $C_1$-$C_3$ alkyl;

$R_b$ and $R_c$ are independently $C_1$-$C_3$ alkyl;

Z is CH, N, CCH₃, CC₂H₅, CCl or CBr;

$Y_1$ is O or CH₂;

$X_1$ is CH₃, OCH₃, OC₂H₅ or OCF₂H;

$X_2$ is CH₃, C₂H₅ or CH₂CF₃;

$Y_2$ is OCH₃, OC₂H₅, SCH₃, SC₂H₅, CH₃ or CH₂CH₃;

$X_3$ is CH₃ or OCH₃; and $Y_3$ is H or CH₃;

provided that 1. when X is halogen, then Z is CH and Y is OCH₃, OC₂H₅, NH₂, NHCH₃, N(CH₃)₂ or OCF₂H;
2. when $R_3$ is $R_4$, then $R_4$ is other than $C_1$-$C_3$ alkyl or CF₂H;
3. the total number of carbon atoms in $R_3$ does not exceed 13;
4. when $R_6$ is H, then $R_{11}$ is other than $SOR_6$, $SO_2R_6$, $OSO_2R_6$ or $NR_5CO_2R_6$; and
5. when X or Y is OCF₂H, then Z is CH Preferred for reasons of their higher herbicidal activity, greater plant growth regulant activity or more favorable ease of synthesis are:

(1) Compounds of Formula I wherein

A is A-1;

X is CH₃, OCH₃, OCH₂CH₃, Cl, F, Br, OCF₂H, CH₂F, CF₃ or cyclopropyl;

Y is H, $C_1$-$C_3$ alkyl, OCH₃, OC₂H₅, CH₂OCH₃, NH₂, NHCH₃, N(OCH₃)CH₃, N(CH₃)₂, C₂H₅, CF₃, SCH₃, OCH₂CH=CH₂, OCH₂C≡CH, OCH₂CF₃, CN, N₃, OCH₂CH₂OCH₃, CH₂SCH₃,

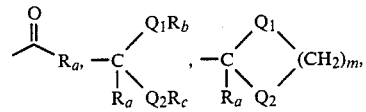

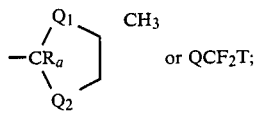 or QCF₂T;

Q is O or S; and

T is H, CHClF, CHBrF or CHFCF₃;

(2) Compounds of Preferred 1 wherein $R_3$ is $C_4$-$C_6$ alkyl, $C_1$-$C_6$ alkylcarbonyl, $C_1$-$C_6$ alkoxycarbonyl, $C_1$-$C_6$ alkyl substituted by 1-3 atoms of F, Cl or 1 Br, or by 1 or 2 groups selected from $C_1$-$C_2$ alkoxy, CN, $C_1$-$C_2$ alkoxycarbonyl, $C_1$-$C_2$ alkylcarbonyl, OH, $C_1$-$C_2$ alkylthio, $C_1$-$C_2$ alkylsulfonyl, $C_1$-$C_2$ alkylsulfonyloxy or $C_1$-$C_2$ alkylcarbonyloxy, $C_3$-$C_4$ alkenyl, $C_3$-$C_4$ haloalkenyl, $C_3$-$C_4$ alkynyl, $C_4$ alkynyl substituted by 1 atom of F or Cl, phenyl or phenyl substituted with Cl, CF₃, NO₂, CN or SO₂CH₃;

(3) Compounds of Preferred 2 wherein $R_1$ is H, $C_1$-$C_3$ alkyl, allyl, propargyl, CH₂CF₃ or CHF₂;

(4) Compounds of Preferred 3 wherein R is H, Y is CH₃, C₂H₅, OCH₃, CH₂OCH₃, OCF₂H or CH(OCH₃)₂, and Z is CH or N;

(5) Compounds of Preferred 4 wherein Z is CH; and $R_3$ is $C_4$ alkyl, $C_1$-$C_3$ haloalkyl substituted by 1-3 atoms of F or Cl or 1 Br, $C_1$-$C_3$ alkyl substituted with C-$C_2$ alkoxy, $C_1$-$C_2$ alkylthio, $C_1$-$C_2$ alkylsulfonyl or CN, $C_3$-$C_4$ alkenyl, $C_3$-$C_4$ haloalkenyl, $C_3$-$C_4$ alkynyl, $C_1$-$C_3$ alkoxycarbonyl or $C_1$-$C_3$ alkylcarbonyl; and (6) Compounds of Preferred 4 wherein Z is N; and $R_3$ is $C_1$-$C_3$ alkoxycarbonyl or $C_1$-$C_3$ alkylcarbonyl.

Specifically preferred for reasons of their expected highest herbicidal activity, greatest plant growth regulant activity or most favorable ease of synthesis are:

N-[(4,6-dimethoxypyrimidin-2-yl)aminocarbonyl]-5-(2-fluoroethyl)-2,5,6,7-tetrahydro-2-methylpyrazolo[3,4-e][1,2]thiazine-3-sulfonamide, 4,4-dioxide;

5-butyl-N-[(4,6-dimethoxypyrimidin-2-yl)aminocarbonyl]-2,5,6,7-tetrahydro-2-methylpyrazolo[3,4-e][1,2]thiazine-3-sulfonamide, 4,4-dioxide; and 5-acetyl-2,5,6,7-tetrahydro-N-[(4-methoxy-6-methyl-1,3,5-triazin-2-yl)aminocarbonyl]-2-methylpyrazolo[3,4-e]thiazine-3-sulfonamide, 4,4-dioxide.

In the above definitions, the term "alkyl", used either alone or in compound words such as "alkylthio" or "haloalkyl", denotes straight chain or branched alkyl, e.g. methyl, ethyl, n-propyl, isopropyl or the different butyl, pentyl, hexyl, heptyl, octyl, nonyl or decyl isomers.

Alkoxy denotes methoxy, ethoxy, n-propyloxy, isopropyloxy and the different butyl, pentyl, hexyl, heptyl, oxtyl or nonyl isomers.

Alkenyl denotes straight chain or branched alkenes, e.g. vinyl, 1-propenyl, 2-propenyl, isopropenyl and the different butenyl, pentenyl, hexenyl, heptenyl, octenyl, nonenyl or decenyl isomers.

Alkynyl denotes straight chain or branch alkynes, e.g. ethynyl, 1-propynyl, 2-propynyl and the different butynyl, pentynyl, hexynyl, heptynyl, octynyl, nonynyl and the decynyl isomers.

Alkylcarbonyl denotes e.g. acetyl, propionyl and isopropionyl.

Alkoxycarbonyl denotes, e.g., methoxycarbonyl and ethoxycarbonyl.

Alkylsulfonyl denotes, e.g., methylsulfonyl and ethylsulfonyl.

Alkylthio, alkylsulfinyl, alkylamino, alkylsulfamoyl, etc. are defined analogously to the above examples.

Cycloalkyl denotes cyclopropyl, cyclobutyl, cyclopentyl and cyclohexyl.

Cycloalkylalkyl denotes, for example, cyclopropylmethyl, 2-cyclopropylethyl and cyclohexylmethyl.

The term "halogen", either alone or in compound words such as "haloalkyl", denotes fluorine, chlorine, bromine or iodine. Further, when used in compound words such as "haloalkyl" said alkyl may be monohalogenated, substituted with more than one halogen, or fully substituted with halogen atoms. When more than one halogen is present said halogen may be the same or different. Examples of haloalkyl include CH₂CH₂F, CH₂CF₃ and CH₂CHFCl The total number of carbon atoms in a substitutent group is indicated by the $C_i$-$C_j$ prefix where i and j are numbers from 1 to 10. For example, $C_1$-$C_3$ alkylsulfonyl would designate methylsulfonyl through propylsulfonyl, $C_2$ alkoxyalkoxy would designate OCH₂OCH₃, $C_2$ cyanoalkyl would designate CH₂CN and $C_3$ cyanoalkyl would designate CH₂CH₂CN and CH(CN)CH₃

DETAILED DESCRIPTION OF THE INVENTION

Synthesis

Compounds of the Invention

The sulfonylureas of Formula I may be prepared by a number of methods. These methods are described below, along with the appropriate references for greater detail.

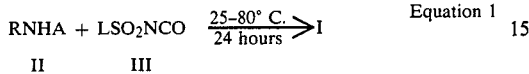

Equation 1

U.S. Pat. Nos. 4,127,405, 4,257,802 and 4,221,585 disclose these equations and are herein incorporated by reference.

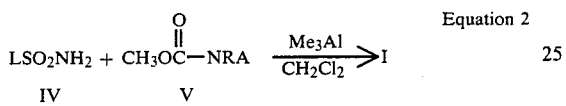

Equation 2

This reaction is taught in EPO Publication No. 83,975 (published July 20, 1983).

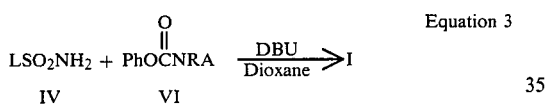

Equation 3

The reaction is taught in EPO Publication No. 44,807 (published Jan. 27, 1982).

Intermediate Compounds

Heterocyclic sulfonyl isocyanates of Formula III may be prepared by procedures taught in U.S. Pat. No. 4,127,405.

Heterocyclic amines of Formula II may be prepared from procedures taught in U.S. Pat. No. 4,127,405 and U.S. Pat. No. 4,221,585.

Heterocyclic carbamates of Formula V are prepared by procedures taught in EPO Publication No. 83,975. The heterocyclic carbamates of Formula VI may be prepared by procedures taught in EPO No. 44,807 and references cited therein.

The preparation of the intermedite pyrazole sulfonamides such as VII and VIII where $R_1$, $R_2$ and $R_3$ *l are as previously described and n is* 0, may be accomplished in one or more of the ways described below in Equations 4, 5 and 6.

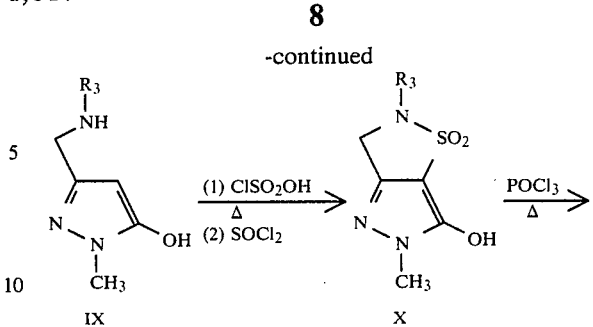

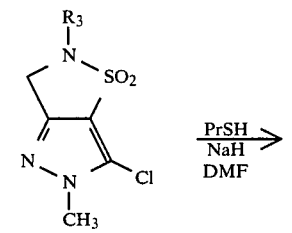

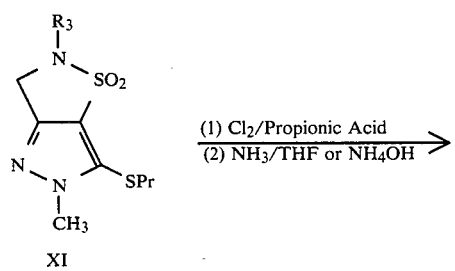

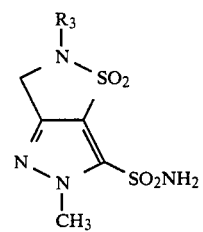

VII

In Equation 4, condensation of a hydrazine with an amine derivative of a β-keto ester affords the pyrazole IX. Reaction of IX with chlorosulfonic acid and subsequent ring closure yields the cyclic sulfonamide X. Conversion to the chloride followed by displacement of the activated chloride would then afford the propylthio derivative XI. Standard oxidative chlorination in the appropriate solvent, followed by amination would then yield the desired 5-sulfonamide XII. The conditions for carrying out the transformation described in Equation 4 would be known to one skilled in the art. For example, the final transformation, a conversion of a thiol to a sulfonamide is taught by R. V. Robin and J. W. Clapp, *J. Am. Chem. Soc.*, 72, 4890 (1950).

An alternate synthesis of sulfonamides VII and VIII is described in Equation 5. This route is the same as that taught in Equation 4 with hydrazine substituted for methylhydrazine.

Equation 4

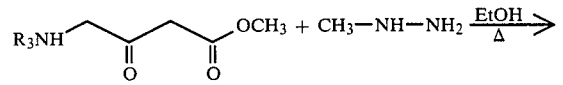

Equation 5

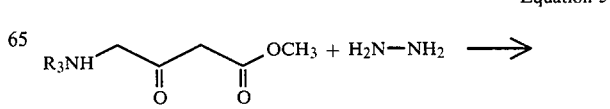

-continued

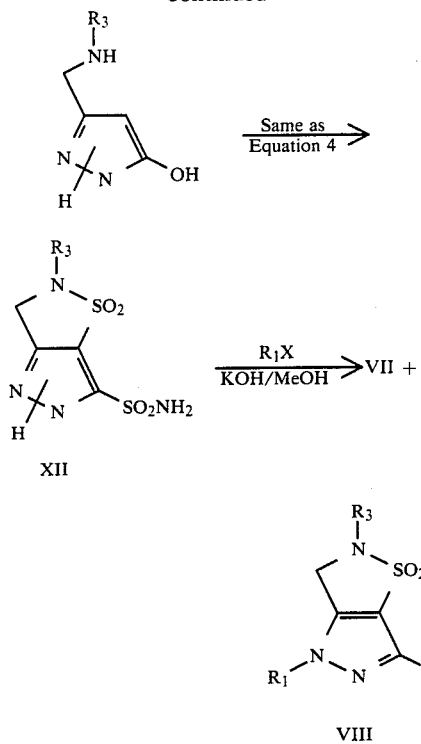

The resulting unsubstituted pyrazole XII may now be alkylated to afford the isomeric sulfonamides VII and VIII. Chromatographic separation of the two isomers then yields the individual sulfonamides. In other words, introduction of the N-substituent, $R_1$ at the end of the synthesis allows for the preparation of both sulfonamides VII and VIII.

Synthesis of sulfonamides XIII and XIV where $R_1$, $R_2$ and $R_3$ are as previously described and n is 1 is described in Equation 6.

Equation 6

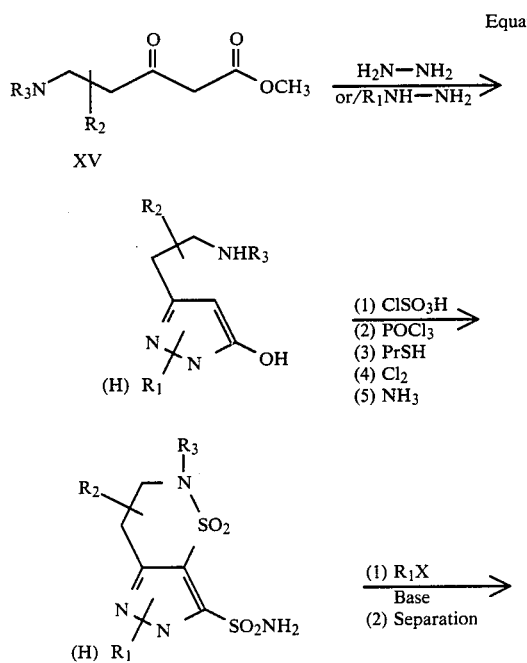

-continued

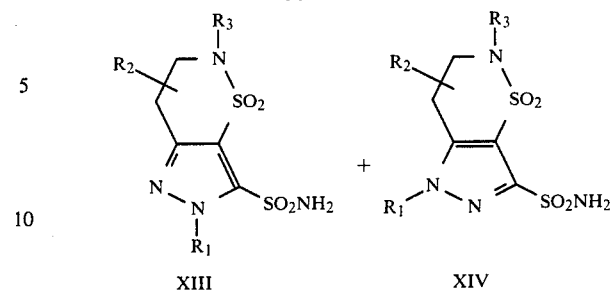

The transformations described in Equation 6, parallel those procedures described in Equations 4 and 5. Here, the homolog amino substituted keto ester XV is employed resulting in the [3.0.4] bicyclic pyrazoles XIII and XIV.

The prerequisite starting amino keto esters may be prepared using standard conditions well known to one skilled in the art. For example, alkylation of glycine with butyl bromide ($R_3$=n-butyl) affords the acid XVI. Esterification followed by condensation with ethyl chloracetate yields the desired keto ester XVII. This sequence is described in Equation 7.

Equation 7

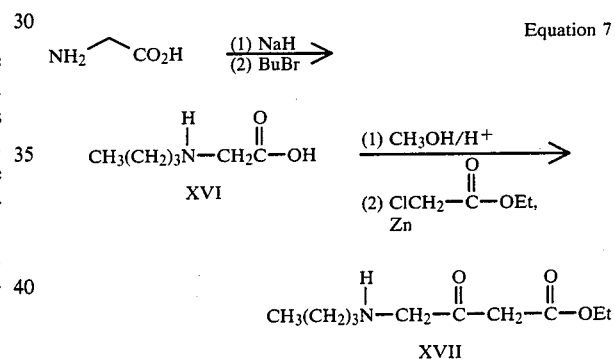

An alternate synthesis of sulfonamides VII and VIII is described in Equation 8. The benzylthio intermediate XIX is oxidatively chlorinated and aminated providing sulfonamides VII and VIII after chromatographic separation of the two isomers. The prerequesite heterocycle XVIII is prepared by the procedures taught in DT No. 2431734.

Equation 8

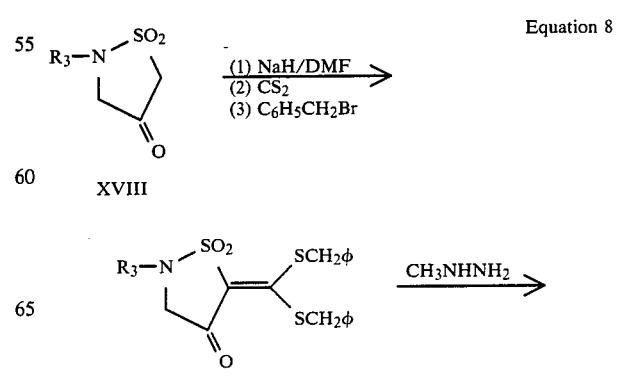

-continued

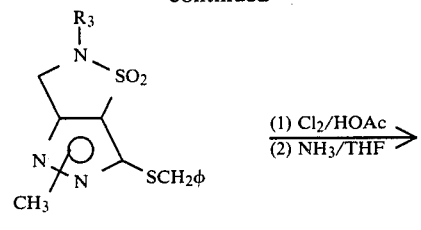

(1) Cl₂/HOAc
(2) NH₃/THF

XIX

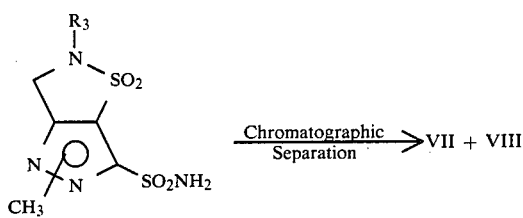

Chromatographic Separation → VII + VIII

In the following examples, all parts are by weight and temperatures in degrees Centigrade unless otherwise stated.

EXAMPLE 1

Preparation of 5-Butyl-2,5,6,7-tetrahydro-2-methylpyrazole[3,4-e][1,2]thiazine-3-sulfonamide, 4,4-dioxide Chlorine gas is bubbled through a stirring solution of 5-Butyl-2,5,6-tetrahydro-2-methyl-3-(propylthio)-pyrazole[3,4-c]-[1,2]thiazine-4-4-dioxide cooled to 5° C. in propionic acid and three equivalents of water. After 30 minutes the solids are filtered off and dried. The resulting solids are dissolved in tetrahydrofuran and added dropwise to a solution of ammonia in tetrahydrofuran. After stirring for 16 hours the solids are filtered and the filtrate is concentrated. The resulting solid is washed with ether and dried to afford the subject sulfonamide.

EXAMPLE 2

Preparation of 5-Butyl-N-[4,6-dimethyoxypyrimidin-2-yl)aminocarbonyl]-2,5,6,7-tetrahydro-2-methylpyrazolo[3,4-e][1,2]thiazine-3-sulfonamide, 4,4-dioxide The sulfonamide from Example 1 is added to a flask containing one equivalent of the phenyl carbamate of 4,6-dimethoxy-2-aminopyrimidine in 10 ml of acetonitrile. One equivalent of diazobicycloundecane is added and the reaction is stirred for 1 hour. Five ml of 10% hydrochloric acid is added and the resulting solids are collected and dried to afford the desired compound.

Structures for Tables

| Table | Structure |
|---|---|
| I n = 1<br>Ia n = 0 | ![structure I] |
| II n = 1<br>IIa n = 0 | ![structure II] |
| III n = 1<br>IIIa n = 0 | ![structure III] |
| IV n = 1<br>IVa n = 0 | ![structure IV] |

TABLE I

General Structure I

| R | R₁ | R₂ | R₃ | X | Y | Z | m.p. (°C.) |
|---|---|---|---|---|---|---|---|
| H | CH₃ | H | CH₂F | CH₃ | CH₃ | CH | |
| H | CH₃ | H | CH₂F | CH₃ | OCH₃ | CH | |
| H | CH₃ | H | CH₂F | OCH₃ | OCH₃ | CH | |
| H | CH₃ | H | CH₂F | CH₃ | CH₃ | N | |
| H | CH₃ | H | CH₂F | CH₃ | OCH₃ | N | |
| H | CH₃ | H | CH₂F | OCH₃ | OCH₃ | N | |
| H | CH₃ | H | CH₂F | OCH₃ | Cl | CH | |
| H | CH₃ | H | CH₂CH₂F | CH₃ | CH₃ | CH | |
| H | CH₃ | H | CH₂CH₂F | CH₃ | OCH₃ | CH | |
| H | CH₃ | H | CH₂CH₂F | OCH₃ | OCH₃ | CH | |
| H | CH₃ | H | CH₂CH₂F | CH₃ | CH₃ | N | |
| H | CH₃ | H | CH₂CH₂F | CH₃ | OCH₃ | N | |
| H | CH₃ | H | CH₂CH₂F | OCH₃ | OCH₃ | N | |
| H | CH₃ | H | CH₂CH₂F | OCH₃ | Cl | CH | |
| H | CH₃ | H | CHFCH₂F | CH₃ | CH₃ | CH | |
| H | CH₃ | H | CHFCH₂F | CH₃ | OCH₃ | CH | |
| H | CH₃ | H | CHFCH₂F | OCH₃ | OCH₃ | CH | |
| H | CH₃ | H | CHFCH₂F | CH₃ | CH₃ | N | |
| H | CH₃ | H | CHFCH₂F | OCH₃ | OCH₃ | N | |
| H | CH₃ | H | CHFCH₂F | OCH₃ | Cl | CH | |

TABLE I-continued

General Structure I

| R | $R_1$ | $R_2$ | $R_3$ | X | Y | Z | m.p. (°C.) |
|---|---|---|---|---|---|---|---|
| H | $CH_3$ | H | $CH_2CHF_2$ | $CH_3$ | $CH_3$ | CH | |
| H | $CH_3$ | H | $CH_2CHF_2$ | $CH_3$ | $OCH_3$ | CH | |
| H | $CH_3$ | H | $CH_2CHF_2$ | $OCH_3$ | $OCH_3$ | CH | |
| H | $CH_3$ | H | $CH_2CHF_2$ | $CH_3$ | $CH_3$ | N | |
| H | $CH_3$ | H | $CH_2CHF_2$ | $CH_3$ | $OCH_3$ | N | |
| H | $CH_3$ | H | $CH_2CHF_2$ | $OCH_3$ | $OCH_3$ | N | |
| H | $CH_3$ | H | $CH_2CHF_2$ | $OCH_3$ | Cl | CH | |
| H | $CH_3$ | H | $CH(CH_2F)_2$ | $CH_3$ | $CH_3$ | CH | |
| H | $CH_3$ | H | $CH(CH_2F)_2$ | $CH_3$ | $OCH_3$ | CH | |
| H | $CH_3$ | H | $CH(CH_2F)_2$ | $OCH_3$ | $OCH_3$ | CH | |
| H | $CH_3$ | H | $CH_2CH_2CH_2F$ | $CH_3$ | $CH_3$ | N | |
| H | $CH_3$ | H | $CH_2CH_2CH_2F$ | $CH_3$ | $OCH_3$ | N | |
| H | $CH_3$ | $CH_3$ | $CH_2CH_2CH_2F$ | $OCH_3$ | $OCH_3$ | N | |
| H | $CH_3$ | H | $CH_2CH_2CH_2F$ | $OCH_3$ | Cl | CH | |
| H | $CH_3$ | H | $CH_2CH_2CH_2F$ | $CH_3$ | $CH_3$ | CH | |
| H | $CH_3$ | H | $CH_2CH_2CH_2F$ | $CH_3$ | $OCH_3$ | CH | |
| H | $CH_3$ | H | $CH_2CH_2CH_2F$ | $OCH_3$ | $OCH_3$ | CH | |
| H | $CH_3$ | H | $CH_2(CH_2)_2CH_2F$ | $CH_3$ | $CH_3$ | N | |
| H | $CH_3$ | H | $CH_2(CH_2)_2CH_2F$ | $CH_3$ | $OCH_3$ | N | |
| H | $CH_3$ | H | $CH_2(CH_2)_2CH_2F$ | $OCH_3$ | $OCH_3$ | N | |
| H | $CH_3$ | H | $CH_2(CH_2)_2CH_2F$ | $OCH_3$ | Cl | CH | |
| H | $CH_3$ | H | $CH_2(CH_2)_2CH_2F$ | $CH_3$ | $CH_3$ | CH | |
| $CH_3$ | $CH_3$ | H | $CH_2(CH_2)_2CH_2F$ | $CH_3$ | $OCH_3$ | CH | |
| H | $CH_3$ | H | $CH_2(CH_2)_2CH_2F$ | $OCH_3$ | $OCH_3$ | CH | |
| H | $CH_3$ | H | $CH(CH_3)CH_2F$ | $CH_3$ | $CH_3$ | N | |
| H | $CH_3$ | H | $CH(CH_3)CH_2F$ | $CH_3$ | $OCH_3$ | N | |
| H | $CH_3$ | H | $CH(CH_3)CH_2F$ | $OCH_3$ | $OCH_3$ | N | |
| H | $CH_3$ | H | $CH(CH_3)CH_2F$ | $OCH_3$ | Cl | CH | |
| H | $CH_3$ | H | $CH_2Br$ | $CH_3$ | $CH_3$ | CH | |
| H | $CH_3$ | H | $CH_2Br$ | $CH_3$ | $OCH_3$ | CH | |
| H | $CH_3$ | H | $CH_2Br$ | $OCH_3$ | $OCH_3$ | CH | |
| H | $CH_3$ | H | $CH_2Br$ | $CH_3$ | $CH_3$ | N | |
| H | $CH_3$ | H | $CH_2Br$ | $CH_3$ | $OCH_3$ | N | |
| H | $CH_3$ | H | $CH_2Br$ | $OCH_3$ | $OCH_3$ | N | |
| H | $CH_3$ | H | $CH_2Br$ | $OCH_3$ | Cl | CH | |
| H | $CH_3$ | H | $CH_2CH_2Br$ | $CH_3$ | $CH_3$ | CH | |
| H | $CH_3$ | H | $CH_2CH_2Br$ | $CH_3$ | $OCH_3$ | CH | |
| H | $CH_3$ | H | $CH_2CH_2Br$ | $OCH_3$ | $OCH_3$ | CH | |
| H | $CH_3$ | H | $CH_2CH_2Br$ | $CH_3$ | $CH_3$ | N | |
| H | $CH_3$ | H | $CH_2CH_2Br$ | $CH_3$ | $OCH_3$ | N | |
| H | $CH_3$ | H | $CH_2CH_2Br$ | $OCH_3$ | $OCH_3$ | N | |
| H | $CH_3$ | H | $CH_2CH_2Br$ | $OCH_3$ | Cl | CH | |
| H | $CH_3$ | H | $CHBrCH_3$ | $CH_3$ | $CH_3$ | CH | |
| H | $CH_3$ | H | $CHBrCH_3$ | $CH_3$ | $OCH_3$ | CH | |
| H | $CH_3$ | H | $CHBrCH_3$ | $OCH_3$ | $OCH_3$ | CH | |
| H | $CH_3$ | H | $CHBrCH_3$ | $CH_3$ | $CH_3$ | N | |
| H | $CH_3$ | H | $CHBrCH_3$ | $CH_3$ | $OCH_3$ | N | |
| H | $CH_3$ | H | $CHBrCH_3$ | $OCH_3$ | Cl | CH | |
| H | $CH_3$ | H | $CH_2CHBr_2$ | $CH_3$ | $CH_3$ | CH | |
| H | $CH_3$ | H | $CH_2CHBr_2$ | $CH_3$ | $OCH_3$ | CH | |
| H | $CH_3$ | H | $CH_2CHBr_2$ | $OCH_3$ | $OCH_3$ | CH | |
| H | $CH_3$ | H | $CH_2CHBr_2$ | $CH_3$ | $CH_3$ | N | |
| H | $CH_3$ | H | $CH_2CHBr_2$ | $CH_3$ | $OCH_3$ | N | |
| H | $CH_3$ | H | $CH_2CHBr_2$ | $OCH_3$ | $OCH_3$ | N | |
| H | $CH_3$ | H | $CH_2CHBr_2$ | $OCH_3$ | Cl | CH | |
| H | $CH_3$ | H | $CH(CH_2Br)_2$ | $CH_3$ | $CH_3$ | CH | |
| H | $CH_3$ | H | $CH(CH_2Br)_2$ | $CH_3$ | $OCH_3$ | CH | |
| H | $CH_3$ | H | $CH(CH_2Br)_2$ | $OCH_3$ | $OCH_3$ | CH | |
| H | $CH_3$ | H | $CH(CH_2Br)_2$ | $CH_3$ | $CH_3$ | N | |
| H | $CH_3$ | H | $CH_2CHBr—CH_3$ | $CH_3$ | $OCH_3$ | N | |
| H | $CH_3$ | $CH_3$ | $CH_2CHBr—CH_3$ | $OCH_3$ | $OCH_3$ | N | |
| H | $CH_3$ | H | $CH_2CHBr—CH_3$ | $OCH_3$ | Cl | CH | |
| H | $CH_3$ | H | $CH_2CHBr—CH_3$ | $CH_3$ | $CH_3$ | CH | |
| H | $CH_3$ | H | $CH_2CHBr—CH_3$ | $CH_3$ | $OCH_3$ | CH | |
| H | $CH_3$ | H | $CH_2(CH_2)_2CH_2Br$ | $OCH_3$ | $OCH_3$ | CH | |
| H | $CH_3$ | H | $CH_2(CH_2)_2CH_2Br$ | $CH_3$ | $CH_3$ | N | |
| H | $CH_3$ | H | $CH_2(CH_2)_2CH_2Br$ | $CH_3$ | $OCH_3$ | N | |
| H | $CH_3$ | H | $CH_2(CH_2)_2CH_2Br$ | $OCH_3$ | $OCH_3$ | N | |
| H | $CH_3$ | H | $CH_2(CH_2)_2CH_2Br$ | $OCH_3$ | Cl | CH | |
| H | $CH_3$ | H | $CH_2(CH_2)_2CH_2Br$ | $CH_3$ | $CH_3$ | CH | |
| $CH_3$ | $CH_3$ | H | $CH_2(CH_2)_2CH_2Br$ | $CH_3$ | $OCH_3$ | CH | |
| H | $CH_3$ | H | $C(CH_3)(CH_2Br)CH_3$ | $OCH_3$ | $OCH_3$ | CH | |
| H | $CH_3$ | H | $CH_2CHBrCH_2CH_3$ | $CH_3$ | $CH_3$ | N | |
| H | $CH_3$ | H | $CH_2CHBrCH_2CH_3$ | $CH_3$ | $OCH_3$ | N | |
| H | $CH_3$ | H | $CH_2CHBrCH_2CH_3$ | $OCH_3$ | $OCH_3$ | N | |
| H | $CH_3$ | H | $CH_2CHBrCH_2CH_3$ | $OCH_3$ | Cl | CH | |
| H | $CH_3$ | H | $CH_2Cl$ | $CH_3$ | $CH_3$ | CH | |
| H | $CH_3$ | H | $CH_2Cl$ | $CH_3$ | $OCH_3$ | CH | |
| H | $CH_3$ | H | $CH_2Cl$ | $OCH_3$ | $OCH_3$ | CH | |
| H | $CH_3$ | H | $CH_2Cl$ | $CH_3$ | $CH_3$ | N | |

TABLE I-continued

General Structure I

| R | $R_1$ | $R_2$ | $R_3$ | X | Y | Z | m.p. (°C.) |
|---|---|---|---|---|---|---|---|
| H | CH$_3$ | H | CH$_2$Cl | CH$_3$ | OCH$_3$ | N | |
| H | CH$_3$ | H | CH$_2$Cl | OCH$_3$ | OCH$_3$ | N | |
| H | CH$_3$ | H | CH$_2$Cl | OCH$_3$ | Cl | CH | |
| H | CH$_3$ | H | CH$_2$CH$_2$Cl | CH$_3$ | CH$_3$ | CH | |
| H | CH$_3$ | H | CH$_2$CH$_2$Cl | CH$_3$ | OCH$_3$ | CH | |
| H | CH$_3$ | H | CH$_2$CH$_2$Cl | OCH$_3$ | OCH$_3$ | CH | |
| H | CH$_3$ | H | CH$_2$CH$_2$Cl | CH$_3$ | CH$_3$ | N | |
| H | CH$_3$ | H | CH$_2$CH$_2$Cl | CH$_3$ | OCH$_3$ | N | |
| H | CH$_3$ | H | CH$_2$CH$_2$Cl | OCH$_3$ | OCH$_3$ | N | |
| H | CH$_3$ | H | CH$_2$CH$_2$Cl | OCH$_3$ | Cl | CH | |
| H | CH$_3$ | H | CHClCH$_2$Cl | CH$_3$ | CH$_3$ | CH | |
| H | CH$_3$ | H | CHClCH$_2$Cl | CH$_3$ | OCH$_3$ | CH | |
| H | CH$_3$ | H | CHClCH$_2$Cl | OCH$_3$ | OCH$_3$ | CH | |
| H | CH$_3$ | H | CHClCH$_2$Cl | CH$_3$ | CH$_3$ | N | |
| H | CH$_3$ | H | CHClCH$_2$Cl | OCH$_3$ | OCH$_3$ | N | |
| H | CH$_3$ | H | CHClCH$_2$Cl | OCH$_3$ | Cl | CH | |
| H | CH$_3$ | H | CH$_2$CCl$_2$CH$_3$ | CH$_3$ | CH$_3$ | CH | |
| H | CH$_3$ | H | CH$_2$CCl$_2$CH$_3$ | CH$_3$ | OCH$_3$ | CH | |
| H | CH$_3$ | H | CH$_2$CCl$_2$CH$_3$ | OCH$_3$ | OCH$_3$ | CH | |
| H | CH$_3$ | H | CH(CH$_2$Cl)$_2$ | CH$_3$ | CH$_3$ | N | |
| H | CH$_3$ | H | CH(CH$_2$Cl)$_2$ | CH$_3$ | OCH$_3$ | N | |
| H | CH$_3$ | H | CH(CH$_2$Cl)$_2$ | OCH$_3$ | OCH$_3$ | N | |
| H | CH$_3$ | H | CH(CH$_2$Cl)$_2$ | OCH$_3$ | Cl | CH | |
| H | CH$_3$ | H | CH(CH$_2$Cl)$_2$ | CH$_3$ | CH$_3$ | CH | |
| H | CH$_3$ | H | CH$_2$CH$_2$CH$_2$Cl | CH$_3$ | OCH$_3$ | CH | |
| H | CH$_3$ | H | CH$_2$CH$_2$CH$_2$Cl | OCH$_3$ | OCH$_3$ | CH | |
| H | CH$_3$ | H | CH$_2$CH$_2$CH$_2$Cl | CH$_3$ | CH$_3$ | N | |
| H | CH$_3$ | H | CH$_2$CH$_2$CH$_2$Cl | CH$_3$ | OCH$_3$ | N | |
| H | CH$_3$ | CH$_3$ | CH$_2$CH$_2$CH$_2$Cl | OCH$_3$ | OCH$_3$ | N | |
| H | CH$_3$ | H | CH$_2$CH$_2$CH$_2$Cl | OCH$_3$ | Cl | CH | |
| H | CH$_3$ | H | CH$_2$CH$_2$CH$_2$Cl | CH$_3$ | CH$_3$ | CH | |
| H | CH$_3$ | H | CH$_2$(CH$_2$)$_2$CH$_2$Cl | CH$_3$ | OCH$_3$ | CH | |
| H | CH$_3$ | H | CH$_2$(CH$_2$)$_2$CH$_2$Cl | OCH$_3$ | OCH$_3$ | CH | |
| H | CH$_3$ | H | CH$_2$(CH$_2$)$_2$CH$_2$Cl | CH$_3$ | CH$_3$ | N | |
| H | CH$_3$ | H | CH$_2$(CH$_2$)$_2$CH$_2$Cl | CH$_3$ | OCH$_3$ | N | |
| H | CH$_3$ | H | CH$_2$(CH$_2$)$_2$CH$_2$Cl | OCH$_3$ | OCH$_3$ | N | |
| H | CH$_3$ | H | CH$_2$(CH$_2$)$_2$CH$_2$Cl | OCH$_3$ | Cl | CH | |
| H | CH$_3$ | H | CH$_2$(CH$_2$)$_2$CH$_2$Cl | CH$_3$ | CH$_3$ | CH | |
| CH$_3$ | CH$_3$ | H | CH(CH$_3$)CH$_2$Cl | CH$_3$ | OCH$_3$ | CH | |
| H | CH$_3$ | H | CH(CH$_3$)CH$_2$Cl | OCH$_3$ | OCH$_3$ | CH | |
| H | CH$_3$ | H | CH(CH$_3$)CH$_2$Cl | CH$_3$ | CH$_3$ | N | |
| H | CH$_3$ | H | CHClCHClCH$_3$ | CH$_3$ | OCH$_3$ | N | |
| H | CH$_3$ | H | CHClCHClCH$_3$ | OCH$_3$ | OCH$_3$ | N | |
| H | CH$_3$ | H | CHClCHClCH$_3$ | OCH$_3$ | Cl | CH | |
| H | CH$_3$ | H | CH$_2$I | CH$_3$ | CH$_3$ | CH | |
| H | CH$_3$ | H | CH$_2$I | CH$_3$ | OCH$_3$ | CH | |
| H | CH$_3$ | H | CH$_2$I | OCH$_3$ | OCH$_3$ | CH | |
| H | CH$_3$ | H | CH$_2$I | CH$_3$ | CH$_3$ | N | |
| H | CH$_3$ | H | CH$_2$I | CH$_3$ | OCH$_3$ | N | |
| H | CH$_3$ | H | CH$_2$I | OCH$_3$ | OCH$_3$ | N | |
| H | CH$_3$ | H | CH$_2$I | OCH$_3$ | Cl | CH | |
| H | CH$_3$ | H | CH$_2$CF$_3$ | CH$_3$ | CH$_3$ | CH | |
| H | CH$_3$ | H | CH$_2$CF$_3$ | CH$_3$ | OCH$_3$ | CH | |
| H | CH$_3$ | H | CH$_2$CF$_3$ | OCH$_3$ | OCH$_3$ | CH | |
| H | CH$_3$ | H | CH$_2$CF$_3$ | CH$_3$ | CH$_3$ | N | |
| H | CH$_3$ | H | CH$_2$CF$_3$ | CH$_3$ | OCH$_3$ | N | |
| H | CH$_3$ | H | CH$_2$CF$_3$ | OCH$_3$ | OCH$_3$ | N | |
| H | CH$_3$ | H | CH$_2$CF$_3$ | OCH$_3$ | Cl | CH | |
| H | CH$_3$ | H | CH$_2$CH$_2$CF$_3$ | CH$_3$ | CH$_3$ | CH | |
| H | CH$_3$ | H | CH$_2$CH$_2$CF$_3$ | CH$_3$ | OCH$_3$ | CH | |
| H | CH$_3$ | H | CH$_2$CH$_2$CF$_3$ | OCH$_3$ | OCH$_3$ | CH | |
| H | CH$_3$ | H | CH$_2$CH$_2$CF$_3$ | CH$_3$ | CH$_3$ | N | |
| H | CH$_3$ | H | CH$_2$CH$_2$CF$_3$ | OCH$_3$ | OCH$_3$ | N | |
| H | CH$_3$ | H | CH$_2$CH$_2$CF$_3$ | OCH$_3$ | Cl | CH | |
| H | CH$_3$ | H | CH$_2$(CH$_2$)$_2$CF$_3$ | CH$_3$ | CH$_3$ | CH | |
| H | CH$_3$ | H | CH$_2$(CH$_2$)$_2$CF$_3$ | CH$_3$ | OCH$_3$ | CH | |
| H | CH$_3$ | H | CH$_2$(CH$_2$)$_2$CF$_3$ | OCH$_3$ | OCH$_3$ | CH | |
| H | CH$_3$ | H | CH$_2$(CH$_2$)$_2$CF$_3$ | CH$_3$ | CH$_3$ | N | |
| H | CH$_3$ | H | CH$_2$(CH$_2$)$_2$CF$_3$ | CH$_3$ | OCH$_3$ | N | |
| H | CH$_3$ | H | CH$_2$(CH$_2$)$_2$CF$_3$ | OCH$_3$ | OCH$_3$ | N | |
| H | CH$_3$ | H | CH$_2$(CH$_2$)$_3$CF$_3$ | OCH$_3$ | Cl | CH | |
| H | CH$_3$ | H | CH$_2$(CH$_2$)$_3$CF$_3$ | CH$_3$ | CH$_3$ | CH | |
| H | CH$_3$ | H | CH$_2$(CH$_2$)$_3$CF$_3$ | CH$_3$ | OCH$_3$ | CH | |
| H | CH$_3$ | H | CH$_2$(CH$_2$)$_3$CF$_3$ | OCH$_3$ | OCH$_3$ | CH | |
| H | CH$_3$ | H | CH$_2$(CH$_2$)$_3$CF$_3$ | CH$_3$ | CH$_3$ | N | |
| H | CH$_3$ | H | CH$_2$(CH$_2$)$_3$CF$_3$ | CH$_3$ | OCH$_3$ | N | |
| H | CH$_3$ | CH$_3$ | CH$_2$(CH$_2$)$_3$CF$_3$ | OCH$_3$ | OCH$_3$ | N | |
| H | CH$_3$ | H | CH(CF$_3$)$_2$ | OCH$_3$ | Cl | CH | |
| H | CH$_3$ | H | CH(CF$_3$)$_2$ | CH$_3$ | CH$_3$ | CH | |
| H | CH$_3$ | H | CH(CF$_3$)$_2$ | CH$_3$ | OCH$_3$ | CH | |

TABLE I-continued

General Structure I

| R | R₁ | R₂ | R₃ | X | Y | Z | m.p. (°C.) |
|---|----|----|----|---|---|---|------------|
| H | CH₃ | H | CH(CF₃)₂ | OCH₃ | OCH₃ | CH | |
| H | CH₃ | H | CH(CF₃)₂ | CH₃ | CH₃ | N | |
| H | CH₃ | H | CH(CF₃)₂ | CH₃ | OCH₃ | N | |
| H | CH₃ | H | CH(CF₃)₂ | OCH₃ | OCH₃ | N | |
| H | CH₃ | H | CH₂(CH₂)₄CF₃ | OCH₃ | Cl | CH | |
| H | CH₃ | H | CH₂(CH₂)₅CF₃ | CH₃ | CH₃ | CH | |
| CH₃ | CH₃ | H | CH₂(CH₂)₆CF₃ | CH₃ | OCH₃ | CH | |
| H | CH₃ | H | CH₂(CH₂)₇CF₃ | OCH₃ | OCH₃ | CH | |
| H | CH₃ | H | CH₂(CH₂)₈CF₃ | CH₃ | CH₃ | N | |
| H | CH₃ | H | CH₂(CH₂)₈CF₃ | CH₃ | OCH₃ | N | |
| H | CH₃ | H | CH(CHF)₈CF₃ | OCH₃ | OCH₃ | N | |
| H | CH₃ | H | CH(CHF)₈CF₃ | OCH₃ | Cl | CH | |
| H | CH₃ | H | CH₂OCH₃ | CH₃ | CH₃ | CH | |
| H | CH₃ | H | CH₂OCH₃ | CH₃ | OCH₃ | CH | |
| H | CH₃ | H | CH₂OCH₃ | OCH₃ | OCH₃ | CH | |
| H | CH₃ | H | CH₂OCH₃ | CH₃ | CH₃ | N | |
| H | CH₃ | H | CH₂OCH₃ | CH₃ | OCH₃ | N | |
| H | CH₃ | H | CH₂OCH₃ | OCH₃ | OCH₃ | N | |
| H | CH₃ | H | CH₂OCH₃ | OCH₃ | Cl | CH | |
| H | CH₃ | H | CH₂OCH₂CH₃ | CH₃ | CH₃ | CH | |
| H | CH₃ | H | CH₂OCH₂CH₃ | CH₃ | OCH₃ | CH | |
| H | CH₃ | H | CH₂OCH₂CH₃ | OCH₃ | OCH₃ | CH | |
| H | CH₃ | H | CH₂—OCH₂F | CH₃ | CH₃ | N | |
| H | CH₃ | H | CH₂—OCH₂F | CH₃ | OCH₃ | N | |
| H | CH₃ | H | CH₂—OCH₂F | OCH₃ | OCH₃ | N | |
| H | CH₃ | H | CH₂—OCH₂F | OCH₃ | Cl | CH | |
| H | CH₃ | H | CH₂—CH₂OCH₃ | CH₃ | CH₃ | CH | |
| H | CH₃ | H | CH₂—CH₂OCH₃ | CH₃ | OCH₃ | CH | |
| H | CH₃ | H | CH₂—CH₂OCH₃ | OCH₃ | OCH₃ | CH | |
| H | CH₃ | H | CH₂—CH₂OCH₃ | CH₃ | CH₃ | N | |
| H | CH₃ | H | CH(OCH₃)₂ | OCH₃ | OCH₃ | N | |
| H | CH₃ | H | CH(OCH₃)₂ | OCH₃ | Cl | CH | |
| H | CH₃ | H | CH₂(CH₂)₂OCH₃ | CH₃ | CH₃ | CH | |
| H | CH₃ | H | CH₂(CH₂)₂OCH₃ | CH₃ | OCH₃ | CH | |
| H | CH₃ | H | CH₂(CH₂)₂OCH₃ | OCH₃ | OCH₃ | CH | |
| H | CH₃ | H | CH₂(CH₂)₂OCH₃ | CH₃ | CH₃ | N | |
| H | CH₃ | H | CH₂(CH₂)₂OCH₃ | CH₃ | OCH₃ | N | |
| H | CH₃ | H | CH₂(CH₂)₂OCH₃ | OCH₃ | OCH₃ | N | |
| H | CH₃ | H | CH₂(CH₂)₂OCH₃ | OCH₃ | Cl | CH | |
| H | CH₃ | H | CH₂(CH₂)₂OCH₃ | CH₃ | CH₃ | CH | |
| H | CH₃ | H | CH₂(CH₂)₂OCH₃ | CH₃ | OCH₃ | CH | |
| H | CH₃ | H | CH₂(CH₂)₂OCH₃ | OCH₃ | OCH₃ | CH | |
| H | CH₃ | H | CH(OCH₃)CH₃ | CH₃ | CH₃ | N | |
| H | CH₃ | H | CH(OCH₃)CH₃ | CH₃ | OCH₃ | N | |
| H | CH₃ | CH₃ | CH(OCH₃)CH₃ | OCH₃ | OCH₃ | N | |
| H | CH₃ | H | CH₂OCH₂C=CH₂ | OCH₃ | Cl | CH | |
| H | CH₃ | H | CH₂OCH₂C=CH₂ | CH₃ | CH₃ | CH | |
| H | CH₃ | H | CH₂OCH₂C=CH₂ | CH₃ | OCH₃ | CH | |
| H | CH₃ | H | CH₂OCH₂C=CH₂ | OCH₃ | OCH₃ | CH | |
| H | CH₃ | H | CH₂OCH₂C=CH₂ | CH₃ | CH₃ | N | |
| H | CH₃ | H | CH₂OCH₂C=CH₂ | CH₃ | OCH₃ | N | |
| H | CH₃ | H | CH₂CH(OCH₃)₂ | OCH₃ | OCH₃ | N | |
| H | CH₃ | H | CH₂CH(OCH₃)₂ | OCH₃ | Cl | CH | |
| H | CH₃ | H | CH₂CH(OCH₃)₂ | CH₃ | CH₃ | CH | |
| H | CH₃ | H | CH₂CH(OCH₃)₂ | CH₃ | OCH₃ | CH | |
| H | CH₃ | H | CH₂C(OCH₃)₂CH₃ | OCH₃ | OCH₃ | CH | |
| H | CH₃ | H | CH₂C(OCH₃)₂CH₃ | CH₃ | CH₃ | N | |
| H | CH₃ | H | CH₂C(OCH₃)₂CH₃ | CH₃ | OCH₃ | N | |
| H | CH₃ | H | CH₂(CH₂)₆OCH₃ | OCH₃ | OCH₃ | N | |
| H | CH₃ | H | CH₂(CH₂)₆OCH₃ | OCH₃ | Cl | CH | |
| H | CH₃ | H | CH₂OC(O)CH₃ | CH₃ | CH₃ | CH | |
| H | CH₃ | H | CH₂OC(O)CH₃ | CH₃ | OCH₃ | CH | |
| H | CH₃ | H | CH₂OC(O)CH₃ | OCH₃ | OCH₃ | CH | |
| H | CH₃ | H | CH₂OC(O)CH₃ | CH₃ | CH₃ | N | |
| H | CH₃ | H | CH₂OC(O)CH₃ | CH₃ | OCH₃ | N | |
| H | CH₃ | H | CH₂OC(O)CH₃ | OCH₃ | OCH₃ | N | |
| H | CH₃ | H | CH₂OC(O)CH₃ | OCH₃ | Cl | CH | |
| H | CH₃ | H | CH₂CH₂OC(O)CH₃ | CH₃ | CH₃ | CH | |
| H | CH₃ | H | CH₂CH₂OC(O)CH₃ | CH₃ | OCH₃ | CH | |
| H | CH₃ | H | CH₂CH₂OC(O)CH₃ | OCH₃ | OCH₃ | CH | |
| H | CH₃ | H | CH₂CH₂OC(O)CH₃ | CH₃ | CH₃ | N | |
| H | CH₃ | H | CH₂CH₂OC(O)CH₃ | CH₃ | OCH₃ | N | |
| H | CH₃ | H | CH₂CH₂OC(O)CH₃ | OCH₃ | OCH₃ | N | |
| H | CH₃ | H | CH₂CH₂OC(O)CH₃ | OCH₃ | Cl | CH | |
| H | CH₃ | H | CH₂(CH₂)₂OC(O)CH₃ | CH₃ | CH₃ | CH | |
| H | CH₃ | H | CH₂(CH₂)₂OC(O)CH₃ | CH₃ | OCH₃ | CH | |
| H | CH₃ | H | CH₂(CH₂)₂OC(O)CH₃ | OCH₃ | OCH₃ | CH | |
| H | CH₃ | H | CH₂(CH₂)₃OC(O)CH₃ | CH₃ | CH₃ | N | |
| H | CH₃ | H | CH₂(CH₂)₃OC(O)CH₃ | OCH₃ | OCH₃ | N | |
| H | CH₃ | H | CH₂(CH₂)₃OC(O)CH₃ | OCH₃ | Cl | CH | |

TABLE I-continued

| | | | | General Structure I | | | |
|---|---|---|---|---|---|---|---|
| R | $R_1$ | $R_2$ | $R_3$ | X | Y | Z | m.p. (°C.) |
| H | $CH_3$ | H | $CH_2(CH_2)_3OC(O)CH_3$ | $CH_3$ | $CH_3$ | CH | |
| H | $CH_3$ | H | $CH_2P(CH_3)(Br)(CH_3)$ | $CH_3$ | $OCH_3$ | CH | |
| H | $CH_3$ | H | $CH_2P(C_6H_5)_3$ | $OCH_3$ | $OCH_3$ | CH | |
| H | $CH_3$ | H | $CH_2OC(O)N(CH_3)_2$ | $CH_3$ | $CH_3$ | N | |
| H | $CH_3$ | H | $CH_2OC(O)N(CH_3)_2$ | $CH_3$ | $OCH_3$ | N | |
| H | $CH_3$ | H | $CH_2OC(O)N(CH_3)_2$ | $OCH_3$ | $OCH_3$ | N | |
| H | $CH_3$ | H | $CH_2OC(O)N(CH_3)_2$ | $OCH_3$ | Cl | CH | |
| H | $CH_3$ | H | $CH_2OC(O)N(CH_3)_2$ | $CH_3$ | $CH_3$ | CH | |
| H | $CH_3$ | H | $CH_2OC(O)N(CH_3)_2$ | $CH_3$ | $OCH_3$ | CH | |
| H | $CH_3$ | H | $CH_2OC(O)N(CH_3)_2$ | $OCH_3$ | $OCH_3$ | CH | |
| H | $CH_3$ | H | $CH_2CH_2OC(O)N(CH_3)_2$ | $CH_3$ | $CH_3$ | N | |
| H | $CH_3$ | H | $CH_2CH_2OC(O)N(CH_3)_2$ | $CH_3$ | $OCH_3$ | N | |
| H | $CH_3$ | $CH_3$ | $CH_2CH_2OC(O)N(CH_3)_2$ | $OCH_3$ | $OCH_3$ | N | |
| H | $CH_3$ | H | $CH_2CH_2OC(O)N(CH_3)_2$ | $OCH_3$ | Cl | CH | |
| H | $CH_3$ | H | $CH_2CH_2OC(O)N(CH_3)_2$ | $CH_3$ | $CH_3$ | CH | |
| H | $CH_3$ | H | $CH_2CH_2OC(O)N(CH_3)_2$ | $CH_3$ | $OCH_3$ | CH | |
| H | $CH_3$ | H | $CH_2OSO_2CH_3$ | $OCH_3$ | $OCH_3$ | CH | |
| H | $CH_3$ | H | $CH_2OSO_2CH_3$ | $CH_3$ | $CH_3$ | N | |
| H | $CH_3$ | H | $CH_2OSO_2CH_3$ | $CH_3$ | $OCH_3$ | N | |
| H | $CH_3$ | H | $CH_2OSO_2CH_3$ | $OCH_3$ | $OCH_3$ | N | |
| H | $CH_3$ | H | $CH_2OSO_2CH_2CH_3$ | $OCH_3$ | Cl | CH | |
| H | $CH_3$ | H | $CH_2OSO_2CH_2CH_3$ | $CH_3$ | $CH_3$ | CH | |
| $CH_3$ | $CH_3$ | H | $CH_2OSO_2CH_2CH_3$ | $CH_3$ | $OCH_3$ | CH | |
| H | $CH_3$ | H | $CH_2(CH_2)_2OSO_2CH_3$ | $OCH_3$ | $OCH_3$ | CH | |
| H | $CH_3$ | H | $CH_2(CH_2)_2OSO_2CH_3$ | $CH_3$ | $CH_3$ | N | |
| H | $CH_3$ | H | $CH_2(CH_2)_2OSO_2CH_3$ | $CH_3$ | $OCH_3$ | N | |
| H | $CH_3$ | H | $CH_2(CH_2)_2OSO_2CH_3$ | $OCH_3$ | $OCH_3$ | N | |
| H | $CH_3$ | H | $CH_2(CH_2)_2OSO_2CH_3$ | $OCH_3$ | Cl | CH | |
| H | $CH_3$ | H | $CH_2OP(O)(CH_3)_2$ | $CH_3$ | $CH_3$ | CH | |
| H | $CH_3$ | H | $CH_2OP(O)(CH_3)_2$ | $CH_3$ | $OCH_3$ | CH | |
| H | $CH_3$ | H | $CH_2OP(O)(CH_3)_2$ | $OCH_3$ | $OCH_3$ | CH | |
| H | $CH_3$ | H | $CH_2OP(O)(CH_3)_2$ | $CH_3$ | $CH_3$ | N | |
| H | $CH_3$ | H | $CH_2OP(O)(CH_3)_2$ | $CH_3$ | $OCH_3$ | N | |
| H | $CH_3$ | H | $CH_2OP(O)(CH_3)_2$ | $OCH_3$ | $OCH_3$ | N | |
| H | $CH_3$ | H | $CH_2OP(O)(CH_3)_2$ | $OCH_3$ | Cl | CH | |
| H | $CH_3$ | H | $CH_2OP(O)(CH_3)Ph$ | $CH_3$ | $CH_3$ | CH | |
| H | $CH_3$ | H | $CH_2OP(O)(CH_3)Ph$ | $CH_3$ | $OCH_3$ | CH | |
| H | $CH_3$ | H | $CH_2OP(O)(CH_3)Ph$ | $OCH_3$ | $OCH_3$ | CH | |
| H | $CH_3$ | H | $CH_2OP(O)(CH_3)Ph$ | $CH_3$ | $CH_3$ | N | |
| H | $CH_3$ | H | $CH_2OP(O)(Ph)_2$ | $CH_3$ | $OCH_3$ | N | |
| H | $CH_3$ | H | $CH_2OP(O)(Ph)_2$ | $OCH_3$ | $OCH_3$ | N | |
| H | $CH_3$ | H | $CH_2OP(O)(Ph)_2$ | $OCH_3$ | Cl | CH | |
| H | $CH_3$ | H | $CH_2OP(O)(Ph)_2$ | $CH_3$ | $CH_3$ | CH | |
| H | $CH_3$ | H | $CH_2OP(O)(Ph)_2$ | $CH_3$ | $OCH_3$ | CH | |
| H | $CH_3$ | H | $CH_2OP(O)(Ph)_2$ | $OCH_3$ | $OCH_3$ | CH | |
| H | $CH_3$ | H | $CH_2CH_2OP(O)(CH_3)_2$ | $CH_3$ | $CH_3$ | N | |
| H | $CH_3$ | H | $CH_2CH_2OP(O)(CH_3)_2$ | $OCH_3$ | $OCH_3$ | N | |
| H | $CH_3$ | H | $CH_2CH_2OP(O)(CH_3)_2$ | $OCH_3$ | Cl | CH | |
| H | $CH_3$ | H | $CH_2CH_2OP(O)(CH_3)_2$ | $CH_3$ | $CH_3$ | CH | |
| H | $CH_3$ | H | $CH_2CH_2OP(O)(CH_3)_2$ | $CH_3$ | $OCH_3$ | CH | |
| H | $CH_3$ | H | $CH_2(CH_2)_2OP(O)(CH_3)_2$ | $OCH_3$ | $OCH_3$ | CH | |
| H | $CH_3$ | H | $CH_2(CH_2)_2OP(O)(CH_3)_2$ | $CH_3$ | $CH_3$ | N | |
| H | $CH_3$ | H | $CH_2(CH_2)_2OP(O)(CH_3)_2$ | $CH_3$ | $OCH_3$ | N | |
| H | $CH_3$ | H | $CH_2(CH_2)_2OP(O)(CH_3)_2$ | $OCH_3$ | $OCH_3$ | N | |
| H | $CH_3$ | H | $CH_2(CH_2)_2OP(O)(CH_3)_2$ | $OCH_3$ | Cl | CH | |
| H | $CH_3$ | H | $CH_2(CH_2)_2OP(O)(CH_3)_2$ | $CH_3$ | $CH_3$ | CH | |
| H | $CH_3$ | H | $CH_2P(O)(CH_3)_2$ | $CH_3$ | $OCH_3$ | CH | |
| H | $CH_3$ | H | $CH_2P(O)(CH_3)_2$ | $OCH_3$ | $OCH_3$ | CH | |
| H | $CH_3$ | H | $CH_2P(O)(CH_3)_2$ | $CH_3$ | $CH_3$ | N | |
| H | $CH_3$ | H | $CH_2P(O)(CH_3)_2$ | $CH_3$ | $OCH_3$ | N | |
| H | $CH_3$ | $CH_3$ | $CH_2P(O)(CH_3)_2$ | $OCH_3$ | $OCH_3$ | N | |
| H | $CH_3$ | H | $CH_2P(O)(CH_3)_2$ | $OCH_3$ | Cl | CH | |
| H | $CH_3$ | H | $CH_2P(O)(CH_3)_2$ | $CH_3$ | $CH_3$ | CH | |
| H | $CH_3$ | H | $CH_2P(O)(CH_3)_2$ | $CH_3$ | $OCH_3$ | CH | |
| H | $CH_3$ | H | $CH_2P(O)(CH_3)_2$ | $OCH_3$ | $OCH_3$ | CH | |
| H | $CH_3$ | H | $CH_2P(O)(CH_3)_2$ | $CH_3$ | $CH_3$ | N | |
| H | $CH_3$ | H | $CH_2P(O)(CH_3)_2$ | $CH_3$ | $OCH_3$ | N | |
| H | $CH_3$ | H | $CH_2P(O)(CH_3)_2$ | $OCH_3$ | $OCH_3$ | N | |
| H | $CH_3$ | H | $CH_2P(O)(CH_3)_2$ | $OCH_3$ | Cl | CH | |
| H | $CH_3$ | H | $CH_2P(O)(CH_3)_2$ | $CH_3$ | $CH_3$ | CH | |
| $CH_3$ | $CH_3$ | H | $CH_2CH_2P(O)(OCH_2CH_3)_2$ | $CH_3$ | $OCH_3$ | CH | |
| H | $CH_3$ | H | $CH_2CH_2P(O)(OCH_2CH_3)_2$ | $OCH_3$ | $OCH_3$ | CH | |
| H | $CH_3$ | H | $CH_2(CH_2)_3P(O)(OCH_3)_2$ | $CH_3$ | $CH_3$ | N | |
| H | $CH_3$ | H | $CH_2(CH_2)_3P(O)(OCH_3)_2$ | $CH_3$ | $OCH_3$ | N | |
| H | $CH_3$ | H | $CH_2(CH_2)_3P(O)(OCH_3)_2$ | $OCH_3$ | $OCH_3$ | N | |
| H | $CH_3$ | H | $CH_2(CH_2)_3P(O)(OCH_3)_2$ | $OCH_3$ | Cl | CH | |
| H | $CH_3$ | H | $CH_2OP(S)(CH_3)_2$ | $CH_3$ | $CH_3$ | CH | |
| H | $CH_3$ | H | $CH_2OP(S)(CH_3)_2$ | $CH_3$ | $OCH_3$ | CH | |
| H | $CH_3$ | H | $CH_2OP(S)(CH_3)_2$ | $OCH_3$ | $OCH_3$ | CH | |
| H | $CH_3$ | H | $CH_2OP(S)(CH_3)_2$ | $CH_3$ | $CH_3$ | N | |

TABLE I-continued

General Structure I

| R | $R_1$ | $R_2$ | $R_3$ | X | Y | Z | m.p. (°C.) |
|---|---|---|---|---|---|---|---|
| H | $CH_3$ | H | $CH_2OP(S)(CH_3)_2$ | $CH_3$ | $OCH_3$ | N | |
| H | $CH_3$ | H | $CH_2OP(S)(CH_3)_2$ | $OCH_3$ | $OCH_3$ | N | |
| H | $CH_3$ | H | $CH_2OP(S)(CH_3)_2$ | $OCH_3$ | Cl | CH | |
| H | $CH_3$ | H | $CH_2OP(S)(OCH_3)_2$ | $CH_3$ | $CH_3$ | CH | |
| H | $CH_3$ | H | $CH_2OP(S)(OCH_3)_2$ | $CH_3$ | $OCH_3$ | CH | |
| H | $CH_3$ | H | $CH_2OP(S)(OCH_3)_2$ | $OCH_3$ | $OCH_3$ | CH | |
| H | $CH_3$ | H | $CH_2OP(S)(OCH_3)_2$ | $CH_3$ | $CH_3$ | N | |
| H | $CH_3$ | H | $CH_2OP(S)(OCH_3)_2$ | $CH_3$ | $OCH_3$ | N | |
| H | $CH_3$ | H | $CH_2OP(S)(OCH_3)_2$ | $OCH_3$ | $OCH_3$ | N | |
| H | $CH_3$ | H | $CH_2OP(S)(OCH_3)_2$ | $OCH_3$ | Cl | CH | |
| H | $CH_3$ | H | $CH_2P(S)(CH_3)_2$ | $CH_3$ | $CH_3$ | CH | |
| H | $CH_3$ | H | $CH_2P(S)(CH_3)_2$ | $CH_3$ | $OCH_3$ | CH | |
| H | $CH_3$ | H | $CH_2P(S)(CH_3)_2$ | $OCH_3$ | $OCH_3$ | CH | |
| H | $CH_3$ | H | $CH_2P(S)(CH_3)_2$ | $CH_3$ | $CH_3$ | N | |
| H | $CH_3$ | H | $CH_2P(S)(CH_3)_2$ | $OCH_3$ | $OCH_3$ | N | |
| H | $CH_3$ | H | $CH_2P(S)(CH_3)_2$ | $OCH_3$ | Cl | CH | |
| H | $CH_3$ | H | $CH_2P(S)(OCH_3)_2$ | $CH_3$ | $CH_3$ | CH | |
| H | $CH_3$ | H | $CH_2P(S)(OCH_3)_2$ | $CH_3$ | $OCH_3$ | CH | |
| H | $CH_3$ | H | $CH_2P(S)(OCH_3)_2$ | $OCH_3$ | $OCH_3$ | CH | |
| H | $CH_3$ | H | $CH_2P(S)(OCH_3)_2$ | $CH_3$ | $CH_3$ | N | |
| H | $CH_3$ | H | $CH_2P(S)(OCH_3)_2$ | $CH_3$ | $OCH_3$ | N | |
| H | $CH_3$ | H | $CH_2P(S)(OCH_3)_2$ | $OCH_3$ | $OCH_3$ | N | |
| H | $CH_3$ | H | $CH_2P(S)(OCH_3)_2$ | $OCH_3$ | Cl | CH | |
| H | $CH_3$ | H | $CH_2CH_2OP(S)(CH_3)_2$ | $CH_3$ | $CH_3$ | CH | |
| H | $CH_3$ | H | $CH_2CH_2OP(S)(CH_3)_2$ | $CH_3$ | $OCH_3$ | CH | |
| H | $CH_3$ | H | $CH_2CH_2OP(S)(CH_3)_2$ | $OCH_3$ | $OCH_3$ | CH | |
| H | $CH_3$ | H | $CH_2CH_2OP(S)(CH_3)_2$ | $CH_3$ | $CH_3$ | N | |
| H | $CH_3$ | H | $CH_2CH_2OP(S)(CH_3)_2$ | $CH_3$ | $OCH_3$ | N | |
| H | $CH_3$ | $CH_3$ | $CH_2CH_2OP(S)(CH_3)_2$ | $OCH_3$ | $OCH_3$ | N | |
| H | $CH_3$ | H | $CH_2CH_2OP(S)(CH_3)_2$ | $OCH_3$ | Cl | CH | |
| H | $CH_3$ | H | $CH_2CH_2P(S)(OCH_3)_2$ | $CH_3$ | $CH_3$ | CH | |
| H | $CH_3$ | H | $CH_2CH_2P(S)(OCH_3)_2$ | $CH_3$ | $OCH_3$ | CH | |
| H | $CH_3$ | H | $CH_2CH_2P(S)(OCH_3)_2$ | $OCH_3$ | $OCH_3$ | CH | |
| H | $CH_3$ | H | $CH_2CH_2P(S)(OCH_3)_2$ | $CH_3$ | $CH_3$ | N | |
| H | $CH_3$ | H | $CH_2CH_2P(S)(OCH_3)_2$ | $CH_3$ | $OCH_3$ | N | |
| H | $CH_3$ | H | $CH_2CH_2P(S)(OCH_3)_2$ | $OCH_3$ | $OCH_3$ | N | |
| H | $CH_3$ | H | $CH_2CH_2P(S)(OCH_3)_2$ | $OCH_3$ | Cl | CH | |
| H | $CH_3$ | H | $CH_2(CH_2)_3OP(S)(CH_3)_2$ | $CH_3$ | $CH_3$ | CH | |
| $CH_3$ | $CH_3$ | H | $CH_2(CH_2)_3OP(S)(CH_3)_2$ | $CH_3$ | $OCH_3$ | CH | |
| H | $CH_3$ | H | $CH_2(CH_2)_3OP(S)(CH_3)_2$ | $OCH_3$ | $OCH_3$ | CH | |
| H | $CH_3$ | H | $CH_2(CH_2)_3OP(S)(CH_3)_2$ | $CH_3$ | $CH_3$ | N | |
| H | $CH_3$ | H | $CH_2(CH_2)_3OP(S)(CH_3)_2$ | $CH_3$ | $OCH_3$ | N | |
| H | $CH_3$ | H | $CH_2(CH_2)_3OP(S)(CH_3)_2$ | $OCH_3$ | $OCH_3$ | N | |
| H | $CH_3$ | H | $CH_2(CH_2)_3OP(S)(CH_3)_2$ | $OCH_3$ | Cl | CH | |
| H | $CH_3$ | H | $CH_2OSi(CH_3)_3$ | $CH_3$ | $CH_3$ | CH | |
| H | $CH_3$ | H | $CH_2OSi(CH_3)_3$ | $CH_3$ | $OCH_3$ | CH | |
| H | $CH_3$ | H | $CH_2OSi(CH_3)_3$ | $OCH_3$ | $OCH_3$ | CH | |
| H | $CH_3$ | H | $CH_2OSi(CH_3)_3$ | $CH_3$ | $CH_3$ | N | |
| H | $CH_3$ | H | $CH_2OSi(CH_3)_3$ | $CH_3$ | $OCH_3$ | N | |
| H | $CH_3$ | H | $CH_2OSi(CH_3)_3$ | $OCH_3$ | $OCH_3$ | N | |
| H | $CH_3$ | H | $CH_2OSi(CH_3)_3$ | $OCH_3$ | Cl | CH | |
| H | $CH_3$ | H | $CH_2CH_2OSi(CH_3)_3$ | $CH_3$ | $CH_3$ | CH | |
| H | $CH_3$ | H | $CH_2CH_2OSi(CH_3)_3$ | $CH_3$ | $OCH_3$ | CH | |
| H | $CH_3$ | H | $CH_2CH_2OSi(CH_3)_3$ | $OCH_3$ | $OCH_3$ | CH | |
| H | $CH_3$ | H | $CH_2CH_2OSi(CH_3)_3$ | $CH_3$ | $CH_3$ | N | |
| H | $CH_3$ | H | $CH_2CH_2OSi(CH_3)_3$ | $CH_3$ | $OCH_3$ | N | |
| H | $CH_3$ | H | $CH_2CH_2OSi(CH_3)_3$ | $OCH_3$ | $OCH_3$ | N | |
| H | $CH_3$ | H | $CH_2CH_2OSi(CH_3)_3$ | $OCH_3$ | Cl | CH | |
| H | $CH_3$ | H | $CH_2(CH_2)_2OSi(CH_3)_3$ | $CH_3$ | $CH_3$ | CH | |
| H | $CH_3$ | H | $CH_2(CH_2)_2OSi(CH_3)_3$ | $CH_3$ | $OCH_3$ | CH | |
| H | $CH_3$ | H | $CH_2(CH_2)_2OSi(CH_3)_3$ | $OCH_3$ | $OCH_3$ | CH | |
| H | $CH_3$ | H | $CH_2(CH_2)_2OSi(CH_3)_3$ | $CH_3$ | $CH_3$ | N | |
| H | $CH_3$ | H | $CH_2(CH_2)_2OSi(CH_3)_3$ | $OCH_3$ | $OCH_3$ | N | |
| H | $CH_3$ | H | $CH_2(CH_2)_2OSi(CH_3)_3$ | $OCH_3$ | Cl | CH | |
| H | $CH_3$ | H | $CH_2(CH_2)_3OSi(CH_3)_3$ | $CH_3$ | $CH_3$ | CH | |
| H | $CH_3$ | H | $CH_2(CH_2)_3OSi(CH_3)_3$ | $CH_3$ | $OCH_3$ | CH | |
| H | $CH_3$ | H | $CH_2(CH_2)_3OSi(CH_3)_3$ | $OCH_3$ | $OCH_3$ | CH | |
| H | $CH_3$ | H | $CH_2(CH_2)_3OSi(CH_3)_3$ | $CH_3$ | $CH_3$ | N | |
| H | $CH_3$ | H | $CH_2(CH_2)_3OSi(CH_3)_3$ | $CH_3$ | $OCH_3$ | N | |
| H | $CH_3$ | H | $CH_2(CH_2)_3OSi(CH_3)_3$ | $OCH_3$ | $OCH_3$ | N | |
| H | $CH_3$ | H | $CH_2(CH_2)_3OSi(CH_3)_3$ | $OCH_3$ | Cl | CH | |
| H | $CH_3$ | H | $CH_2(CH_2)_4OSi(CH_3)_3$ | $CH_3$ | $CH_3$ | CH | |
| H | $CH_3$ | H | $CH_2(CH_2)_5OSi(CH_3)_3$ | $CH_3$ | $OCH_3$ | CH | |
| H | $CH_3$ | H | $CH_2(CH_2)_6OSi(CH_3)_3$ | $OCH_3$ | $OCH_3$ | CH | |
| H | $CH_3$ | H | $CH_2(CH_2)_7OSi(CH_3)_3$ | $CH_3$ | $CH_3$ | N | |
| H | $CH_3$ | H | $CH_2OSi(CH_2CH_3)_3$ | $CH_3$ | $OCH_3$ | N | |
| H | $CH_3$ | H | $CH_2OSi(CH_3)_2(Ph)$ | $OCH_3$ | $OCH_3$ | N | |
| H | $CH_3$ | H | $CH(CH_3)OSi(CH_3)_3$ | $OCH_3$ | Cl | CH | |
| H | $CH_3$ | H | $CH(CH_3)OSi(CH_3)_3$ | $CH_3$ | $CH_3$ | CH | |
| H | $CH_3$ | H | $CH(CH_3)OSi(CH_3)_3$ | $CH_3$ | $OCH_3$ | CH | |

TABLE I-continued

General Structure I

| R | R₁ | R₂ | R₃ | X | Y | Z | m.p. (°C.) |
|---|---|---|---|---|---|---|---|
| H | CH₃ | H | CH(CH₃)OSi(CH₃)₃ | OCH₃ | OCH₃ | CH | |
| H | CH₃ | H | CH(CH₃)OSi(CH₃)₃ | CH₃ | CH₃ | N | |
| H | CH₃ | H | CH₂Si(CH₃)₃ | CH₃ | OCH₃ | N | |
| H | CH₃ | H | CH₂Si(CH₃)₃ | OCH₃ | OCH₃ | N | |
| H | CH₃ | H | CH₂Si(CH₃)₃ | OCH₃ | Cl | CH | |
| H | CH₃ | H | CH₂Si(CH₃)₃ | CH₃ | CH₃ | CH | |
| CH₃ | CH₃ | H | CH₂Si(CH₃)₃ | CH₃ | OCH₃ | CH | |
| H | CH₃ | H | CH₂Si(CH₃)₃ | OCH₃ | OCH₃ | CH | |
| H | CH₃ | H | CH₂Si(CH₃)₃ | CH₃ | CH₃ | N | |
| H | CH₃ | H | CH₂CH₂Si(CH₃)₃ | CH₃ | OCH₃ | N | |
| H | CH₃ | H | CH₂CH₂Si(CH₃)₃ | OCH₃ | OCH₃ | N | |
| H | CH₃ | H | CH₂CH₂Si(CH₃)₃ | OCH₃ | Cl | CH | |
| H | CH₃ | H | CH₂(CH₂)₂Si(CH₃)₃ | CH₃ | CH₃ | CH | |
| H | CH₃ | H | CH₂(CH₂)₂Si(CH₃)₃ | CH₃ | OCH₃ | CH | |
| H | CH₃ | H | CH₂(CH₂)₂Si(CH₃)₃ | OCH₃ | OCH₃ | CH | |
| H | CH₃ | H | CH₂(CH₂)₂Si(CH₃)₃ | CH₃ | CH₃ | N | |
| H | CH₃ | H | CH₂(CH₂)₂Si(CH₃)₃ | CH₃ | OCH₃ | N | |
| H | CH₃ | H | CH₂(CH₂)₂Si(CH₃)₃ | OCH₃ | OCH₃ | N | |
| H | CH₃ | H | CH₂(CH₂)₂Si(CH₃)₃ | OCH₃ | Cl | CH | |
| H | CH₃ | H | C(Si(CH₃)₃)(CH₃)₂ | CH₃ | CH₃ | CH | |
| H | CH₃ | H | C(Si(CH₃)₃)(CH₃)₂ | CH₃ | OCH₃ | CH | |
| H | CH₃ | H | C(Si(CH₃)₃)(CH₃)₂ | OCH₃ | OCH₃ | CH | |
| H | CH₃ | H | C(Si(CH₃)₃)(CH₃)₂ | CH₃ | CH₃ | N | |
| H | CH₃ | H | C(Si(CH₃)₃)(CH₃)₂ | CH₃ | OCH₃ | N | |
| H | CH₃ | H | C(Si(CH₃)₃)(CH₃)₂ | OCH₃ | OCH₃ | N | |
| H | CH₃ | H | C(Si(CH₃)₃)(CH₃)₂ | OCH₃ | Cl | CH | |
| H | CH₃ | H | CH₂SCH₃ | CH₃ | CH₃ | CH | |
| H | CH₃ | H | CH₂SCH₃ | CH₃ | OCH₃ | CH | |
| H | CH₃ | H | CH₂SCH₃ | OCH₃ | OCH₃ | CH | |
| H | CH₃ | H | CH₂SCH₃ | CH₃ | CH₃ | N | |
| H | CH₃ | H | CH₂SCH₃ | OCH₃ | OCH₃ | N | |
| H | CH₃ | H | CH₂SCH₃ | OCH₃ | Cl | CH | |
| H | CH₃ | H | CH₂SCH₂CH₃ | CH₃ | CH₃ | CH | |
| H | CH₃ | H | CH₂CH₂SCH₃ | CH₃ | OCH₃ | CH | |
| H | CH₃ | H | CH₂CH₂SCH₃ | OCH₃ | OCH₃ | CH | |
| H | CH₃ | H | CH₂CH₂SCH₃ | CH₃ | CH₃ | N | |
| H | CH₃ | H | CH₂CH₂SCH₃ | CH₃ | OCH₃ | N | |
| H | CH₃ | H | CH₂CH₂SCH₃ | OCH₃ | OCH₃ | N | |
| H | CH₃ | H | CH₂CH₂SCH₃ | OCH₃ | Cl | CH | |
| H | CH₃ | H | CH₂CH₂SCH₃ | CH₃ | CH₃ | CH | |
| H | CH₃ | H | CH₂(CH₂)₂SCH₃ | CH₃ | OCH₃ | CH | |
| H | CH₃ | H | CH₂(CH₂)₂SCH₃ | OCH₃ | OCH₃ | CH | |
| H | CH₃ | H | CH₂(CH₂)₂SCH₃ | CH₃ | CH₃ | N | |
| H | CH₃ | H | CH₂(CH₂)₂SCH₃ | CH₃ | OCH₃ | N | |
| H | CH₃ | CH₃ | CH₂(CH₂)₂SCH₃ | OCH₃ | OCH₃ | N | |
| H | CH₃ | H | CH₂(CH₂)₂SCH₃ | OCH₃ | Cl | CH | |
| H | CH₃ | H | CH₂(CH₂)₃SCH₃ | CH₃ | CH₃ | CH | |
| H | CH₃ | H | CH₂(CH₂)₃SCH₃ | CH₃ | OCH₃ | CH | |
| H | CH₃ | H | CH₂(CH₂)₃SCH₃ | OCH₃ | OCH₃ | CH | |
| H | CH₃ | H | CH₂(CH₂)₃SCH₃ | CH₃ | CH₃ | N | |
| H | CH₃ | H | CH₂(CH₂)₃SCH₃ | CH₃ | OCH₃ | N | |
| H | CH₃ | H | CH₂(CH₂)₃SCH₃ | OCH₃ | OCH₃ | N | |
| H | CH₃ | H | CH(CH₃)SCH₃ | OCH₃ | Cl | CH | |
| H | CH₃ | H | CH(CH₃)SCH₃ | CH₃ | CH₃ | CH | |
| CH₃ | CH₃ | H | CH(CH₃)SCH₃ | CH₃ | OCH₃ | CH | |
| H | CH₃ | H | CH(SCH₃)₂ | OCH₃ | OCH₃ | CH | |
| H | CH₃ | H | CH₂CH(CH₃)SCH₃ | CH₃ | CH₃ | N | |
| H | CH₃ | H | CH₂CH(CH₃)SCH₃ | CH₃ | OCH₃ | N | |
| H | CH₃ | H | CH₂(CH₂)₈SCH₃ | OCH₃ | OCH₃ | N | |
| H | CH₃ | H | CH₂(CH₂)₈SCH₃ | OCH₃ | Cl | CH | |
| H | CH₃ | H | CH₂SOCH₃ | CH₃ | CH₃ | CH | |
| H | CH₃ | H | CH₂SOCH₃ | CH₃ | OCH₃ | CH | |
| H | CH₃ | H | CH₂SOCH₃ | OCH₃ | OCH₃ | CH | |
| H | CH₃ | H | CH₂SOCH₃ | CH₃ | CH₃ | N | |
| H | CH₃ | H | CH₂SOCH₃ | CH₃ | OCH₃ | N | |
| H | CH₃ | H | CH₂SOCH₃ | OCH₃ | OCH₃ | N | |
| H | CH₃ | H | CH₂SOCH₃ | OCH₃ | Cl | CH | |
| H | CH₃ | H | CH₂CH₂SOCH₃ | CH₃ | CH₃ | CH | |
| H | CH₃ | H | CH₂CH₂SOCH₃ | CH₃ | OCH₃ | CH | |
| H | CH₃ | H | CH₂CH₂SOCH₃ | OCH₃ | OCH₃ | CH | |
| H | CH₃ | H | CH₂CH₂SOCH₃ | CH₃ | CH₃ | N | |
| H | CH₃ | H | CH₂CH₂SOCH₃ | CH₃ | OCH₃ | N | |
| H | CH₃ | H | CH₂CH₂SOCH₃ | OCH₃ | OCH₃ | N | |
| H | CH₃ | H | CH₂CH₂SOCH₃ | OCH₃ | Cl | CH | |
| H | CH₃ | H | CH₂(CH₂)₃SOCH₃ | CH₃ | CH₃ | CH | |
| H | CH₃ | H | CH₂(CH₂)₃SOCH₃ | CH₃ | OCH₃ | CH | |
| H | CH₃ | H | CH₂(CH₂)₃SOCH₃ | OCH₃ | OCH₃ | CH | |
| H | CH₃ | H | CH₂(CH₂)₃SOCH₃ | CH₃ | CH₃ | N | |
| H | CH₃ | H | CH₂(CH₂)₃SOCH₃ | OCH₃ | OCH₃ | N | |
| H | CH₃ | H | CH₂(CH₂)₃SOCH₃ | OCH₃ | Cl | CH | |

TABLE I-continued

General Structure I

| R | $R_1$ | $R_2$ | $R_3$ | X | Y | Z | m.p. (°C.) |
|---|---|---|---|---|---|---|---|
| H | $CH_3$ | H | $CH_2SO_2CH_3$ | $CH_3$ | $CH_3$ | CH | |
| H | $CH_3$ | H | $CH_2SO_2CH_3$ | $CH_3$ | $OCH_3$ | CH | |
| H | $CH_3$ | H | $CH_2SO_2CH_3$ | $OCH_3$ | $OCH_3$ | CH | |
| H | $CH_3$ | H | $CH_2SO_2CH_3$ | $CH_3$ | $CH_3$ | N | |
| H | $CH_3$ | H | $CH_2SO_2CH_3$ | $CH_3$ | $OCH_3$ | N | |
| H | $CH_3$ | H | $CH_2SO_2CH_3$ | $OCH_3$ | $OCH_3$ | N | |
| H | $CH_3$ | H | $CH_2SO_2CH_3$ | $OCH_3$ | Cl | CH | |
| H | $CH_3$ | H | $CH_2CH_2SO_2CH_3$ | $CH_3$ | $CH_3$ | CH | |
| H | $CH_3$ | H | $CH_2CH_2SO_2CH_3$ | $CH_3$ | $OCH_3$ | CH | |
| H | $CH_3$ | H | $CH_2CH_2SO_2CH_3$ | $OCH_3$ | $OCH_3$ | CH | |
| H | $CH_3$ | H | $CH_2CH_2SO_2CH_3$ | $CH_3$ | $CH_3$ | N | |
| H | $CH_3$ | H | $CH_2CH_2SO_2CH_3$ | $CH_3$ | $OCH_3$ | N | |
| H | $CH_3$ | $CH_3$ | $CH_2CH_2SO_2CH_3$ | $OCH_3$ | $OCH_3$ | N | |
| H | $CH_3$ | H | $CH_2CH_2SO_2CH_3$ | $OCH_3$ | Cl | CH | |
| H | $CH_3$ | H | $CH_2(CH_2)_3SO_2CH_3$ | $CH_3$ | $CH_3$ | CH | |
| H | $CH_3$ | H | $CH_2(CH_2)_3SO_2CH_3$ | $CH_3$ | $OCH_3$ | CH | |
| H | $CH_3$ | H | $CH_2(CH_2)_3SO_3CH_3$ | $OCH_3$ | $OCH_3$ | CH | |
| H | $CH_3$ | H | $CH_2(CH_2)_3SO_2CH_3$ | $CH_3$ | $CH_3$ | N | |
| H | $CH_3$ | H | $CH_2(CH_2)_3SO_2CH_3$ | $CH_3$ | $OCH_3$ | N | |
| H | $CH_3$ | $CH_3$ | $CH_2(CH_2)_3SO_2CH_3$ | $OCH_3$ | $OCH_3$ | N | |
| H | $CH_3$ | H | $CH_2(CH_2)_3SO_2CH_3$ | $OCH_3$ | Cl | CH | |
| H | $CH_3$ | H | $CH_2SOCH_2CH_3$ | $CH_3$ | $CH_3$ | CH | |
| $CH_3$ | $CH_3$ | H | $CH_2SOCH_2CH_3$ | $CH_3$ | $OCH_3$ | CH | |
| H | $CH_3$ | H | $CH_2SO_2CH_2CH_3$ | $OCH_3$ | $OCH_3$ | CH | |
| H | $CH_3$ | H | $CH_2(CH_2)_6SOCH_3$ | $CH_3$ | $CH_3$ | N | |
| H | $CH_3$ | H | $CH_2(CH_2)_6SOCH_3$ | $CH_3$ | $OCH_3$ | N | |
| H | $CH_3$ | H | $CH_2(CH_2)_4SO_2CH_3$ | $OCH_3$ | $OCH_3$ | N | |
| H | $CH_3$ | H | $CH_2(CH_2)_4SO_2CH_3$ | $OCH_3$ | Cl | CH | |
| H | $CH_3$ | H | $CH_2SCN$ | $CH_3$ | $CH_3$ | CH | |
| H | $CH_3$ | H | $CH_2SCN$ | $CH_3$ | $OCH_3$ | CH | |
| H | $CH_3$ | H | $CH_2SCN$ | $OCH_3$ | $OCH_3$ | CH | |
| H | $CH_3$ | H | $CH_2SCN$ | $CH_3$ | $CH_3$ | N | |
| H | $CH_3$ | H | $CH_2SCN$ | $CH_3$ | $OCH_3$ | N | |
| H | $CH_3$ | H | $CH_2SCN$ | $OCH_3$ | $OCH_3$ | N | |
| H | $CH_3$ | H | $CH_2SCN$ | $OCH_3$ | Cl | CH | |
| H | $CH_3$ | H | $CH_2CH_2SCN$ | $CH_3$ | $CH_3$ | CH | |
| H | $CH_3$ | H | $CH_2CH_2SCN$ | $CH_3$ | $OCH_3$ | CH | |
| H | $CH_3$ | H | $CH_2CH_2SCN$ | $OCH_3$ | $OCH_3$ | CH | |
| H | $CH_3$ | H | $CH_2CH_2SCN$ | $CH_3$ | $CH_3$ | N | |
| H | $CH_3$ | H | $CH_2CH_2SCN$ | $CH_3$ | $OCH_3$ | N | |
| H | $CH_3$ | H | $CH_2CH_2SCN$ | $OCH_3$ | $OCH_3$ | N | |
| H | $CH_3$ | H | $CH_2CH_2SCN$ | $OCH_3$ | Cl | CH | |
| H | $CH_3$ | H | $CH_2(CH_2)_2SCN$ | $CH_3$ | $CH_3$ | CH | |
| H | $CH_3$ | H | $CH_2(CH_2)_2SCN$ | $CH_3$ | $OCH_3$ | CH | |
| H | $CH_3$ | H | $CH_2(CH_2)_2SCN$ | $OCH_3$ | $OCH_3$ | CH | |
| H | $CH_3$ | H | $CH_2(CH_2)_2SCN$ | $CH_3$ | $CH_3$ | N | |
| H | $CH_3$ | H | $CH_2(CH_2)_2SCN$ | $OCH_3$ | $OCH_3$ | N | |
| H | $CH_3$ | H | $CH_2(CH_2)_2SCN$ | $OCH_3$ | Cl | CH | |
| H | $CH_3$ | H | $CH_2(CH_2)_3SCN$ | $CH_3$ | $CH_3$ | CH | |
| H | $CH_3$ | H | $CH_2(CH_2)_3SCN$ | $CH_3$ | $OCH_3$ | CH | |
| H | $CH_3$ | H | $CH_2(CH_2)_3SCN$ | $OCH_3$ | $OCH_3$ | CH | |
| H | $CH_3$ | H | $CH_2(CH_2)_3SCN$ | $CH_3$ | $CH_3$ | N | |
| H | $CH_3$ | H | $CH_2(CH_2)_3SCN$ | $CH_3$ | $OCH_3$ | N | |
| H | $CH_3$ | H | $CH_2(CH_2)_3SCN$ | $OCH_3$ | $OCH_3$ | N | |
| H | $CH_3$ | H | $CH_2(CH_2)_3SCN$ | $OCH_3$ | Cl | CH | |
| H | $CH_3$ | H | $CH_2CHFSCN$ | $CH_3$ | $CH_3$ | CH | |
| H | $CH_3$ | H | $CH(CF_3)SCN$ | $CH_3$ | $OCH_3$ | CH | |
| H | $CH_3$ | H | $CH_2(CH_2)_5SCN$ | $OCH_3$ | $OCH_3$ | CH | |
| H | $CH_3$ | H | $CH_2CN$ | $CH_3$ | $CH_3$ | N | |
| H | $CH_3$ | H | $CH_2CN$ | $CH_3$ | $OCH_3$ | N | |
| H | $CH_3$ | $CH_3$ | $CH_2CN$ | $OCH_3$ | $OCH_3$ | N | |
| H | $CH_3$ | H | $CH_2CN$ | $OCH_3$ | Cl | CH | |
| H | $CH_3$ | H | $CH_2CN$ | $CH_3$ | $CH_3$ | CH | |
| H | $CH_3$ | H | $CH_2CN$ | $CH_3$ | $OCH_3$ | CH | |
| H | $CH_3$ | H | $CH_2CH_2CN$ | $OCH_3$ | $OCH_3$ | CH | |
| H | $CH_3$ | H | $CH_2CH_2CN$ | $CH_3$ | $CH_3$ | N | |
| H | $CH_3$ | H | $CH_2CH_2CN$ | $CH_3$ | $OCH_3$ | N | |
| H | $CH_3$ | H | $CH_2CH_2CN$ | $OCH_3$ | $OCH_3$ | N | |
| H | $CH_3$ | H | $CH_2CH_2CN$ | $OCH_3$ | Cl | CH | |
| H | $CH_3$ | H | $CH_2CH_2CN$ | $CH_3$ | $CH_3$ | CH | |
| $CH_3$ | $CH_3$ | H | $CH_2CH_2CN$ | $CH_3$ | $OCH_3$ | CH | |
| H | $CH_3$ | H | $CH_2CH_2CN$ | $OCH_3$ | $OCH_3$ | CH | |
| H | $CH_3$ | H | $CH_2(CH_2)_3CN$ | $CH_3$ | $CH_3$ | N | |
| H | $CH_3$ | H | $CH_2(CH_2)_3CN$ | $CH_3$ | $OCH_3$ | N | |
| H | $CH_3$ | H | $CH_2(CH_2)_3CN$ | $OCH_3$ | $OCH_3$ | N | |
| H | $CH_3$ | H | $CH_2(CH_2)_3CN$ | $OCH_3$ | Cl | CH | |
| H | $CH_3$ | H | $CH_2(CH_2)_4CN$ | $CH_3$ | $CH_3$ | CH | |
| H | $CH_3$ | H | $CH_2(CH_2)_2CH(CN)_2$ | $CH_3$ | $OCH_3$ | CH | |
| H | $CH_3$ | H | $CH(CH_3)CH_2CN$ | $OCH_3$ | $OCH_3$ | CH | |
| H | $CH_3$ | H | $CH(CH_3)CH_2CN$ | $CH_3$ | $CH_3$ | N | |

TABLE I-continued

General Structure I

| R | R₁ | R₂ | R₃ | X | Y | Z | m.p. (°C.) |
|---|---|---|---|---|---|---|---|
| H | CH₃ | H | CH(CH₃)CH₂CN | CH₃ | OCH₃ | N | |
| H | CH₃ | H | CH(CH₃)CH₂CN | OCH₃ | OCH₃ | N | |
| H | CH₃ | H | CH(CH₃)CH₂CN | OCH₃ | Cl | CH | |
| H | CH₃ | H | CH₂SP(O)(CH₃)₂ | CH₃ | CH₃ | CH | |
| H | CH₃ | H | CH₂SP(O)(CH₃)₂ | CH₃ | OCH₃ | CH | |
| H | CH₃ | H | CH₂SP(O)(CH₃)₂ | OCH₃ | OCH₃ | CH | |
| H | CH₃ | H | CH₂CH₂SP(O)(CH₃)₂ | CH₃ | CH₃ | N | |
| H | CH₃ | H | CH₂CH₂SP(O)(CH₃)₂ | CH₃ | OCH₃ | N | |
| H | CH₃ | H | CH₂CH₂SP(O)(CH₃)₂ | OCH₃ | OCH₃ | N | |
| H | CH₃ | H | CH₂P(S)(CH₃)₂ | OCH₃ | Cl | CH | |
| H | CH₃ | H | CH₂P(S)(CH₃)₂ | CH₃ | CH₃ | CH | |
| H | CH₃ | H | CH₂P(S)(CH₃)₂ | CH₃ | OCH₃ | CH | |
| H | CH₃ | H | CH₂—CH₂P(S)(CH₃)₂ | OCH₃ | OCH₃ | CH | |
| H | CH₃ | H | CH₂—CH₂P(S)(CH₃)₂ | CH₃ | CH₃ | N | |
| H | CH₃ | H | CH₂—CH₂P(S)(CH₃)₂ | OCH₃ | OCH₃ | N | |
| H | CH₃ | H | CH₂—CH₂P(S)(CH₃)₂ | OCH₃ | Cl | CH | |
| H | CH₃ | H | CH₂—CH₂P(S)(CH₃)₂ | CH₃ | CH₃ | CH | |
| H | CH₃ | H | CH₂N(CH₃)₂ | CH₃ | OCH₃ | CH | |
| H | CH₃ | H | CH₂N(CH₃)₂ | OCH₃ | OCH₃ | CH | |
| H | CH₃ | H | CH₂N(CH₃)₂ | CH₃ | CH₃ | N | |
| H | CH₃ | H | CH₂N(CH₃)₂ | CH₃ | OCH₃ | N | |
| H | CH₃ | H | CH₂N(CH₃)₂ | OCH₃ | OCH₃ | N | |
| H | CH₃ | H | CH₂N(CH₃)₂ | OCH₃ | Cl | CH | |
| H | CH₃ | H | CH₂N(CH₃)₂ | CH₃ | CH₃ | CH | |
| H | CH₃ | H | CH₂(CH₂)₃N(CH₃)₂ | CH₃ | OCH₃ | CH | |
| H | CH₃ | H | CH₂(CH₂)₃N(CH₃)₂ | OCH₃ | OCH₃ | CH | |
| H | CH₃ | H | CH₂(CH₂)₃N(CH₃)₂ | CH₃ | CH₃ | N | |
| H | CH₃ | H | CH₂(CH₂)₃N(CH₃)₂ | CH₃ | OCH₃ | N | |
| H | CH₃ | CH₃ | CH₂(CH₂)₃N(CH₃)₂ | OCH₃ | OCH₃ | N | |
| H | CH₃ | H | CH₂(CH₂)₃N(CH₃)₂ | OCH₃ | Cl | CH | |
| H | CH₃ | H | CH₂(CH₂)₃N(CH₃)₂ | CH₃ | CH₃ | CH | |
| H | CH₃ | H | CH₂N(CH₃)₂Ph | CH₃ | OCH₃ | CH | |
| H | CH₃ | H | CH₂N(CH₃)₂Ph | OCH₃ | OCH₃ | CH | |
| H | CH₃ | H | CH₂N(CH₃)₂Ph | CH₃ | CH₃ | N | |
| H | CH₃ | H | CH₂N(CH₃)₂Ph | CH₃ | OCH₃ | N | |
| H | CH₃ | H | CH₂—CH(CH₃)N(CH₃)₂ | OCH₃ | OCH₃ | N | |
| H | CH₃ | H | CH₂—CH(CH₃)N(CH₃)₂ | OCH₃ | Cl | CH | |
| H | CH₃ | H | CH₂—CH(CH₃)N(CH₃)₂ | CH₃ | CH₃ | CH | |
| CH₃ | CH₃ | H | CH₂—CH(CH₃)N(CH₃)₂ | CH₃ | OCH₃ | CH | |
| H | CH₃ | H | CH₂—CH(CH₃)N(CH₃)₂ | OCH₃ | OCH₃ | CH | |
| H | CH₃ | H | CH₂CH₂CH(CH₃)₂ | CH₃ | CH₃ | N | |
| H | CH₃ | H | CH₂CH₂CH(CH₃)₂ | CH₃ | OCH₃ | N | |
| H | CH₃ | H | CH₂CH₂CH(CH₃)₂ | OCH₃ | OCH₃ | N | |
| H | CH₃ | H | CH₂CH₂CH(CH₃)₂ | OCH₃ | Cl | CH | |
| H | CH₃ | H | CH₂NHC(O)CH₃ | CH₃ | CH₃ | CH | |
| H | CH₃ | H | CH₂NHC(O)CH₃ | CH₃ | OCH₃ | CH | |
| H | CH₃ | H | CH₂NHC(O)CH₃ | OCH₃ | OCH₃ | CH | |
| H | CH₃ | H | CH₂NHC(O)CH₃ | CH₃ | CH₃ | N | |
| H | CH₃ | H | CH₂NHC(O)CH₃ | CH₃ | OCH₃ | N | |
| H | CH₃ | H | CH₂NHC(O)CH₃ | OCH₃ | OCH₃ | N | |
| H | CH₃ | H | CH₂NHC(O)CH₃ | OCH₃ | Cl | CH | |
| H | CH₃ | H | CH₂CH₂N(CH₃)C(O)CH₃ | CH₃ | CH₃ | CH | |
| H | CH₃ | H | CH₂CH₂N(CH₃)C(O)CH₃ | CH₃ | OCH₃ | CH | |
| H | CH₃ | H | CH₂CH₂N(CH₃)C(O)CH₃ | OCH₃ | OCH₃ | CH | |
| H | CH₃ | H | CH₂CH₂N(CH₃)C(O)CH₃ | CH₃ | CH₃ | N | |
| H | CH₃ | H | CH₂(CH₂)₃NHC(O)CH₃ | CH₃ | OCH₃ | N | |
| H | CH₃ | H | CH₂(CH₂)₃NHC(O)CH₃ | OCH₃ | OCH₃ | N | |
| H | CH₃ | H | CH₂N(CH₃)C(O)OCH₃ | OCH₃ | Cl | CH | |
| H | CH₃ | H | CH₂N(CH₃)C(O)OCH₃ | CH₃ | CH₃ | CH | |
| H | CH₃ | H | CH₂NHC(O)OCH₃ | CH₃ | OCH₃ | CH | |
| H | CH₃ | H | CH₂NHC(O)OCH₃ | OCH₃ | OCH₃ | CH | |
| H | CH₃ | H | CH₂NHC(O)OCH₃ | CH₃ | CH₃ | N | |
| H | CH₃ | H | CH₂NHC(O)OCH₃ | OCH₃ | OCH₃ | N | |
| H | CH₃ | H | CH₂NHC(O)OCH₃ | OCH₃ | Cl | CH | |
| H | CH₃ | H | CH₂NHC(O)OCH₃ | CH₃ | CH₃ | CH | |
| H | CH₃ | H | CH₂(CH₂)₃NHC(O)OCH₃ | CH₃ | OCH₃ | CH | |
| H | CH₃ | H | CH₂(CH₂)₃NHC(O)OCH₃ | OCH₃ | OCH₃ | CH | |
| H | CH₃ | H | CH₂(CH₂)₃NHC(O)OCH₃ | CH₃ | CH₃ | CH | |
| H | CH₃ | H | CH₂N(CH₃)C(O)OCH₂CH₃ | CH₃ | OCH₃ | N | |
| H | CH₃ | H | CH(CH₃)NHC(O)OCH₃ | OCH₃ | OCH₃ | N | |
| H | CH₃ | H | CH(CH₃)NHC(O)OCH₃ | OCH₃ | Cl | CH | |
| H | CH₃ | H | CH(CH₃)NHC(O)OCH₃ | CH₃ | CH₃ | CH | |
| H | CH₃ | H | CH₂NHSO₂CH₃ | CH₃ | OCH₃ | CH | |
| H | CH₃ | H | CH₂NHSO₂CH₃ | OCH₃ | OCH₃ | CH | |
| H | CH₃ | H | CH₂NHSO₂CH₃ | CH₃ | CH₃ | N | |
| H | CH₃ | H | CH₂NHSO₂CH₃ | CH₃ | OCH₃ | N | |
| H | CH₃ | CH₃ | CH₂NHSO₂CH₃ | OCH₃ | OCH₃ | N | |
| H | CH₃ | H | CH₂NHSO₂CH₃ | OCH₃ | Cl | CH | |
| H | CH₃ | H | CH₂NHSO₂CH₃ | CH₃ | CH₃ | CH | |
| H | CH₃ | H | CH₂CH₂NHSO₂CH₃ | CH₃ | OCH₃ | CH | |

TABLE I-continued

General Structure I

| R | R₁ | R₂ | R₃ | X | Y | Z | m.p. (°C.) |
|---|---|---|---|---|---|---|---|
| H | CH₃ | H | CH₂CH₂NHSO₂CH₃ | OCH₃ | OCH₃ | CH | |
| H | CH₃ | H | CH₂CH₂NHSO₂CH₃ | CH₃ | CH₃ | N | |
| H | CH₃ | H | CH₂CH₂NHSO₂CH₃ | CH₃ | OCH₃ | N | |
| H | CH₃ | H | CH₂(CH₂)₃NHSO₂CH₃ | OCH₃ | OCH₃ | N | |
| H | CH₃ | H | CH₂(CH₂)₃NHSO₂CH₃ | OCH₃ | Cl | CH | |
| H | CH₃ | H | CH₂(CH₂)₃NHSO₂CH₃ | CH₃ | CH₃ | CH | |
| CH₃ | CH₃ | H | CH₂NHP(O)(CH₃)₂ | CH₃ | OCH₃ | CH | |
| H | CH₃ | H | CH₂NHP(O)(CH₃)₂ | OCH₃ | OCH₃ | CH | |
| H | CH₃ | H | CH₂NHP(O)(CH₃)₂ | CH₃ | CH₃ | N | |
| H | CH₃ | H | CH₂NHP(O)(OCH₃)₂ | CH₃ | OCH₃ | N | |
| H | CH₃ | H | CH₂NHP(O)(OCH₃)₂ | OCH₃ | OCH₃ | N | |
| H | CH₃ | H | CH₂NHP(O)(OCH₃)₂ | OCH₃ | Cl | CH | |
| H | CH₃ | H | CH=CH₂ | CH₃ | CH₃ | CH | |
| H | CH₃ | H | CH=CH₂ | CH₃ | OCH₃ | CH | |
| H | CH₃ | H | CH₂NO₂ | CH₃ | CH₃ | CH | |
| H | CH₃ | H | CH₂NO₂ | CH₃ | OCH₃ | CH | |
| H | CH₃ | H | CH₂NO₂ | OCH₃ | OCH₃ | CH | |
| H | CH₃ | H | CH₂NO₂ | CH₃ | CH₃ | N | |
| H | CH₃ | H | CH₂NO₂ | CH₃ | OCH₃ | N | |
| H | CH₃ | H | CH₂NO₂ | OCH₃ | OCH₃ | N | |
| H | CH₃ | H | CH₂NO₂ | OCH₃ | Cl | CH | |
| H | CH₃ | H | CH₂CH₂NO₂ | CH₃ | CH₃ | CH | |
| H | CH₃ | H | CH₂CH₂NO₂ | CH₃ | OCH₃ | CH | |
| H | CH₃ | H | CH₂CH₂NO₂ | OCH₃ | OCH₃ | CH | |
| H | CH₃ | H | CH₂CH₂NO₂ | CH₃ | CH₃ | N | |
| H | CH₃ | H | CH₂CH₂NO₂ | CH₃ | OCH₃ | N | |
| H | CH₃ | H | CH₂CH₂NO₂ | OCH₃ | OCH₃ | N | |
| H | CH₃ | H | CH₂CH₂NO₂ | OCH₃ | Cl | CH | |
| H | CH₃ | H | CH₂C(O)CH₃ | CH₃ | CH₃ | CH | |
| H | CH₃ | H | CH₂C(O)CH₃ | CH₃ | OCH₃ | CH | |
| H | CH₃ | H | CH₂C(O)CH₃ | OCH₃ | OCH₃ | N | |
| H | CH₃ | H | CH₂C(O)CH₃ | CH₃ | CH₃ | N | |
| H | CH₃ | H | CH₂C(O)CH₃ | OCH₃ | OCH₃ | N | |
| H | CH₃ | H | CH₂C(O)CH₃ | OCH₃ | Cl | CH | |
| H | CH₃ | H | CH₂C(O)CH₂CH₃ | CH₃ | CH₃ | CH | |
| H | CH₃ | H | CH₂C(O)CH₂CH₃ | CH₃ | OCH₃ | CH | |
| H | CH₃ | H | CH₂C(O)CH₂CH₃ | OCH₃ | OCH₃ | CH | |
| H | CH₃ | H | CH₂C(O)CH₂CH₃ | CH₃ | CH₃ | N | |
| H | CH₃ | H | CH₂C(O)CH₂CH₃ | CH₃ | OCH₃ | N | |
| H | CH₃ | H | CH₂C(O)CH₂CH₃ | OCH₃ | OCH₃ | N | |
| H | CH₃ | H | CH₂C(O)CH₂CH₃ | OCH₃ | Cl | CH | |
| H | CH₃ | H | CH₂(CH₂)₃C(O)CH₃ | CH₃ | CH₃ | CH | |
| H | CH₃ | H | CH₂(CH₂)₃C(O)CH₃ | CH₃ | OCH₃ | CH | |
| H | CH₃ | H | CH₂(CH₂)₃C(O)CH₃ | OCH₃ | OCH₃ | CH | |
| H | CH₃ | H | CH₂(CH₂)₃C(O)CH₃ | CH₃ | CH₃ | N | |
| H | CH₃ | H | CH₂(CH₂)₃C(O)CH₃ | CH₃ | OCH₃ | N | |
| H | CH₃ | CH₃ | CH₂(CH₂)₃C(O)CH₃ | OCH₃ | OCH₃ | N | |
| H | CH₃ | H | CH₂(CH₂)₃C(O)CH₃ | OCH₃ | Cl | CH | |
| H | CH₃ | H | CH₂CH₂C(O)CH₃ | CH₃ | CH₃ | CH | |
| H | CH₃ | H | CH₂CH₂C(O)CH₃ | CH₃ | OCH₃ | CH | |
| H | CH₃ | H | CH₂CH₂C(O)CH₃ | OCH₃ | OCH₃ | CH | |
| H | CH₃ | H | CH₂CH₂C(O)CH₃ | CH₃ | CH₃ | N | |
| H | CH₃ | H | CH₂—CH(CH₃)C(O)CH₃ | CH₃ | OCH₃ | N | |
| H | CH₃ | H | CH₂—CH(CH₂)C(O)CH₃ | OCH₃ | OCH₃ | N | |
| H | CH₃ | H | CH₂—CH(CH₂)C(O)CH₃ | OCH₃ | Cl | CH | |
| H | CH₃ | H | CH₂—CH(CH₃)C(O)CH₃ | CH₃ | CH₃ | CH | |
| CH₃ | CH₃ | CH₃ | CH₂—CH(CH₂)C(O)CH₃ | CH₃ | OCH₃ | CH | |
| H | CH₃ | H | CH₂(CH₂)₆C(O)CH₂CH₃ | OCH₃ | OCH₃ | CH | |
| H | CH₃ | H | CH₂(CH₂)₆C(O)CH₂CH₃ | CH₃ | CH₃ | N | |
| H | CH₃ | H | CH₂(CH₂)₆C(O)CH₂CH₃ | CH₃ | OCH₃ | N | |
| H | CH₃ | H | CH₂(CH₂)₆C(O)CH₂CH₃ | OCH₃ | OCH₃ | N | |
| H | CH₃ | H | CH₂(CH₂)₆C(O)CH₂CH₃ | OCH₃ | Cl | CH | |
| H | CH₃ | H | CH₂C(O)OCH₃ | CH₃ | CH₃ | CH | |
| H | CH₃ | H | CH₂C(O)OCH₃ | CH₃ | OCH₃ | CH | |
| H | CH₃ | H | CH₂C(O)OCH₃ | OCH₃ | OCH₃ | CH | |
| H | CH₃ | H | CH₂C(O)OCH₃ | CH₃ | CH₃ | N | |
| H | CH₃ | H | CH₂C(O)OCH₃ | CH₃ | OCH₃ | N | |
| H | CH₃ | H | CH₂C(O)OCH₃ | OCH₃ | OCH₃ | N | |
| H | CH₃ | H | CH₂C(O)OCH₃ | OCH₃ | Cl | CH | |
| H | CH₃ | H | CH₂C(O)OCH₂CH₃ | CH₃ | CH₃ | CH | |
| H | CH₃ | H | CH₂C(O)OCH₂CH₃ | CH₃ | OCH₃ | CH | |
| H | CH₃ | H | CH₂C(O)OCH₂CH₃ | OCH₃ | OCH₃ | CH | |
| H | CH₃ | H | CH₂C(O)OCH₂CH₃ | CH₃ | CH₃ | N | |
| H | CH₃ | H | CH₂C(O)OCH₂CH₃ | CH₃ | OCH₃ | N | |
| H | CH₃ | H | CH₂C(O)OCH₂CH₃ | OCH₃ | OCH₃ | N | |
| H | CH₃ | H | CH₂C(O)OCH₂CH₃ | OCH₃ | Cl | CH | |
| H | CH₃ | H | CH₂CH₂C(O)CH₃ | CH₃ | CH₃ | CH | |
| H | CH₃ | H | CH₂CH₂C(O)CH₃ | CH₃ | OCH₃ | CH | |
| H | CH₃ | H | CH₂CH₂C(O)CH₃ | OCH₃ | OCH₃ | N | |
| H | CH₃ | H | CH₂CH₂C(O)CH₃ | CH₃ | CH₃ | N | |

TABLE I-continued

General Structure I

| R | $R_1$ | $R_2$ | $R_3$ | X | Y | Z | m.p. (°C.) |
|---|---|---|---|---|---|---|---|
| H | $CH_3$ | H | $CH_2CH_2C(O)CH_3$ | $OCH_3$ | $OCH_3$ | N | |
| H | $CH_3$ | H | $CH_2CH_2C(O)CH_3$ | $OCH_3$ | Cl | CH | |
| H | $CH_3$ | H | $CH_2C(O)N(CH_3)_2$ | $CH_3$ | $CH_3$ | CH | |
| H | $CH_3$ | H | $CH_2C(O)N(CH_3)_2$ | $CH_3$ | $OCH_3$ | CH | |
| H | $CH_3$ | H | $CH_2C(O)N(CH_3)_2$ | $OCH_3$ | $OCH_3$ | CH | |
| H | $CH_3$ | H | $CH_2C(O)N(CH_3)_2$ | $CH_3$ | $CH_3$ | N | |
| H | $CH_3$ | H | $CH_2C(O)N(CH_3)_2$ | $CH_3$ | $OCH_3$ | N | |
| H | $CH_3$ | H | $CH_2C(O)N(CH_3)_2$ | $OCH_3$ | $OCH_3$ | N | |
| H | $CH_3$ | H | $CH_2C(O)N(CH_3)_2$ | $OCH_3$ | Cl | CH | |
| H | $CH_3$ | H | $CH_2C(O)N(CH_3)_2$ | $CH_3$ | $CH_3$ | CH | |
| H | $CH_3$ | H | $CH_2CH_2C(O)N(CH_3)_2$ | $CH_3$ | $OCH_3$ | CH | |
| H | $CH_3$ | H | $CH_2CH_2C(O)N(CH_3)_2$ | $OCH_3$ | $OCH_3$ | CH | |
| H | $CH_3$ | H | $CH_2CH_2C(O)N(CH_3)_2$ | $CH_3$ | $CH_3$ | N | |
| H | $CH_3$ | H | $CH_2CH_2C(O)N(CH_3)_2$ | $CH_3$ | $OCH_3$ | N | |
| H | $CH_3$ | $CH_3$ | $CH_2CH_2C(O)N(CH_3)_2$ | $OCH_3$ | $OCH_3$ | N | |
| H | $CH_3$ | H | $CH_2CH_2C(O)N(CH_3)_2$ | $OCH_3$ | Cl | CH | |
| H | $CH_3$ | H | $CH_2C(O)N(CH_3)CH_2CH_3$ | $CH_3$ | $CH_3$ | CH | |
| H | $CH_3$ | H | $CH_2C(O)N(CH_3)CH_2CH_3$ | $CH_3$ | $OCH_3$ | CH | |
| H | $CH_3$ | H | $CH_2C(O)N(CH_3)CH_2CH_3$ | $OCH_3$ | $OCH_3$ | CH | |
| H | $CH_3$ | H | $CH_2C(O)N(CH_3)CH_2CH_3$ | $CH_3$ | $CH_3$ | N | |
| H | $CH_3$ | H | $CH_2C(O)N(CH_3)CH_2OCH_3$ | $CH_3$ | $OCH_3$ | N | |
| H | $CH_3$ | H | $CH_2C(O)N(CH_3)CH_2OCH_3$ | $OCH_3$ | $OCH_3$ | N | |
| H | $CH_3$ | H | $CH_2C(O)N(CH_3)CH_2OCH_3$ | $OCH_3$ | Cl | CH | |
| H | $CH_3$ | H | $CH_2SeCH_3$ | $CH_3$ | $CH_3$ | CH | |
| $CH_3$ | $CH_3$ | H | $CH_2SeCH_3$ | $CH_3$ | $OCH_3$ | CH | |
| H | $CH_3$ | H | $CH_2SeCH_3$ | $OCH_3$ | $OCH_3$ | CH | |
| H | $CH_3$ | H | $CH_2SePh$ | $CH_3$ | $CH_3$ | N | |
| H | $CH_3$ | H | $CH_2SePh$ | $CH_3$ | $OCH_3$ | N | |
| H | $CH_3$ | H | $CH_2-CH_2SeCH_3$ | $OCH_3$ | $OCH_3$ | N | |
| H | $CH_3$ | H | $CH_2-CH_2SeCH_3$ | $OCH_3$ | Cl | CH | |
| H | $CH_3$ | H | $CH=CH_2$ | $OCH_3$ | $OCH_3$ | CH | |
| H | $CH_3$ | H | $CH=CH_2$ | $CH_3$ | $CH_3$ | N | |
| H | $CH_3$ | H | $CH=CH_2$ | $CH_3$ | $OCH_3$ | N | |
| H | $CH_3$ | H | $CH=CH_2$ | $OCH_3$ | $OCH_3$ | N | |
| H | $CH_3$ | H | $CH=CH_2$ | $OCH_3$ | Cl | CH | |
| H | $CH_3$ | H | $CH=CH-CH_3$ | $CH_3$ | $CH_3$ | CH | |
| H | $CH_3$ | H | $CH=CH-CH_3$ | $CH_3$ | $OCH_3$ | CH | |
| H | $CH_3$ | H | $CH=CH-CH_3$ | $OCH_3$ | $OCH_3$ | CH | |
| H | $CH_3$ | H | $CH=CH-CH_3$ | $CH_3$ | $CH_3$ | N | |
| H | $CH_3$ | H | $CH=CH-CH_3$ | $CH_3$ | $OCH_3$ | N | |
| H | $CH_3$ | H | $CH=CH-CH_3$ | $OCH_3$ | $OCH_3$ | N | |
| H | $CH_3$ | H | $CH=CH-CH_3$ | $OCH_3$ | Cl | CH | |
| H | $CH_3$ | H | $CH=CH-CH_2-CH_3$ | $CH_3$ | $CH_3$ | CH | |
| H | $CH_3$ | H | $CH=CH-CH_2-CH_3$ | $CH_3$ | $OCH_3$ | CH | |
| H | $CH_3$ | H | $CH=CH-CH_2-CH_3$ | $OCH_3$ | $OCH_3$ | CH | |
| H | $CH_3$ | H | $CH=CH-CH_2-CH_3$ | $CH_3$ | $CH_3$ | N | |
| H | $CH_3$ | H | $CH=CH-CH_2-CH_3$ | $OCH_3$ | $OCH_3$ | N | |
| H | $CH_3$ | H | $CH=CH-CH_2-CH_3$ | $OCH_3$ | Cl | CH | |
| H | $CH_3$ | H | $CH=C(CH_3)_2$ | $CH_3$ | $CH_3$ | CH | |
| H | $CH_3$ | H | $CH=C(CH_3)_2$ | $CH_3$ | $OCH_3$ | CH | |
| H | $CH_3$ | H | $CH=C(CH_3)_2$ | $OCH_3$ | $OCH_3$ | CH | |
| H | $CH_3$ | H | $CH=C(CH_3)_2$ | $CH_3$ | $CH_3$ | N | |
| H | $CH_3$ | H | $CH=C(CH_3)_2$ | $CH_3$ | $OCH_3$ | N | |
| H | $CH_3$ | H | $CH=C(CH_3)_2$ | $OCH_3$ | $OCH_3$ | N | |
| H | $CH_3$ | H | $CH=C(CH_3)_2$ | $OCH_3$ | Cl | CH | |
| H | $CH_3$ | H | $CH=CH(CH_2)_3CH_3$ | $CH_3$ | $CH_3$ | CH | |
| H | $CH_3$ | H | $CH=CH(CH_2)_3CH_3$ | $CH_3$ | $OCH_3$ | CH | |
| H | $CH_3$ | H | $CH=CH(CH_2)_3CH_3$ | $OCH_3$ | $OCH_3$ | CH | |
| H | $CH_3$ | H | $CH=CH(CH_2)_3CH_3$ | $CH_3$ | $CH_3$ | N | |
| H | $CH_3$ | H | $CH=CH(CH_2)_3CH_3$ | $CH_3$ | $OCH_3$ | N | |
| H | $CH_3$ | $CH_3$ | $CH=CH(CH_2)_3CH_3$ | $OCH_3$ | $OCH_3$ | N | |
| H | $CH_3$ | H | $CH=CH(CH_2)_3CH_3$ | $OCH_3$ | Cl | CH | |
| H | $CH_3$ | H | $CH=C(CH_3)CH_2CH_3$ | $CH_3$ | $CH_3$ | CH | |
| H | $CH_3$ | H | $CH=C(CH_3)CH_2CH_3$ | $CH_3$ | $OCH_3$ | CH | |
| H | $CH_3$ | H | $CH=C(CH_3)CH_2CH_3$ | $OCH_3$ | $OCH_3$ | CH | |
| H | $CH_3$ | H | $CH=CH-CH(CH_3)_2$ | $CH_3$ | $CH_3$ | N | |
| H | $CH_3$ | H | $CH=CH-CH(CH_3)_2$ | $CH_3$ | $OCH_3$ | N | |
| H | $CH_3$ | H | $CH=CH-CH(CH_3)_2$ | $OCH_3$ | $OCH_3$ | N | |
| H | $CH_3$ | H | $CH=CH-CH(CH_3)_2$ | $OCH_3$ | Cl | CH | |
| H | $CH_3$ | H | $CH=CH(CH_2)_4CH_3$ | $CH_3$ | $CH_3$ | CH | |
| $CH_3$ | $CH_3$ | H | $CH=CH(CH_2)_4CH_3$ | $CH_3$ | $OCH_3$ | CH | |
| H | $CH_3$ | H | $CH=CH(CH_2)_6CH_3$ | $OCH_3$ | $OCH_3$ | CH | |
| H | $CH_3$ | H | $CH=CH(CH_2)_6CH_3$ | $CH_3$ | $CH_3$ | N | |
| H | $CH_3$ | H | $CH=CH(CH_2)_6CH_3$ | $CH_3$ | $OCH_3$ | N | |
| H | $CH_3$ | H | $CH=C(CH_3)(CH_2)_3CH_3$ | $OCH_3$ | $OCH_3$ | N | |
| H | $CH_3$ | H | $CH=C(CH_3)(CH_2)_3CH_3$ | $OCH_3$ | Cl | CH | |
| H | $CH_3$ | H | $CH_2CH=CH_2$ | $CH_3$ | $CH_3$ | CH | |
| H | $CH_3$ | H | $CH_2CH=CH_2$ | $CH_3$ | $OCH_3$ | CH | |
| H | $CH_3$ | H | $CH_2CH=CH_2$ | $OCH_3$ | $OCH_3$ | CH | |
| H | $CH_3$ | H | $CH_2CH=CH_2$ | $CH_3$ | $CH_3$ | N | |

TABLE I-continued

General Structure I

| R | R₁ | R₂ | R₃ | X | Y | Z | m.p. (°C.) |
|---|---|---|---|---|---|---|---|
| H | CH₃ | H | CH₂CH=CH₂ | CH₃ | OCH₃ | N | |
| H | CH₃ | H | CH₂CH=CH₂ | OCH₃ | OCH₃ | N | |
| H | CH₃ | H | CH₂CH=CH₂ | OCH₃ | Cl | CH | |
| H | CH₃ | H | CH₂CH=CH₂ | CH₃ | CH₃ | CH | |
| H | CH₃ | H | CH₂CH=CH₂ | CH₃ | OCH₃ | CH | |
| H | CH₃ | H | CH₂CH=CH₂ | OCH₃ | OCH₃ | CH | |
| H | CH₃ | H | CH₂CH=CH₂ | CH₃ | CH₃ | N | |
| H | CH₃ | H | CH₂CH=CH₂ | CH₃ | OCH₃ | N | |
| H | CH₃ | H | CH₂CH=CH₂ | OCH₃ | OCH₃ | N | |
| H | CH₃ | H | CH₂CH=CH₂ | OCH₃ | Cl | CH | |
| H | CH₃ | H | CH₂CH₂CH=CH₂ | CH₃ | CH₃ | CH | |
| H | CH₃ | H | CH₂CH₂CH=CH₂ | CH₃ | OCH₃ | CH | |
| H | CH₃ | H | CH₂CH₂CH=CH₂ | OCH₃ | OCH₃ | CH | |
| H | CH₃ | H | CH₂CH₂CH=CH₂ | CH₃ | CH₃ | N | |
| H | CH₃ | H | CH₂CH₂CH=CH₂ | CH₃ | OCH₃ | N | |
| H | CH₃ | H | CH₂CH₂CH=CH₂ | OCH₃ | OCH₃ | N | |
| H | CH₃ | H | CH₂CH₂CH=CH₂ | OCH₃ | Cl | CH | |
| H | CH₃ | H | CH₂CH=CHCH₃ | CH₃ | CH₃ | CH | |
| H | CH₃ | H | CH₂CH=CHCH₃ | CH₃ | OCH₃ | CH | |
| H | CH₃ | H | CH₂CH=CHCH₃ | OCH₃ | OCH₃ | CH | |
| H | CH₃ | H | CH₂CH=CHCH₃ | CH₃ | CH₃ | N | |
| H | CH₃ | H | CH₂—CH=CH—CH₃ | OCH₃ | OCH₃ | N | |
| H | CH₃ | H | CH₂—CH=CH—CH₃ | OCH₃ | Cl | CH | |
| H | CH₃ | H | CH₂—CH=C(CH₃)₂ | CH₃ | CH₃ | CH | |
| H | CH₃ | H | CH₂—CH=C(CH₃)₂ | CH₃ | OCH₃ | CH | |
| H | CH₃ | H | CH₂—CH=C(CH₃)₂ | OCH₃ | OCH₃ | CH | |
| H | CH₃ | H | CH₂—CH=C(CH₃)₂ | CH₃ | CH₃ | N | |
| H | CH₃ | H | CH₂—CH=C(CH₃)₂ | CH₃ | OCH₃ | N | |
| H | CH₃ | H | CH₂—CH=C(CH₃)₂ | OCH₃ | OCH₃ | N | |
| H | CH₃ | H | CH₂—CH=CH(CH₂)₃CH₃ | OCH₃ | Cl | CH | |
| H | CH₃ | H | CH₂—CH=CH(CH₂)₃CH₃ | CH₃ | CH₃ | CH | |
| H | CH₃ | H | CH₂—CH=CH(CH₂)₃CH₃ | CH₃ | OCH₃ | CH | |
| H | CH₃ | H | CH₂—CH=CH(CH₂)₃CH₃ | OCH₃ | OCH₃ | CH | |
| H | CH₃ | H | CH₂—CH=CH(CH₂)₃CH₃ | CH₃ | CH₃ | N | |
| H | CH₃ | H | CH₂—CH=CH(CH₂)₃CH₃ | CH₃ | OCH₃ | N | |
| H | CH₃ | H | CH₂—CH=CH(CH₂)₃CH₃ | OCH₃ | OCH₃ | N | |
| H | CH₃ | H | CH₂—CH₂—CH=CH₂ | OCH₃ | Cl | CH | |
| H | CH₃ | H | CH₂—CH₂—CH=CH₂ | CH₃ | CH₃ | CH | |
| H | CH₃ | H | CH₂—CH₂—CH=CH₂ | CH₃ | OCH₃ | CH | |
| H | CH₃ | H | CH₂—CH₂—CH=CH₂ | OCH₃ | OCH₃ | CH | |
| H | CH₃ | H | CH₂—CH₂—CH=CH₂ | CH₃ | CH₃ | N | |
| H | CH₃ | H | CH₂—(CH₂)₄CH=CH₂ | CH₃ | OCH₃ | N | |
| H | CH₃ | H | CH₂—CH=CH—CH(CH₃)₂ | OCH₃ | OCH₃ | N | |
| H | CH₃ | H | CH₂—CH=CH—CH(CH₃)₂ | OCH₃ | Cl | CH | |
| H | CH₃ | H | CH₂—CH=CH—CH(CH₃)₂ | CH₃ | CH₃ | CH | |
| H | CH₃ | H | CH₂—CH=CH—CH(CH₃)₂ | CH₃ | OCH₃ | CH | |
| H | CH₃ | H | CH₂—CH=CH—CH(CH₃)₂ | OCH₃ | OCH₃ | CH | |
| H | CH₃ | H | CH₂—CH=CH—CH=CH₂ | CH₃ | CH₃ | N | |
| H | CH₃ | H | CH₂—CH=CH—CH=CH₂ | CH₃ | OCH₃ | N | |
| H | CH₃ | H | CH₂—CH=CH—CH=CH₂ | OCH₃ | OCH₃ | N | |
| H | CH₃ | H | CH₂—CH=CH—CH=CH₂ | OCH₃ | Cl | CH | |
| H | CH₃ | H | C≡CH | CH₃ | CH₃ | CH | |
| H | CH₃ | H | C≡CH | CH₃ | OCH₃ | CH | |
| H | CH₃ | H | C≡CH | OCH₃ | OCH₃ | CH | |
| H | CH₃ | H | C≡CH | CH₃ | CH₃ | N | |
| H | CH₃ | H | C≡CH | CH₃ | OCH₃ | N | |
| H | CH₃ | H | C≡CH | OCH₃ | OCH₃ | N | |
| H | CH₃ | H | C≡CH | OCH₃ | Cl | CH | |
| H | CH₃ | H | C≡C—CH₃ | CH₃ | CH₃ | CH | |
| H | CH₃ | H | C≡C—CH₃ | CH₃ | OCH₃ | CH | |
| H | CH₃ | H | C≡C—CH₃ | OCH₃ | OCH₃ | CH | |
| H | CH₃ | H | C≡C—CH₃ | CH₃ | CH₃ | N | |
| H | CH₃ | H | C≡C—CH₃ | CH₃ | OCH₃ | N | |
| H | CH₃ | H | C≡C—CH₃ | OCH₃ | OCH₃ | N | |
| H | CH₃ | H | C≡C—CH₃ | OCH₃ | Cl | CH | |
| H | CH₃ | H | C≡C(CH₂)₂CH₃ | CH₃ | CH₃ | CH | |
| H | CH₃ | H | C≡C(CH₂)₂CH₃ | CH₃ | OCH₃ | CH | |
| H | CH₃ | H | C≡C(CH₂)₂CH₃ | OCH₃ | OCH₃ | CH | |
| H | CH₃ | H | C≡C(CH₂)₂CH₃ | CH₃ | CH₃ | N | |
| H | CH₃ | H | C≡C(CH₂)₂CH₃ | OCH₃ | OCH₃ | N | |
| H | CH₃ | H | CH₂—C≡CH | OCH₃ | Cl | CH | |
| H | CH₃ | H | CH₂—C≡CH | CH₃ | CH₃ | CH | |
| H | CH₃ | H | CH₂—C≡CH | CH₃ | OCH₃ | CH | |
| H | CH₃ | H | CH₂—C≡CH | OCH₃ | OCH₃ | CH | |
| H | CH₃ | H | CH₂—C≡CH | CH₃ | CH₃ | N | |
| H | CH₃ | H | CH₂—C≡CH | CH₃ | OCH₃ | N | |
| H | CH₃ | H | CH₂—C≡CH | OCH₃ | OCH₃ | N | |
| H | CH₃ | H | CH₂—C≡C—CH₃ | OCH₃ | Cl | CH | |
| H | CH₃ | H | CH₂—C≡C—CH₃ | CH₃ | CH₃ | CH | |
| H | CH₃ | H | CH₂—C≡C—CH₃ | CH₃ | OCH₃ | CH | |

TABLE I-continued

General Structure I

| R | R₁ | R₂ | R₃ | X | Y | Z | m.p. (°C) |
|---|---|---|---|---|---|---|---|
| H | CH₃ | H | CH₂—C≡C—CH₃ | OCH₃ | OCH₃ | CH | |
| H | CH₃ | H | CH₂—C≡C—CH₃ | CH₃ | CH₃ | N | |
| H | CH₃ | H | CH₂—C≡C—CH₃ | CH₃ | OCH₃ | N | |
| H | CH₃ | CH₃ | CH₂—C≡C—CH₃ | OCH₃ | OCH₃ | N | |
| H | CH₃ | H | CH₂—CH₂—C≡CH | OCH₃ | Cl | CH | |
| H | CH₃ | H | CH₂—CH₂—C≡CH | CH₃ | CH₃ | CH | |
| H | CH₃ | H | CH₂—CH₂—C≡CH | CH₃ | OCH₃ | CH | |
| H | CH₃ | H | CH₂—CH₂—C≡CH | OCH₃ | OCH₃ | CH | |
| H | CH₃ | H | CH₂—CH₂—C≡CH | CH₃ | CH₃ | N | |
| H | CH₃ | H | CH₂—CH₂—C≡CH | CH₃ | OCH₃ | N | |
| H | CH₃ | H | CH₂—CH₂—C≡CH | OCH₃ | OCH₃ | N | |
| H | CH₃ | H | CH₂—C≡C—CH(CH₃)₂ | OCH₃ | Cl | CH | |
| CH₃ | CH₃ | H | CH₂—C≡C—CH(CH₃)₂ | CH₃ | CH₃ | CH | |
| H | CH₃ | H | CH₂—C≡C—CH(CH₃)₂ | CH₃ | OCH₃ | CH | |
| H | CH₃ | H | C≡C—(CH₂)₆CH₃ | OCH₃ | OCH₃ | CH | |
| H | CH₃ | H | C≡C—(CH₂)₆CH₃ | CH₃ | CH₃ | N | |
| H | CH₃ | H | C≡C—(CH₂)₆CH₃ | CH₃ | OCH₃ | N | |
| H | CH₃ | H | CH₂(CH₂)₇C≡CH | OCH₃ | OCH₃ | N | |
| H | CH₃ | H | CH₂(CH₂)₇C≡CH | OCH₃ | Cl | CH | |
| H | CH₃ | H | CH₂—CH(O)CH₂ (epoxide) | CH₃ | CH₃ | CH | |
| H | CH₃ | H | CH₂—CH(O)CH₂ (epoxide) | CH₃ | OCH₃ | CH | |
| H | CH₃ | H | CH₂—CH(O)CH₂ (epoxide) | OCH₃ | OCH₃ | CH | |
| H | CH₃ | H | CH₂—CH(O)CH₂ (epoxide) | CH₃ | CH₃ | N | |
| H | CH₃ | H | CH₂—CH(O)CH₂ (epoxide) | CH₃ | OCH₃ | N | |
| H | CH₃ | H | CH₂—CH(O)CH₂ (epoxide) | OCH₃ | OCH₃ | N | |
| H | CH₃ | H | CH₂—CH(O)CH₂ (epoxide) | OCH₃ | Cl | CH | |
| H | CH₃ | H | CH₂—CH(O)CH—CH₃ (epoxide) | CH₃ | CH₃ | CH | |
| H | CH₃ | H | CH₂—CH(O)CH—CH₃ (epoxide) | CH₃ | OCH₃ | CH | |
| H | CH₃ | H | CH₂—CH(O)CH—CH₃ (epoxide) | OCH₃ | OCH₃ | CH | |
| H | CH₃ | H | CH₂—CH(O)CH—CH₃ (epoxide) | CH₃ | CH₃ | N | |
| H | CH₃ | H | CH₂—CH(O)CH—CH₃ (epoxide) | CH₃ | OCH₃ | N | |
| H | CH₃ | H | CH₂—CH(O)CH—CH₃ (epoxide) | OCH₃ | OCH₃ | N | |
| H | CH₃ | H | CH₂—CH(O)CH—CH₃ (epoxide) | OCH₃ | Cl | CH | |
| H | CH₃ | H | CH₂—CH₂—CH(O)CH₂ (epoxide) | CH₃ | CH₃ | CH | |
| H | CH₃ | H | CH₂—CH₂—CH(O)CH₂ (epoxide) | CH₃ | OCH₃ | CH | |
| H | CH₃ | H | CH₂—CH₂—CH(O)CH₂ (epoxide) | OCH₃ | OCH₃ | CH | |
| H | CH₃ | H | CH₂—CH₂—CH(O)CH₂ (epoxide) | CH₃ | CH₃ | N | |
| H | CH₃ | H | CH₂—CH₂—CH(O)CH₂ (epoxide) | OCH₃ | OCH₃ | N | |
| H | CH₃ | H | CH₂—CH₂—CH(O)CH₂ (epoxide) | OCH₃ | Cl | CH | |
| H | CH₃ | H | cyclobutyl | CH₃ | CH₃ | CH | |
| H | CH₃ | H | cyclobutyl | CH₃ | OCH₃ | CH | |

TABLE I-continued

General Structure I

| R | $R_1$ | $R_2$ | $R_3$ | X | Y | Z | m.p. (°C.) |
|---|---|---|---|---|---|---|---|
| H | $CH_3$ | H | cyclobutyl | $OCH_3$ | $OCH_3$ | CH | |
| H | $CH_3$ | H | cyclobutyl | $CH_3$ | $CH_3$ | N | |
| H | $CH_3$ | H | cyclobutyl | $CH_3$ | $OCH_3$ | N | |
| H | $CH_3$ | H | cyclobutyl | $OCH_3$ | $OCH_3$ | N | |
| H | $CH_3$ | H | cyclobutyl | $OCH_3$ | Cl | CH | |
| H | $CH_3$ | H | cyclopentyl | $CH_3$ | $CH_3$ | CH | |
| H | $CH_3$ | H | cyclopentyl | $CH_3$ | $OCH_3$ | CH | |
| H | $CH_3$ | H | cyclopentyl | $OCH_3$ | $OCH_3$ | CH | |
| H | $CH_3$ | H | cyclopentyl | $CH_3$ | $CH_3$ | N | |
| H | $CH_3$ | H | cyclopentyl | $CH_3$ | $OCH_3$ | N | |
| H | $CH_3$ | $CH_3$ | cyclopentyl | $OCH_3$ | $OCH_3$ | N | |
| H | $CH_3$ | H | cyclopentyl | $OCH_3$ | Cl | CH | |
| H | $CH_3$ | H | cyclohexyl | $CH_3$ | $CH_3$ | CH | |
| H | $CH_3$ | H | cyclohexyl | $CH_3$ | $OCH_3$ | CH | |
| H | $CH_3$ | H | cyclohexyl | $OCH_3$ | $OCH_3$ | CH | |
| H | $CH_3$ | H | cyclohexyl | $CH_3$ | $CH_3$ | N | |
| H | $CH_3$ | H | cyclohexyl | $CH_3$ | $OCH_3$ | N | |
| H | $CH_3$ | $CH_3$ | cyclohexyl | $OCH_3$ | $OCH_3$ | N | |
| H | $CH_3$ | H | cyclohexyl | $OCH_3$ | Cl | CH | |
| H | $CH_3$ | H | cyclopropyl | $CH_3$ | $CH_3$ | CH | |
| $CH_3$ | $CH_3$ | H | cyclopropyl | $CH_3$ | $OCH_3$ | CH | |
| H | $CH_3$ | H | cyclopropyl | $OCH_3$ | $OCH_3$ | CH | |
| H | $CH_3$ | H | cyclopropyl | $CH_3$ | $CH_3$ | N | |
| H | $CH_3$ | H | cyclopropyl | $CH_3$ | $OCH_3$ | N | |
| H | $CH_3$ | H | cyclopropyl | $OCH_3$ | $OCH_3$ | N | |
| H | $CH_3$ | H | cyclopropyl | $OCH_3$ | Cl | CH | |
| H | $CH_3$ | H | $CH_2$—cyclopropyl | $CH_3$ | $CH_3$ | CH | |
| H | $CH_3$ | H | $CH_2$—cyclopropyl | $CH_3$ | $OCH_3$ | CH | |
| H | $CH_3$ | H | $CH_2$—cyclopropyl | $OCH_3$ | $OCH_3$ | CH | |
| H | $CH_3$ | H | $CH_2$—cyclopropyl | $CH_3$ | $CH_3$ | N | |
| H | $CH_3$ | H | $CH_2$—cyclopropyl | $CH_3$ | $OCH_3$ | N | |
| H | $CH_3$ | H | $CH_2$—cyclopropyl | $OCH_3$ | $OCH_3$ | N | |
| H | $CH_3$ | H | $CH_2$—cyclopropyl | $OCH_3$ | Cl | CH | |
| H | $CH_3$ | H | $CH_2$—cyclopentyl | $CH_3$ | $CH_3$ | CH | |
| H | $CH_3$ | H | $CH_2$—cyclopentyl | $CH_3$ | $OCH_3$ | CH | |
| H | $CH_3$ | H | $CH_2$—cyclopentyl | $OCH_3$ | $OCH_3$ | CH | |
| H | $CH_3$ | H | $CH_2$—cyclopentyl | $CH_3$ | $CH_3$ | N | |
| H | $CH_3$ | H | $CH_2$—cyclopentyl | $CH_3$ | $OCH_3$ | N | |
| H | $CH_3$ | H | $CH_2$—cyclopentyl | $OCH_3$ | $OCH_3$ | N | |
| H | $CH_3$ | H | $CH_2$—cyclopentyl | $OCH_3$ | Cl | CH | |
| H | $CH_3$ | H | $C_6H_5$ | $CH_3$ | $CH_3$ | CH | |
| H | $CH_3$ | H | $C_6H_5$ | $CH_3$ | $OCH_3$ | CH | |
| H | $CH_3$ | H | $C_6H_5$ | $OCH_3$ | $OCH_3$ | CH | |
| H | $CH_3$ | H | $C_6H_5$ | $CH_3$ | $CH_3$ | N | |
| H | $CH_3$ | H | $C_6H_5$ | $OCH_3$ | $OCH_3$ | N | |
| H | $CH_3$ | H | $C_6H_5$ | $OCH_3$ | Cl | CH | |
| H | $CH_3$ | H | CH=CH—$CF_3$ | $CH_3$ | $CH_3$ | CH | |
| H | $CH_3$ | H | CH=CH—$CF_3$ | $CH_3$ | $OCH_3$ | CH | |
| H | $CH_3$ | H | CH=CH—$CF_3$ | $OCH_3$ | $OCH_3$ | CH | |
| H | $CH_3$ | H | CH=CH—$CF_3$ | $CH_3$ | $CH_3$ | N | |
| H | $CH_3$ | H | CH=CH—$CF_3$ | $CH_3$ | $OCH_3$ | N | |
| H | $CH_3$ | H | CH=CH—$CF_3$ | $OCH_3$ | $OCH_3$ | N | |
| H | $CH_3$ | H | CH=CH—$CF_3$ | $OCH_3$ | Cl | CH | |
| H | $CH_3$ | H | $CH_2$—C≡C—$CF_3$ | $CH_3$ | $CH_3$ | CH | |
| H | $CH_3$ | H | $CH_2$—C≡C—$CF_3$ | $CH_3$ | $OCH_3$ | CH | |
| H | $CH_3$ | H | $CH_2$—C≡C—$CF_3$ | $OCH_3$ | $OCH_3$ | CH | |
| H | $CH_3$ | H | $CH_2$—C≡C—$CF_3$ | $CH_3$ | $CH_3$ | N | |
| H | $CH_3$ | H | $CH_2$—C≡C—$CF_3$ | $CH_3$ | $OCH_3$ | N | |
| H | $CH_3$ | $CH_3$ | $CH_2$—C≡C—$CF_3$ | $OCH_3$ | $OCH_3$ | N | |
| H | $CH_3$ | H | $CH_2$—CH=$CF_2$ | $OCH_3$ | Cl | CH | |
| H | $CH_3$ | H | CH=CH—$CH_2Cl$ | $CH_3$ | $CH_3$ | CH | |
| H | $CH_3$ | H | CH=CH—$CH_2Cl$ | $CH_3$ | $OCH_3$ | CH | |
| H | $CH_3$ | H | CH=CH—$CH_2Cl$ | $OCH_3$ | $OCH_3$ | CH | |
| H | $CH_3$ | H | CH=CH—$CH_2Cl$ | $CH_3$ | $CH_3$ | N | |
| H | $CH_3$ | H | CH=CH—$CH_2Cl$ | $CH_3$ | $OCH_3$ | N | |
| H | $CH_3$ | H | CH=CH—$CH_2Cl$ | $OCH_3$ | $OCH_3$ | N | |
| H | $CH_3$ | H | $CH_2$—C(CHF)(CH_2)(CH_2) (cyclopropyl with F) | $OCH_3$ | Cl | CH | |
| H | $CH_3$ | H | $CH_2$—C(CHF)(CH_2)(CH_2) (cyclopropyl with F) | $CH_3$ | $CH_3$ | CH | |

TABLE I-continued

General Structure I

| R | R₁ | R₂ | R₃ | X | Y | Z | m.p. (°C.) |
|---|---|---|---|---|---|---|---|
| CH₃ | CH₃ | H | CH₂—C(CHF)(CH₂) (cyclopropane with CHF) | CH₃ | OCH₃ | CH | |
| H | CH₃ | H | CH₂—C(CHF)(CH₂) (cyclopropane with CHF) | OCH₃ | OCH₃ | CH | |
| H | CH₃ | H | CH₂—C(CHF)(CH₂) (cyclopropane with CHF) | CH₃ | CH₃ | N | |
| H | CH₃ | H | CH₂—C(CHF)(CH₂) (cyclopropane with CHF) | CH₃ | OCH₃ | N | |
| H | CH₃ | H | CH₂—C≡C—CH₂Br | OCH₃ | OCH₃ | N | |
| H | CH₃ | H | CH₂—C≡C—CH₂Br | OCH₃ | Cl | CH | |
| H | CH₃ | H | CH₂—CH=CHOCH₃ | CH₃ | CH₃ | CH | |
| H | CH₃ | H | CH₂—CH=CHOCH₃ | CH₃ | OCH₃ | CH | |
| H | CH₃ | H | CH₂—CH=CHOCH₃ | OCH₃ | OCH₃ | CH | |
| H | CH₃ | H | CH₂—CH=CHOCH₃ | CH₃ | CH₃ | N | |
| H | CH₃ | H | CH₂—C≡C—OCH₃ | CH₃ | OCH₃ | N | |
| H | CH₃ | H | CH₂—C≡C—OCH₃ | OCH₃ | OCH₃ | N | |
| H | CH₃ | H | CH₂—CH₂—CH=CHCN | OCH₃ | Cl | CH | |
| H | CH₃ | H | CH₂—CH₂—CH=CHCN | CH₃ | CH₃ | CH | |
| H | CH₃ | H | CH₂—CH₂—CH=CHCN | CH₃ | OCH₃ | CH | |
| H | CH₃ | H | CH(OSO₂CH₃)C≡CH | OCH₃ | OCH₃ | CH | |
| H | CH₃ | H | CH(OSO₂CH₃)C≡CH | CH₃ | CH₃ | N | |
| H | CH₃ | H | CH(OSO₂CH₃)C≡CH | CH₃ | OCH₃ | N | |
| H | CH₃ | H | CH(OSO₂CH₃)C≡CH | OCH₃ | OCH₃ | N | |
| H | CH₃ | H | CH(OSO₂CH₃)C≡CH | OCH₃ | Cl | CH | |
| H | CH₃ | H | C≡C—Si(CH₃)₃ | CH₃ | CH₃ | CH | |
| H | CH₃ | H | C≡C—Si(CH₃)₃ | CH₃ | OCH₃ | CH | |
| H | CH₃ | H | C≡C—Si(CH₃)₃ | OCH₃ | OCH₃ | CH | |
| H | CH₃ | H | CH₂—CH=CHP(O)(CH₃)₂ | CH₃ | CH₃ | N | |
| H | CH₃ | H | CH₂—CH=CHP(O)(CH₃)₂ | CH₃ | OCH₃ | N | |
| H | CH₃ | H | CH₂—CH=CHP(O)(CH₃)₂ | OCH₃ | Cl | CH | |
| H | CH₃ | H | CH₂—CH=CHP(O)(CH₃)₂ | CH₃ | CH₃ | CH | |
| H | CH₃ | H | CH₂—CH=CHP(O)(CH₃)₂ | CH₃ | OCH₃ | CH | |
| H | CH₃ | H | CH=CH—OSi(CH₃)₃ | OCH₃ | OCH₃ | CH | |
| H | CH₃ | H | CH=CH—OSi(CH₃)₃ | CH₃ | CH₃ | N | |
| H | CH₃ | H | CH=CH—OSi(CH₃)₃ | CH₃ | OCH₃ | N | |
| H | CH₃ | H | CH=CH—OSi(CH₃)₃ | OCH₃ | OCH₃ | N | |
| H | CH₃ | H | CH₂(CH₂)₅CH=CH—CN | OCH₃ | Cl | CH | |
| H | CH₃ | H | CH₂(CH₂)₅CH=CH—CN | CH₃ | CH₃ | CH | |
| H | CH₃ | H | CH₂(CH₂)₅CH=CH—CN | CH₃ | OCH₃ | CH | |
| H | CH₃ | H | CH₂(CH₂)₅CH=CH—CN | OCH₃ | OCH₃ | CH | |
| H | CH₃ | H | CH₂(CH₂)₅CH=CH—CN | CH₃ | CH₃ | N | |
| H | CH₃ | H | CH=CH—CH₂SCN | CH₃ | OCH₃ | N | |
| H | CH₃ | H | CH=CH—CH₂SCN | CH₃ | OCH₃ | N | |
| H | CH₃ | H | CH=CH—CH₂SCN | OCH₃ | OCH₃ | N | |
| H | CH₃ | H | CH=CH—CH₂SCN | OCH₃ | Cl | CH | |
| H | CH₃ | H | C≡C—C≡C—CH₂OCH₃ | CH₃ | CH₃ | CH | |
| H | CH₃ | H | C≡C—C≡C—CH₂OCH₃ | CH₃ | OCH₃ | CH | |
| H | CH₃ | H | C≡C—C≡C—CH₂OCH₃ | OCH₃ | OCH₃ | CH | |
| H | CH₃ | H | CH₂—CH=CH—CH₂SCH₃ | CH₃ | CH₃ | N | |
| H | CH₃ | H | CH₂—CH=CH—CH₂SCH₃ | CH₃ | OCH₃ | N | |
| H | CH₃ | H | CH₂—CH=CH—CH₂SCH₃ | OCH₃ | OCH₃ | N | |
| H | CH₃ | H | CH₂—CH=CH—CH₂SCH₃ | OCH₃ | Cl | CH | |
| H | CH₃ | H | CH=CH—CH₂N(CH₃)₂ | CH₃ | CH₃ | CH | |
| CH₃ | CH₃ | H | CH=CH₂N(CH₃)₂ | CH₃ | OCH₃ | CH | |
| H | CH₃ | H | CH=CH—CH₂N(CH₃)₂ | OCH₃ | OCH₃ | CH | |
| H | CH₃ | H | CH₂—CH=CH—P(O)(OCH₃)₂ | CH₃ | CH₃ | N | |
| H | CH₃ | H | CH₂—CH=CH—P(O)(OCH₃)₂ | CH₃ | CH₃ | N | |
| H | CH₃ | H | CH₂—CH=CH—P(O)(OCH₃)₂ | OCH₃ | OCH₃ | N | |
| H | CH₃ | H | CH₂—CH=CH—P(O)(OCH₃)₂ | OCH₃ | Cl | CH | |
| H | CH₃ | H | SCH₃ | CH₃ | CH₃ | CH | |
| H | CH₃ | H | SCH₃ | CH₃ | OCH₃ | CH | |
| H | CH₃ | H | SCH₃ | OCH₃ | OCH₃ | CH | |
| H | CH₃ | H | SCH₃ | CH₃ | CH₃ | N | |
| H | CH₃ | H | SCH₃ | CH₃ | OCH₃ | N | |
| H | CH₃ | H | SCH₃ | OCH₃ | OCH₃ | N | |
| H | CH₃ | H | SCH₃ | OCH₃ | Cl | CH | |
| H | CH₃ | H | SCH₂CF₃ | CH₃ | CH₃ | CH | |
| H | CH₃ | H | SCH₂CH₃ | CH₃ | OCH₃ | CH | |

TABLE I-continued

General Structure I

| R | R$_1$ | R$_2$ | R$_3$ | X | Y | Z | m.p. (°C.) |
|---|---|---|---|---|---|---|---|
| H | CH$_3$ | H | SCH$_2$CH$_3$ | OCH$_3$ | OCH$_3$ | CH | |
| H | CH$_3$ | H | SCH$_2$CH$_3$ | CH$_3$ | CH$_3$ | N | |
| H | CH$_3$ | H | SCH$_2$CH$_3$ | CH$_3$ | OCH$_3$ | N | |
| H | CH$_3$ | H | SCH$_2$CH$_3$ | OCH$_3$ | OCH$_3$ | N | |
| H | CH$_3$ | H | SCH$_2$CH$_3$ | OCH$_3$ | Cl | CH | |
| H | CH$_3$ | H | SO$_2$CH$_3$ | CH$_3$ | CH$_3$ | CH | |
| H | CH$_3$ | H | SO$_2$CH$_3$ | CH$_3$ | OCH$_3$ | CH | |
| H | CH$_3$ | H | SO$_2$CH$_3$ | OCH$_3$ | OCH$_3$ | CH | |
| H | CH$_3$ | H | SO$_2$CH$_3$ | CH$_3$ | CH$_3$ | N | |
| H | CH$_3$ | H | SO$_2$CH$_3$ | OCH$_3$ | OCH$_3$ | N | |
| H | CH$_3$ | H | SO$_2$CH$_3$ | OCH$_3$ | Cl | CH | |
| H | CH$_3$ | H | SO$_2$CH$_2$CH$_3$ | CH$_3$ | CH$_3$ | CH | |
| H | CH$_3$ | H | SO$_2$CH$_2$CH$_3$ | CH$_3$ | OCH$_3$ | CH | |
| H | CH$_3$ | H | SO$_2$CH$_2$CH$_3$ | OCH$_3$ | OCH$_3$ | CH | |
| H | CH$_3$ | H | SO$_2$CH$_2$CH$_3$ | CH$_3$ | CH$_3$ | N | |
| H | CH$_3$ | H | SO$_2$CH$_2$CH$_3$ | CH$_3$ | OCH$_3$ | N | |
| H | CH$_3$ | H | SO$_2$CH$_2$CH$_3$ | OCH$_3$ | OCH$_3$ | N | |
| H | CH$_3$ | H | SO$_2$CH$_2$CH$_3$ | OCH$_3$ | Cl | CH | |
| H | CH$_3$ | H | OCH$_3$ | CH$_3$ | CH$_3$ | CH | |
| H | CH$_3$ | H | OCH$_3$ | CH$_3$ | OCH$_3$ | CH | |
| H | CH$_3$ | H | OCH$_3$ | OCH$_3$ | OCH$_3$ | CH | |
| H | CH$_3$ | H | OCH$_3$ | CH$_3$ | CH$_3$ | N | |
| H | CH$_3$ | H | OCH$_3$ | CH$_3$ | OCH$_3$ | N | |
| H | CH$_3$ | CH$_3$ | OCH$_3$ | OCH$_3$ | OCH$_3$ | N | |
| H | CH$_3$ | H | OCH$_3$ | OCH$_3$ | Cl | CH | |
| H | CH$_3$ | H | OCH$_2$CH$_3$ | CH$_3$ | CH$_3$ | CH | |
| H | CH$_3$ | H | OCH$_2$CH$_3$ | CH$_3$ | OCH$_3$ | CH | |
| H | CH$_3$ | H | OCH$_2$CH$_3$ | OCH$_3$ | OCH$_3$ | CH | |
| H | CH$_3$ | H | OCH$_2$CH$_3$ | CH$_3$ | CH$_3$ | N | |
| H | CH$_3$ | H | OCH$_2$CH$_3$ | CH$_3$ | OCH$_3$ | N | |
| H | CH$_3$ | H | OCH$_2$CH$_3$ | OCH$_3$ | OCH$_3$ | N | |
| H | CH$_3$ | H | OCH$_2$CH$_3$ | OCH$_3$ | Cl | CH | |
| H | CH$_3$ | H | OCH(CH$_3$)$_2$ | CH$_3$ | CH$_3$ | CH | |
| CH$_3$ | CH$_3$ | H | OCH(CH$_3$)$_2$ | CH$_3$ | OCH$_3$ | CH | |
| H | CH$_3$ | H | OCH(CH$_3$)$_2$ | OCH$_3$ | OCH$_3$ | CH | |
| H | CH$_3$ | H | OCH(CH$_3$)$_2$ | CH$_3$ | CH$_3$ | N | |
| H | CH$_3$ | H | OCH(CH$_3$)$_2$ | CH$_3$ | OCH$_3$ | N | |
| H | CH$_3$ | H | OCH(CH$_3$)$_2$ | OCH$_3$ | OCH$_3$ | N | |
| H | CH$_3$ | H | OCH(CH$_3$)$_2$ | OCH$_3$ | Cl | CH | |
| H | CH$_3$ | H | C(O)CH$_3$ | CH$_3$ | CH$_3$ | CH | |
| H | CH$_3$ | H | C(O)CH$_3$ | CH$_3$ | OCH$_3$ | CH | |
| H | CH$_3$ | H | C(O)CH$_3$ | OCH$_3$ | OCH$_3$ | CH | |
| H | CH$_3$ | H | C(O)CH$_3$ | CH$_3$ | CH$_3$ | N | |
| H | CH$_3$ | H | C(O)CH$_3$ | CH$_3$ | OCH$_3$ | N | |
| H | CH$_3$ | H | C(O)CH$_3$ | OCH$_3$ | OCH$_3$ | N | |
| H | CH$_3$ | H | C(O)CH$_3$ | OCH$_3$ | Cl | CH | |
| H | CH$_3$ | H | C(O)CH$_2$CH$_3$ | CH$_3$ | CH$_3$ | CH | |
| H | CH$_3$ | H | C(O)CH$_2$CH$_3$ | CH$_3$ | OCH$_3$ | CH | |
| H | CH$_3$ | H | C(O)CH$_2$CH$_3$ | OCH$_3$ | OCH$_3$ | CH | |
| H | CH$_3$ | H | C(O)CH$_2$CH$_3$ | CH$_3$ | CH$_3$ | N | |
| H | CH$_3$ | H | C(O)CH$_2$CH$_3$ | CH$_3$ | OCH$_3$ | N | |
| H | CH$_3$ | H | C(O)CH$_2$CH$_3$ | OCH$_3$ | OCH$_3$ | N | |
| H | CH$_3$ | H | C(O)CH$_2$CH$_3$ | OCH$_3$ | Cl | CH | |
| H | CH$_3$ | H | C(O)(CH)(CH$_3$)$_2$ | CH$_3$ | CH$_3$ | CH | |
| H | CH$_3$ | H | C(O)(CH)(CH$_3$)$_2$ | CH$_3$ | OCH$_3$ | CH | |
| H | CH$_3$ | H | C(O)(CH)(CH$_3$)$_2$ | OCH$_3$ | OCH$_3$ | CH | |
| H | CH$_3$ | H | C(O)(CH)(CH$_3$)$_2$ | CH$_3$ | CH$_3$ | N | |
| H | CH$_3$ | H | C(O)(CH)(CH$_3$)$_2$ | OCH$_3$ | OCH$_3$ | N | |
| H | CH$_3$ | H | C(O)(CH)(CH$_3$)$_2$ | OCH$_3$ | Cl | CH | |
| H | CH$_3$ | H | C(O)CHF$_2$ | CH$_3$ | CH$_3$ | CH | |
| H | CH$_3$ | H | C(O)CHF$_2$ | CH$_3$ | OCH$_3$ | CH | |
| H | CH$_3$ | H | C(O)CHF$_2$ | OCH$_3$ | OCH$_3$ | CH | |
| H | CH$_3$ | H | C(O)CF$_3$ | CH$_3$ | CH$_3$ | N | |
| H | CH$_3$ | H | C(O)CF$_3$ | CH$_3$ | OCH$_3$ | N | |
| H | CH$_3$ | H | C(O)CF$_3$ | OCH$_3$ | OCH$_3$ | N | |
| H | CH$_3$ | H | C(O)CF$_3$ | OCH$_3$ | Cl | CH | |
| H | CH$_3$ | H | C(O)CH$_2$CH$_2$CH$_3$ | CH$_3$ | CH$_3$ | CH | |
| H | CH$_3$ | H | C(O)CH$_2$CH$_2$CH$_3$ | CH$_3$ | OCH$_3$ | CH | |
| H | CH$_3$ | H | C(O)CH$_2$CH$_2$CH$_3$ | OCH$_3$ | OCH$_3$ | CH | |
| H | CH$_3$ | H | C(O)CH$_2$CH$_2$CH$_3$ | CH$_3$ | CH$_3$ | N | |
| H | CH$_3$ | H | C(O)CH$_2$CH$_2$CH$_3$ | CH$_3$ | OCH$_3$ | N | |
| H | CH$_3$ | CH$_3$ | C(O)CH$_2$CH$_2$CH$_3$ | OCH$_3$ | OCH$_3$ | N | |
| H | CH$_3$ | H | C(O)CH$_2$CH$_2$CH$_3$ | OCH$_3$ | Cl | CH | |
| H | CH$_3$ | H | C(O)CH$_2$OCH$_3$ | CH$_3$ | CH$_3$ | CH | |
| H | CH$_3$ | H | C(O)CH$_2$OCH$_3$ | CH$_3$ | OCH$_3$ | CH | |
| H | CH$_3$ | H | C(O)CH$_2$OCH$_3$ | OCH$_3$ | OCH$_3$ | CH | |
| H | CH$_3$ | H | C(O)CH$_2$OCH$_3$ | CH$_3$ | CH$_3$ | N | |
| H | CH$_3$ | H | C(O)CH$_2$Cl | CH$_3$ | OCH$_3$ | N | |
| H | CH$_3$ | H | C(O)CH$_2$Cl | OCH$_3$ | OCH$_3$ | N | |
| H | CH$_3$ | H | C(O)CH$_2$Cl | OCH$_3$ | Cl | CH | |

TABLE I-continued

General Structure I

| R | R$_1$ | R$_2$ | R$_3$ | X | Y | Z | m.p. (°C.) |
|---|---|---|---|---|---|---|---|
| H | CH$_3$ | H | C(O)CH$_2$CH(CH$_3$)CN | CH$_3$ | CH$_3$ | CH | |
| CH$_3$ | CH$_3$ | H | C(O)CH$_2$CH(CH$_3$)CN | CH$_3$ | OCH$_3$ | CH | |
| H | CH$_3$ | H | C(O)CH$_2$N(CH$_3$)$_2$ | OCH$_3$ | OCH$_3$ | CH | |
| H | CH$_3$ | H | C(O)CH$_2$N(CH$_3$)$_2$ | CH$_3$ | CH$_3$ | N | |
| H | CH$_3$ | H | C(O)CH$_2$CH=CH$_2$ | CH$_3$ | OCH$_3$ | N | |
| H | CH$_3$ | H | C(O)CH$_2$CH=CH$_2$ | OCH$_3$ | OCH$_3$ | N | |
| H | CH$_3$ | H | C(O)CH$_2$C≡CH | OCH$_3$ | Cl | CH | |
| H | CH$_3$ | H | CO$_2$CH$_3$ | CH$_3$ | CH$_3$ | CH | |
| H | CH$_3$ | H | CO$_2$CH$_3$ | CH$_3$ | OCH$_3$ | CH | |
| H | CH$_3$ | H | CO$_2$CH$_3$ | OCH$_3$ | OCH$_3$ | CH | |
| H | CH$_3$ | H | CO$_2$CH$_3$ | CH$_3$ | CH$_3$ | N | |
| H | CH$_3$ | H | CO$_2$CH$_3$ | CH$_3$ | OCH$_3$ | N | |
| H | CH$_3$ | H | CO$_2$CH$_3$ | OCH$_3$ | OCH$_3$ | N | |
| H | CH$_3$ | H | CO$_2$CH$_3$ | OCH$_3$ | Cl | CH | |
| H | CH$_3$ | H | CO$_2$CH$_2$CH$_3$ | CH$_3$ | CH$_3$ | CH | |
| H | CH$_3$ | H | CO$_2$CH$_2$CH$_3$ | CH$_3$ | OCH$_3$ | CH | |
| H | CH$_3$ | H | CO$_2$CH$_2$CH$_3$ | OCH$_3$ | OCH$_3$ | CH | |
| H | CH$_3$ | H | CO$_2$CH$_2$CH$_3$ | CH$_3$ | CH$_3$ | N | |
| H | CH$_3$ | H | CO$_2$CH$_2$CH$_3$ | CH$_3$ | OCH$_3$ | N | |
| H | CH$_3$ | H | CO$_2$CH$_2$CH$_3$ | OCH$_3$ | OCH$_3$ | N | |
| H | CH$_3$ | H | CO$_2$CH$_2$CH$_3$ | OCH$_3$ | Cl | CH | |
| H | CH$_3$ | H | CO$_2$CH$_2$CF$_3$ | CH$_3$ | CH$_3$ | CH | |
| H | CH$_3$ | H | CO$_2$CH$_2$CF$_3$ | CH$_3$ | OCH$_3$ | CH | |
| H | CH$_3$ | H | CO$_2$CH$_2$CF$_3$ | OCH$_3$ | OCH$_3$ | CH | |
| H | CH$_3$ | H | CO$_2$CH$_2$CF$_3$ | CH$_3$ | CH$_3$ | N | |
| H | CH$_3$ | H | CO$_2$CF$_3$ | OCH$_3$ | OCH$_3$ | N | |
| H | CH$_3$ | H | CO$_2$CF$_3$ | OCH$_3$ | Cl | CH | |
| H | CH$_3$ | H | CO$_2$CF$_3$ | CH$_3$ | CH$_3$ | CH | |
| H | CH$_3$ | H | CO$_2$CH$_2$C≡CH | CH$_3$ | OCH$_3$ | CH | |
| H | CH$_3$ | H | CO$_2$CH$_2$C≡CH | OCH$_3$ | OCH$_3$ | CH | |
| H | CH$_3$ | H | CO$_2$CH$_2$C≡CH | CH$_3$ | CH$_3$ | N | |
| H | CH$_3$ | H | CO$_2$CH$_2$C≡CH | CH$_3$ | OCH$_3$ | N | |
| H | CH$_3$ | H | CO$_2$CH$_2$C≡CH | OCH$_3$ | OCH$_3$ | N | |
| H | CH$_3$ | H | CO$_2$CH$_2$CH=CH$_2$ | OCH$_3$ | Cl | CH | |
| H | CH$_3$ | H | CO$_2$CH$_2$CH=CH$_2$ | CH$_3$ | CH$_3$ | CH | |
| H | CH$_3$ | H | CO$_2$CH$_2$CH=CH$_2$ | CH$_3$ | OCH$_3$ | CH | |
| H | CH$_3$ | H | CO$_2$CH$_2$CH=CH$_2$ | OCH$_3$ | OCH$_3$ | CH | |
| H | CH$_3$ | H | CO$_2$CH$_2$CH=CH$_2$ | CH$_3$ | CH$_3$ | N | |
| H | CH$_3$ | H | CO$_2$CH$_2$CH=CH$_2$ | CH$_3$ | OCH$_3$ | N | |
| H | CH$_3$ | CH$_3$ | CO$_2$CH$_3$ | OCH$_3$ | OCH$_3$ | N | |
| H | CH$_3$ | H | CO$_2$CF$_3$ | OCH$_3$ | Cl | CH | |
| H | CH$_3$ | H | CO$_2$CF$_3$ | CH$_3$ | CH$_3$ | CH | |
| H | CH$_3$ | H | CO$_2$CF$_3$ | CH$_3$ | OCH$_3$ | CH | |
| H | CH$_3$ | H | CO$_2$CF$_3$ | OCH$_3$ | OCH$_3$ | CH | |
| H | CH$_3$ | H | CO$_2$CH$_2$CH$_2$Cl | CH$_3$ | CH$_3$ | N | |
| H | CH$_3$ | H | CO$_2$CH$_2$CH$_2$Cl | CH$_3$ | OCH$_3$ | N | |
| H | CH$_3$ | H | CO$_2$CH$_2$CH$_2$Cl | OCH$_3$ | OCH$_3$ | N | |
| H | CH$_3$ | H | CO$_2$CH$_2$CH$_2$P(O)(CH$_3$)$_2$ | OCH$_3$ | Cl | CH | |
| H | CH$_3$ | H | CO$_2$CH$_2$CH$_2$P(O)(CH$_3$)$_2$ | CH$_3$ | CH$_3$ | CH | |
| CH$_3$ | CH$_3$ | H | CO$_2$C(CH$_3$)$_3$ | CH$_3$ | OCH$_3$ | CH | |
| H | CH$_3$ | H | CO$_2$C(CH$_3$)$_3$ | OCH$_3$ | OCH$_3$ | CH | |
| H | CH$_3$ | H | CO$_2$CH$_2$(CH$_2$)$_4$CH$_3$ | CH$_3$ | CH$_3$ | N | |
| H | CH$_3$ | H | CO$_2$CH$_2$(CH$_2$)$_4$CH$_3$ | CH$_3$ | OCH$_3$ | N | |
| H | CH$_3$ | H | CO$_2$CH$_2$OCH$_3$ | OCH$_3$ | OCH$_3$ | N | |
| H | CH$_3$ | H | CO$_2$CH$_2$OCH$_3$ | OCH$_3$ | Cl | CH | |
| H | CH$_3$ | H | (C(O))$_2$OCH$_3$ | CH$_3$ | CH$_3$ | CH | |
| H | CH$_3$ | H | (C(O))$_2$OCH$_3$ | CH$_3$ | OCH$_3$ | CH | |
| H | CH$_3$ | H | (C(O))$_2$OCH$_3$ | OCH$_3$ | OCH$_3$ | CH | |
| H | CH$_3$ | H | (C(O))$_2$OCH$_3$ | CH$_3$ | CH$_3$ | N | |
| H | CH$_3$ | H | (C(O))$_2$OCH$_3$ | CH$_3$ | OCH$_3$ | N | |
| H | CH$_3$ | H | (C(O))$_2$OCH$_3$ | OCH$_3$ | OCH$_3$ | N | |
| H | CH$_3$ | H | (C(O))$_2$OCH$_3$ | OCH$_3$ | Cl | CH | |
| H | CH$_3$ | H | (CO)$_2$CH$_3$ | CH$_3$ | CH$_3$ | CH | |
| H | CH$_3$ | H | (CO)$_2$CH$_3$ | CH$_3$ | OCH$_3$ | CH | |
| H | CH$_3$ | H | (CO)$_2$CH$_3$ | OCH$_3$ | OCH$_3$ | CH | |
| H | CH$_3$ | H | (CO)$_2$CH$_3$ | CH$_3$ | CH$_3$ | N | |
| H | CH$_3$ | H | (CO)$_2$CH$_3$ | CH$_3$ | OCH$_3$ | N | |
| H | CH$_3$ | H | (CO)$_2$CH$_3$ | OCH$_3$ | OCH$_3$ | N | |
| H | CH$_3$ | H | (CO)$_2$CH$_3$ | OCH$_3$ | Cl | CH | |
| H | CH$_3$ | H | C(O)N(CH$_3$)$_2$ | CH$_3$ | CH$_3$ | CH | |
| H | CH$_3$ | H | C(O)N(CH$_3$)$_2$ | CH$_3$ | OCH$_3$ | CH | |
| H | CH$_3$ | H | C(O)N(CH$_3$)$_2$ | OCH$_3$ | OCH$_3$ | CH | |
| H | CH$_3$ | H | C(O)N(CH$_3$)$_2$ | CH$_3$ | CH$_3$ | N | |
| H | CH$_3$ | H | C(O)N(CH$_3$)$_2$ | OCH$_3$ | OCH$_3$ | N | |
| H | CH$_3$ | H | C(O)N(CH$_3$)$_2$ | OCH$_3$ | Cl | CH | |
| H | CH$_3$ | H | C(O)N(CH$_2$CH$_3$)$_2$ | CH$_3$ | CH$_3$ | CH | |
| H | CH$_3$ | H | C(O)N(CH$_2$CH$_3$)$_2$ | CH$_3$ | OCH$_3$ | CH | |
| H | CH$_3$ | H | C(O)N(CH$_2$CH$_3$)$_2$ | OCH$_3$ | OCH$_3$ | CH | |
| H | CH$_3$ | H | C(O)N(CH$_2$CH$_3$)$_2$ | CH$_3$ | CH$_3$ | N | |
| H | CH$_3$ | H | C(O)N(CH$_2$CH$_3$)$_2$ | CH$_3$ | OCH$_3$ | N | |

TABLE I-continued

General Structure I

| R | R₁ | R₂ | R₃ | X | Y | Z | m.p. (°C.) |
|---|---|---|---|---|---|---|---|
| H | CH₃ | H | C(O)N(CH₂CH₃)₂ | OCH₃ | OCH₃ | N | |
| H | CH₃ | H | C(O)N(CH₃)CH₂CH₃ | OCH₃ | Cl | CH | |
| H | CH₃ | H | C(O)N(CH₃)CH₂CH₃ | CH₃ | CH₃ | CH | |
| H | CH₃ | H | C(O)N(CH₃)CH₂CH₃ | CH₃ | OCH₃ | CH | |
| H | CH₃ | H | C(O)N(CH₃)CH₂CH₃ | OCH₃ | OCH₃ | CH | |
| H | CH₃ | H | C(O)N(CH₃)CH₂CH₃ | CH₃ | CH₃ | N | |
| H | CH₃ | H | C(O)N(CF₃)CH₃ | CH₃ | OCH₃ | N | |
| H | CH₃ | CH₃ | C(O)N(CF₃)CH₃ | OCH₃ | OCH₃ | N | |
| H | CH₃ | H | C(O)N(CF₃)CH₃ | OCH₃ | Cl | CH | |
| H | CH₃ | H | C(O)N(CH₃)OCH₃ | CH₃ | CH₃ | CH | |
| H | CH₃ | H | C(O)N(CH₃)OCH₃ | CH₃ | OCH₃ | CH | |
| H | CH₃ | H | C(O)N(CH₃)OCH₃ | OCH₃ | OCH₃ | CH | |
| H | CH₃ | H | C(O)N(CH₃)OCH₃ | CH₃ | CH₃ | N | |
| H | CH₃ | H | C(O)N(CH=CH₂)CH₃ | CH₃ | OCH₃ | N | |
| H | CH₃ | H | C(O)N(CH=CH₂)CH₃ | OCH₃ | OCH₃ | N | |
| H | CH₃ | H | C(O)N(CH=CH₂)CH₃ | OCH₃ | Cl | CH | |
| H | CH₃ | H | C(O)N(CH=CH₂)CH₃ | CH₃ | CH₃ | CH | |
| CH₃ | CH₃ | H | C(O)N(CH=CH₂)CH₃ | CH₃ | OCH₃ | CH | |
| H | CH₃ | H | C(O)N(CH₃)Ph | OCH₃ | OCH₃ | CH | |
| H | CH₃ | H | C(O)N(CH₃)Ph | CH₃ | CH₃ | N | |
| H | CH₃ | H | C(O)N(CH₃)Ph | CH₃ | OCH₃ | N | |
| H | CH₃ | H | C(O)N(OCH₃)₂ | OCH₃ | OCH₃ | N | |
| H | CH₃ | H | C(O)N(OCH₃)₂ | OCH₃ | Cl | CH | |
| H | CH₃ | H | CS₂CH₃ | CH₃ | CH₃ | CH | |
| H | CH₃ | H | CS₂CH₃ | CH₃ | OCH₃ | CH | |
| H | CH₃ | H | CS₂CH₃ | OCH₃ | OCH₃ | CH | |
| H | CH₃ | H | CS₂CH₃ | CH₃ | CH₃ | N | |
| H | CH₃ | H | CS₂CH₃ | CH₃ | OCH₃ | N | |
| H | CH₃ | H | CS₂CH₃ | OCH₃ | OCH₃ | N | |
| H | CH₃ | H | CS₂CH₃ | OCH₃ | Cl | CH | |
| H | CH₃ | H | CS₂CH₂CH₃ | CH₃ | CH₃ | N | |
| H | CH₃ | H | CS₂CH₂CH₃ | CH₃ | OCH₃ | N | |
| H | CH₃ | H | CS₂CH₂CH=CH₂ | OCH₃ | OCH₃ | N | |
| H | CH₃ | H | CS₂CH₂CH=CH₂ | OCH₃ | Cl | CH | |
| H | CH₃ | H | CS₂CH₂CH=CH₂ | CH₃ | CH₃ | CH | |
| H | CH₃ | H | NH₂ | CH₃ | CH₃ | CH | |
| H | CH₃ | H | NH₂ | CH₃ | OCH₃ | CH | |
| H | CH₃ | H | NH₂ | OCH₃ | OCH₃ | CH | |
| H | CH₃ | H | NH₂ | CH₃ | CH₃ | N | |
| H | CH₃ | H | NH₂ | CH₃ | OCH₃ | N | |
| H | CH₃ | H | NH₂ | OCH₃ | OCH₃ | N | |
| H | CH₃ | H | NH₂ | OCH₃ | Cl | CH | |
| H | CH₃ | H | N(CH₃)₂ | CH₃ | CH₃ | CH | |
| H | CH₃ | H | N(CH₃)₂ | CH₃ | OCH₃ | CH | |
| H | CH₃ | H | N(CH₃)₂ | OCH₃ | OCH₃ | CH | |
| H | CH₃ | H | N(CH₃)₂ | CH₃ | CH₃ | N | |
| H | CH₃ | H | N(CH₃)₂ | CH₃ | OCH₃ | N | |
| H | CH₃ | CH₃ | N(CH₃)₂ | OCH₃ | OCH₃ | N | |
| H | CH₃ | H | N(CH₃)₂ | OCH₃ | Cl | CH | |
| H | CH₃ | H | N(CH₃)(CH₂CH₃) | CH₃ | CH₃ | CH | |
| H | CH₃ | H | N(CH₃)(CH₂CH₃) | CH₃ | OCH₃ | CH | |
| H | CH₃ | H | N(CH₃)(CH₂CH₃) | OCH₃ | OCH₃ | CH | |
| H | CH₃ | H | N(CH₃)OCH₃ | CH₃ | CH₃ | N | |
| H | CH₃ | H | N(CH₃)OCH₃ | CH₃ | OCH₃ | N | |
| H | CH₃ | H | N(CH₃)OCH₃ | OCH₃ | OCH₃ | N | |
| H | CH₃ | H | N(CH₃)CH=CH₂ | OCH₃ | Cl | CH | |
| H | CH₃ | H | N(CH₃)CH=CH₂ | CH₃ | CH₃ | CH | |
| CH₃ | CH₃ | H | N(CH₃)CH=CH₂ | CH₃ | OCH₃ | CH | |
| H | CH₃ | H | N(CH₃)CH=CH₂ | OCH₃ | OCH₃ | CH | |
| H | CH₃ | H | N(CH₂CH₃)₂ | CH₃ | CH₃ | N | |
| H | CH₃ | H | N(CH₂CH₃)₂ | CH₃ | OCH₃ | N | |
| H | CH₃ | H | N(CH₂CH₃)₂ | OCH₃ | OCH₃ | N | |
| H | CH₃ | H | N(CH₂CH₃)₂ | OCH₃ | Cl | CH | |
| H | CH₃ | H | OH | CH₃ | CH₃ | CH | |
| H | CH₃ | H | OH | CH₃ | OCH₃ | CH | |
| H | CH₃ | H | OH | OCH₃ | OCH₃ | CH | |
| H | CH₃ | H | OH | CH₃ | CH₃ | N | |
| H | CH₃ | H | OH | CH₃ | OCH₃ | N | |
| H | CH₃ | H | OH | OCH₃ | OCH₃ | N | |
| H | CH₃ | H | OH | OCH₃ | Cl | CH | |
| H | CH₃ | H | CN | CH₃ | CH₃ | CH | |
| H | CH₃ | H | CN | CH₃ | OCH₃ | CH | |
| H | CH₃ | H | CN | OCH₃ | OCH₃ | CH | |
| H | CH₃ | H | CN | CH₃ | CH₃ | N | |
| H | CH₃ | H | CN | CH₃ | OCH₃ | N | |
| H | CH₃ | H | CN | OCH₃ | OCH₃ | N | |
| H | CH₃ | H | CN | OCH₃ | Cl | CH | |
| H | CH₃ | H | P(O)(CH₃)₂ | CH₃ | CH₃ | CH | |
| H | CH₃ | H | P(O)(CH₃)₂ | CH₃ | OCH₃ | CH | |
| H | CH₃ | H | P(O)(CH₃)₂ | OCH₃ | OCH₃ | CH | |

TABLE I-continued

General Structure I

| R | R₁ | R₂ | R₃ | X | Y | Z | m.p. (°C.) |
|---|---|---|---|---|---|---|---|
| H | CH₃ | H | P(O)(CH₃)₂ | CH₃ | CH₃ | N | |
| H | CH₃ | H | P(O)(CH₃)₂ | OCH₃ | OCH₃ | N | |
| H | CH₃ | H | P(O)(OCH₃)₂ | OCH₃ | Cl | CH | |
| H | CH₃ | H | P(O)(OCH₃)₂ | CH₃ | CH₃ | CH | |
| H | CH₃ | H | P(O)(OCH₃)₂ | CH₃ | OCH₃ | CH | |
| H | CH₃ | H | P(O)(OCH₃)₂ | OCH₃ | OCH₃ | CH | |
| H | CH₃ | H | P(O)(OCH₃)SCH₃ | CH₃ | CH₃ | N | |
| H | CH₃ | H | P(O)(OCH₃)SCH₃ | CH₃ | OCH₃ | N | |
| H | CH₃ | H | P(O)(OCH₃)SCH₃ | OCH₃ | OCH₃ | N | |
| H | CH₃ | H | P(O)(OCH₃)SCH₃ | OCH₃ | Cl | CH | |
| H | CH₃ | H | P(O)(OCH₃)SCH₂CH₂CH₃ | CH₃ | CH₃ | CH | |
| H | CH₃ | H | P(O)(OCH₃)SCH₂CH₂CH₃ | CH₃ | OCH₃ | CH | |
| H | CH₃ | H | P(O)(OCH₃)SCH₂CH₂CH₃ | OCH₃ | OCH₃ | CH | |
| H | CH₃ | H | P(O)(OCH₃)SCH₂CH₂CH₃ | CH₃ | CH₃ | N | |
| H | CH₃ | H | P(O)(OCH₃)SCH₂CH₂CH₃ | CH₃ | OCH₃ | N | |
| H | CH₃ | CH₃ | OH | OCH₃ | OCH₃ | N | |
| H | CH₃ | H | P(S)(CH₃)₂ | OCH₃ | Cl | CH | |
| H | CH₃ | H | P(S)(CH₃)₂ | CH₃ | CH₃ | CH | |
| H | CH₃ | H | P(S)(CH₃)₂ | CH₃ | OCH₃ | CH | |
| H | CH₃ | H | P(S)(CH₃)₂ | OCH₃ | OCH₃ | CH | |
| H | CH₃ | H | P(S)(CH₃)₂ | CH₃ | CH₃ | N | |
| H | CH₃ | H | P(S)(CH₃)₂ | CH₃ | OCH₃ | N | |
| H | CH₃ | H | P(S)(CH₃)₂ | OCH₃ | OCH₃ | N | |
| H | CH₃ | H | P(S)(OCH₃)₂ | CH₃ | CH₃ | CH | |
| CH₃ | CH₃ | H | P(S)(OCH₃)₂ | CH₃ | OCH₃ | CH | |
| H | CH₃ | H | P(S)(OCH₃)₂ | OCH₃ | OCH₃ | CH | |
| H | CH₃ | H | P(S)(OCH₃)₂ | CH₃ | CH₃ | N | |
| H | CH₃ | H | P(S)(OCH₃)₂ | CH₃ | OCH₃ | N | |
| H | CH₃ | H | P(S)(OCH₃)₂ | OCH₃ | OCH₃ | N | |
| H | CH₃ | H | P(S)(OCH₃)SCH₃ | OCH₃ | Cl | CH | |
| H | CH₃ | H | NO₂ | CH₃ | CH₃ | CH | |
| H | CH₃ | H | NO₂ | CH₃ | OCH₃ | CH | |
| H | CH₃ | H | NO₂ | OCH₃ | OCH₃ | CH | |
| H | CH₃ | H | NO₂ | CH₃ | CH₃ | N | |
| H | CH₃ | H | NO₂ | CH₃ | OCH₃ | N | |
| H | CH₃ | H | NO₂ | OCH₃ | OCH₃ | N | |
| H | CH₃ | H | CH₂C(O)CH(CH₂CH₂CH₂) | CH₃ | CH₃ | N | |
| H | CH₃ | H | CH₂C(O)CH(CH₂CH₂CH₂) | CH₃ | OCH₃ | N | |
| H | CH₃ | H | CH₂C(O)CH(CH₂CH₂CH₂) | OCH₃ | OCH₃ | N | |
| H | CH₃ | H | CH₂C(O)CH(CH₂CH₂CH₂) | OCH₃ | Cl | CH | |
| H | CH₃ | H | CH₂C(O)CH(CH₂CH₂CH₂) | CH₃ | CH₃ | CH | |
| H | CH₃ | H | CH₂C(O)CH(CH₂CH₂CH₂) | CH₃ | OCH₃ | CH | |
| H | CH₃ | H | CH₂C(O)Ph | OCH₃ | OCH₃ | CH | |
| H | CH₃ | H | CH₂C(O)Ph | CH₃ | CH₃ | N | |
| H | CH₃ | H | CH₂C(O)Ph | CH₃ | OCH₃ | N | |
| H | CH₃ | CH₃ | CH₂C(O)Ph | OCH₃ | OCH₃ | N | |
| H | CH₃ | H | CH₂C(O)Ph | OCH₃ | Cl | CH | |
| H | CH₃ | H | CH₂C(O)Ph | CH₃ | CH₃ | CH | |
| H | CH₃ | H | CH₂C(O)Ph | CH₃ | OCH₃ | CH | |
| H | CH₃ | H | CH(CH₃)C(O)CH₃ | OCH₃ | OCH₃ | CH | |
| H | CH₃ | H | CH(CH₃)C(O)CH₃ | CH₃ | CH₃ | N | |
| H | CH₃ | H | CH(CH₃)C(O)CH₃ | CH₃ | OCH₃ | N | |
| H | CH₃ | H | CH(CH₃)C(O)CH₃ | OCH₃ | OCH₃ | N | |
| H | CH₃ | H | CH₂CF₂—C(O)CH₃ | OCH₃ | Cl | CH | |
| H | CH₃ | H | CH₂CF₂—C(O)CH₃ | CH₃ | CH₃ | CH | |
| CH₃ | CH₃ | H | CH₂CF₂—C(O)CH₃ | CH₃ | OCH₃ | CH | |

TABLE I-continued

General Structure I

| R | $R_1$ | $R_2$ | $R_3$ | X | Y | Z | m.p. (°C.) |
|---|---|---|---|---|---|---|---|
| H | $CH_3$ | H | $CH_2CF_2$—$C(O)CH_3$ | $OCH_3$ | $OCH_3$ | CH | |
| H | $CH_3$ | H | $CH_2C(O)CH_2OCH_3$ | $CH_3$ | $CH_3$ | N | |
| H | $CH_3$ | H | $CH_2C(O)CH_2OCH_3$ | $CH_3$ | $OCH_3$ | N | |
| H | $CH_3$ | H | $CH_2C(O)CH_2OCH_3$ | $OCH_3$ | $OCH_3$ | N | |
| H | $CH_3$ | H | $CH_2C(O)CH_2OCH_3$ | $OCH_3$ | Cl | CH | |
| H | $CH_3$ | H | $CH_2CO_2CH_3$ | $CH_3$ | $CH_3$ | CH | |
| H | $CH_3$ | H | $CH_2CO_2CH_3$ | $CH_3$ | $OCH_3$ | CH | |
| H | $CH_3$ | H | $CH_2CO_2CH_3$ | $OCH_3$ | $OCH_3$ | CH | |
| H | $CH_3$ | H | $CH_2CO_2CH_3$ | $CH_3$ | $CH_3$ | N | |
| H | $CH_3$ | H | $CH_2CO_2CH_3$ | $CH_3$ | $OCH_3$ | N | |
| H | $CH_3$ | H | $CH_2CO_2CH_3$ | $OCH_3$ | $OCH_3$ | N | |
| H | $CH_3$ | H | $CH_2CO_2CH_3$ | $OCH_3$ | Cl | CH | |
| H | $CH_3$ | H | $CH_2CO_2CH_2CH_3$ | $CH_3$ | $CH_3$ | CH | |
| H | $CH_3$ | H | $CH_2CO_2CH_2CH_3$ | $CH_3$ | $OCH_3$ | CH | |
| H | $CH_3$ | H | $CH_2CO_2CH_2CH_3$ | $OCH_3$ | $OCH_3$ | CH | |
| H | $CH_3$ | H | $CH_2CO_2CH_2CH_3$ | $CH_3$ | $CH_3$ | N | |
| H | $CH_3$ | H | $CH_2CO_2CH_2CH_3$ | $CH_3$ | $OCH_3$ | N | |
| H | $CH_3$ | H | $CH_2CO_2CH_2CH_3$ | $OCH_3$ | $OCH_3$ | N | |
| H | $CH_3$ | H | $CH_2CO_2CH_2CH_3$ | $OCH_3$ | Cl | CH | |
| H | $CH_3$ | H | $CH_2CH_2CO_2CH_3$ | $CH_3$ | $CH_3$ | CH | |
| H | $CH_3$ | H | $CH_2CH_2CO_2CH_3$ | $CH_3$ | $OCH_3$ | CH | |
| H | $CH_3$ | H | $CH_2CH_2CO_2CH_3$ | $OCH_3$ | $OCH_3$ | CH | |
| H | $CH_3$ | H | $CH_2CH_2CO_2CH_3$ | $CH_3$ | $CH_3$ | N | |
| H | $CH_3$ | H | $CH_2CH_2CO_2CH_3$ | $OCH_3$ | $OCH_3$ | N | |
| H | $CH_3$ | H | $CH_2CH_2CO_2CH_3$ | $OCH_3$ | Cl | CH | |
| H | $CH_3$ | H | $CH_2$—$CO_2CH_2CH$=$CH_2$ | $CH_3$ | $CH_3$ | CH | |
| H | $CH_3$ | H | $CH_2$—$CO_2CH_2CH$=$CH_2$ | $CH_3$ | $OCH_3$ | CH | |
| H | $CH_3$ | H | $CH_2$—$CO_2CH_2CH$=$CH_2$ | $OCH_3$ | $OCH_3$ | CH | |
| H | $CH_3$ | H | $CH_2$—$CO_2CH_2CH$=$CH_2$ | $CH_3$ | $CH_3$ | N | |
| H | $CH_3$ | H | $CH_2$—$CO_2CH_2CH$=$CH_2$ | $CH_3$ | $OCH_3$ | N | |
| H | $CH_3$ | H | $CH_2$—$CO_2CH_2CH$=$CH_2$ | $OCH_3$ | $OCH_3$ | N | |
| H | $CH_3$ | H | $CH_2$—$CO_2CH_2CH$=$CH_2$ | $OCH_3$ | Cl | CH | |
| H | $CH_3$ | H | $CH_2(CH_2)_4CO_2CH_3$ | $CH_3$ | $CH_3$ | CH | |
| H | $CH_3$ | H | $CH_2(CH_2)_4CO_2CH_3$ | $CH_3$ | $OCH_3$ | CH | |
| H | $CH_3$ | H | $CH_2(CH_2)_4CO_2CH_3$ | $OCH_3$ | $OCH_3$ | CH | |
| H | $CH_3$ | H | $CH_2(CH_2)_4CO_2CH_3$ | $CH_3$ | $CH_3$ | N | |
| H | $CH_3$ | H | $CH_2(CH_2)_4CO_2CH_3$ | $CH_3$ | $OCH_3$ | N | |
| H | $CH_3$ | $CH_3$ | $CH_2(CH_2)_4CO_2CH_3$ | $OCH_3$ | $OCH_3$ | N | |
| H | $CH_3$ | H | $CH_2(CH_2)_4CO_2CH_3$ | $OCH_3$ | Cl | CH | |
| H | $CH_3$ | H | $CH_2CO_2CH_2C$≡$CH$ | $CH_3$ | $CH_3$ | CH | |
| H | $CH_3$ | H | $CH_2CO_2CH_2C$≡$CH$ | $CH_3$ | $OCH_3$ | CH | |
| H | $CH_3$ | H | $CH_2CO_2CH_2C$≡$CH$ | $OCH_3$ | $OCH_3$ | CH | |
| H | $CH_3$ | H | $CH_2CO_2CH_2C$≡$CH$ | $CH_3$ | $CH_3$ | N | |
| H | $CH_3$ | H | $CH_2CO_2CH_2C$≡$CH$ | $CH_3$ | $OCH_3$ | N | |
| H | $CH_3$ | H | $CH_2CO_2CH_2C$≡$CH$ | $OCH_3$ | $OCH_3$ | N | |
| H | $CH_3$ | H | $CH_2CO_2CH_2C$≡$CH$ | $OCH_3$ | Cl | CH | |
| H | $CH_3$ | H | $CH_2CO_2CF_3$ | $CH_3$ | $CH_3$ | CH | |
| $CH_3$ | $CH_3$ | H | $CH_2CO_2CF_3$ | $CH_3$ | $OCH_3$ | CH | |
| H | $CH_3$ | H | $CH_2CO_2CF_3$ | $OCH_3$ | $OCH_3$ | CH | |
| H | $CH_3$ | H | $CH_2CO_2CF_3$ | $CH_3$ | $CH_3$ | N | |
| H | $CH_3$ | H | $CH_2CO_2CF_3$ | $CH_3$ | $OCH_3$ | N | |
| H | $CH_3$ | H | $CH_2CO_2CF_3$ | $OCH_3$ | $OCH_3$ | N | |
| H | $CH_3$ | H | $CH_2CO_2CF_3$ | $OCH_3$ | Cl | CH | |
| H | $CH_3$ | H | $CH_2C(O)N(CH_3)_2$ | $CH_3$ | $CH_3$ | CH | |
| H | $CH_3$ | H | $CH_2C(O)N(CH_3)_2$ | $CH_3$ | $OCH_3$ | CH | |
| H | $CH_3$ | H | $CH_2C(O)N(CH_3)_2$ | $OCH_3$ | $OCH_3$ | CH | |
| H | $CH_3$ | H | $CH_2C(O)N(CH_3)_2$ | $CH_3$ | $CH_3$ | N | |
| H | $CH_3$ | H | $CH_2C(O)N(CH_3)_2$ | $CH_3$ | $OCH_3$ | N | |
| H | $CH_3$ | H | $CH_2C(O)N(CH_3)_2$ | $OCH_3$ | $OCH_3$ | N | |
| H | $CH_3$ | H | $CH_2C(O)N(CH_3)_2$ | $OCH_3$ | Cl | CH | |
| H | $CH_3$ | H | $SeCH_3$ | $CH_3$ | $CH_3$ | CH | |
| H | $CH_3$ | H | $SeCH_3$ | $CH_3$ | $OCH_3$ | CH | |
| H | $CH_3$ | H | $SeCH_3$ | $OCH_3$ | $OCH_3$ | CH | |
| H | $CH_3$ | H | $SeCH_3$ | $CH_3$ | $CH_3$ | N | |
| H | $CH_3$ | H | $SeCH_3$ | $CH_3$ | $OCH_3$ | N | |
| H | $CH_3$ | H | $SeCH_3$ | $OCH_3$ | $OCH_3$ | N | |
| H | $CH_3$ | H | $SeCH_3$ | $OCH_3$ | Cl | CH | |
| H | $CH_3$ | H | $CH_2Ph$ | $CH_3$ | $CH_3$ | CH | |
| H | $CH_3$ | H | $CH_2Ph$ | $CH_3$ | $OCH_3$ | CH | |
| H | $CH_3$ | H | $CH_2Ph$ | $OCH_3$ | $OCH_3$ | CH | |
| H | $CH_3$ | H | $CH_2Ph$ | $CH_3$ | $CH_3$ | N | |
| H | $CH_3$ | H | $CH_2Ph$ | $OCH_3$ | $OCH_3$ | N | |
| H | $CH_3$ | H | $CH_2Ph$ | $OCH_3$ | Cl | CH | |
| H | $CH_3$ | H | $CH_2$—(1,3-dioxolan-2-yl) | $CH_3$ | $CH_3$ | CH | |
| H | $CH_3$ | H | $CH_2$—(1,3-dioxolan-2-yl) | $CH_3$ | $OCH_3$ | CH | |
| H | $CH_3$ | H | $CH_2$—(1,3-dioxolan-2-yl) | $OCH_3$ | $OCH_3$ | CH | |
| H | $CH_3$ | H | $CH_2$—(1,3-dioxolan-2-yl) | $CH_3$ | $CH_3$ | N | |
| H | $CH_3$ | H | $CH_2$—(1,3-dioxolan-2-yl) | $CH_3$ | $OCH_3$ | N | |
| H | $CH_3$ | H | $CH_2$—(1,3-dioxolan-2-yl) | $OCH_3$ | $OCH_3$ | N | |
| H | $CH_3$ | H | $CH_2$—OTHP | $OCH_3$ | Cl | CH | |

TABLE I-continued

General Structure I

| R | R₁ | R₂ | R₃ | X | Y | Z | m.p. (°C.) |
|---|---|---|---|---|---|---|---|
| H | CH₃ | H | CH₂—OTHP | CH₃ | CH₃ | CH | |
| H | CH₃ | H | CH₂—OTHP | CH₃ | OCH₃ | CH | |
| H | CH₃ | H | CH₂—OTHP | OCH₃ | OCH₃ | CH | |
| H | CH₃ | H | CH₂—OTHP | CH₃ | CH₃ | N | |
| H | CH₃ | H | CH₂—OTHP | CH₃ | OCH₃ | N | |
| H | CH₃ | CH₃ | CH₂—OTHP | OCH₃ | OCH₃ | N | |
| H | CH₃ | H | Si(CH₃)₃ | CH₃ | CH₃ | CH | |
| H | CH₃ | H | Si(CH₃)₃ | CH₃ | OCH₃ | CH | |
| H | CH₃ | H | Si(CH₃)₃ | OCH₃ | OCH₃ | CH | |
| H | CH₃ | H | Si(CH₃)₃ | CH₃ | CH₃ | N | |
| H | CH₃ | H | Si(CH₃)₃ | CH₃ | OCH₃ | N | |
| H | CH₃ | H | Si(CH₃)₃ | OCH₃ | OCH₃ | N | |
| H | CH₃ | H | Si(CH₃)₃ | OCH₃ | Cl | CH | |
| H | CH₃ | H | Si(CH₃)₂Ph | CH₃ | CH₃ | CH | |
| H | CH₃ | H | Si(CH₃)₂Ph | CH₃ | OCH₃ | CH | |
| H | CH₃ | H | Si(CH₃)₂Ph | OCH₃ | OCH₃ | CH | |
| H | CH₃ | H | Si(CH₃)₂Ph | CH₃ | CH₃ | N | |
| H | CH₃ | H | Si(CH₃)₂Ph | CH₃ | OCH₃ | N | |
| H | CH₃ | H | Si(CH₃)₂Ph | OCH₃ | OCH₃ | N | |
| H | CH₃ | H | Si(CH₃)₂Ph | OCH₃ | Cl | CH | |
| H | CH₃ | H | Si(CH₃)₂CH₂CH₃ | CH₃ | CH₃ | CH | |
| H | CH₃ | H | Si(CH₃)₂CH₂CH₃ | CH₃ | OCH₃ | CH | |
| H | CH₃ | H | Si(CH₃)₂CH₂CH₃ | OCH₃ | OCH₃ | CH | |
| H | CH₃ | H | Si(CH₃)₂CH₂CH₃ | CH₃ | CH₃ | N | |
| H | CH₃ | H | Si(CH₃)₂CH₂CH₃ | OCH₃ | OCH₃ | N | |
| H | CH₃ | H | Si(CH₃)₂CH₂CH₃ | OCH₃ | Cl | CH | |
| H | CH₃ | H | A-HET | CH₃ | CH₃ | CH | |
| H | CH₃ | H | A-HET | CH₃ | OCH₃ | CH | |
| H | CH₃ | H | A-HET | OCH₃ | OCH₃ | CH | |
| H | CH₃ | H | A-HET | CH₃ | CH₃ | N | |
| H | CH₃ | H | A-HET | CH₃ | OCH₃ | N | |
| H | CH₃ | H | A-HET | OCH₃ | OCH₃ | N | |
| H | CH₃ | H | A-HET | OCH₃ | Cl | CH | |
| H | CH₃ | H | B-HET | CH₃ | CH₃ | CH | |
| H | CH₃ | H | B-HET | CH₃ | OCH₃ | CH | |
| H | CH₃ | H | B-HET | OCH₃ | OCH₃ | CH | |
| H | CH₃ | H | B-HET | CH₃ | CH₃ | N | |
| H | CH₃ | H | B-HET | CH₃ | OCH₃ | N | |
| H | CH₃ | CH₃ | B-HET | OCH₃ | OCH₃ | N | |
| H | CH₃ | H | B-HET | OCH₃ | Cl | CH | |
| H | CH₃ | H | C-HET | CH₃ | CH₃ | CH | |
| H | CH₃ | H | C-HET | CH₃ | OCH₃ | CH | |
| H | CH₃ | H | C-HET | OCH₃ | OCH₃ | CH | |
| H | CH₃ | H | C-HET | CH₃ | CH₃ | N | |
| H | CH₃ | H | C-HET | CH₃ | OCH₃ | N | |
| H | CH₃ | H | C-HET | OCH₃ | Cl | CH | |
| H | CH₃ | H | D-HET | CH₃ | CH₃ | CH | |
| CH₃ | CH₃ | H | D-HET | CH₃ | OCH₃ | CH | |
| H | CH₃ | H | D-HET | OCH₃ | OCH₃ | CH | |
| H | CH₃ | H | D-HET | CH₃ | CH₃ | N | |
| H | CH₃ | H | D-HET | CH₃ | OCH₃ | N | |
| H | CH₃ | H | D-HET | OCH₃ | OCH₃ | N | |
| H | CH₃ | H | D-HET | OCH₃ | Cl | CH | |
| H | CH₃ | H | C(O)A-HET | CH₃ | CH₃ | CH | |
| H | CH₃ | H | C(O)A-HET | CH₃ | OCH₃ | CH | |
| H | CH₃ | H | C(O)A-HET | OCH₃ | OCH₃ | CH | |
| H | CH₃ | H | C(O)A-HET | CH₃ | CH₃ | N | |
| H | CH₃ | H | C(O)A-HET | CH₃ | OCH₃ | N | |
| H | CH₃ | H | C(O)A-HET | OCH₃ | OCH₃ | N | |
| H | CH₃ | H | C(O)A-HET | OCH₃ | Cl | CH | |
| H | CH₃ | H | C(O)B-HET | CH₃ | CH₃ | CH | |
| H | CH₃ | H | C(O)B-HET | CH₃ | OCH₃ | CH | |
| H | CH₃ | H | C(O)B-HET | OCH₃ | OCH₃ | CH | |
| H | CH₃ | H | C(O)B-HET | CH₃ | CH₃ | N | |
| H | CH₃ | H | C(O)B-HET | CH₃ | OCH₃ | N | |
| H | CH₃ | H | C(O)B-HET | OCH₃ | OCH₃ | N | |
| H | CH₃ | H | C(O)B-HET | OCH₃ | Cl | CH | |
| H | CH₃ | H | C(O)C-HET | CH₃ | CH₃ | CH | |
| H | CH₃ | H | C(O)C-HET | CH₃ | OCH₃ | CH | |
| H | CH₃ | H | C(O)C-HET | OCH₃ | OCH₃ | CH | |
| H | CH₃ | H | C(O)C-HET | CH₃ | CH₃ | N | |
| H | CH₃ | H | C(O)C-HET | CH₃ | OCH₃ | N | |
| H | CH₃ | H | C(O)C-HET | OCH₃ | Cl | CH | |
| H | CH₃ | H | C(O)D-HET | CH₃ | CH₃ | CH | |
| H | CH₃ | H | C(O)D-HET | CH₃ | OCH₃ | CH | |
| H | CH₃ | H | C(O)D-HET | OCH₃ | OCH₃ | CH | |
| H | CH₃ | H | C(O)D-HET | CH₃ | CH₃ | N | |
| H | CH₃ | H | C(O)D-HET | CH₃ | OCH₃ | N | |
| H | CH₃ | H | C(O)D-HET | OCH₃ | OCH₃ | N | |

TABLE I-continued

General Structure I

| R | R₁ | R₂ | R₃ | X | Y | Z | m.p. (°C.) |
|---|----|----|----|---|---|---|---|
| H | CH₃ | H | C(O)D-HET | OCH₃ | Cl | CH | | wherein

A-HET is 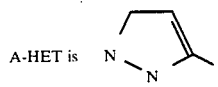

B-HET is 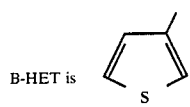

C-HET is 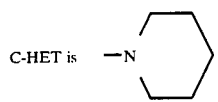

D-HET is 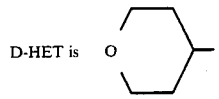

TABLE Ia

General Structure Ia

| R | R₁ | R₂ | R₃ | X | Y | Z | m.p. (°C.) |
|---|----|----|----|---|---|---|---|
| H | CH₃ | H | CH₂F | CH₃ | CH₃ | CH | |
| H | CH₃ | H | CH₂F | CH₃ | OCH₃ | CH | |
| H | CH₃ | H | CH₂F | OCH₃ | OCH₃ | CH | |
| H | CH₃ | H | CH₂F | CH₃ | CH₃ | N | |
| H | CH₃ | H | CH₂F | CH₃ | OCH₃ | N | |
| H | CH₃ | H | CH₂F | OCH₃ | OCH₃ | N | |
| H | CH₃ | H | CH₂F | OCH₃ | Cl | CH | |
| H | CH₃ | H | CH₂CH₂F | CH₃ | CH₃ | CH | |
| H | CH₃ | H | CH₂CH₂F | CH₃ | OCH₃ | CH | |
| H | CH₃ | H | CH₂CH₂F | OCH₃ | OCH₃ | CH | |
| H | CH₃ | H | CH₂CH₂F | CH₃ | CH₃ | N | |
| H | CH₃ | H | CH₂CH₂F | CH₃ | OCH₃ | N | |
| H | CH₃ | H | CH₂CH₂F | OCH₃ | OCH₃ | N | |
| H | CH₃ | H | CH₂CH₂F | OCH₃ | Cl | CH | |
| H | CH₃ | H | CHFCH₂F | CH₃ | CH₃ | CH | |
| H | CH₃ | H | CHFCH₂F | CH₃ | OCH₃ | CH | |
| H | CH₃ | H | CHFCH₂F | OCH₃ | OCH₃ | CH | |
| H | CH₃ | H | CHFCH₂F | CH₃ | CH₃ | N | |
| H | CH₃ | H | CHFCH₂F | OCH₃ | OCH₃ | N | |
| H | CH₃ | H | CHFCH₂F | OCH₃ | Cl | CH | |
| H | CH₃ | H | CH₂CHF₂ | CH₃ | CH₃ | CH | |
| H | CH₃ | H | CH₂CHF₂ | CH₃ | OCH₃ | CH | |
| H | CH₃ | H | CH₂CHF₂ | OCH₃ | OCH₃ | CH | |
| H | CH₃ | H | CH₂CHF₂ | CH₃ | CH₃ | N | |
| H | CH₃ | H | CH₂CHF₂ | CH₃ | OCH₃ | N | |
| H | CH₃ | H | CH₂CHF₂ | OCH₃ | OCH₃ | N | |
| H | CH₃ | H | CH₂CHF₂ | OCH₃ | Cl | CH | |
| H | CH₃ | H | CH(CH₂F)₂ | CH₃ | CH₃ | CH | |
| H | CH₃ | H | CH(CH₂F)₂ | CH₃ | OCH₃ | CH | |
| H | CH₃ | H | CH(CH₂F)₂ | OCH₃ | OCH₃ | CH | |
| H | CH₃ | H | CH₂CH₂CH₂F | CH₃ | CH₃ | N | |
| H | CH₃ | H | CH₂CH₂CH₂F | CH₃ | OCH₃ | N | |
| H | CH₃ | CH₃ | CH₂CH₂CH₂F | OCH₃ | OCH₃ | N | |
| H | CH₃ | H | CH₂CH₂CH₂F | OCH₃ | Cl | CH | |
| H | CH₃ | H | CH₂CH₂CH₂F | CH₃ | CH₃ | CH | |
| H | CH₃ | H | CH₂CH₂CH₂F | CH₃ | OCH₃ | CH | |
| H | CH₃ | H | CH₂CH₂CH₂F | OCH₃ | OCH₃ | CH | |
| H | CH₃ | H | CH₂(CH₂)₂CH₂F | CH₃ | CH₃ | N | |
| H | CH₃ | H | CH₂(CH₂)₂CH₂F | CH₃ | OCH₃ | N | |
| H | CH₃ | H | CH₂(CH₂)₂CH₂F | OCH₃ | OCH₃ | N | |
| H | CH₃ | H | CH₂(CH₂)₂CH₂F | OCH₃ | Cl | CH | |
| H | CH₃ | H | CH₂(CH₂)₂CH₂F | CH₃ | CH₃ | CH | |
| CH₃ | CH₃ | H | CH₂(CH₂)₂CH₂F | CH₃ | OCH₃ | CH | |
| H | CH₃ | H | CH₂(CH₂)₂CH₂F | OCH₃ | OCH₃ | CH | |
| H | CH₃ | H | CH(CH₃)CH₂F | CH₃ | CH₃ | N | |
| H | CH₃ | H | CH(CH₃)CH₂F | CH₃ | OCH₃ | N | |
| H | CH₃ | H | CH(CH₃)CH₂F | OCH₃ | OCH₃ | N | |
| H | CH₃ | H | CH(CH₃)CH₂F | OCH₃ | Cl | CH | |
| H | CH₃ | H | CH₂Br | CH₃ | CH₃ | CH | |
| H | CH₃ | H | CH₂Br | CH₃ | OCH₃ | CH | |
| H | CH₃ | H | CH₂Br | OCH₃ | OCH₃ | CH | |
| H | CH₃ | H | CH₂Br | CH₃ | CH₃ | N | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂Br | CH₃ | OCH₃ | N | |
| H | CH₃ | H | CH₂Br | OCH₃ | OCH₃ | N | |
| H | CH₃ | H | CH₂Br | OCH₃ | Cl | CH | |
| H | CH₃ | H | CH₂CH₂Br | CH₃ | CH₃ | CH | |
| H | CH₃ | H | CH₂CH₂Br | CH₃ | OCH₃ | CH | |
| H | CH₃ | H | CH₂CH₂Br | OCH₃ | OCH₃ | CH | |
| H | CH₃ | H | CH₂CH₂Br | CH₃ | CH₃ | N | |
| H | CH₃ | H | CH₂CH₂Br | CH₃ | OCH₃ | N | |
| H | CH₃ | H | CH₂CH₂Br | OCH₃ | OCH₃ | N | |
| H | CH₃ | H | CH₂CH₂Br | OCH₃ | Cl | CH | |
| H | CH₃ | H | CHBrCH₃ | CH₃ | CH₃ | CH | |
| H | CH₃ | H | CHBrCH₃ | CH₃ | OCH₃ | CH | |
| H | CH₃ | H | CHBrCH₃ | OCH₃ | OCH₃ | CH | |
| H | CH₃ | H | CHBrCH₃ | CH₃ | CH₃ | N | |
| H | CH₃ | H | CHBrCH₃ | OCH₃ | OCH₃ | N | |
| H | CH₃ | H | CHBrCH₃ | OCH₃ | Cl | CH | |
| H | CH₃ | H | CH₂CHBr₂ | CH₃ | CH₃ | CH | |
| H | CH₃ | H | CH₂CHBr₂ | CH₃ | OCH₃ | CH | |
| H | CH₃ | H | CH₂CHBr₂ | OCH₃ | OCH₃ | CH | |
| H | CH₃ | H | CH₂CHBr₂ | CH₃ | CH₃ | N | |
| H | CH₃ | H | CH₂CHBr₂ | CH₃ | OCH₃ | N | |
| H | CH₃ | H | CH₂CHBr₂ | OCH₃ | OCH₃ | N | |
| H | CH₃ | H | CH₂CHBr₂ | OCH₃ | Cl | CH | |
| H | CH₃ | H | CH(CH₂Br)₂ | CH₃ | CH₃ | CH | |
| H | CH₃ | H | CH(CH₂Br)₂ | CH₃ | OCH₃ | CH | |
| H | CH₃ | H | CH(CH₂Br)₂ | OCH₃ | OCH₃ | CH | |
| H | CH₃ | H | CH(CH₂Br)₂ | CH₃ | CH₃ | N | |
| H | CH₃ | H | CH₂CHBrCH₃ | CH₃ | OCH₃ | N | |
| H | CH₃ | CH₃ | CH₂CHBrCH₃ | OCH₃ | OCH₃ | N | |
| H | CH₃ | H | CH₂CHBrCH₃ | OCH₃ | Cl | CH | |
| H | CH₃ | H | CH₂CHBrCH₃ | CH₃ | CH₃ | CH | |
| H | CH₃ | H | CH₂CHBrCH₃ | CH₃ | OCH₃ | CH | |
| H | CH₃ | H | CH₂(CH₂)₂CH₂Br | OCH₃ | OCH₃ | CH | |
| H | CH₃ | H | CH₂(CH₂)₂CH₂Br | CH₃ | CH₃ | N | |
| H | CH₃ | H | CH₂(CH₂)₂CH₂Br | CH₃ | OCH₃ | N | |
| H | CH₃ | H | CH₂(CH₂)₂CH₂Br | OCH₃ | OCH₃ | N | |
| H | CH₃ | H | CH₂(CH₂)₂CH₂Br | OCH₃ | Cl | CH | |
| H | CH₃ | H | CH₂(CH₂)₂CH₂Br | CH₃ | CH₃ | CH | |
| CH₃ | CH₃ | H | CH₂(CH₂)₂CH₂Br | CH₃ | OCH₃ | CH | |
| H | CH₃ | H | C(CH₃)(CH₂Br)CH₃ | OCH₃ | OCH₃ | CH | |
| H | CH₃ | H | CH₂CHBrCH₂CH₃ | CH₃ | CH₃ | N | |
| H | CH₃ | H | CH₂CHBrCH₂CH₃ | CH₃ | OCH₃ | N | |
| H | CH₃ | H | CH₂CHBrCH₂CH₃ | OCH₃ | OCH₃ | N | |
| H | CH₃ | H | CH₂CHBrCH₂CH₃ | OCH₃ | Cl | CH | |
| H | CH₃ | H | CH₂Cl | CH₃ | CH₃ | CH | |
| H | CH₃ | H | CH₂Cl | CH₃ | OCH₃ | CH | |
| H | CH₃ | H | CH₂Cl | OCH₃ | OCH₃ | CH | |
| H | CH₃ | H | CH₂Cl | CH₃ | CH₃ | N | |
| H | CH₃ | H | CH₂Cl | CH₃ | OCH₃ | N | |
| H | CH₃ | H | CH₂Cl | OCH₃ | OCH₃ | N | |
| H | CH₃ | H | CH₂Cl | OCH₃ | Cl | CH | |
| H | CH₃ | H | CH₂CH₂Cl | CH₃ | CH₃ | CH | |
| H | CH₃ | H | CH₂CH₂Cl | CH₃ | OCH₃ | CH | |
| H | CH₃ | H | CH₂CH₂Cl | OCH₃ | OCH₃ | CH | |
| H | CH₃ | H | CH₂CH₂Cl | CH₃ | CH₃ | N | |
| H | CH₃ | H | CH₂CH₂Cl | CH₃ | OCH₃ | N | |
| H | CH₃ | H | CH₂CH₂Cl | OCH₃ | OCH₃ | N | |
| H | CH₃ | H | CH₂CH₂Cl | OCH₃ | Cl | CH | |
| H | CH₃ | H | CHClCH₂Cl | CH₃ | CH₃ | CH | |
| H | CH₃ | H | CHClCH₂Cl | CH₃ | OCH₃ | CH | |
| H | CH₃ | H | CHClCH₂Cl | OCH₃ | OCH₃ | CH | |
| H | CH₃ | H | CHClCH₂Cl | CH₃ | CH₃ | N | |
| H | CH₃ | H | CHClCH₂Cl | OCH₃ | OCH₃ | N | |
| H | CH₃ | H | CHClCH₂Cl | OCH₃ | Cl | CH | |
| H | CH₃ | H | CH₂CCl₂CH₃ | CH₃ | CH₃ | CH | |
| H | CH₃ | H | CH₂CCl₂CH₃ | CH₃ | OCH₃ | CH | |
| H | CH₃ | H | CH₂CCl₂CH₃ | OCH₃ | OCH₃ | CH | |
| H | CH₃ | H | CH(CH₂Cl)₂ | CH₃ | CH₃ | N | |
| H | CH₃ | H | CH(CH₂Cl)₂ | CH₃ | OCH₃ | N | |
| H | CH₃ | H | CH(CH₂Cl)₂ | OCH₃ | OCH₃ | N | |
| H | CH₃ | H | CH(CH₂Cl)₂ | OCH₃ | Cl | CH | |
| H | CH₃ | H | CH(CH₂Cl)₂ | CH₃ | CH₃ | CH | |
| H | CH₃ | H | CH₂CH₂CH₂Cl | CH₃ | OCH₃ | CH | |
| H | CH₃ | H | CH₂CH₂CH₂Cl | OCH₃ | OCH₃ | CH | |
| H | CH₃ | H | CH₂CH₂CH₂Cl | CH₃ | CH₃ | N | |
| H | CH₃ | H | CH₂CH₂CH₂Cl | CH₃ | OCH₃ | N | |
| H | CH₃ | CH₃ | CH₂CH₂CH₂Cl | OCH₃ | OCH₃ | N | |
| H | CH₃ | H | CH₂CH₂CH₂Cl | OCH₃ | Cl | CH | |
| H | CH₃ | H | CH₂CH₂CH₂Cl | CH₃ | CH₃ | CH | |
| H | CH₃ | H | CH₂(CH₂)₂CH₂Cl | CH₃ | OCH₃ | CH | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂(CH₂)₂CH₂Cl | OCH₃ | OCH₃ | CH | |
| H | CH₃ | H | CH₂(CH₂)₂CH₂Cl | CH₃ | CH₃ | N | |
| H | CH₃ | H | CH₂(CH₂)₂CH₂Cl | CH₃ | OCH₃ | N | |
| H | CH₃ | H | CH₂(CH₂)₂CH₂Cl | OCH₃ | OCH₃ | N | |
| H | CH₃ | H | CH₂(CH₂)₂CH₂Cl | OCH₃ | Cl | CH | |
| H | CH₃ | H | CH₂(CH₂)₂CH₂Cl | CH₃ | CH₃ | CH | |
| CH₃ | CH₃ | H | CH(CH₃)CH₂Cl | CH₃ | OCH₃ | CH | |
| H | CH₃ | H | CH(CH₃)CH₂Cl | OCH₃ | OCH₃ | CH | |
| H | CH₃ | H | CH(CH₃)CH₂Cl | CH₃ | CH₃ | N | |
| H | CH₃ | H | CHClCHClCH₃ | CH₃ | OCH₃ | N | |
| H | CH₃ | H | CHClCHClCH₃ | OCH₃ | OCH₃ | N | |
| H | CH₃ | H | CHClCHClCH₃ | OCH₃ | Cl | CH | |
| H | CH₃ | H | CH₂I | CH₃ | CH₃ | CH | |
| H | CH₃ | H | CH₂I | CH₃ | OCH₃ | CH | |
| H | CH₃ | H | CH₂I | OCH₃ | OCH₃ | CH | |
| H | CH₃ | H | CH₂I | CH₃ | CH₃ | N | |
| H | CH₃ | H | CH₂I | CH₃ | OCH₃ | N | |
| H | CH₃ | H | CH₂I | OCH₃ | OCH₃ | N | |
| H | CH₃ | H | CH₂I | OCH₃ | Cl | CH | |
| H | CH₃ | H | CH₂CF₃ | CH₃ | CH₃ | CH | |
| H | CH₃ | H | CH₂CF₃ | CH₃ | OCH₃ | CH | |
| H | CH₃ | H | CH₂CF₃ | OCH₃ | OCH₃ | CH | |
| H | CH₃ | H | CH₂CF₃ | CH₃ | CH₃ | N | |
| H | CH₃ | H | CH₂CF₃ | CH₃ | OCH₃ | N | |
| H | CH₃ | H | CH₂CF₃ | OCH₃ | OCH₃ | N | |
| H | CH₃ | H | CH₂CF₃ | OCH₃ | Cl | CH | |
| H | CH₃ | H | CH₂CH₂CF₃ | CH₃ | CH₃ | CH | |
| H | CH₃ | H | CH₂CH₂CF₃ | CH₃ | OCH₃ | CH | |
| H | CH₃ | H | CH₂CH₂CF₃ | OCH₃ | OCH₃ | CH | |
| H | CH₃ | H | CH₂CH₂CF₃ | CH₃ | CH₃ | N | |
| H | CH₃ | H | CH₂CH₂CF₃ | OCH₃ | OCH₃ | N | |
| H | CH₃ | H | CH₂CH₂CF₃ | OCH₃ | Cl | CH | |
| H | CH₃ | H | CH₂(CH₂)₂CF₃ | CH₃ | CH₃ | CH | |
| H | CH₃ | H | CH₂(CH₂)₂CF₃ | CH₃ | OCH₃ | CH | |
| H | CH₃ | H | CH₂(CH₂)₂CF₃ | OCH₃ | OCH₃ | CH | |
| H | CH₃ | H | CH₂(CH₂)₂CF₃ | CH₃ | CH₃ | N | |
| H | CH₃ | H | CH₂(CH₂)₂CF₃ | CH₃ | OCH₃ | N | |
| H | CH₃ | H | CH₂(CH₂)₂CF₃ | OCH₃ | OCH₃ | N | |
| H | CH₃ | H | CH₂(CH₂)₃CF₃ | OCH₃ | Cl | CH | |
| H | CH₃ | H | CH₂(CH₂)₃CF₃ | CH₃ | CH₃ | CH | |
| H | CH₃ | H | CH₂(CH₂)₃CF₃ | CH₃ | OCH₃ | CH | |
| H | CH₃ | H | CH₂(CH₂)₃CF₃ | OCH₃ | OCH₃ | CH | |
| H | CH₃ | H | CH₂(CH₂)₃CF₃ | CH₃ | CH₃ | N | |
| H | CH₃ | H | CH₂(CH₂)₃CF₃ | CH₃ | OCH₃ | N | |
| H | CH₃ | CH₃ | CH₂(CH₂)₃CF₃ | OCH₃ | OCH₃ | N | |
| H | CH₃ | H | CH(CF₃)₂ | OCH₃ | Cl | CH | |
| H | CH₃ | H | CH(CF₃)₂ | CH₃ | CH₃ | CH | |
| H | CH₃ | H | CH(CF₃)₂ | CH₃ | OCH₃ | CH | |
| H | CH₃ | H | CH(CF₃)₂ | OCH₃ | OCH₃ | CH | |
| H | CH₃ | H | CH(CF₃)₂ | CH₃ | CH₃ | N | |
| H | CH₃ | H | CH(CF₃)₂ | CH₃ | OCH₃ | N | |
| H | CH₃ | H | CH(CF₃)₂ | OCH₃ | OCH₃ | N | |
| H | CH₃ | H | CH₂(CH₂)₄CF₃ | OCH₃ | Cl | CH | |
| H | CH₃ | H | CH₂(CH₂)₅CF₃ | CH₃ | CH₃ | CH | |
| CH₃ | CH₃ | H | CH₂(CH₂)₆CF₃ | CH₃ | OCH₃ | CH | |
| H | CH₃ | H | CH₂(CH₂)₇CF₃ | OCH₃ | OCH₃ | CH | |
| H | CH₃ | H | CH₂(CH₂)₈CF₃ | CH₃ | CH₃ | N | |
| H | CH₃ | H | CHF(CH₂)₈CF₃ | CH₃ | OCH₃ | N | |
| H | CH₃ | H | CH(CHF)₈CF₃ | OCH₃ | OCH₃ | N | |
| H | CH₃ | H | CH(CHF)₈CF₃ | OCH₃ | Cl | CH | |
| H | CH₃ | H | CH₂OCH₃ | CH₃ | CH₃ | CH | |
| H | CH₃ | H | CH₂OCH₃ | CH₃ | OCH₃ | CH | |
| H | CH₃ | H | CH₂OCH₃ | OCH₃ | OCH₃ | CH | |
| H | CH₃ | H | CH₂OCH₃ | CH₃ | CH₃ | N | |
| H | CH₃ | H | CH₂OCH₃ | CH₃ | OCH₃ | N | |
| H | CH₃ | H | CH₂OCH₃ | OCH₃ | OCH₃ | N | |
| H | CH₃ | H | CH₂OCH₃ | OCH₃ | Cl | CH | |
| H | CH₃ | H | CH₂OCH₂CH₃ | CH₃ | CH₃ | CH | |
| H | CH₃ | H | CH₂OCH₂CH₃ | CH₃ | OCH₃ | CH | |
| H | CH₃ | H | CH₂OCH₂CH₃ | OCH₃ | OCH₃ | CH | |
| H | CH₃ | H | CH₂—OCH₂F | CH₃ | CH₃ | N | |
| H | CH₃ | H | CH₂—OCH₂F | CH₃ | OCH₃ | N | |
| H | CH₃ | H | CH₂—OCH₂F | OCH₃ | OCH₃ | N | |
| H | CH₃ | H | CH₂—OCH₂F | OCH₃ | Cl | CH | |
| H | CH₃ | H | CH₂—CH₂OCH₃ | CH₃ | CH₃ | CH | |
| H | CH₃ | H | CH₂—CH₂OCH₃ | CH₃ | OCH₃ | CH | |
| H | CH₃ | H | CH₂—CH₂OCH₃ | OCH₃ | OCH₃ | CH | |
| H | CH₃ | H | CH₂—CH₂OCH₃ | CH₃ | CH₃ | N | |
| H | CH₃ | H | CH(OCH₃)₂ | OCH₃ | OCH₃ | N | |
| H | CH₃ | H | CH(OCH₃)₂ | OCH₃ | Cl | CH | |

TABLE Ia-continued

General Structure Ia

| R | R$_1$ | R$_2$ | R$_3$ | X | Y | Z | m.p. (°C.) |
|---|---|---|---|---|---|---|---|
| H | CH$_3$ | H | CH$_2$(CH$_2$)$_2$OCH$_3$ | CH$_3$ | CH$_3$ | CH | |
| H | CH$_3$ | H | CH$_2$(CH$_2$)$_2$OCH$_3$ | CH$_3$ | OCH$_3$ | CH | |
| H | CH$_3$ | H | CH$_2$(CH$_2$)$_2$OCH$_3$ | OCH$_3$ | OCH$_3$ | CH | |
| H | CH$_3$ | H | CH$_2$(CH$_2$)$_2$OCH$_3$ | CH$_3$ | CH$_3$ | N | |
| H | CH$_3$ | H | CH$_2$(CH$_2$)$_2$OCH$_3$ | CH$_3$ | OCH$_3$ | N | |
| H | CH$_3$ | H | CH$_2$(CH$_2$)$_3$OCH$_3$ | OCH$_3$ | OCH$_3$ | N | |
| H | CH$_3$ | H | CH$_2$(CH$_2$)$_3$OCH$_3$ | OCH$_3$ | Cl | CH | |
| H | CH$_3$ | H | CH$_2$(CH$_2$)$_3$OCH$_3$ | CH$_3$ | CH$_3$ | CH | |
| H | CH$_3$ | H | CH$_2$(CH$_2$)$_3$OCH$_3$ | CH$_3$ | OCH$_3$ | CH | |
| H | CH$_3$ | H | CH$_2$(CH$_2$)$_3$OCH$_3$ | OCH$_3$ | OCH$_3$ | CH | |
| H | CH$_3$ | H | CH(OCH$_3$)CH$_3$ | CH$_3$ | CH$_3$ | N | |
| H | CH$_3$ | H | CH(OCH$_3$)CH$_3$ | CH$_3$ | OCH$_3$ | N | |
| H | CH$_3$ | CH$_3$ | CH(OCH$_3$)CH$_3$ | OCH$_3$ | OCH$_3$ | N | |
| H | CH$_3$ | H | CH$_2$OCH$_2$C=CH$_2$ | OCH$_3$ | Cl | CH | |
| H | CH$_3$ | H | CH$_2$OCH$_2$C=CH$_2$ | CH$_3$ | CH$_3$ | CH | |
| H | CH$_3$ | H | CH$_2$OCH$_2$C=CH$_2$ | CH$_3$ | OCH$_3$ | CH | |
| H | CH$_3$ | H | CH$_2$OCH$_2$C=CH$_2$ | OCH$_3$ | OCH$_3$ | CH | |
| H | CH$_3$ | H | CH$_2$OCH$_2$C=CH$_2$ | CH$_3$ | CH$_3$ | N | |
| H | CH$_3$ | H | CH$_2$OCH$_2$C=CH$_2$ | CH$_3$ | OCH$_3$ | N | |
| H | CH$_3$ | H | CH$_2$CH(OCH$_3$)$_2$ | OCH$_3$ | OCH$_3$ | N | |
| H | CH$_3$ | H | CH$_2$CH(OCH$_3$)$_2$ | OCH$_3$ | Cl | CH | |
| H | CH$_3$ | H | CH$_2$CH(OCH$_3$)$_2$ | CH$_3$ | CH$_3$ | CH | |
| CH$_3$ | CH$_3$ | H | CH$_2$CH(OCH$_3$)$_2$ | CH$_3$ | OCH$_3$ | CH | |
| H | CH$_3$ | H | CH$_2$C(OCH$_3$)$_2$CH$_3$ | OCH$_3$ | OCH$_3$ | CH | |
| H | CH$_3$ | H | CH$_2$C(OCH$_3$)$_2$CH$_3$ | CH$_3$ | CH$_3$ | N | |
| H | CH$_3$ | H | CH$_2$C(OCH$_3$)$_2$CH$_3$ | CH$_3$ | OCH$_3$ | N | |
| H | CH$_3$ | H | CH$_2$(CH$_2$)$_6$OCH$_3$ | OCH$_3$ | OCH$_3$ | N | |
| H | CH$_3$ | H | CH$_2$(CH$_2$)$_6$OCH$_3$ | OCH$_3$ | Cl | CH | |
| H | CH$_3$ | H | CH$_2$OC(O)CH$_3$ | CH$_3$ | CH$_3$ | CH | |
| H | CH$_3$ | H | CH$_2$OC(O)CH$_3$ | CH$_3$ | OCH$_3$ | CH | |
| H | CH$_3$ | H | CH$_2$OC(O)CH$_3$ | OCH$_3$ | OCH$_3$ | CH | |
| H | CH$_3$ | H | CH$_2$OC(O)CH$_3$ | CH$_3$ | CH$_3$ | N | |
| H | CH$_3$ | H | CH$_2$OC(O)CH$_3$ | CH$_3$ | OCH$_3$ | N | |
| H | CH$_3$ | H | CH$_2$OC(O)CH$_3$ | OCH$_3$ | OCH$_3$ | N | |
| H | CH$_3$ | H | CH$_2$OC(O)CH$_3$ | OCH$_3$ | Cl | CH | |
| H | CH$_3$ | H | CH$_2$CH$_2$OC(O)CH$_3$ | CH$_3$ | CH$_3$ | CH | |
| H | CH$_3$ | H | CH$_2$CH$_2$OC(O)CH$_3$ | CH$_3$ | OCH$_3$ | CH | |
| H | CH$_3$ | H | CH$_2$CH$_2$OC(O)CH$_3$ | OCH$_3$ | OCH$_3$ | CH | |
| H | CH$_3$ | H | CH$_2$CH$_2$OC(O)CH$_3$ | CH$_3$ | CH$_3$ | N | |
| H | CH$_3$ | H | CH$_2$CH$_2$OC(O)CH$_3$ | CH$_3$ | OCH$_3$ | N | |
| H | CH$_3$ | H | CH$_2$CH$_2$OC(O)CH$_3$ | OCH$_3$ | OCH$_3$ | N | |
| H | CH$_3$ | H | CH$_2$CH$_2$OC(O)CH$_3$ | OCH$_3$ | Cl | CH | |
| H | CH$_3$ | H | CH$_2$(CH$_2$)$_2$OC(O)CH$_3$ | CH$_3$ | CH$_3$ | CH | |
| H | CH$_3$ | H | CH$_2$(CH$_2$)$_2$OC(O)CH$_3$ | CH$_3$ | OCH$_3$ | CH | |
| H | CH$_3$ | H | CH$_2$(CH$_2$)$_2$OC(O)CH$_3$ | OCH$_3$ | OCH$_3$ | CH | |
| H | CH$_3$ | H | CH$_2$(CH$_2$)$_3$OC(O)CH$_3$ | CH$_3$ | CH$_3$ | N | |
| H | CH$_3$ | H | CH$_2$(CH$_2$)$_3$OC(O)CH$_3$ | OCH$_3$ | OCH$_3$ | N | |
| H | CH$_3$ | H | CH$_2$(CH$_2$)$_3$OC(O)CH$_3$ | OCH$_3$ | Cl | CH | |
| H | CH$_3$ | H | CH$_2$(CH$_2$)$_3$OC(O)CH$_3$ | CH$_3$ | CH$_3$ | CH | |
| H | CH$_3$ | H | CH$_2$P(CH$_3$)(Br)(CH$_3$) | CH$_3$ | OCH$_3$ | CH | |
| H | CH$_3$ | H | CH$_2$P(C$_6$H$_5$)$_3$ | OCH$_3$ | OCH$_3$ | CH | |
| H | CH$_3$ | H | CH$_2$OC(O)N(CH$_3$)$_2$ | CH$_3$ | CH$_3$ | N | |
| H | CH$_3$ | H | CH$_2$OC(O)N(CH$_3$)$_2$ | CH$_3$ | OCH$_3$ | N | |
| H | CH$_3$ | H | CH$_2$OC(O)N(CH$_3$)$_2$ | OCH$_3$ | OCH$_3$ | N | |
| H | CH$_3$ | H | CH$_2$OC(O)N(CH$_3$)$_2$ | OCH$_3$ | Cl | CH | |
| H | CH$_3$ | H | CH$_2$OC(O)N(CH$_3$)$_2$ | CH$_3$ | CH$_3$ | CH | |
| H | CH$_3$ | H | CH$_2$OC(O)N(CH$_3$)$_2$ | CH$_3$ | OCH$_3$ | CH | |
| H | CH$_3$ | H | CH$_2$OC(O)N(CH$_3$)$_2$ | OCH$_3$ | OCH$_3$ | CH | |
| H | CH$_3$ | H | CH$_2$CH$_2$OC(O)N(CH$_3$)$_2$ | CH$_3$ | CH$_3$ | N | |
| H | CH$_3$ | H | CH$_2$CH$_2$OC(O)N(CH$_3$)$_2$ | CH$_3$ | OCH$_3$ | N | |
| H | CH$_3$ | CH$_3$ | CH$_2$CH$_2$OC(O)N(CH$_3$)$_2$ | OCH$_3$ | OCH$_3$ | N | |
| H | CH$_3$ | H | CH$_2$CH$_2$OC(O)N(CH$_3$)$_2$ | OCH$_3$ | Cl | CH | |
| H | CH$_3$ | H | CH$_2$CH$_2$OC(O)N(CH$_3$)$_2$ | CH$_3$ | CH$_3$ | CH | |
| H | CH$_3$ | H | CH$_2$CH$_2$OC(O)N(CH$_3$)$_2$ | CH$_3$ | OCH$_3$ | CH | |
| H | CH$_3$ | H | CH$_2$OSO$_2$CH$_3$ | OCH$_3$ | OCH$_3$ | CH | |
| H | CH$_3$ | H | CH$_2$OSO$_2$CH$_3$ | CH$_3$ | CH$_3$ | N | |
| H | CH$_3$ | H | CH$_2$OSO$_2$CH$_3$ | CH$_3$ | OCH$_3$ | N | |
| H | CH$_3$ | H | CH$_2$OSO$_2$CH$_3$ | OCH$_3$ | OCH$_3$ | N | |
| H | CH$_3$ | H | CH$_2$OSO$_2$CH$_2$CH$_3$ | OCH$_3$ | Cl | CH | |
| H | CH$_3$ | H | CH$_2$OSO$_2$CH$_2$CH$_3$ | CH$_3$ | CH$_3$ | CH | |
| CH$_3$ | CH$_3$ | H | CH$_2$OSO$_2$CH$_2$CH$_3$ | CH$_3$ | OCH$_3$ | CH | |
| H | CH$_3$ | H | CH$_2$(CH$_2$)$_2$OSO$_2$CH$_3$ | OCH$_3$ | OCH$_3$ | CH | |
| H | CH$_3$ | H | CH$_2$(CH$_2$)$_2$OSO$_2$CH$_3$ | CH$_3$ | CH$_3$ | N | |
| H | CH$_3$ | H | CH$_2$(CH$_2$)$_2$OSO$_2$CH$_3$ | CH$_3$ | OCH$_3$ | N | |
| H | CH$_3$ | H | CH$_2$(CH$_2$)$_2$OSO$_2$CH$_3$ | OCH$_3$ | OCH$_3$ | N | |
| H | CH$_3$ | H | CH$_2$(CH$_2$)$_2$OSO$_2$CH$_3$ | OCH$_3$ | Cl | CH | |
| H | CH$_3$ | H | CH$_2$OP(O)(CH$_3$)$_2$ | CH$_3$ | CH$_3$ | CH | |
| H | CH$_3$ | H | CH$_2$OP(O)(CH$_3$)$_2$ | CH$_3$ | OCH$_3$ | CH | |
| H | CH$_3$ | H | CH$_2$OP(O)(CH$_3$)$_2$ | OCH$_3$ | OCH$_3$ | CH | |
| H | CH$_3$ | H | CH$_2$OP(O)(CH$_3$)$_2$ | CH$_3$ | CH$_3$ | N | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂OP(O)(CH₃)₂ | CH₃ | OCH₃ | N | |
| H | CH₃ | H | CH₂OP(O)(CH₃)₂ | OCH₃ | OCH₃ | N | |
| H | CH₃ | H | CH₂OP(O)(CH₃)₂ | OCH₃ | Cl | CH | |
| H | CH₃ | H | CH₂OP(O)(CH₃)Ph | CH₃ | CH₃ | CH | |
| H | CH₃ | H | CH₂OP(O)(CH₃)Ph | CH₃ | OCH₃ | CH | |
| H | CH₃ | H | CH₂OP(O)(CH₃)Ph | OCH₃ | OCH₃ | CH | |
| H | CH₃ | H | CH₂OP(O)(CH₃)Ph | CH₃ | CH₃ | N | |
| H | CH₃ | H | CH₂OP(O)(Ph)₂ | CH₃ | OCH₃ | N | |
| H | CH₃ | H | CH₂OP(O)(Ph)₂ | OCH₃ | OCH₃ | N | |
| H | CH₃ | H | CH₂OP(O)(Ph)₂ | OCH₃ | Cl | CH | |
| H | CH₃ | H | CH₂OP(O)(Ph)₂ | CH₃ | CH₃ | CH | |
| H | CH₃ | H | CH₂OP(O)(Ph)₂ | CH₃ | OCH₃ | CH | |
| H | CH₃ | H | CH₂OP(O)(Ph)₂ | OCH₃ | OCH₃ | CH | |
| H | CH₃ | H | CH₂CH₂OP(O)(CH₃)₂ | CH₃ | CH₃ | N | |
| H | CH₃ | H | CH₂CH₂OP(O)(CH₃)₂ | OCH₃ | OCH₃ | N | |
| H | CH₃ | H | CH₂CH₂OP(O)(CH₃)₂ | OCH₃ | Cl | CH | |
| H | CH₃ | H | CH₂CH₂OP(O)(CH₃)₂ | CH₃ | CH₃ | CH | |
| H | CH₃ | H | CH₂CH₂OP(O)CH₃)₂ | CH₃ | OCH₃ | CH | |
| H | CH₃ | H | CH₂(CH₂)₂OP(O)(CH₃)₂ | OCH₃ | OCH₃ | CH | |
| H | CH₃ | H | CH₂(CH₂)₂OP(O)(CH₃)₂ | CH₃ | CH₃ | N | |
| H | CH₃ | H | CH₂(CH₂)₂OP(O)(CH₃)₂ | CH₃ | OCH₃ | N | |
| H | CH₃ | H | CH₂(CH₂)₂OP(O)(CH₃)₂ | OCH₃ | OCH₃ | N | |
| H | CH₃ | H | CH₂(CH₂)₂OP(O)(CH₃)₂ | OCH₃ | Cl | CH | |
| H | CH₃ | H | CH₂(CH₂)₂OP(O)(CH₃)₂ | CH₃ | CH₃ | CH | |
| H | CH₃ | H | CH₂P(O)(CH₃)₂ | CH₃ | OCH₃ | CH | |
| H | CH₃ | H | CH₂P(O)(CH₃)₂ | OCH₃ | OCH₃ | CH | |
| H | CH₃ | H | CH₂P(O)(CH₃)₂ | CH₃ | CH₃ | N | |
| H | CH₃ | H | CH₂P(O)(CH₃)₂ | CH₃ | OCH₃ | N | |
| H | CH₃ | CH₃ | CH₂P(O)(CH₃)₂ | OCH₃ | OCH₃ | N | |
| H | CH₃ | H | CH₂P(O)(CH₃)₂ | OCH₃ | Cl | CH | |
| H | CH₃ | H | CH₂P(O)(CH₃)₂ | CH₃ | CH₃ | CH | |
| H | CH₃ | H | CH₂P(O)(OCH₃)₂ | CH₃ | OCH₃ | CH | |
| H | CH₃ | H | CH₂P(O)(OCH₃)₂ | OCH₃ | OCH₃ | CH | |
| H | CH₃ | H | CH₂P(O)(OCH₃)₂ | CH₃ | CH₃ | N | |
| H | CH₃ | H | CH₂P(O)(OCH₃)₂ | CH₃ | OCH₃ | N | |
| H | CH₃ | H | CH₂P(O)(OCH₃)₂ | OCH₃ | OCH₃ | N | |
| H | CH₃ | H | CH₂P(O)(OCH₃)₂ | OCH₃ | Cl | CH | |
| H | CH₃ | H | CH₂P(O)(OCH₃)₂ | CH₃ | CH₃ | CH | |
| CH₃ | CH₃ | H | CH₂CH₂P(O)(OCH₂CH₃)₂ | CH₃ | OCH₃ | CH | |
| H | CH₃ | H | CH₂CH₂P(O)(OCH₂CH₃)₂ | OCH₃ | OCH₃ | CH | |
| H | CH₃ | H | CH₂(CH₂)₃P(O)(OCH₃)₂ | CH₃ | CH₃ | N | |
| H | CH₃ | H | CH₂(CH₂)₃P(O)(OCH₃)₂ | CH₃ | OCH₃ | N | |
| H | CH₃ | H | CH₂(CH₂)₃P(O)(OCH₃)₂ | OCH₃ | OCH₃ | N | |
| H | CH₃ | H | CH₂(CH₂)₃P(O)(OCH₃)₂ | OCH₃ | Cl | CH | |
| H | CH₃ | H | CH₂OP(S)(CH₃)₂ | CH₃ | CH₃ | CH | |
| H | CH₃ | H | CH₂OP(S)(CH₃)₂ | CH₃ | OCH₃ | CH | |
| H | CH₃ | H | CH₂OP(S)(CH₃)₂ | OCH₃ | OCH₃ | CH | |
| H | CH₃ | H | CH₂OP(S)(CH₃)₂ | CH₃ | CH₃ | N | |
| H | CH₃ | H | CH₂OP(S)(CH₃)₂ | CH₃ | OCH₃ | N | |
| H | CH₃ | H | CH₂OP(S)(CH₃)₂ | OCH₃ | OCH₃ | N | |
| H | CH₃ | H | CH₂OP(S)(CH₃)₂ | OCH₃ | Cl | CH | |
| H | CH₃ | H | CH₂OP(S)(OCH₃)₂ | CH₃ | CH₃ | CH | |
| H | CH₃ | H | CH₂OP(S)(OCH₃)₂ | CH₃ | OCH₃ | CH | |
| H | CH₃ | H | CH₂OP(S)(OCH₃)₂ | OCH₃ | OCH₃ | CH | |
| H | CH₃ | H | CH₂OP(S)(OCH₃)₂ | CH₃ | CH₃ | N | |
| H | CH₃ | H | CH₂OP(S)(OCH₃)₂ | CH₃ | OCH₃ | N | |
| H | CH₃ | H | CH₂OP(S)(OCH₃)₂ | OCH₃ | OCH₃ | N | |
| H | CH₃ | H | CH₂OP(S)(OCH₃)₂ | OCH₃ | Cl | CH | |
| H | CH₃ | H | CH₂P(S)(CH₃)₂ | CH₃ | CH₃ | CH | |
| H | CH₃ | H | CH₂P(S)(CH₃)₂ | CH₃ | OCH₃ | CH | |
| H | CH₃ | H | CH₂P(S)(CH₃)₂ | OCH₃ | OCH₃ | CH | |
| H | CH₃ | H | CH₂P(S)(CH₃)₂ | CH₃ | CH₃ | N | |
| H | CH₃ | H | CH₂P(S)(CH₃)₂ | OCH₃ | OCH₃ | N | |
| H | CH₃ | H | CH₂P(S)(CH₃)₂ | OCH₃ | Cl | CH | |
| H | CH₃ | H | CH₂P(S)(OCH₃)₂ | CH₃ | CH₃ | CH | |
| H | CH₃ | H | CH₂P(S)(OCH₃)₂ | CH₃ | OCH₃ | CH | |
| H | CH₃ | H | CH₂P(S)(OCH₃)₂ | OCH₃ | OCH₃ | CH | |
| H | CH₃ | H | CH₂P(S)(OCH₃)₂ | CH₃ | CH₃ | N | |
| H | CH₃ | H | CH₂P(S)(OCH₃)₂ | CH₃ | OCH₃ | N | |
| H | CH₃ | H | CH₂P(S)(OCH₃)₂ | OCH₃ | OCH₃ | N | |
| H | CH₃ | H | CH₂P(S)(OCH₃)₂ | OCH₃ | Cl | CH | |
| H | CH₃ | H | CH₂CH₂OP(S)(CH₃)₂ | CH₃ | CH₃ | CH | |
| H | CH₃ | H | CH₂CH₂OP(S)(CH₃)₂ | CH₃ | OCH₃ | CH | |
| H | CH₃ | H | CH₂CH₂OP(S)(CH₃)₂ | OCH₃ | OCH₃ | CH | |
| H | CH₃ | H | CH₂CH₂OP(S)(CH₃)₂ | CH₃ | CH₃ | N | |
| H | CH₃ | H | CH₂CH₂OP(S)(CH₃)₂ | CH₃ | OCH₃ | N | |
| H | CH₃ | CH₃ | CH₂CH₂OP(S)(CH₃)₂ | OCH₃ | OCH₃ | N | |
| H | CH₃ | H | CH₂CH₂OP(S)(CH₃)₂ | OCH₃ | Cl | CH | |
| H | CH₃ | H | CH₂CH₂P(S)(OCH₃)₂ | CH₃ | CH₃ | CH | |
| H | CH₃ | H | CH₂CH₂P(S)(OCH₃)₂ | CH₃ | OCH₃ | CH | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂CH₂P(S)(OCH₃)₂ | OCH₃ | OCH₃ | CH | |
| H | CH₃ | H | CH₂CH₂P(S)(OCH₃)₂ | CH₃ | CH₃ | N | |
| H | CH₃ | H | CH₂CH₂P(S)(OCH₃)₂ | CH₃ | OCH₃ | N | |
| H | CH₃ | H | CH₂CH₂P(S)(OCH₃)₂ | OCH₃ | OCH₃ | N | |
| H | CH₃ | H | CH₂CH₂P(S)(OCH₃)₂ | OCH₃ | Cl | CH | |
| H | CH₃ | H | CH₂(CH₂)₃OP(S)(CH₃)₂ | CH₃ | CH₃ | CH | |
| CH₃ | CH₃ | H | CH₂(CH₂)₃OP(S)(CH₃)₂ | CH₃ | OCH₃ | CH | |
| H | CH₃ | H | CH₂(CH₂)₃OP(S)(CH₃)₂ | OCH₃ | OCH₃ | CH | |
| H | CH₃ | H | CH₂(CH₂)₃OP(S)(CH₃)₂ | CH₃ | CH₃ | N | |
| H | CH₃ | H | CH₂(CH₂)₃OP(S)(CH₃)₂ | CH₃ | OCH₃ | N | |
| H | CH₃ | H | CH₂(CH₂)₃OP(S)(CH₃)₂ | OCH₃ | OCH₃ | N | |
| H | CH₃ | H | CH₂(CH₂)₃OP(S)(CH₃)₂ | OCH₃ | Cl | CH | |
| H | CH₃ | H | CH₂OSi(CH₃)₃ | CH₃ | CH₃ | CH | |
| H | CH₃ | H | CH₂OSi(CH₃)₃ | CH₃ | OCH₃ | CH | |
| H | CH₃ | H | CH₂OSi(CH₃)₃ | OCH₃ | OCH₃ | CH | |
| H | CH₃ | H | CH₂OSi(CH₃)₃ | CH₃ | CH₃ | N | |
| H | CH₃ | H | CH₂OSi(CH₃)₃ | CH₃ | OCH₃ | N | |
| H | CH₃ | H | CH₂OSi(CH₃)₃ | OCH₃ | OCH₃ | N | |
| H | CH₃ | H | CH₂OSi(CH₃)₃ | OCH₃ | Cl | CH | |
| H | CH₃ | H | CH₂CH₂OSi(CH₃)₃ | CH₃ | CH₃ | CH | |
| H | CH₃ | H | CH₂CH₂OSi(CH₃)₃ | CH₃ | OCH₃ | CH | |
| H | CH₃ | H | CH₂CH₂OSi(CH₃)₃ | OCH₃ | OCH₃ | CH | |
| H | CH₃ | H | CH₂CH₂OSi(CH₃)₃ | CH₃ | CH₃ | N | |
| H | CH₃ | H | CH₂CH₂OSi(CH₃)₃ | CH₃ | OCH₃ | N | |
| H | CH₃ | H | CH₂CH₂OSi(CH₃)₃ | OCH₃ | OCH₃ | N | |
| H | CH₃ | H | CH₂CH₂OSi(CH₃)₃ | OCH₃ | Cl | CH | |
| H | CH₃ | H | CH₂(CH₂)₂OSi(CH₃)₃ | CH₃ | CH₃ | CH | |
| H | CH₃ | H | CH₂(CH₂)₂OSi(CH₃)₃ | CH₃ | OCH₃ | CH | |
| H | CH₃ | H | CH₂(CH₂)₂OSi(CH₃)₃ | OCH₃ | OCH₃ | CH | |
| H | CH₃ | H | CH₂(CH₂)₂OSi(CH₃)₃ | CH₃ | CH₃ | N | |
| H | CH₃ | H | CH₂(CH₂)₂OSi(CH₃)₃ | OCH₃ | OCH₃ | N | |
| H | CH₃ | H | CH₂(CH₂)₂OSi(CH₃)₃ | OCH₃ | Cl | CH | |
| H | CH₃ | H | CH₂(CH₂)₃OSi(CH₃)₃ | CH₃ | CH₃ | CH | |
| H | CH₃ | H | CH₂(CH₂)₃OSi(CH₃)₃ | CH₃ | OCH₃ | CH | |
| H | CH₃ | H | CH₂(CH₂)₃OSi(CH₃)₃ | OCH₃ | OCH₃ | CH | |
| H | CH₃ | H | CH₂(CH₂)₃OSi(CH₃)₃ | CH₃ | CH₃ | N | |
| H | CH₃ | H | CH₂(CH₂)₃OSi(CH₃)₃ | CH₃ | OCH₃ | N | |
| H | CH₃ | H | CH₂(CH₂)₃OSi(CH₃)₃ | OCH₃ | OCH₃ | N | |
| H | CH₃ | H | CH₂(CH₂)₃OSi(CH₃)₃ | OCH₃ | Cl | CH | |
| H | CH₃ | H | CH₂(CH₂)₄OSi(CH₃)₃ | CH₃ | CH₃ | CH | |
| H | CH₃ | H | CH₂(CH₂)₅OSi(CH₃)₃ | CH₃ | OCH₃ | CH | |
| H | CH₃ | H | CH₂(CH₂)₆OSi(CH₃)₃ | OCH₃ | OCH₃ | CH | |
| H | CH₃ | H | CH₂(CH₂)₇OSi(CH₃)₃ | CH₃ | CH₃ | N | |
| H | CH₃ | H | CH₂OSi(CH₂CH₃)₃ | CH₃ | OCH₃ | N | |
| H | CH₃ | CH₃ | CH₂OSi(CH₃)₂(Ph) | OCH₃ | OCH₃ | N | |
| H | CH₃ | H | CH(CH₃)OSi(CH₃)₃ | OCH₃ | Cl | CH | |
| H | CH₃ | H | CH(CH₃)OSi(CH₃)₃ | CH₃ | CH₃ | CH | |
| H | CH₃ | H | CH(CH₃)OSi(CH₃)₃ | CH₃ | OCH₃ | CH | |
| H | CH₃ | H | CH(CH₃)OSi(CH₃)₃ | OCH₃ | OCH₃ | CH | |
| H | CH₃ | H | CH(CH₃)OSi(CH₃)₃ | CH₃ | CH₃ | N | |
| H | CH₃ | H | CH₂Si(CH₃)₃ | CH₃ | OCH₃ | N | |
| H | CH₃ | H | CH₂Si(CH₃)₃ | OCH₃ | OCH₃ | N | |
| H | CH₃ | H | CH₂Si(CH₃)₃ | OCH₃ | Cl | CH | |
| H | CH₃ | H | CH₂Si(CH₃)₃ | CH₃ | CH₃ | CH | |
| CH₃ | CH₃ | H | CH₂Si(CH₃)₃ | CH₃ | OCH₃ | CH | |
| H | CH₃ | H | CH₂Si(CH₃)₃ | OCH₃ | OCH₃ | CH | |
| H | CH₃ | H | CH₂Si(CH₃)₃ | CH₃ | CH₃ | N | |
| H | CH₃ | H | CH₂CH₂Si(CH₃)₃ | CH₃ | OCH₃ | N | |
| H | CH₃ | H | CH₂CH₂Si(CH₃)₃ | OCH₃ | OCH₃ | N | |
| H | CH₃ | H | CH₂CH₂Si(CH₃)₃ | OCH₃ | Cl | CH | |
| H | CH₃ | H | CH₂(CH₂)₂Si(CH₃)₃ | CH₃ | CH₃ | CH | |
| H | CH₃ | H | CH₂(CH₂)₂Si(CH₃)₃ | CH₃ | OCH₃ | CH | |
| H | CH₃ | H | CH₂(CH₂)₂Si(CH₃)₃ | OCH₃ | OCH₃ | CH | |
| H | CH₃ | H | CH₂(CH₂)₂Si(CH₃)₃ | CH₃ | CH₃ | N | |
| H | CH₃ | H | CH₂(CH₂)₂Si(CH₃)₃ | CH₃ | OCH₃ | N | |
| H | CH₃ | H | CH₂(CH₂)₂Si(CH₃)₃ | OCH₃ | OCH₃ | N | |
| H | CH₃ | H | CH₂(CH₂)₂Si(CH₃)₃ | OCH₃ | Cl | CH | |
| H | CH₃ | H | C(Si(CH₃)₃)(CH₃)₂ | CH₃ | CH₃ | CH | |
| H | CH₃ | H | C(Si(CH₃)₃)(CH₃)₂ | CH₃ | OCH₃ | CH | |
| H | CH₃ | H | C(Si(CH₃)₃)(CH₃)₂ | OCH₃ | OCH₃ | CH | |
| H | CH₃ | H | C(Si(CH₃)₃)(CH₃)₂ | CH₃ | CH₃ | N | |
| H | CH₃ | H | C(Si(CH₃)₃)(CH₃)₂ | CH₃ | OCH₃ | N | |
| H | CH₃ | H | C(Si(CH₃)₃)(CH₃)₂ | OCH₃ | OCH₃ | N | |
| H | CH₃ | H | C(Si(CH₃)₃)(CH₃)₂ | OCH₃ | Cl | CH | |
| H | CH₃ | H | CH₂SCH₃ | CH₃ | CH₃ | CH | |
| H | CH₃ | H | CH₂SCH₃ | CH₃ | OCH₃ | CH | |
| H | CH₃ | H | CH₂SCH₃ | OCH₃ | OCH₃ | CH | |
| H | CH₃ | H | CH₂SCH₃ | CH₃ | CH₃ | N | |
| H | CH₃ | H | CH₂SCH₃ | OCH₃ | OCH₃ | N | |
| H | CH₃ | H | CH₂SCH₃ | OCH₃ | Cl | CH | |

TABLE Ia-continued

General Structure Ia

| R | $R_1$ | $R_2$ | $R_3$ | X | Y | Z | m.p. (°C.) |
|---|---|---|---|---|---|---|---|
| H | $CH_3$ | H | $CH_2SCH_2CH_3$ | $CH_3$ | $CH_3$ | CH | |
| H | $CH_3$ | H | $CH_2CH_2SCH_3$ | $CH_3$ | $OCH_3$ | CH | |
| H | $CH_3$ | H | $CH_2CH_2SCH_3$ | $OCH_3$ | $OCH_3$ | CH | |
| H | $CH_3$ | H | $CH_2CH_2SCH_3$ | $CH_3$ | $CH_3$ | N | |
| H | $CH_3$ | H | $CH_2CH_2SCH_3$ | $CH_3$ | $OCH_3$ | N | |
| H | $CH_3$ | H | $CH_2CH_2SCH_3$ | $OCH_3$ | $OCH_3$ | N | |
| H | $CH_3$ | H | $CH_2CH_2SCH_3$ | $OCH_3$ | Cl | CH | |
| H | $CH_3$ | H | $CH_2CH_2SCH_3$ | $CH_3$ | $CH_3$ | CH | |
| H | $CH_3$ | H | $CH_2(CH_2)_2SCH_3$ | $CH_3$ | $OCH_3$ | CH | |
| H | $CH_3$ | H | $CH_2(CH_2)_2SCH_3$ | $OCH_3$ | $OCH_3$ | CH | |
| H | $CH_3$ | H | $CH_2(CH_2)_2SCH_3$ | $CH_3$ | $CH_3$ | N | |
| H | $CH_3$ | H | $CH_2(CH_2)_2SCH_3$ | $CH_3$ | $OCH_3$ | N | |
| H | $CH_3$ | $CH_3$ | $CH_2(CH_2)_2SCH_3$ | $OCH_3$ | $OCH_3$ | N | |
| H | $CH_3$ | H | $CH_2(CH_2)_2SCH_3$ | $OCH_3$ | Cl | CH | |
| H | $CH_3$ | H | $CH_2(CH_2)_3SCH_3$ | $CH_3$ | $CH_3$ | CH | |
| H | $CH_3$ | H | $CH_2(CH_2)_3SCH_3$ | $CH_3$ | $OCH_3$ | CH | |
| H | $CH_3$ | H | $CH_2(CH_2)_3SCH_3$ | $OCH_3$ | $OCH_3$ | CH | |
| H | $CH_3$ | H | $CH_2(CH_2)_3SCH_3$ | $CH_3$ | $CH_3$ | N | |
| H | $CH_3$ | H | $CH_2(CH_2)_3SCH_3$ | $CH_3$ | $OCH_3$ | N | |
| H | $CH_3$ | H | $CH_2(CH_2)_3SCH_3$ | $OCH_3$ | $OCH_3$ | N | |
| H | $CH_3$ | H | $CH(CH_3)SCH_3$ | $OCH_3$ | Cl | CH | |
| H | $CH_3$ | H | $CH(CH_3)SCH_3$ | $CH_3$ | $CH_3$ | CH | |
| $CH_3$ | $CH_3$ | H | $CH(CH_3)SCH_3$ | $CH_3$ | $OCH_3$ | CH | |
| H | $CH_3$ | H | $CH(SCH_3)_2$ | $OCH_3$ | $OCH_3$ | CH | |
| H | $CH_3$ | H | $CH_2CH(CH_3)SCH_3$ | $CH_3$ | $CH_3$ | N | |
| H | $CH_3$ | H | $CH_2CH(CH_3)SCH_3$ | $CH_3$ | $OCH_3$ | N | |
| H | $CH_3$ | H | $CH_2(CH_2)_8SCH_3$ | $OCH_3$ | $OCH_3$ | N | |
| H | $CH_3$ | H | $CH_2(CH_2)_8SCH_3$ | $OCH_3$ | Cl | CH | |
| H | $CH_3$ | H | $CH_2SOCH_3$ | $CH_3$ | $CH_3$ | CH | |
| H | $CH_3$ | H | $CH_2SOCH_3$ | $CH_3$ | $OCH_3$ | CH | |
| H | $CH_3$ | H | $CH_2SOCH_3$ | $OCH_3$ | $OCH_3$ | CH | |
| H | $CH_3$ | H | $CH_2SOCH_3$ | $CH_3$ | $CH_3$ | N | |
| H | $CH_3$ | H | $CH_2SOCH_3$ | $CH_3$ | $OCH_3$ | N | |
| H | $CH_3$ | H | $CH_2SOCH_3$ | $OCH_3$ | $OCH_3$ | N | |
| H | $CH_3$ | H | $CH_2SOCH_3$ | $OCH_3$ | Cl | CH | |
| H | $CH_3$ | H | $CH_2CH_2SOCH_3$ | $CH_3$ | $CH_3$ | CH | |
| H | $CH_3$ | H | $CH_2CH_2SOCH_3$ | $CH_3$ | $OCH_3$ | CH | |
| H | $CH_3$ | H | $CH_2CH_2SOCH_3$ | $OCH_3$ | $OCH_3$ | CH | |
| H | $CH_3$ | H | $CH_2CH_2SOCH_3$ | $CH_3$ | $CH_3$ | N | |
| H | $CH_3$ | H | $CH_2CH_2SOCH_3$ | $CH_3$ | $OCH_3$ | N | |
| H | $CH_3$ | H | $CH_2CH_2SOCH_3$ | $OCH_3$ | $OCH_3$ | N | |
| H | $CH_3$ | H | $CH_2CH_2SOCH_3$ | $OCH_3$ | Cl | CH | |
| H | $CH_3$ | H | $CH_2(CH_2)_3SOCH_3$ | $CH_3$ | $CH_3$ | CH | |
| H | $CH_3$ | H | $CH_2(CH_2)_3SOCH_3$ | $CH_3$ | $OCH_3$ | CH | |
| H | $CH_3$ | H | $CH_2(CH_2)_3SOCH_3$ | $OCH_3$ | $OCH_3$ | CH | |
| H | $CH_3$ | H | $CH_2(CH_2)_3SOCH_3$ | $CH_3$ | $CH_3$ | N | |
| H | $CH_3$ | H | $CH_2(CH_2)_3SOCH_3$ | $OCH_3$ | $OCH_3$ | N | |
| H | $CH_3$ | H | $CH_2(CH_2)_3SOCH_3$ | $OCH_3$ | Cl | CH | |
| H | $CH_3$ | H | $CH_2SO_2CH_3$ | $CH_3$ | $CH_3$ | CH | |
| H | $CH_3$ | H | $CH_2SO_2CH_3$ | $CH_3$ | $OCH_3$ | CH | |
| H | $CH_3$ | H | $CH_2SO_2CH_3$ | $OCH_3$ | $OCH_3$ | CH | |
| H | $CH_3$ | H | $CH_2SO_2CH_3$ | $CH_3$ | $CH_3$ | N | |
| H | $CH_3$ | H | $CH_2SO_2CH_3$ | $CH_3$ | $OCH_3$ | N | |
| H | $CH_3$ | H | $CH_2SO_2CH_3$ | $OCH_3$ | $OCH_3$ | N | |
| H | $CH_3$ | H | $CH_2SO_2CH_3$ | $OCH_3$ | Cl | CH | |
| H | $CH_3$ | H | $CH_2CH_2SO_2CH_3$ | $CH_3$ | $CH_3$ | CH | |
| H | $CH_3$ | H | $CH_2CH_2SO_2CH_3$ | $CH_3$ | $OCH_3$ | CH | |
| H | $CH_3$ | H | $CH_2CH_2SO_2CH_3$ | $OCH_3$ | $OCH_3$ | CH | |
| H | $CH_3$ | H | $CH_2CH_2SO_2CH_3$ | $CH_3$ | $CH_3$ | N | |
| H | $CH_3$ | H | $CH_2CH_2SO_2CH_3$ | $CH_3$ | $OCH_3$ | N | |
| H | $CH_3$ | $CH_3$ | $CH_2CH_2SO_2CH_3$ | $OCH_3$ | $OCH_3$ | N | |
| H | $CH_3$ | H | $CH_2CH_2SO_2CH_3$ | $OCH_3$ | Cl | CH | |
| H | $CH_3$ | H | $CH_2(CH_2)_3SO_2CH_3$ | $CH_3$ | $CH_3$ | CH | |
| H | $CH_3$ | H | $CH_2(CH_2)_3SO_2CH_3$ | $CH_3$ | $OCH_3$ | CH | |
| H | $CH_3$ | H | $CH_2(CH_2)_3SO_2CH_3$ | $OCH_3$ | $OCH_3$ | CH | |
| H | $CH_3$ | H | $CH_2(CH_2)_3SO_2CH_3$ | $CH_3$ | $CH_3$ | N | |
| H | $CH_3$ | H | $CH_2(CH_2)_3SO_2CH_3$ | $CH_3$ | $OCH_3$ | N | |
| H | $CH_3$ | $CH_3$ | $CH_2(CH_2)_3SO_2CH_3$ | $OCH_3$ | $OCH_3$ | N | |
| H | $CH_3$ | H | $CH_2(CH_2)_3SO_2CH_3$ | $OCH_3$ | Cl | CH | |
| H | $CH_3$ | H | $CH_2SOCH_2CH_3$ | $CH_3$ | $CH_3$ | CH | |
| $CH_3$ | $CH_3$ | H | $CH_2SOCH_2CH_3$ | $CH_3$ | $OCH_3$ | CH | |
| H | $CH_3$ | H | $CH_2SO_2CH_2CH_3$ | $OCH_3$ | $OCH_3$ | CH | |
| H | $CH_3$ | H | $CH_2(CH_2)_6SOCH_3$ | $CH_3$ | $CH_3$ | N | |
| H | $CH_3$ | H | $CH_2(CH_2)_6SOCH_3$ | $CH_3$ | $OCH_3$ | N | |
| H | $CH_3$ | H | $CH_2(CH_2)_4SO_2CH_3$ | $OCH_3$ | $OCH_3$ | N | |
| H | $CH_3$ | H | $CH_2(CH_2)_4SO_2CH_3$ | $OCH_3$ | Cl | CH | |
| H | $CH_3$ | H | $CH_2SCN$ | $CH_3$ | $CH_3$ | CH | |
| H | $CH_3$ | H | $CH_2SCN$ | $CH_3$ | $OCH_3$ | CH | |
| H | $CH_3$ | H | $CH_2SCN$ | $OCH_3$ | $OCH_3$ | CH | |
| H | $CH_3$ | H | $CH_2SCN$ | $CH_3$ | $CH_3$ | N | |

TABLE Ia-continued

General Structure Ia

| R | $R_1$ | $R_2$ | $R_3$ | X | Y | Z | m.p. (°C.) |
|---|---|---|---|---|---|---|---|
| H | $CH_3$ | H | $CH_2SCN$ | $CH_3$ | $OCH_3$ | N | |
| H | $CH_3$ | H | $CH_2SCN$ | $OCH_3$ | $OCH_3$ | N | |
| H | $CH_3$ | H | $CH_2SCN$ | $OCH_3$ | Cl | CH | |
| H | $CH_3$ | H | $CH_2CH_2SCN$ | $CH_3$ | $CH_3$ | CH | |
| H | $CH_3$ | H | $CH_2CH_2SCN$ | $CH_3$ | $OCH_3$ | CH | |
| H | $CH_3$ | H | $CH_2CH_2SCN$ | $OCH_3$ | $OCH_3$ | CH | |
| H | $CH_3$ | H | $CH_2CH_2SCN$ | $CH_3$ | $CH_3$ | N | |
| H | $CH_3$ | H | $CH_2CH_2SCN$ | $CH_3$ | $OCH_3$ | N | |
| H | $CH_3$ | H | $CH_2CH_2SCN$ | $OCH_3$ | $OCH_3$ | N | |
| H | $CH_3$ | H | $CH_2CH_2SCN$ | $OCH_3$ | Cl | CH | |
| H | $CH_3$ | H | $CH_2(CH_2)_2SCN$ | $CH_3$ | $CH_3$ | CH | |
| H | $CH_3$ | H | $CH_2(CH_2)_2SCN$ | $CH_3$ | $OCH_3$ | CH | |
| H | $CH_3$ | H | $CH_2(CH_2)_2SCN$ | $OCH_3$ | $OCH_3$ | CH | |
| H | $CH_3$ | H | $CH_2(CH_2)_2SCN$ | $CH_3$ | $CH_3$ | N | |
| H | $CH_3$ | H | $CH_2(CH_2)_2SCN$ | $OCH_3$ | $OCH_3$ | N | |
| H | $CH_3$ | H | $CH_2(CH_2)_2SCN$ | $OCH_3$ | Cl | CH | |
| H | $CH_3$ | H | $CH_2(CH_2)_3SCN$ | $CH_3$ | $CH_3$ | CH | |
| H | $CH_3$ | H | $CH_2(CH_2)_3SCN$ | $CH_3$ | $OCH_3$ | CH | |
| H | $CH_3$ | H | $CH_2(CH_2)_3SCN$ | $OCH_3$ | $OCH_3$ | CH | |
| H | $CH_3$ | H | $CH_2(CH_2)_3SCN$ | $CH_3$ | $CH_3$ | N | |
| H | $CH_3$ | H | $CH_2(CH_2)_3SCN$ | $CH_3$ | $OCH_3$ | N | |
| H | $CH_3$ | H | $CH_2(CH_2)_3SCN$ | $OCH_3$ | $OCH_3$ | N | |
| H | $CH_3$ | H | $CH_2(CH_2)_3SCN$ | $OCH_3$ | Cl | CH | |
| H | $CH_3$ | H | $CH_2CHFSCN$ | $CH_3$ | $CH_3$ | CH | |
| H | $CH_3$ | H | $CH(CF_3)SCN$ | $CH_3$ | $OCH_3$ | CH | |
| H | $CH_3$ | H | $CH_2(CH_2)_5SCN$ | $OCH_3$ | $OCH_3$ | CH | |
| H | $CH_3$ | H | $CH_2CN$ | $CH_3$ | $CH_3$ | N | |
| H | $CH_3$ | H | $CH_2CN$ | $CH_3$ | $OCH_3$ | N | |
| H | $CH_3$ | $CH_3$ | $CH_2CN$ | $OCH_3$ | $OCH_3$ | N | |
| H | $CH_3$ | H | $CH_2CN$ | $OCH_3$ | Cl | CH | |
| H | $CH_3$ | H | $CH_2CN$ | $CH_3$ | $CH_3$ | CH | |
| H | $CH_3$ | H | $CH_2CN$ | $CH_3$ | $OCH_3$ | CH | |
| H | $CH_3$ | H | $CH_2CH_2CN$ | $OCH_3$ | $OCH_3$ | CH | |
| H | $CH_3$ | H | $CH_2CH_2CN$ | $CH_3$ | $CH_3$ | N | |
| H | $CH_3$ | H | $CH_2CH_2CN$ | $CH_3$ | $OCH_3$ | N | |
| H | $CH_3$ | H | $CH_2CH_2CN$ | $OCH_3$ | $OCH_3$ | N | |
| H | $CH_3$ | H | $CH_2CH_2CN$ | $OCH_3$ | Cl | CH | |
| H | $CH_3$ | H | $CH_2CH_2CN$ | $CH_3$ | $CH_3$ | CH | |
| $CH_3$ | $CH_3$ | H | $CH_2CH_2CN$ | $CH_3$ | $OCH_3$ | CH | |
| H | $CH_3$ | H | $CH_2CH_2CN$ | $OCH_3$ | $OCH_3$ | CH | |
| H | $CH_3$ | H | $CH_2(CH_2)_3CN$ | $CH_3$ | $CH_3$ | N | |
| H | $CH_3$ | H | $CH_2(CH_2)_3CN$ | $CH_3$ | $OCH_3$ | N | |
| H | $CH_3$ | H | $CH_2(CH_2)_3CN$ | $OCH_3$ | $OCH_3$ | N | |
| H | $CH_3$ | H | $CH_2(CH_2)_3CN$ | $OCH_3$ | Cl | CH | |
| H | $CH_3$ | H | $CH_2(CH_2)_4CN$ | $CH_3$ | $CH_3$ | CH | |
| H | $CH_3$ | H | $CH_2(CH_2)_2CH(CN)_2$ | $CH_3$ | $OCH_3$ | CH | |
| H | $CH_3$ | H | $CH(CH_3)CH_2CN$ | $OCH_3$ | $OCH_3$ | CH | |
| H | $CH_3$ | H | $CH(CH_3)CH_2CN$ | $CH_3$ | $CH_3$ | N | |
| H | $CH_3$ | H | $CH(CH_3)CH_2CN$ | $CH_3$ | $OCH_3$ | N | |
| H | $CH_3$ | H | $CH(CH_3)CH_2CN$ | $OCH_3$ | $OCH_3$ | N | |
| H | $CH_3$ | H | $CH(CH_3)CH_2CN$ | $OCH_3$ | Cl | CH | |
| H | $CH_3$ | H | $CH_2SP(O)(CH_3)_2$ | $CH_3$ | $CH_3$ | CH | |
| H | $CH_3$ | H | $CH_2SP(O)(CH_3)_2$ | $CH_3$ | $OCH_3$ | CH | |
| H | $CH_3$ | H | $CH_2SP(O)(CH_3)_2$ | $OCH_3$ | $OCH_3$ | CH | |
| H | $CH_3$ | H | $CH_2CH_2SP(O)(CH_3)_2$ | $CH_3$ | $CH_3$ | N | |
| H | $CH_3$ | H | $CH_2CH_2SP(O)(CH_3)_2$ | $CH_3$ | $OCH_3$ | N | |
| H | $CH_3$ | H | $CH_2CH_2SP(O)(CH_3)_2$ | $OCH_3$ | $OCH_3$ | N | |
| H | $CH_3$ | H | $CH_2P(S)(CH_3)_2$ | $OCH_3$ | Cl | CH | |
| H | $CH_3$ | H | $CH_2P(S)(CH_3)_2$ | $CH_3$ | $CH_3$ | CH | |
| H | $CH_3$ | H | $CH_2P(S)(CH_3)_2$ | $CH_3$ | $OCH_3$ | CH | |
| H | $CH_3$ | H | $CH_2-CH_2P(S)(CH_3)_2$ | $OCH_3$ | $OCH_3$ | CH | |
| H | $CH_3$ | H | $CH_2-CH_2P(S)(CH_3)_2$ | $CH_3$ | $CH_3$ | N | |
| H | $CH_3$ | H | $CH_2-CH_2P(S)(CH_3)_2$ | $OCH_3$ | $OCH_3$ | N | |
| H | $CH_3$ | H | $CH_2-CH_2P(S)(CH_3)_2$ | $OCH_3$ | Cl | CH | |
| H | $CH_3$ | H | $CH_2-CH_2P(S)(CH_3)_2$ | $CH_3$ | $CH_3$ | CH | |
| H | $CH_3$ | H | $CH_2N(CH_3)_2$ | $CH_3$ | $OCH_3$ | CH | |
| H | $CH_3$ | H | $CH_2N(CH_3)_2$ | $OCH_3$ | $OCH_3$ | CH | |
| H | $CH_3$ | H | $CH_2N(CH_3)_2$ | $CH_3$ | $CH_3$ | N | |
| H | $CH_3$ | H | $CH_2N(CH_3)_2$ | $OCH_3$ | $OCH_3$ | N | |
| H | $CH_3$ | H | $CH_2N(CH_3)_2$ | $OCH_3$ | Cl | CH | |
| H | $CH_3$ | H | $CH_2N(CH_3)_2$ | $CH_3$ | $CH_3$ | CH | |
| H | $CH_3$ | H | $CH_2(CH_2)_3N(CH_3)_2$ | $CH_3$ | $OCH_3$ | CH | |
| H | $CH_3$ | H | $CH_2(CH_2)_3N(CH_3)_2$ | $OCH_3$ | $OCH_3$ | CH | |
| H | $CH_3$ | H | $CH_2(CH_2)_3N(CH_3)_2$ | $CH_3$ | $CH_3$ | N | |
| H | $CH_3$ | H | $CH_2(CH_2)_3N(CH_3)_2$ | $CH_3$ | $OCH_3$ | N | |
| H | $CH_3$ | $CH_3$ | $CH_2(CH_2)_3N(CH_3)_2$ | $OCH_3$ | $OCH_3$ | N | |
| H | $CH_3$ | H | $CH_2(CH_2)_3N(CH_3)_2$ | $OCH_3$ | Cl | CH | |
| H | $CH_3$ | H | $CH_2(CH_2)_3N(CH_3)_2$ | $CH_3$ | $CH_3$ | CH | |
| H | $CH_3$ | H | $CH_2N(CH_3)_2Ph$ | $CH_3$ | $OCH_3$ | CH | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂N(CH₃)₂Ph | OCH₃ | OCH₃ | CH | |
| H | CH₃ | H | CH₂N(CH₃)₂Ph | CH₃ | CH₃ | N | |
| H | CH₃ | H | CH₂N(CH₃)₂Ph | CH₃ | OCH₃ | N | |
| H | CH₃ | H | CH₂—CH(CH₃)N(CH₃)₂ | OCH₃ | OCH₃ | N | |
| H | CH₃ | H | CH₂—CH(CH₃)N(CH₃)₂ | OCH₃ | Cl | CH | |
| H | CH₃ | H | CH₂—CH(CH₃)N(CH₃)₂ | CH₃ | CH₃ | CH | |
| CH₃ | CH₃ | H | CH₂—CH(CH₃)N(CH₃)₂ | CH₃ | OCH₃ | CH | |
| H | CH₃ | H | CH₂—CH(CH₃)N(CH₃)₂ | OCH₃ | OCH₃ | CH | |
| H | CH₃ | H | CH₂CH₂CH(CH₃)₂ | CH₃ | CH₃ | N | |
| H | CH₃ | H | CH₂CH₂CH(CH₃)₂ | CH₃ | OCH₃ | N | |
| H | CH₃ | H | CH₂CH₂CH(CH₃)₂ | OCH₃ | OCH₃ | N | |
| H | CH₃ | H | CH₂CH₂CH(CH₃)₂ | OCH₃ | Cl | CH | |
| H | CH₃ | H | CH₂NHC(O)CH₃ | CH₃ | CH₃ | CH | |
| H | CH₃ | H | CH₂NHC(O)CH₃ | CH₃ | OCH₃ | CH | |
| H | CH₃ | H | CH₂NHC(O)CH₃ | OCH₃ | OCH₃ | CH | |
| H | CH₃ | H | CH₂NHC(O)CH₃ | CH₃ | CH₃ | N | |
| H | CH₃ | H | CH₂NHC(O)CH₃ | CH₃ | OCH₃ | N | |
| H | CH₃ | H | CH₂NHC(O)CH₃ | OCH₃ | OCH₃ | N | |
| H | CH₃ | H | CH₂NHC(O)CH₃ | OCH₃ | Cl | CH | |
| H | CH₃ | H | CH₂CH₂N(CH₃)C(O)CH₃ | CH₃ | CH₃ | CH | |
| H | CH₃ | H | CH₂CH₂N(CH₃)C(O)CH₃ | CH₃ | OCH₃ | CH | |
| H | CH₃ | H | CH₂CH₂N(CH₃)C(O)CH₃ | OCH₃ | OCH₃ | CH | |
| H | CH₃ | H | CH₂CH₂N(CH₃)C(O)CH₃ | CH₃ | CH₃ | N | |
| H | CH₃ | H | CH₂(CH₂)₃NHC(O)CH₃ | CH₃ | OCH₃ | N | |
| H | CH₃ | H | CH₂(CH₂)₃NHC(O)CH₃ | OCH₃ | OCH₃ | N | |
| H | CH₃ | H | CH₂N(CH₃)C(O)OCH₃ | OCH₃ | Cl | CH | |
| H | CH₃ | H | CH₂N(CH₃)C(O)OCH₃ | CH₃ | CH₃ | CH | |
| H | CH₃ | H | CH₂NHC(O)OCH₃ | CH₃ | OCH₃ | CH | |
| H | CH₃ | H | CH₂NHC(O)OCH₃ | OCH₃ | OCH₃ | CH | |
| H | CH₃ | H | CH₂NHC(O)OCH₃ | CH₃ | CH₃ | N | |
| H | CH₃ | H | CH₂NHC(O)OCH₃ | OCH₃ | OCH₃ | N | |
| H | CH₃ | H | CH₂NHC(O)OCH₃ | OCH₃ | Cl | CH | |
| H | CH₃ | H | CH₂NHC(O)OCH₃ | CH₃ | CH₃ | CH | |
| H | CH₃ | H | CH₂(CH₂)₃NHC(O)OCH₃ | CH₃ | OCH₃ | CH | |
| H | CH₃ | H | CH₂(CH₂)₃NHC(O)OCH₃ | OCH₃ | OCH₃ | CH | |
| H | CH₃ | H | CH₂(CH₂)₃NHC(O)OCH₃ | CH₃ | CH₃ | N | |
| H | CH₃ | H | CH₂N(CH₃)C(O)OCH₂CH₃ | CH₃ | OCH₃ | N | |
| H | CH₃ | H | CH(CH₃)NHC(O)OCH₃ | OCH₃ | OCH₃ | N | |
| H | CH₃ | H | CH(CH₃)NHC(O)OCH₃ | OCH₃ | Cl | CH | |
| H | CH₃ | H | CH(CH₃)NHC(O)OCH₃ | CH₃ | CH₃ | CH | |
| H | CH₃ | H | CH₂NHSO₂CH₃ | CH₃ | OCH₃ | CH | |
| H | CH₃ | H | CH₂NHSO₂CH₃ | OCH₃ | OCH₃ | CH | |
| H | CH₃ | H | CH₂NHSO₂CH₃ | CH₃ | CH₃ | N | |
| H | CH₃ | H | CH₂NHSO₂CH₃ | CH₃ | OCH₃ | N | |
| H | CH₃ | CH₃ | CH₂NHSO₂CH₃ | OCH₃ | OCH₃ | N | |
| H | CH₃ | H | CH₂CH₂NHSO₂CH₃ | OCH₃ | Cl | CH | |
| H | CH₃ | H | CH₂CH₂NHSO₂CH₃ | CH₃ | CH₃ | CH | |
| H | CH₃ | H | CH₂CH₂NHSO₂CH₃ | CH₃ | OCH₃ | CH | |
| H | CH₃ | H | CH₂CH₂NHSO₂CH₃ | OCH₃ | OCH₃ | CH | |
| H | CH₃ | H | CH₂CH₂NHSO₂CH₃ | CH₃ | CH₃ | N | |
| H | CH₃ | H | CH₂CH₂NHSO₂CH₃ | CH₃ | OCH₃ | N | |
| H | CH₃ | H | CH₂(CH₂)₃NHSO₂CH₃ | OCH₃ | OCH₃ | N | |
| H | CH₃ | H | CH₂(CH₂)₃NHSO₂CH₃ | OCH₃ | Cl | CH | |
| H | CH₃ | H | CH₂(CH₂)₃NHSO₂CH₃ | CH₃ | CH₃ | CH | |
| CH₃ | CH₃ | H | CH₂NHP(O)(CH₃)₂ | CH₃ | OCH₃ | CH | |
| H | CH₃ | H | CH₂NHP(O)(CH₃)₂ | OCH₃ | OCH₃ | CH | |
| H | CH₃ | H | CH₂NHP(O)(CH₃)₂ | CH₃ | CH₃ | N | |
| H | CH₃ | H | CH₂NHP(O)(OCH₃)₂ | CH₃ | OCH₃ | N | |
| H | CH₃ | H | CH₂NHP(O)(OCH₃)₂ | OCH₃ | OCH₃ | N | |
| H | CH₃ | H | CH₂NHP(O)(OCH₃)₂ | OCH₃ | Cl | CH | |
| H | CH₃ | H | CH=CH₂ | CH₃ | CH₃ | CH | |
| H | CH₃ | H | CH=CH₂ | CH₃ | OCH₃ | CH | |
| H | CH₃ | H | CH₂NO₂ | CH₃ | CH₃ | CH | |
| H | CH₃ | H | CH₂NO₂ | CH₃ | OCH₃ | CH | |
| H | CH₃ | H | CH₂NO₂ | OCH₃ | OCH₃ | CH | |
| H | CH₃ | H | CH₂NO₂ | CH₃ | CH₃ | N | |
| H | CH₃ | H | CH₂NO₂ | CH₃ | OCH₃ | N | |
| H | CH₃ | H | CH₂NO₂ | OCH₃ | OCH₃ | N | |
| H | CH₃ | H | CH₂NO₂ | OCH₃ | Cl | CH | |
| H | CH₃ | H | CH₂CH₂NO₂ | CH₃ | CH₃ | CH | |
| H | CH₃ | H | CH₂CH₂NO₂ | CH₃ | OCH₃ | CH | |
| H | CH₃ | H | CH₂CH₂NO₂ | OCH₃ | OCH₃ | CH | |
| H | CH₃ | H | CH₂CH₂NO₂ | CH₃ | CH₃ | N | |
| H | CH₃ | H | CH₂CH₂NO₂ | CH₃ | OCH₃ | N | |
| H | CH₃ | H | CH₂CH₂NO₂ | OCH₃ | OCH₃ | N | |
| H | CH₃ | H | CH₂CH₂NO₂ | OCH₃ | Cl | CH | |
| H | CH₃ | H | CH₂C(O)CH₃ | CH₃ | CH₃ | CH | |
| H | CH₃ | H | CH₂C(O)CH₃ | CH₃ | OCH₃ | CH | |
| H | CH₃ | H | CH₂C(O)CH₃ | OCH₃ | OCH₃ | N | |
| H | CH₃ | H | CH₂C(O)CH₃ | CH₃ | CH₃ | N | |

TABLE Ia-continued

General Structure Ia

| R | $R_1$ | $R_2$ | $R_3$ | X | Y | Z | m.p. (°C.) |
|---|---|---|---|---|---|---|---|
| H | $CH_3$ | H | $CH_2C(O)CH_3$ | $OCH_3$ | $OCH_3$ | N | |
| H | $CH_3$ | H | $CH_2C(O)CH_3$ | $OCH_3$ | Cl | CH | |
| H | $CH_3$ | H | $CH_2C(O)CH_2CH_3$ | $CH_3$ | $CH_3$ | CH | |
| H | $CH_3$ | H | $CH_2C(O)CH_2CH_3$ | $CH_3$ | $OCH_3$ | CH | |
| H | $CH_3$ | H | $CH_2C(O)CH_2CH_3$ | $OCH_3$ | $OCH_3$ | CH | |
| H | $CH_3$ | H | $CH_2C(O)CH_2CH_3$ | $CH_3$ | $CH_3$ | N | |
| H | $CH_3$ | H | $CH_2C(O)CH_2CH_3$ | $CH_3$ | $OCH_3$ | N | |
| H | $CH_3$ | H | $CH_2C(O)CH_2CH_3$ | $OCH_3$ | $OCH_3$ | N | |
| H | $CH_3$ | H | $CH_2C(O)CH_2CH_3$ | $OCH_3$ | Cl | CH | |
| H | $CH_3$ | H | $CH_2(CH_2)_3C(O)CH_3$ | $CH_3$ | $CH_3$ | CH | |
| H | $CH_3$ | H | $CH_2(CH_2)_3C(O)CH_3$ | $CH_3$ | $OCH_3$ | CH | |
| H | $CH_3$ | H | $CH_2(CH_2)_3C(O)CH_3$ | $OCH_3$ | $OCH_3$ | CH | |
| H | $CH_3$ | H | $CH_2(CH_2)_3C(O)CH_3$ | $CH_3$ | $CH_3$ | N | |
| H | $CH_3$ | H | $CH_2(CH_2)_3C(O)CH_3$ | $CH_3$ | $OCH_3$ | N | |
| H | $CH_3$ | $CH_3$ | $CH_2(CH_2)_3C(O)CH_3$ | $OCH_3$ | $OCH_3$ | N | |
| H | $CH_3$ | H | $CH_2(CH_2)_3C(O)CH_3$ | $OCH_3$ | Cl | CH | |
| H | $CH_3$ | H | $CH_2CH_2C(O)CH_3$ | $CH_3$ | $CH_3$ | CH | |
| H | $CH_3$ | H | $CH_2CH_2C(O)CH_3$ | $CH_3$ | $OCH_3$ | CH | |
| H | $CH_3$ | H | $CH_2CH_2C(O)CH_3$ | $OCH_3$ | $OCH_3$ | CH | |
| H | $CH_3$ | H | $CH_2CH_2C(O)CH_3$ | $CH_3$ | $CH_3$ | N | |
| H | $CH_3$ | H | $CH_2-CH(CH_3)C(O)CH_3$ | $CH_3$ | $OCH_3$ | N | |
| H | $CH_3$ | $CH_3$ | $CH_2-CH(CH_2)C(O)CH_3$ | $OCH_3$ | $OCH_3$ | N | |
| H | $CH_3$ | H | $CH_2-CH(CH_2)C(O)CH_3$ | $OCH_3$ | Cl | CH | |
| H | $CH_3$ | H | $CH_2-CH(CH_3)C(O)CH_3$ | $CH_3$ | $CH_3$ | CH | |
| $CH_3$ | $CH_3$ | $CH_3$ | $CH_2-CH(CH_2)C(O)CH_3$ | $CH_3$ | $OCH_3$ | CH | |
| H | $CH_3$ | H | $CH_2(CH_2)_6C(O)CH_2CH_3$ | $OCH_3$ | $OCH_3$ | CH | |
| H | $CH_3$ | H | $CH_2(CH_2)_6C(O)CH_2CH_3$ | $CH_3$ | $CH_3$ | N | |
| H | $CH_3$ | H | $CH_2(CH_2)_6C(O)CH_2CH_3$ | $CH_3$ | $OCH_3$ | N | |
| H | $CH_3$ | H | $CH_2(CH_2)_6C(O)CH_2CH_3$ | $OCH_3$ | $OCH_3$ | N | |
| H | $CH_3$ | H | $CH_2(CH_2)_6C(O)CH_2CH_3$ | $OCH_3$ | Cl | CH | |
| H | $CH_3$ | H | $CH_2C(O)OCH_3$ | $CH_3$ | $CH_3$ | CH | |
| H | $CH_3$ | H | $CH_2C(O)OCH_3$ | $CH_3$ | $OCH_3$ | CH | |
| H | $CH_3$ | H | $CH_2C(O)OCH_3$ | $OCH_3$ | $OCH_3$ | CH | |
| H | $CH_3$ | H | $CH_2C(O)OCH_3$ | $CH_3$ | $CH_3$ | N | |
| H | $CH_3$ | H | $CH_2C(O)OCH_3$ | $CH_3$ | $OCH_3$ | N | |
| H | $CH_3$ | H | $CH_2C(O)OCH_3$ | $OCH_3$ | $OCH_3$ | N | |
| H | $CH_3$ | H | $CH_2C(O)OCH_3$ | $OCH_3$ | Cl | CH | |
| H | $CH_3$ | H | $CH_2C(O)OCH_2CH_3$ | $CH_3$ | $CH_3$ | CH | |
| H | $CH_3$ | H | $CH_2C(O)OCH_2CH_3$ | $CH_3$ | $OCH_3$ | CH | |
| H | $CH_3$ | H | $CH_2C(O)OCH_2CH_3$ | $OCH_3$ | $OCH_3$ | CH | |
| H | $CH_3$ | H | $CH_2C(O)OCH_2CH_3$ | $CH_3$ | $CH_3$ | N | |
| H | $CH_3$ | H | $CH_2C(O)OCH_2CH_3$ | $CH_3$ | $OCH_3$ | N | |
| H | $CH_3$ | H | $CH_2C(O)OCH_2CH_3$ | $OCH_3$ | $OCH_3$ | N | |
| H | $CH_3$ | H | $CH_2C(O)OCH_2CH_3$ | $OCH_3$ | Cl | CH | |
| H | $CH_3$ | H | $CH_2CH_2C(O)CH_3$ | $CH_3$ | $CH_3$ | CH | |
| H | $CH_3$ | H | $CH_2CH_2C(O)CH_3$ | $CH_3$ | $OCH_3$ | CH | |
| H | $CH_3$ | H | $CH_2CH_2C(O)CH_3$ | $OCH_3$ | $OCH_3$ | N | |
| H | $CH_3$ | H | $CH_2CH_2C(O)CH_3$ | $CH_3$ | $CH_3$ | N | |
| H | $CH_3$ | H | $CH_2CH_2C(O)CH_3$ | $OCH_3$ | $OCH_3$ | N | |
| H | $CH_3$ | H | $CH_2CH_2C(O)CH_3$ | $OCH_3$ | Cl | CH | |
| H | $CH_3$ | H | $CH_2C(O)N(CH_3)_2$ | $CH_3$ | $CH_3$ | CH | |
| H | $CH_3$ | H | $CH_2C(O)N(CH_3)_2$ | $CH_3$ | $OCH_3$ | CH | |
| H | $CH_3$ | H | $CH_2C(O)N(CH_3)_2$ | $OCH_3$ | $OCH_3$ | CH | |
| H | $CH_3$ | H | $CH_2C(O)N(CH_3)_2$ | $CH_3$ | $CH_3$ | N | |
| H | $CH_3$ | H | $CH_2C(O)N(CH_3)_2$ | $CH_3$ | $OCH_3$ | N | |
| H | $CH_3$ | H | $CH_2C(O)N(CH_3)_2$ | $OCH_3$ | $OCH_3$ | N | |
| H | $CH_3$ | H | $CH_2C(O)N(CH_3)_2$ | $OCH_3$ | Cl | CH | |
| H | $CH_3$ | H | $CH_2CH_2C(O)N(CH_3)_2$ | $CH_3$ | $CH_3$ | CH | |
| H | $CH_3$ | H | $CH_2CH_2C(O)N(CH_3)_2$ | $CH_3$ | $OCH_3$ | CH | |
| H | $CH_3$ | H | $CH_2CH_2C(O)N(CH_3)_2$ | $OCH_3$ | $OCH_3$ | CH | |
| H | $CH_3$ | H | $CH_2CH_2C(O)N(CH_3)_2$ | $CH_3$ | $CH_3$ | N | |
| H | $CH_3$ | H | $CH_2CH_2C(O)N(CH_3)_2$ | $CH_3$ | $OCH_3$ | N | |
| H | $CH_3$ | $CH_3$ | $CH_2CH_2C(O)N(CH_3)_2$ | $OCH_3$ | $OCH_3$ | N | |
| H | $CH_3$ | H | $CH_2CH_2C(O)N(CH_3)_2$ | $OCH_3$ | Cl | CH | |
| H | $CH_3$ | H | $CH_2C(O)N(CH_3)CH_2CH_3$ | $CH_3$ | $CH_3$ | CH | |
| H | $CH_3$ | H | $CH_2C(O)N(CH_3)CH_2CH_3$ | $CH_3$ | $OCH_3$ | CH | |
| H | $CH_3$ | H | $CH_2C(O)N(CH_3)CH_2CH_3$ | $OCH_3$ | $OCH_3$ | CH | |
| H | $CH_3$ | H | $CH_2C(O)N(CH_3)CH_2CH_3$ | $CH_3$ | $CH_3$ | N | |
| H | $CH_3$ | H | $CH_2C(O)N(CH_3)CH_2OCH_3$ | $CH_3$ | $OCH_3$ | N | |
| H | $CH_3$ | H | $CH_2C(O)N(CH_3)CH_2OCH_3$ | $OCH_3$ | $OCH_3$ | N | |
| H | $CH_3$ | H | $CH_2C(O)N(CH_3)CH_2OCH_3$ | $OCH_3$ | Cl | CH | |
| H | $CH_3$ | H | $CH_2SeCH_3$ | $CH_3$ | $CH_3$ | CH | |
| $CH_3$ | $CH_3$ | H | $CH_2SeCH_3$ | $CH_3$ | $OCH_3$ | CH | |
| H | $CH_3$ | H | $CH_2SeCH_3$ | $OCH_3$ | $OCH_3$ | CH | |
| H | $CH_3$ | H | $CH_2SePh$ | $CH_3$ | $CH_3$ | N | |
| H | $CH_3$ | H | $CH_2SePh$ | $CH_3$ | $OCH_3$ | N | |
| H | $CH_3$ | H | $CH_2-CH_2SeCH_3$ | $OCH_3$ | $OCH_3$ | N | |
| H | $CH_3$ | H | $CH_2-CH_2SeCH_3$ | $OCH_3$ | Cl | CH | |
| H | $CH_3$ | H | $CH=CH_2$ | $OCH_3$ | $OCH_3$ | CH | |
| H | $CH_3$ | H | $CH=CH_2$ | $CH_3$ | $CH_3$ | N | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH=CH₂ | CH₃ | OCH₃ | N | |
| H | CH₃ | H | CH=CH₂ | OCH₃ | OCH₃ | N | |
| H | CH₃ | H | CH=CH₂ | OCH₃ | Cl | CH | |
| H | CH₃ | H | CH=CH—CH₃ | CH₃ | CH₃ | CH | |
| H | CH₃ | H | CH=CH—CH₃ | CH₃ | OCH₃ | CH | |
| H | CH₃ | H | CH=CH—CH₃ | OCH₃ | OCH₃ | CH | |
| H | CH₃ | H | CH=CH—CH₃ | CH₃ | CH₃ | N | |
| H | CH₃ | H | CH=CH—CH₃ | CH₃ | OCH₃ | N | |
| H | CH₃ | H | CH=CH—CH₃ | OCH₃ | OCH₃ | N | |
| H | CH₃ | H | CH=CH—CH₃ | OCH₃ | Cl | CH | |
| H | CH₃ | H | CH=CH—CH₂—CH₃ | CH₃ | CH₃ | CH | |
| H | CH₃ | H | CH=CH—CH₂—CH₃ | CH₃ | OCH₃ | CH | |
| H | CH₃ | H | CH=CH—CH₂—CH₃ | OCH₃ | OCH₃ | CH | |
| H | CH₃ | H | CH=CH—CH₂—CH₃ | CH₃ | CH₃ | N | |
| H | CH₃ | H | CH=CH—CH₂—CH₃ | OCH₃ | OCH₃ | N | |
| H | CH₃ | H | CH=CH—CH₂—CH₃ | OCH₃ | Cl | CH | |
| H | CH₃ | H | CH=C(CH₃)₂ | CH₃ | CH₃ | CH | |
| H | CH₃ | H | CH=C(CH₃)₂ | CH₃ | OCH₃ | CH | |
| H | CH₃ | H | CH=C(CH₃)₂ | OCH₃ | OCH₃ | CH | |
| H | CH₃ | H | CH=C(CH₃)₂ | CH₃ | CH₃ | N | |
| H | CH₃ | H | CH=C(CH₃)₂ | CH₃ | OCH₃ | N | |
| H | CH₃ | H | CH=C(CH₃)₂ | OCH₃ | OCH₃ | N | |
| H | CH₃ | H | CH=C(CH₃)₂ | OCH₃ | Cl | CH | |
| H | CH₃ | H | CH=CH(CH₂)₃CH₃ | CH₃ | CH₃ | CH | |
| H | CH₃ | H | CH=CH(CH₂)₃CH₃ | CH₃ | OCH₃ | CH | |
| H | CH₃ | H | CH=CH(CH₂)₃CH₃ | OCH₃ | OCH₃ | CH | |
| H | CH₃ | H | CH=CH(CH₂)₃CH₃ | CH₃ | CH₃ | N | |
| H | CH₃ | H | CH=CH(CH₂)₃CH₃ | CH₃ | OCH₃ | N | |
| H | CH₃ | CH₃ | CH=CH(CH₂)₃CH₃ | OCH₃ | OCH₃ | N | |
| H | CH₃ | H | CH=CH(CH₂)₃CH₃ | OCH₃ | Cl | CH | |
| H | CH₃ | H | CH=C(CH₃)CH₂CH₃ | CH₃ | CH₃ | CH | |
| H | CH₃ | H | CH=C(CH₃)CH₂CH₃ | CH₃ | OCH₃ | CH | |
| H | CH₃ | H | CH=C(CH₃)CH₂CH₃ | OCH₃ | OCH₃ | CH | |
| H | CH₃ | H | CH=CH—CH(CH₃)₂ | CH₃ | CH₃ | N | |
| H | CH₃ | H | CH=CH—CH(CH₃)₂ | CH₃ | OCH₃ | N | |
| H | CH₃ | H | CH=CH—CH(CH₃)₂ | OCH₃ | OCH₃ | N | |
| H | CH₃ | H | CH=CH—CH(CH₃)₂ | OCH₃ | Cl | CH | |
| H | CH₃ | H | CH=CH(CH₂)₄CH₃ | CH₃ | CH₃ | CH | |
| CH₃ | CH₃ | H | CH=CH(CH₂)₄CH₃ | CH₃ | OCH₃ | CH | |
| H | CH₃ | H | CH=CH(CH₂)₆CH₃ | OCH₃ | OCH₃ | CH | |
| H | CH₃ | H | CH=CH(CH₂)₆CH₃ | CH₃ | CH₃ | N | |
| H | CH₃ | H | CH=CH(CH₂)₆CH₃ | CH₃ | OCH₃ | N | |
| H | CH₃ | H | CH=C(CH₃)(CH₂)₃CH₃ | OCH₃ | OCH₃ | N | |
| H | CH₃ | H | CH=C(CH₃)(CH₂)₃CH₃ | OCH₃ | Cl | CH | |
| H | CH₃ | H | CH₂CH=CH₂ | CH₃ | CH₃ | CH | |
| H | CH₃ | H | CH₂CH=CH₂ | CH₃ | OCH₃ | CH | |
| H | CH₃ | H | CH₂CH=CH₂ | OCH₃ | OCH₃ | CH | |
| H | CH₃ | H | CH₂CH=CH₂ | CH₃ | CH₃ | N | |
| H | CH₃ | H | CH₂CH=CH₂ | CH₃ | OCH₃ | N | |
| H | CH₃ | H | CH₂CH=CH₂ | OCH₃ | OCH₃ | N | |
| H | CH₃ | H | CH₂CH=CH₂ | OCH₃ | Cl | CH | |
| H | CH₃ | H | CH₂CH₂CH=CH₂ | CH₃ | CH₃ | CH | |
| H | CH₃ | H | CH₂CH₂CH=CH₂ | CH₃ | OCH₃ | CH | |
| H | CH₃ | H | CH₂CH₂CH=CH₂ | OCH₃ | OCH₃ | CH | |
| H | CH₃ | H | CH₂CH₂CH=CH₂ | CH₃ | CH₃ | N | |
| H | CH₃ | H | CH₂CH₂CH=CH₂ | CH₃ | OCH₃ | N | |
| H | CH₃ | H | CH₂CH₂CH=CH₂ | OCH₃ | OCH₃ | N | |
| H | CH₃ | H | CH₂CH₂CH=CH₂ | OCH₃ | Cl | CH | |
| H | CH₃ | H | CH₂CH=CHCH₃ | CH₃ | CH₃ | CH | |
| H | CH₃ | H | CH₂CH=CHCH₃ | CH₃ | OCH₃ | CH | |
| H | CH₃ | H | CH₂CH=CHCH₃ | OCH₃ | OCH₃ | CH | |
| H | CH₃ | H | CH₂CH=CHCH₃ | CH₃ | CH₃ | N | |
| H | CH₃ | H | CH₂—CH=CH—CH₃ | OCH₃ | OCH₃ | N | |
| H | CH₃ | H | CH₂—CH=CH—CH₃ | OCH₃ | Cl | CH | |
| H | CH₃ | H | CH₂—CH=C(CH₃)₂ | CH₃ | CH₃ | CH | |
| H | CH₃ | H | CH₂—CH=C(CH₃)₂ | CH₃ | OCH₃ | CH | |
| H | CH₃ | H | CH₂—CH=C(CH₃)₂ | OCH₃ | OCH₃ | CH | |
| H | CH₃ | H | CH₂—CH=C(CH₃)₂ | CH₃ | CH₃ | N | |
| H | CH₃ | H | CH₂—CH=C(CH₃)₂ | CH₃ | OCH₃ | N | |
| H | CH₃ | H | CH₂—CH=C(CH₃)₂ | OCH₃ | OCH₃ | N | |
| H | CH₃ | H | CH₂—CH=CH(CH₂)₃CH₃ | OCH₃ | Cl | CH | |
| H | CH₃ | H | CH₂—CH=CH(CH₂)₃CH₃ | CH₃ | CH₃ | CH | |
| H | CH₃ | H | CH₂—CH=CH(CH₂)₃CH₃ | CH₃ | OCH₃ | CH | |
| H | CH₃ | H | CH₂—CH=CH(CH₂)₃CH₃ | OCH₃ | OCH₃ | CH | |
| H | CH₃ | H | CH₂—CH=CH(CH₂)₃CH₃ | CH₃ | CH₃ | N | |
| H | CH₃ | H | CH₂—CH=CH(CH₂)₃CH₃ | CH₃ | OCH₃ | N | |
| H | CH₃ | CH₃ | CH₂—CH=CH(CH₂)₃CH₃ | OCH₃ | OCH₃ | N | |
| H | CH₃ | H | CH₂—CH₂—CH=CH₂ | OCH₃ | Cl | CH | |
| H | CH₃ | H | CH₂—CH₂—CH=CH₂ | CH₃ | CH₃ | CH | |
| H | CH₃ | H | CH₂=CH₂—CH=CH₂ | CH₃ | OCH₃ | CH | |

TABLE Ia-continued

General Structure Ia

| R | R₁ | R₂ | R₃ | X | Y | Z | m.p. (°C.) |
|---|----|----|----|---|---|---|---|
| H | CH₃ | H | CH₂—CH₂—CH=CH₂ | OCH₃ | OCH₃ | CH | |
| H | CH₃ | H | CH₂—CH₂—CH=CH₂ | CH₃ | CH₃ | N | |
| H | CH₃ | H | CH₂—(CH₂)₄CH=CH₂ | CH₃ | OCH₃ | N | |
| H | CH₃ | H | CH₂—CH=CH—CH(CH₃)₂ | OCH₃ | OCH₃ | N | |
| H | CH₃ | H | CH₂—CH=CH—CH(CH₃)₂ | OCH₃ | Cl | CH | |
| H | CH₃ | H | CH₂—CH=CH—CH(CH₃)₂ | CH₃ | CH₃ | CH | |
| CH₃ | CH₃ | H | CH₂—CH=CH—CH(CH₃)₂ | CH₃ | OCH₃ | CH | |
| H | CH₃ | H | CH₂—CH=CH—CH(CH₃)₂ | OCH₃ | OCH₃ | CH | |
| H | CH₃ | H | CH₂—CH=CH—CH=CH₂ | CH₃ | CH₃ | N | |
| H | CH₃ | H | CH₂—CH=CH—CH=CH₂ | CH₃ | OCH₃ | N | |
| H | CH₃ | H | CH₂—CH=CH—CH=CH₂ | OCH₃ | OCH₃ | N | |
| H | CH₃ | H | CH₂—CH=CH—CH=CH₂ | OCH₃ | Cl | CH | |
| H | CH₃ | H | C≡CH | CH₃ | CH₃ | CH | |
| H | CH₃ | H | C≡CH | CH₃ | OCH₃ | CH | |
| H | CH₃ | H | C≡CH | OCH₃ | OCH₃ | CH | |
| H | CH₃ | H | C≡CH | CH₃ | CH₃ | N | |
| H | CH₃ | H | C≡CH | CH₃ | OCH₃ | N | |
| H | CH₃ | H | C≡CH | OCH₃ | OCH₃ | N | |
| H | CH₃ | H | C≡CH | OCH₃ | Cl | CH | |
| H | CH₃ | H | C≡C—CH₃ | CH₃ | CH₃ | CH | |
| H | CH₃ | H | C≡C—CH₃ | CH₃ | OCH₃ | CH | |
| H | CH₃ | H | C≡C—CH₃ | OCH₃ | OCH₃ | CH | |
| H | CH₃ | H | C≡C—CH₃ | CH₃ | CH₃ | N | |
| H | CH₃ | H | C≡C—CH₃ | CH₃ | OCH₃ | N | |
| H | CH₃ | H | C≡C—CH₃ | OCH₃ | OCH₃ | N | |
| H | CH₃ | H | C≡C—CH₃ | OCH₃ | Cl | CH | |
| H | CH₃ | H | C≡C(CH₂)₂CH₃ | CH₃ | CH₃ | CH | |
| H | CH₃ | H | C≡C(CH₂)₂CH₃ | CH₃ | OCH₃ | CH | |
| H | CH₃ | H | C≡C(CH₂)₂CH₃ | OCH₃ | OCH₃ | CH | |
| H | CH₃ | H | C≡C(CH₂)₂CH₃ | CH₃ | CH₃ | N | |
| H | CH₃ | H | C≡C(CH₂)₂CH₃ | OCH₃ | OCH₃ | N | |
| H | CH₃ | H | CH₂—C≡CH | OCH₃ | Cl | CH | |
| H | CH₃ | H | CH₂—C≡CH | CH₃ | CH₃ | CH | |
| H | CH₃ | H | CH₂—C≡CH | OCH₃ | OCH₃ | CH | |
| H | CH₃ | H | CH₂—C≡CH | CH₃ | CH₃ | N | |
| H | CH₃ | H | CH₂—C≡CH | CH₃ | OCH₃ | N | |
| H | CH₃ | H | CH₂—C≡CH | OCH₃ | OCH₃ | N | |
| H | CH₃ | H | CH₂—C≡C—CH₃ | OCH₃ | Cl | CH | |
| H | CH₃ | H | CH₂—C≡C—CH₃ | CH₃ | CH₃ | CH | |
| H | CH₃ | H | CH₂—C≡C—CH₃ | CH₃ | OCH₃ | CH | |
| H | CH₃ | H | CH₂—C≡C—CH₃ | OCH₃ | OCH₃ | CH | |
| H | CH₃ | H | CH₂—C≡C—CH₃ | CH₃ | CH₃ | N | |
| H | CH₃ | H | CH₂—C≡C—CH₃ | CH₃ | OCH₃ | N | |
| H | CH₃ | CH₃ | CH₂—C≡C—CH₃ | OCH₃ | OCH₃ | N | |
| H | CH₃ | H | CH₂—CH₂—C≡CH | OCH₃ | Cl | CH | |
| H | CH₃ | H | CH₂—CH₂—C≡CH | CH₃ | CH₃ | CH | |
| H | CH₃ | H | CH₂—CH₂—C≡CH | CH₃ | OCH₃ | CH | |
| H | CH₃ | H | CH₂—CH₂—C≡CH | OCH₃ | OCH₃ | CH | |
| H | CH₃ | H | CH₂—CH₂—C≡CH | CH₃ | CH₃ | N | |
| H | CH₃ | H | CH₂—CH₂—C≡CH | CH₃ | OCH₃ | N | |
| H | CH₃ | H | CH₂—CH₂—C≡CH | OCH₃ | OCH₃ | N | |
| H | CH₃ | H | CH₂—C≡C—CH(CH₃)₂ | OCH₃ | Cl | CH | |
| H | CH₃ | H | CH₂—C≡C—CH(CH₃)₂ | CH₃ | CH₃ | CH | |
| CH₃ | CH₃ | H | CH₂—C≡C—CH(CH₃)₂ | CH₃ | OCH₃ | CH | |
| H | CH₃ | H | C≡C—(CH₂)₆CH₃ | OCH₃ | OCH₃ | CH | |
| H | CH₃ | H | C≡C—(CH₂)₆CH₃ | CH₃ | CH₃ | N | |
| H | CH₃ | H | C≡C—(CH₂)₆CH₃ | CH₃ | OCH₃ | N | |
| H | CH₃ | H | CH₂(CH₂)₇C≡CH | OCH₃ | OCH₃ | N | |
| H | CH₃ | H | CH₂(CH₂)₇C≡CH | OCH₃ | Cl | CH | |
| H | CH₃ | H | 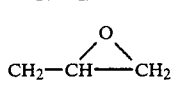 | CH₃ | CH₃ | CH | |
| H | CH₃ | H | 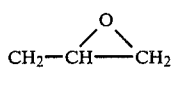 | CH₃ | OCH₃ | CH | |
| H | CH₃ | H | 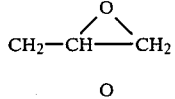 | OCH₃ | OCH₃ | CH | |
| H | CH₃ | H | 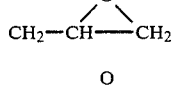 | CH₃ | CH₃ | N | |
| H | CH₃ | H | 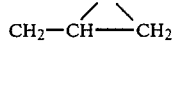 | CH₃ | OCH₃ | N | |

TABLE Ia-continued

General Structure Ia

| R | R₁ | R₂ | R₃ | X | Y | Z | m.p. (°C.) |
|---|----|----|----|---|---|---|------------|
| H | CH₃ | H | 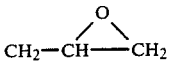 | OCH₃ | OCH₃ | N | |
| H | CH₃ | H | 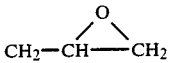 | OCH₃ | Cl | CH | |
| H | CH₃ | H | 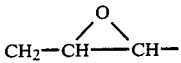 | CH₃ | CH₃ | CH | |
| H | CH₃ | H | 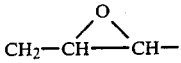 | CH₃ | OCH₃ | CH | |
| H | CH₃ | H | 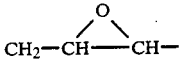 | OCH₃ | OCH₃ | CH | |
| H | CH₃ | H | 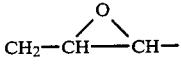 | CH₃ | CH₃ | N | |
| H | CH₃ | H | 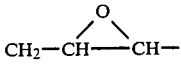 | CH₃ | OCH₃ | N | |
| H | CH₃ | H | 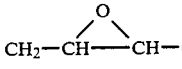 | OCH₃ | OCH₃ | N | |
| H | CH₃ | H | 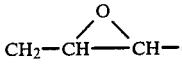 | OCH₃ | Cl | CH | |
| H | CH₃ | H | 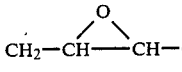 | CH₃ | CH₃ | CH | |
| H | CH₃ | H | 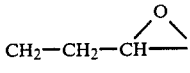 | CH₃ | OCH₃ | CH | |
| H | CH₃ | H | 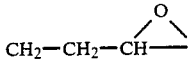 | OCH₃ | OCH₃ | CH | |
| H | CH₃ | H | 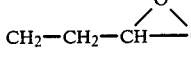 | CH₃ | CH₃ | N | |
| H | CH₃ | H | 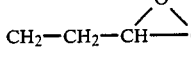 | OCH₃ | OCH₃ | N | |
| H | CH₃ | H | 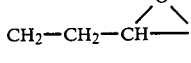 | OCH₃ | Cl | CH | |
| H | CH₃ | H | cyclobutyl | CH₃ | CH₃ | CH | |
| H | CH₃ | H | cyclobutyl | CH₃ | OCH₃ | CH | |
| H | CH₃ | H | cyclobutyl | OCH₃ | OCH₃ | CH | |
| H | CH₃ | H | cyclobutyl | CH₃ | CH₃ | N | |
| H | CH₃ | H | cyclobutyl | CH₃ | OCH₃ | N | |
| H | CH₃ | H | cyclobutyl | OCH₃ | OCH₃ | N | |
| H | CH₃ | H | cyclobutyl | OCH₃ | Cl | CH | |
| H | CH₃ | H | cyclopentyl | CH₃ | CH₃ | CH | |
| H | CH₃ | H | cyclopentyl | CH₃ | OCH₃ | CH | |
| H | CH₃ | H | cyclopentyl | OCH₃ | OCH₃ | CH | |
| H | CH₃ | H | cyclopentyl | CH₃ | CH₃ | N | |
| H | CH₃ | H | cyclopentyl | CH₃ | OCH₃ | N | |
| H | CH₃ | CH₃ | cyclopentyl | OCH₃ | OCH₃ | N | |
| H | CH₃ | H | cyclopentyl | OCH₃ | Cl | CH | |
| H | CH₃ | H | cyclohexyl | CH₃ | CH₃ | CH | |
| H | CH₃ | H | cyclohexyl | CH₃ | OCH₃ | CH | |
| H | CH₃ | H | cyclohexyl | OCH₃ | OCH₃ | CH | |
| H | CH₃ | H | cyclohexyl | CH₃ | CH₃ | N | |
| H | CH₃ | H | cyclohexyl | CH₃ | OCH₃ | N | |
| H | CH₃ | CH₃ | cyclohexyl | OCH₃ | OCH₃ | N | |

TABLE Ia-continued

General Structure Ia

| R | R₁ | R₂ | R₃ | X | Y | Z | m.p. (°C.) |
|---|----|----|----|----|----|----|----|
| H | CH₃ | H | cyclohexyl | OCH₃ | Cl | CH | |
| H | CH₃ | H | cyclopropyl | CH₃ | CH₃ | CH | |
| CH₃ | CH₃ | H | cyclopropyl | CH₃ | OCH₃ | CH | |
| H | CH₃ | H | cyclopropyl | OCH₃ | OCH₃ | CH | |
| H | CH₃ | H | cyclopropyl | CH₃ | CH₃ | N | |
| H | CH₃ | H | cyclopropyl | CH₃ | OCH₃ | N | |
| H | CH₃ | H | cyclopropyl | OCH₃ | OCH₃ | N | |
| H | CH₃ | H | cyclopropyl | OCH₃ | Cl | CH | |
| H | CH₃ | H | CH₂—cyclopropyl | CH₃ | CH₃ | CH | |
| H | CH₃ | H | CH₂—cyclopropyl | CH₃ | OCH₃ | CH | |
| H | CH₃ | H | CH₂—cyclopropyl | OCH₃ | OCH₃ | CH | |
| H | CH₃ | H | CH₂—cyclopropyl | CH₃ | CH₃ | N | |
| H | CH₃ | H | CH₂—cyclopropyl | CH₃ | OCH₃ | N | |
| H | CH₃ | H | CH₂—cyclopropyl | OCH₃ | OCH₃ | N | |
| H | CH₃ | H | CH₂—cyclopropyl | OCH₃ | Cl | CH | |
| H | CH₃ | H | CH₂—cyclopentyl | CH₃ | CH₃ | CH | |
| H | CH₃ | H | CH₂—cyclopentyl | CH₃ | OCH₃ | CH | |
| H | CH₃ | H | CH₂—cyclopentyl | OCH₃ | OCH₃ | CH | |
| H | CH₃ | H | CH₂—cyclopentyl | CH₃ | CH₃ | N | |
| H | CH₃ | H | CH₂—cyclopentyl | CH₃ | OCH₃ | N | |
| H | CH₃ | H | CH₂—cyclopentyl | OCH₃ | OCH₃ | N | |
| H | CH₃ | H | CH₂—cyclopentyl | OCH₃ | Cl | CH | |
| H | CH₃ | H | C₆H₅ | CH₃ | CH₃ | CH | |
| H | CH₃ | H | C₆H₅ | CH₃ | OCH₃ | CH | |
| H | CH₃ | H | C₆H₅ | OCH₃ | OCH₃ | CH | |
| H | CH₃ | H | C₆H₅ | CH₃ | CH₃ | N | |
| H | CH₃ | H | C₆H₅ | OCH₃ | OCH₃ | N | |
| H | CH₃ | H | C₆H₅ | OCH₃ | Cl | CH | |
| H | CH₃ | H | CH=CH—CF₃ | CH₃ | CH₃ | CH | |
| H | CH₃ | H | CH=CH—CF₃ | CH₃ | OCH₃ | CH | |
| H | CH₃ | H | CH=CH—CF₃ | OCH₃ | OCH₃ | CH | |
| H | CH₃ | H | CH=CH—CF₃ | CH₃ | CH₃ | N | |
| H | CH₃ | H | CH=CH—CF₃ | CH₃ | OCH₃ | N | |
| H | CH₃ | H | CH=CH—CF₃ | OCH₃ | OCH₃ | N | |
| H | CH₃ | H | CH=CH—CF₃ | OCH₃ | Cl | CH | |
| H | CH₃ | H | CH₂—C≡C—CF₃ | CH₃ | CH₃ | CH | |
| H | CH₃ | H | CH₂—C≡C—CF₃ | CH₃ | OCH₃ | CH | |
| H | CH₃ | H | CH₂—C≡C—CF₃ | OCH₃ | OCH₃ | CH | |
| H | CH₃ | H | CH₂—C≡C—CF₃ | CH₃ | CH₃ | N | |
| H | CH₃ | H | CH₂—C≡C—CF₃ | CH₃ | OCH₃ | N | |
| H | CH₃ | CH₃ | CH₂—C≡C—CF₃ | OCH₃ | OCH₃ | N | |
| H | CH₃ | H | CH₂—CH=CF₂ | OCH₃ | Cl | CH | |
| H | CH₃ | H | CH=CH—CH₂Cl | CH₃ | CH₃ | CH | |
| H | CH₃ | H | CH=CH—CH₂Cl | CH₃ | OCH₃ | CH | |
| H | CH₃ | H | CH=CH—CH₂Cl | OCH₃ | OCH₃ | CH | |
| H | CH₃ | H | CH=CH—CH₂Cl | CH₃ | CH₃ | N | |
| H | CH₃ | H | CH=CH—CH₂Cl | CH₃ | OCH₃ | N | |
| H | CH₃ | H | CH=CH—CH₂Cl | OCH₃ | OCH₃ | N | |
| H | CH₃ | H | CH₂—C(CHF)(CH₂) (fluorocyclopropyl-CH₂) | OCH₃ | Cl | CH | |
| H | CH₃ | H | CH₂—C(CHF)(CH₂) | CH₃ | CH₃ | CH | |
| CH₃ | CH₃ | H | CH₂—C(CHF)(CH₂) | CH₃ | OCH₃ | CH | |
| H | CH₃ | H | CH₂—C(CHF)(CH₂) | OCH₃ | OCH₃ | CH | |
| H | CH₃ | H | CH₂—C(CHF)(CH₂) | CH₃ | CH₃ | N | |

TABLE Ia-continued

General Structure Ia

| R | R$_1$ | R$_2$ | R$_3$ | X | Y | Z | m.p. (°C.) |
|---|---|---|---|---|---|---|---|
| H | CH$_3$ | H | CH$_2$—C(CHF)(CH$_2$) (cyclopropane) | CH$_3$ | OCH$_3$ | N | |
| H | CH$_3$ | H | CH$_2$—C≡C—CH$_2$Br | OCH$_3$ | OCH$_3$ | N | |
| H | CH$_3$ | H | CH$_2$—C≡C—CH$_2$Br | OCH$_3$ | Cl | CH | |
| H | CH$_3$ | H | CH$_2$—CH=CHOCH$_3$ | CH$_3$ | CH$_3$ | CH | |
| H | CH$_3$ | H | CH$_2$—CH=CHOCH$_3$ | CH$_3$ | OCH$_3$ | CH | |
| H | CH$_3$ | H | CH$_2$—CH=CHOCH$_3$ | OCH$_3$ | OCH$_3$ | CH | |
| H | CH$_3$ | H | CH$_2$—CH=CHOCH$_3$ | CH$_3$ | CH$_3$ | N | |
| H | CH$_3$ | H | CH$_2$—C≡CHOCH$_3$ | CH$_3$ | OCH$_3$ | N | |
| H | CH$_3$ | H | CH$_2$—C≡CHOCH$_3$ | OCH$_3$ | OCH$_3$ | N | |
| H | CH$_3$ | H | CH$_2$—CH$_2$—CH=CHCN | OCH$_3$ | Cl | CH | |
| H | CH$_3$ | H | CH$_2$—CH$_2$—CH=CHCN | CH$_3$ | CH$_3$ | CH | |
| H | CH$_3$ | H | CH$_2$—CH$_2$—CH=CHCN | CH$_3$ | OCH$_3$ | CH | |
| H | CH$_3$ | H | CH(OSO$_2$CH$_3$)C≡CH | OCH$_3$ | OCH$_3$ | CH | |
| H | CH$_3$ | H | CH(OSO$_2$CH$_3$)C≡CH | CH$_3$ | CH$_3$ | N | |
| H | CH$_3$ | H | CH(OSO$_2$CH$_3$)C≡CH | CH$_3$ | OCH$_3$ | N | |
| H | CH$_3$ | H | CH(OSO$_2$CH$_3$)C≡CH | OCH$_3$ | OCH$_3$ | N | |
| H | CH$_3$ | H | CH(OSO$_2$CH$_3$)C≡CH | OCH$_3$ | Cl | CH | |
| H | CH$_3$ | H | C≡C—Si(CH$_3$)$_3$ | CH$_3$ | CH$_3$ | CH | |
| H | CH$_3$ | H | C≡C—Si(CH$_3$)$_3$ | CH$_3$ | OCH$_3$ | CH | |
| H | CH$_3$ | H | C≡C—Si(CH$_3$)$_3$ | OCH$_3$ | OCH$_3$ | CH | |
| H | CH$_3$ | H | CH$_2$—CH=CHP(O)(CH$_3$)$_2$ | CH$_3$ | CH$_3$ | N | |
| H | CH$_3$ | H | CH$_2$—CH=CHP(O)(CH$_3$)$_2$ | OCH$_3$ | OCH$_3$ | N | |
| H | CH$_3$ | H | CH$_2$—CH=CHP(O)(CH$_3$)$_2$ | OCH$_3$ | Cl | CH | |
| H | CH$_3$ | H | CH$_2$—CH=CHP(O)(CH$_3$)$_2$ | CH$_3$ | CH$_3$ | CH | |
| H | CH$_3$ | H | CH$_2$—CH=CHP(O)(CH$_3$)$_2$ | CH$_3$ | OCH$_3$ | CH | |
| H | CH$_3$ | H | CH=CH—OSi(CH$_3$)$_3$ | OCH$_3$ | OCH$_3$ | CH | |
| H | CH$_3$ | H | CH=CH—OSi(CH$_3$)$_3$ | CH$_3$ | CH$_3$ | N | |
| H | CH$_3$ | H | CH=CH—OSi(CH$_3$)$_3$ | CH$_3$ | OCH$_3$ | N | |
| H | CH$_3$ | H | CH=CH—OSi(CH$_3$)$_3$ | OCH$_3$ | OCH$_3$ | N | |
| H | CH$_3$ | H | CH$_2$(CH$_2$)$_5$CH=CH—CN | OCH$_3$ | Cl | CH | |
| H | CH$_3$ | H | CH$_2$(CH$_2$)$_5$CH=CH—CN | CH$_3$ | CH$_3$ | CH | |
| H | CH$_3$ | H | CH$_2$(CH$_2$)$_5$CH=CH—CN | CH$_3$ | OCH$_3$ | CH | |
| H | CH$_3$ | H | CH$_2$(CH$_2$)$_5$CH=CH—CN | OCH$_3$ | OCH$_3$ | CH | |
| H | CH$_3$ | H | CH$_2$(CH$_2$)$_5$CH=CH—CN | CH$_3$ | CH$_3$ | N | |
| H | CH$_3$ | H | CH=CH—CH$_2$SCN | CH$_3$ | OCH$_3$ | N | |
| H | CH$_3$ | CH$_3$ | CH=CH—CH$_2$SCN | OCH$_3$ | OCH$_3$ | N | |
| H | CH$_3$ | H | CH=CH—CH$_2$SCN | OCH$_3$ | Cl | CH | |
| H | CH$_3$ | H | C≡C—C≡C—CH$_2$OCH$_3$ | CH$_3$ | CH$_3$ | CH | |
| H | CH$_3$ | H | C≡C—C≡C—CH$_2$OCH$_3$ | CH$_3$ | OCH$_3$ | CH | |
| H | CH$_3$ | H | C≡C—C≡C—CH$_2$OCH$_3$ | OCH$_3$ | OCH$_3$ | CH | |
| H | CH$_3$ | H | CH$_2$—CH=CH=CH$_2$SCH$_3$ | CH$_3$ | CH$_3$ | N | |
| H | CH$_3$ | H | CH$_2$—CH=CH—CH$_2$SCH$_3$ | CH$_3$ | OCH$_3$ | N | |
| H | CH$_3$ | H | CH$_2$—CH=CH—CH$_2$SCH$_3$ | OCH$_3$ | OCH$_3$ | N | |
| H | CH$_3$ | H | CH$_2$—CH=CH—CH$_2$SCH$_3$ | OCH$_3$ | Cl | CH | |
| H | CH$_3$ | H | CH=CH—CH$_2$N(CH$_3$)$_2$ | CH$_3$ | CH$_3$ | CH | |
| CH$_3$ | CH$_3$ | H | CH=CH—CH$_2$N(CH$_3$)$_2$ | CH$_3$ | OCH$_3$ | CH | |
| H | CH$_3$ | H | CH=CH—CH$_2$N(CH$_3$)$_2$ | OCH$_3$ | OCH$_3$ | CH | |
| H | CH$_3$ | H | CH$_2$—CH=CH—P(O)(OCH$_3$)$_2$ | CH$_3$ | CH$_3$ | N | |
| H | CH$_3$ | H | CH$_2$—CH=CH—P(O)(OCH$_3$)$_2$ | CH$_3$ | OCH$_3$ | N | |
| H | CH$_3$ | H | CH$_2$—CH=CH—P(O)(OCH$_3$)$_2$ | OCH$_3$ | OCH$_3$ | N | |
| H | CH$_3$ | H | CH$_2$—CH=CH—P(O)(OCH$_3$)$_2$ | OCH$_3$ | Cl | CH | |
| H | CH$_3$ | H | SCH$_3$ | CH$_3$ | CH$_3$ | CH | |
| H | CH$_3$ | H | SCH$_3$ | CH$_3$ | OCH$_3$ | CH | |
| H | CH$_3$ | H | SCH$_3$ | OCH$_3$ | OCH$_3$ | CH | |
| H | CH$_3$ | H | SCH$_3$ | CH$_3$ | CH$_3$ | N | |
| H | CH$_3$ | H | SCH$_3$ | CH$_3$ | OCH$_3$ | N | |
| H | CH$_3$ | H | SCH$_3$ | OCH$_3$ | OCH$_3$ | N | |
| H | CH$_3$ | H | SCH$_3$ | OCH$_3$ | Cl | CH | |
| H | CH$_3$ | H | SCH$_2$CF$_3$ | CH$_3$ | CH$_3$ | CH | |
| H | CH$_3$ | H | SCH$_2$CH$_3$ | CH$_3$ | OCH$_3$ | CH | |
| H | CH$_3$ | H | SCH$_2$CH$_3$ | OCH$_3$ | OCH$_3$ | CH | |
| H | CH$_3$ | H | SCH$_2$CH$_3$ | CH$_3$ | CH$_3$ | N | |
| H | CH$_3$ | H | SCH$_2$CH$_3$ | CH$_3$ | OCH$_3$ | N | |
| H | CH$_3$ | H | SCH$_2$CH$_3$ | OCH$_3$ | OCH$_3$ | N | |
| H | CH$_3$ | H | SCH$_2$CH$_3$ | OCH$_3$ | Cl | CH | |
| H | CH$_3$ | H | SO$_2$CH$_3$ | CH$_3$ | CH$_3$ | CH | |
| H | CH$_3$ | H | SO$_2$CH$_3$ | CH$_3$ | OCH$_3$ | CH | |
| H | CH$_3$ | H | SO$_2$CH$_3$ | OCH$_3$ | OCH$_3$ | CH | |
| H | CH$_3$ | H | SO$_2$CH$_3$ | CH$_3$ | CH$_3$ | N | |
| H | CH$_3$ | H | SO$_2$CH$_3$ | OCH$_3$ | OCH$_3$ | N | |
| H | CH$_3$ | H | SO$_2$CH$_3$ | OCH$_3$ | Cl | CH | |
| H | CH$_3$ | H | SO$_2$CH$_2$CH$_3$ | CH$_3$ | CH$_3$ | CH | |
| H | CH$_3$ | H | SO$_2$CH$_2$CH$_3$ | CH$_3$ | OCH$_3$ | CH | |
| H | CH$_3$ | H | SO$_2$CH$_2$CH$_3$ | OCH$_3$ | OCH$_3$ | CH | |
| H | CH$_3$ | H | SO$_2$CH$_2$CH$_3$ | CH$_3$ | CH$_3$ | N | |

TABLE Ia-continued

General Structure Ia

| R | R$_1$ | R$_2$ | R$_3$ | X | Y | Z | m.p. (°C.) |
|---|---|---|---|---|---|---|---|
| H | CH$_3$ | H | SO$_2$CH$_2$CH$_3$ | CH$_3$ | OCH$_3$ | N | |
| H | CH$_3$ | H | SO$_2$CH$_2$CH$_3$ | OCH$_3$ | OCH$_3$ | N | |
| H | CH$_3$ | H | SO$_2$CH$_2$CH$_3$ | OCH$_3$ | Cl | CH | |
| H | CH$_3$ | H | OCH$_3$ | CH$_3$ | CH$_3$ | CH | |
| H | CH$_3$ | H | OCH$_3$ | CH$_3$ | OCH$_3$ | CH | |
| H | CH$_3$ | H | OCH$_3$ | OCH$_3$ | OCH$_3$ | CH | |
| H | CH$_3$ | H | OCH$_3$ | CH$_3$ | CH$_3$ | N | |
| H | CH$_3$ | H | OCH$_3$ | CH$_3$ | OCH$_3$ | N | |
| H | CH$_3$ | CH$_3$ | OCH$_3$ | OCH$_3$ | OCH$_3$ | N | |
| H | CH$_3$ | H | OCH$_3$ | OCH$_3$ | Cl | CH | |
| H | CH$_3$ | H | OCH$_2$CH$_3$ | CH$_3$ | CH$_3$ | CH | |
| H | CH$_3$ | H | OCH$_2$CH$_3$ | CH$_3$ | OCH$_3$ | CH | |
| H | CH$_3$ | H | OCH$_2$CH$_3$ | OCH$_3$ | OCH$_3$ | CH | |
| H | CH$_3$ | H | OCH$_2$CH$_3$ | CH$_3$ | CH$_3$ | N | |
| H | CH$_3$ | H | OCH$_2$CH$_3$ | CH$_3$ | OCH$_3$ | N | |
| H | CH$_3$ | H | OCH$_2$CH$_3$ | OCH$_3$ | OCH$_3$ | N | |
| H | CH$_3$ | H | OCH$_2$CH$_3$ | OCH$_3$ | Cl | CH | |
| H | CH$_3$ | H | OCH(CH$_3$)$_2$ | CH$_3$ | CH$_3$ | CH | |
| CH$_3$ | CH$_3$ | H | OCH(CH$_3$)$_2$ | CH$_3$ | OCH$_3$ | CH | |
| H | CH$_3$ | H | OCH(CH$_3$)$_2$ | OCH$_3$ | OCH$_3$ | CH | |
| H | CH$_3$ | H | OCH(CH$_3$)$_2$ | CH$_3$ | CH$_3$ | N | |
| H | CH$_3$ | H | OCH(CH$_3$)$_2$ | CH$_3$ | OCH$_3$ | N | |
| H | CH$_3$ | H | OCH(CH$_3$)$_2$ | OCH$_3$ | OCH$_3$ | N | |
| H | CH$_3$ | H | OCH(CH$_3$)$_2$ | OCH$_3$ | Cl | CH | |
| H | CH$_3$ | H | C(O)CH$_3$ | CH$_3$ | CH$_3$ | CH | |
| H | CH$_3$ | H | C(O)CH$_3$ | CH$_3$ | OCH$_3$ | CH | |
| H | CH$_3$ | H | C(O)CH$_3$ | OCH$_3$ | OCH$_3$ | CH | |
| H | CH$_3$ | H | C(O)CH$_3$ | CH$_3$ | CH$_3$ | N | |
| H | CH$_3$ | H | C(O)CH$_3$ | CH$_3$ | OCH$_3$ | N | |
| H | CH$_3$ | H | C(O)CH$_3$ | OCH$_3$ | OCH$_3$ | N | |
| H | CH$_3$ | H | C(O)CH$_3$ | OCH$_3$ | Cl | CH | |
| H | CH$_3$ | H | C(O)CH$_2$CH$_3$ | CH$_3$ | CH$_3$ | CH | |
| H | CH$_3$ | H | C(O)CH$_2$CH$_3$ | CH$_3$ | OCH$_3$ | CH | |
| H | CH$_3$ | H | C(O)CH$_2$CH$_3$ | OCH$_3$ | OCH$_3$ | CH | |
| H | CH$_3$ | H | C(O)CH$_2$CH$_3$ | CH$_3$ | CH$_3$ | N | |
| H | CH$_3$ | H | C(O)CH$_2$CH$_3$ | CH$_3$ | OCH$_3$ | N | |
| H | CH$_3$ | H | C(O)CH$_2$CH$_3$ | OCH$_3$ | OCH$_3$ | N | |
| H | CH$_3$ | H | C(O)CH$_2$CH$_3$ | OCH$_3$ | Cl | CH | |
| H | CH$_3$ | H | C(O)(CH)(CH$_3$)$_2$ | CH$_3$ | CH$_3$ | CH | |
| H | CH$_3$ | H | C(O)(CH)(CH$_3$)$_2$ | CH$_3$ | OCH$_3$ | CH | |
| H | CH$_3$ | H | C(O)(CH)(CH$_3$)$_2$ | OCH$_3$ | OCH$_3$ | CH | |
| H | CH$_3$ | H | C(O)(CH)(CH$_3$)$_2$ | CH$_3$ | CH$_3$ | N | |
| H | CH$_3$ | H | C(O)(CH)(CH$_3$)$_2$ | OCH$_3$ | OCH$_3$ | N | |
| H | CH$_3$ | H | C(O)(CH)(CH$_3$)$_2$ | OCH$_3$ | Cl | CH | |
| H | CH$_3$ | H | C(O)CHF$_2$ | CH$_3$ | CH$_3$ | CH | |
| H | CH$_3$ | H | C(O)CHF$_2$ | CH$_3$ | OCH$_3$ | CH | |
| H | CH$_3$ | H | C(O)CHF$_2$ | OCH$_3$ | OCH$_3$ | CH | |
| H | CH$_3$ | H | C(O)CF$_3$ | CH$_3$ | CH$_3$ | N | |
| H | CH$_3$ | H | C(O)CF$_3$ | CH$_3$ | OCH$_3$ | N | |
| H | CH$_3$ | H | C(O)CF$_3$ | OCH$_3$ | OCH$_3$ | N | |
| H | CH$_3$ | H | C(O)CF$_3$ | OCH$_3$ | Cl | CH | |
| H | CH$_3$ | H | C(O)CH$_2$CH$_2$CH$_3$ | CH$_3$ | CH$_3$ | CH | |
| H | CH$_3$ | H | C(O)CH$_2$CH$_2$CH$_3$ | CH$_3$ | OCH$_3$ | CH | |
| H | CH$_3$ | H | C(O)CH$_2$CH$_2$CH$_3$ | OCH$_3$ | OCH$_3$ | CH | |
| H | CH$_3$ | H | C(O)CH$_2$CH$_2$CH$_3$ | CH$_3$ | CH$_3$ | N | |
| H | CH$_3$ | H | C(O)CH$_2$CH$_2$CH$_3$ | CH$_3$ | OCH$_3$ | N | |
| H | CH$_3$ | CH$_3$ | C(O)CH$_2$CH$_2$CH$_3$ | OCH$_3$ | OCH$_3$ | N | |
| H | CH$_3$ | H | C(O)CH$_2$CH$_2$CH$_3$ | OCH$_3$ | Cl | CH | |
| H | CH$_3$ | H | C(O)CH$_2$OCH$_3$ | CH$_3$ | CH$_3$ | CH | |
| H | CH$_3$ | H | C(O)CH$_2$OCH$_3$ | CH$_3$ | OCH$_3$ | CH | |
| H | CH$_3$ | H | C(O)CH$_2$OCH$_3$ | OCH$_3$ | OCH$_3$ | CH | |
| H | CH$_3$ | H | C(O)CH$_2$OCH$_3$ | CH$_3$ | CH$_3$ | N | |
| H | CH$_3$ | H | C(O)CH$_2$Cl | CH$_3$ | OCH$_3$ | N | |
| H | CH$_3$ | H | C(O)CH$_2$Cl | OCH$_3$ | OCH$_3$ | N | |
| H | CH$_3$ | H | C(O)CH$_2$Cl | OCH$_3$ | Cl | CH | |
| H | CH$_3$ | H | C(O)CH$_2$CH(CH$_3$)CN | CH$_3$ | CH$_3$ | CH | |
| CH$_3$ | CH$_3$ | H | C(O)CH$_2$CH(CH$_3$)CN | CH$_3$ | OCH$_3$ | CH | |
| H | CH$_3$ | H | C(O)CH$_2$N(CH$_3$)$_2$ | OCH$_3$ | OCH$_3$ | CH | |
| H | CH$_3$ | H | C(O)CH$_2$N(CH$_3$)$_2$ | CH$_3$ | CH$_3$ | CH | |
| H | CH$_3$ | H | C(O)CH$_2$CH=CH$_2$ | CH$_3$ | OCH$_3$ | N | |
| H | CH$_3$ | H | C(O)CH$_2$CH=CH$_2$ | OCH$_3$ | OCH$_3$ | N | |
| H | CH$_3$ | H | C(O)CH$_2$C≡CH | OCH$_3$ | Cl | CH | |
| H | CH$_3$ | H | CO$_2$CH$_3$ | CH$_3$ | CH$_3$ | CH | |
| H | CH$_3$ | H | CO$_2$CH$_3$ | CH$_3$ | OCH$_3$ | CH | |
| H | CH$_3$ | H | CO$_2$CH$_3$ | OCH$_3$ | OCH$_3$ | CH | |
| H | CH$_3$ | H | CO$_2$CH$_3$ | CH$_3$ | CH$_3$ | N | |
| H | CH$_3$ | H | CO$_2$CH$_3$ | CH$_3$ | OCH$_3$ | N | |
| H | CH$_3$ | H | CO$_2$CH$_3$ | OCH$_3$ | OCH$_3$ | N | |
| H | CH$_3$ | H | CO$_2$CH$_3$ | OCH$_3$ | Cl | CH | |
| H | CH$_3$ | H | CO$_2$CH$_2$CH$_3$ | CH$_3$ | CH$_3$ | CH | |

TABLE Ia-continued

General Structure Ia

| R | $R_1$ | $R_2$ | $R_3$ | X | Y | Z | m.p. (°C.) |
|---|---|---|---|---|---|---|---|
| H | $CH_3$ | H | $CO_2CH_2CH_3$ | $CH_3$ | $OCH_3$ | CH | |
| H | $CH_3$ | H | $CO_2CH_2CH_3$ | $OCH_3$ | $OCH_3$ | CH | |
| H | $CH_3$ | H | $CO_2CH_2CH_3$ | $CH_3$ | $CH_3$ | N | |
| H | $CH_3$ | H | $CO_2CH_2CH_3$ | $CH_3$ | $OCH_3$ | N | |
| H | $CH_3$ | H | $CO_2CH_2CH_3$ | $OCH_3$ | $OCH_3$ | N | |
| H | $CH_3$ | H | $CO_2CH_2CH_3$ | $OCH_3$ | Cl | CH | |
| H | $CH_3$ | H | $CO_2CH_2CF_3$ | $CH_3$ | $CH_3$ | CH | |
| H | $CH_3$ | H | $CO_2CH_2CF_3$ | $CH_3$ | $OCH_3$ | CH | |
| H | $CH_3$ | H | $CO_2CH_2CF_3$ | $OCH_3$ | $OCH_3$ | CH | |
| H | $CH_3$ | H | $CO_2CH_2CF_3$ | $CH_3$ | $CH_3$ | N | |
| H | $CH_3$ | H | $CO_2CF_3$ | $OCH_3$ | $OCH_3$ | N | |
| H | $CH_3$ | H | $CO_2CF_3$ | $OCH_3$ | Cl | CH | |
| H | $CH_3$ | H | $CO_2CF_3$ | $CH_3$ | $CH_3$ | CH | |
| H | $CH_3$ | H | $CO_2CH_2C\equiv CH$ | $CH_3$ | $OCH_3$ | CH | |
| H | $CH_3$ | H | $CO_2CH_2C\equiv CH$ | $OCH_3$ | $OCH_3$ | CH | |
| H | $CH_3$ | H | $CO_2CH_2C\equiv CH$ | $CH_3$ | $CH_3$ | N | |
| H | $CH_3$ | H | $CO_2CH_2C\equiv CH$ | $CH_3$ | $OCH_3$ | N | |
| H | $CH_3$ | H | $CO_2CH_2C\equiv CH$ | $OCH_3$ | $OCH_3$ | N | |
| H | $CH_3$ | H | $CO_2CH_2CH=CH_2$ | $OCH_3$ | Cl | CH | |
| H | $CH_3$ | H | $CO_2CH_2CH=CH_2$ | $CH_3$ | $CH_3$ | CH | |
| H | $CH_3$ | H | $CO_2CH_2CH=CH_2$ | $CH_3$ | $OCH_3$ | CH | |
| H | $CH_3$ | H | $CO_2CH_2CH=CH_2$ | $OCH_3$ | $OCH_3$ | CH | |
| H | $CH_3$ | H | $CO_2CH_2CH=CH_2$ | $CH_3$ | $CH_3$ | N | |
| H | $CH_3$ | H | $CO_2CH_2CH=CH_2$ | $CH_3$ | $OCH_3$ | N | |
| H | $CH_3$ | $CH_3$ | $CO_2CH_3$ | $OCH_3$ | $OCH_3$ | N | |
| H | $CH_3$ | H | $CO_2CF_3$ | $OCH_3$ | Cl | CH | |
| H | $CH_3$ | H | $CO_2CF_3$ | $CH_3$ | $CH_3$ | CH | |
| H | $CH_3$ | H | $CO_2CF_3$ | $CH_3$ | $OCH_3$ | CH | |
| H | $CH_3$ | H | $CO_2CF_3$ | $OCH_3$ | $OCH_3$ | CH | |
| H | $CH_3$ | H | $CO_2CH_2CH_2Cl$ | $CH_3$ | $CH_3$ | N | |
| H | $CH_3$ | H | $CO_2CH_2CH_2Cl$ | $CH_3$ | $OCH_3$ | N | |
| H | $CH_3$ | H | $CO_2CH_2CH_2Cl$ | $OCH_3$ | $OCH_3$ | N | |
| H | $CH_3$ | H | $CO_2CH_2CH_2P(O)(CH_3)_2$ | $OCH_3$ | Cl | CH | |
| H | $CH_3$ | H | $CO_2CH_2CH_2P(O)(CH_3)_2$ | $CH_3$ | $CH_3$ | CH | |
| $CH_3$ | $CH_3$ | H | $CO_2C(CH_3)_3$ | $CH_3$ | $OCH_3$ | CH | |
| H | $CH_3$ | H | $CO_2C(CH_3)_3$ | $OCH_3$ | $OCH_3$ | CH | |
| H | $CH_3$ | H | $CO_2CH_2(CH_2)_4CH_3$ | $CH_3$ | $CH_3$ | N | |
| H | $CH_3$ | H | $CO_2CH_2(CH_2)_4CH_4$ | $CH_3$ | $OCH_3$ | N | |
| H | $CH_3$ | H | $CO_2CH_2OCH_3$ | $OCH_3$ | $OCH_3$ | N | |
| H | $CH_3$ | H | $CO_2CH_2OCH_3$ | $OCH_3$ | Cl | CH | |
| H | $CH_3$ | H | $(C(O))_2OCH_3$ | $CH_3$ | $CH_3$ | CH | |
| H | $CH_3$ | H | $(C(O))_2OCH_3$ | $CH_3$ | $OCH_3$ | CH | |
| H | $CH_3$ | H | $(C(O))_2OCH_3$ | $OCH_3$ | $OCH_3$ | CH | |
| H | $CH_3$ | H | $(C(O))_2OCH_3$ | $CH_3$ | $CH_3$ | N | |
| H | $CH_3$ | H | $(C(O))_2OCH_3$ | $CH_3$ | $OCH_3$ | N | |
| H | $CH_3$ | H | $(C(O))_2OCH_3$ | $OCH_3$ | $OCH_3$ | N | |
| H | $CH_3$ | H | $(C(O))_2OCH_3$ | $OCH_3$ | Cl | CH | |
| H | $CH_3$ | H | $(CO)_2CH_3$ | $CH_3$ | $CH_3$ | CH | |
| H | $CH_3$ | H | $(CO)_2CH_3$ | $CH_3$ | $OCH_3$ | CH | |
| H | $CH_3$ | H | $(CO)_2CH_3$ | $OCH_3$ | $OCH_3$ | CH | |
| H | $CH_3$ | H | $(CO)_2CH_3$ | $CH_3$ | $CH_3$ | N | |
| H | $CH_3$ | H | $(CO)_2CH_3$ | $CH_3$ | $OCH_3$ | N | |
| H | $CH_3$ | H | $(CO)_2CH_3$ | $OCH_3$ | $OCH_3$ | N | |
| H | $CH_3$ | H | $(CO)_2CH_3$ | $OCH_3$ | Cl | CH | |
| H | $CH_3$ | H | $C(O)N(CH_3)_2$ | $CH_3$ | $CH_3$ | CH | |
| H | $CH_3$ | H | $C(O)N(CH_3)_2$ | $CH_3$ | $OCH_3$ | CH | |
| H | $CH_3$ | H | $C(O)N(CH_3)_2$ | $OCH_3$ | $OCH_3$ | CH | |
| H | $CH_3$ | H | $C(O)N(CH_3)_2$ | $CH_3$ | $CH_3$ | N | |
| H | $CH_3$ | H | $C(O)N(CH_3)_2$ | $OCH_3$ | $OCH_3$ | N | |
| H | $CH_3$ | H | $C(O)N(CH_3)_2$ | $OCH_3$ | Cl | CH | |
| H | $CH_3$ | H | $C(O)N(CH_2CH_3)_2$ | $CH_3$ | $CH_3$ | CH | |
| H | $CH_3$ | H | $C(O)N(CH_2CH_3)_2$ | $CH_3$ | $OCH_3$ | CH | |
| H | $CH_3$ | H | $C(O)N(CH_2CH_3)_2$ | $OCH_3$ | $OCH_3$ | CH | |
| H | $CH_3$ | H | $C(O)N(CH_2CH_3)_2$ | $CH_3$ | $CH_3$ | N | |
| H | $CH_3$ | H | $C(O)N(CH_2CH_3)_2$ | $CH_3$ | $OCH_3$ | N | |
| H | $CH_3$ | H | $C(O)N(CH_2CH_3)_2$ | $OCH_3$ | $OCH_3$ | N | |
| H | $CH_3$ | H | $C(O)N(CH_3)CH_2CH_3$ | $OCH_3$ | Cl | CH | |
| H | $CH_3$ | H | $C(O)N(CH_3)CH_2CH_3$ | $CH_3$ | $CH_3$ | CH | |
| H | $CH_3$ | H | $C(O)N(CH_3)CH_2CH_3$ | $CH_3$ | $OCH_3$ | CH | |
| H | $CH_3$ | H | $C(O)N(CH_3)CH_2CH_3$ | $OCH_3$ | $OCH_3$ | CH | |
| H | $CH_3$ | H | $C(O)N(CH_3)CH_2CH_3$ | $CH_3$ | $CH_3$ | N | |
| H | $CH_3$ | H | $C(O)N(CF_3)CH_3$ | $CH_3$ | $OCH_3$ | N | |
| H | $CH_3$ | $CH_3$ | $C(O)N(CF_3)CH_3$ | $OCH_3$ | $OCH_3$ | N | |
| H | $CH_3$ | H | $C(O)N(CF_3)CH_3$ | $OCH_3$ | Cl | CH | |
| H | $CH_3$ | H | $C(O)N(CH_3)OCH_3$ | $CH_3$ | $CH_3$ | CH | |
| H | $CH_3$ | H | $C(O)N(CH_3)OCH_3$ | $CH_3$ | $OCH_3$ | CH | |
| H | $CH_3$ | H | $C(O)N(CH_3)OCH_3$ | $OCH_3$ | $OCH_3$ | CH | |
| H | $CH_3$ | H | $C(O)N(CH_3)OCH_3$ | $CH_3$ | $CH_3$ | N | |
| H | $CH_3$ | H | $C(O)N(CH=CH_2)CH_3$ | $CH_3$ | $OCH_3$ | N | |
| H | $CH_3$ | H | $C(O)N(CH=CH_2)CH_3$ | $OCH_3$ | $OCH_3$ | N | |

TABLE Ia-continued

General Structure Ia

| R | R₁ | R₂ | R₃ | X | Y | Z | m.p. (°C.) |
|---|----|----|----|----|----|----|------------|
| H | CH₃ | H | C(O)N(CH=CH₂)CH₃ | OCH₃ | Cl | CH | |
| H | CH₃ | H | C(O)N(CH=CH₂)CH₃ | CH₃ | CH₃ | CH | |
| CH₃ | CH₃ | H | C(O)N(CH=CH₂)CH₃ | CH₃ | OCH₃ | CH | |
| H | CH₃ | H | C(O)N(CH₃)Ph | OCH₃ | OCH₃ | CH | |
| H | CH₃ | H | C(O)N(CH₃)Ph | CH₃ | CH₃ | N | |
| H | CH₃ | H | C(O)N(CH₃)Ph | CH₃ | OCH₃ | N | |
| H | CH₃ | H | C(O)N(OCH₃)₂ | OCH₃ | OCH₃ | N | |
| H | CH₃ | H | C(O)N(OCH₃)₂ | OCH₃ | Cl | CH | |
| H | CH₃ | H | CS₂CH₃ | CH₃ | CH₃ | CH | |
| H | CH₃ | H | CS₂CH₃ | CH₃ | OCH₃ | CH | |
| H | CH₃ | H | CS₂CH₃ | OCH₃ | OCH₃ | CH | |
| H | CH₃ | H | CS₂CH₃ | CH₃ | CH₃ | N | |
| H | CH₃ | H | CS₂CH₃ | CH₃ | OCH₃ | N | |
| H | CH₃ | H | CS₂CH₃ | OCH₃ | OCH₃ | N | |
| H | CH₃ | H | CS₂CH₃ | OCH₃ | Cl | CH | |
| H | CH₃ | H | CS₂CH₂CH₃ | CH₃ | CH₃ | CH | |
| H | CH₃ | H | CS₂CH₂CH₃ | CH₃ | OCH₃ | CH | |
| H | CH₃ | H | CS₂CH₂CH₃ | OCH₃ | OCH₃ | CH | |
| H | CH₃ | H | CS₂CH₂CH₃ | CH₃ | CH₃ | N | |
| H | CH₃ | H | CS₂CH₂CH₃ | CH₃ | OCH₃ | N | |
| H | CH₃ | H | CS₂CH₂CH=CH₂ | OCH₃ | OCH₃ | N | |
| H | CH₃ | H | CS₂CH₂CH=CH₂ | OCH₃ | Cl | CH | |
| H | CH₃ | H | CS₂CH₂CH=CH₂ | CH₃ | CH₃ | CH | |
| H | CH₃ | H | NH₂ | CH₃ | CH₃ | CH | |
| H | CH₃ | H | NH₂ | CH₃ | OCH₃ | CH | |
| H | CH₃ | H | NH₂ | OCH₃ | OCH₃ | CH | |
| H | CH₃ | H | NH₂ | CH₃ | CH₃ | N | |
| H | CH₃ | H | NH₂ | CH₃ | OCH₃ | N | |
| H | CH₃ | H | NH₂ | OCH₃ | OCH₃ | N | |
| H | CH₃ | H | NH₂ | OCH₃ | Cl | CH | |
| H | CH₃ | H | N(CH₃)₂ | CH₃ | CH₃ | CH | |
| H | CH₃ | H | N(CH₃)₂ | CH₃ | OCH₃ | CH | |
| H | CH₃ | H | N(CH₃)₂ | OCH₃ | OCH₃ | CH | |
| H | CH₃ | H | N(CH₃)₂ | CH₃ | CH₃ | N | |
| H | CH₃ | H | N(CH₃)₂ | CH₃ | OCH₃ | N | |
| H | CH₃ | CH₃ | N(CH₃)₂ | OCH₃ | OCH₃ | N | |
| H | CH₃ | H | N(CH₃)₂ | OCH₃ | Cl | CH | |
| H | CH₃ | H | N(CH₃)(CH₂CH₃) | CH₃ | CH₃ | CH | |
| H | CH₃ | H | N(CH₃)(CH₂CH₃) | CH₃ | OCH₃ | CH | |
| H | CH₃ | H | N(CH₃)(CH₂CH₃) | OCH₃ | OCH₃ | CH | |
| H | CH₃ | H | N(CH₃)OCH₃ | CH₃ | CH₃ | N | |
| H | CH₃ | H | N(CH₃)OCH₃ | CH₃ | OCH₃ | N | |
| H | CH₃ | H | N(CH₃)OCH₃ | OCH₃ | OCH₃ | N | |
| H | CH₃ | H | N(CH₃)CH=CH₂ | OCH₃ | Cl | CH | |
| H | CH₃ | H | N(CH₃)CH=CH₂ | CH₃ | CH₃ | CH | |
| CH₃ | CH₃ | H | N(CH₃)CH=CH₂ | CH₃ | OCH₃ | CH | |
| H | CH₃ | H | N(CH₃)CH=CH₂ | OCH₃ | OCH₃ | CH | |
| H | CH₃ | H | N(CH₂CH₃)₂ | CH₃ | CH₃ | N | |
| H | CH₃ | H | N(CH₂CH₃)₂ | CH₃ | OCH₃ | N | |
| H | CH₃ | H | N(CH₂CH₃)₂ | OCH₃ | OCH₃ | N | |
| H | CH₃ | H | N(CH₂CH₃)₂ | OCH₃ | Cl | CH | |
| H | CH₃ | H | OH | CH₃ | CH₃ | CH | |
| H | CH₃ | H | OH | CH₃ | OCH₃ | CH | |
| H | CH₃ | H | OH | OCH₃ | OCH₃ | CH | |
| H | CH₃ | H | OH | CH₃ | CH₃ | N | |
| H | CH₃ | H | OH | CH₃ | OCH₃ | N | |
| H | CH₃ | H | OH | OCH₃ | OCH₃ | N | |
| H | CH₃ | H | OH | OCH₃ | Cl | CH | |
| H | CH₃ | H | CN | CH₃ | CH₃ | CH | |
| H | CH₃ | H | CN | CH₃ | OCH₃ | CH | |
| H | CH₃ | H | CN | OCH₃ | OCH₃ | CH | |
| H | CH₃ | H | CN | CH₃ | CH₃ | N | |
| H | CH₃ | H | CN | CH₃ | OCH₃ | N | |
| H | CH₃ | H | CN | OCH₃ | OCH₃ | N | |
| H | CH₃ | H | CN | OCH₃ | Cl | CH | |
| H | CH₃ | H | P(O)(CH₃)₂ | CH₃ | CH₃ | CH | |
| H | CH₃ | H | P(O)(CH₃)₂ | CH₃ | OCH₃ | CH | |
| H | CH₃ | H | P(O)(CH₃)₂ | OCH₃ | OCH₃ | CH | |
| H | CH₃ | H | P(O)(CH₃)₂ | CH₃ | CH₃ | N | |
| H | CH₃ | H | P(O)(CH₃)₂ | OCH₃ | OCH₃ | N | |
| H | CH₃ | H | P(O)(OCH₃)₂ | OCH₃ | Cl | CH | |
| H | CH₃ | H | P(O)(OCH₃)₂ | CH₃ | CH₃ | CH | |
| H | CH₃ | H | P(O)(OCH₃)₂ | CH₃ | OCH₃ | CH | |
| H | CH₃ | H | P(O)(OCH₃)₂ | OCH₃ | OCH₃ | CH | |
| H | CH₃ | H | P(O)(OCH₃)SCH₃ | CH₃ | CH₃ | N | |
| H | CH₃ | H | P(O)(OCH₃)SCH₃ | CH₃ | OCH₃ | N | |
| H | CH₃ | H | P(O)(OCH₃)SCH₃ | OCH₃ | OCH₃ | N | |
| H | CH₃ | H | P(O)(OCH₃)SCH₃ | OCH₃ | Cl | CH | |
| H | CH₃ | H | P(O)(OCH₃)SCH₂CH₂CH₃ | CH₃ | CH₃ | CH | |
| H | CH₃ | H | P(O)(OCH₃)SCH₂CH₂CH₃ | CH₃ | OCH₃ | CH | |

TABLE Ia-continued

General Structure Ia

| R | R₁ | R₂ | R₃ | X | Y | Z | m.p. (°C.) |
|---|----|----|----|---|---|---|------------|
| H | CH₃ | H | P(O)(OCH₃)SCH₂CH₂CH₃ | OCH₃ | OCH₃ | CH | |
| H | CH₃ | H | P(O)(OCH₃)SCH₂CH₂CH₃ | CH₃ | CH₃ | N | |
| H | CH₃ | H | P(O)(OCH₃)SCH₂CH₂CH₃ | CH₃ | OCH₃ | N | |
| H | CH₃ | CH₃ | OH | OCH₃ | OCH₃ | N | |
| H | CH₃ | H | P(S)(CH₃)₂ | OCH₃ | Cl | CH | |
| H | CH₃ | H | P(S)(CH₃)₂ | CH₃ | CH₃ | CH | |
| H | CH₃ | H | P(S)(CH₃)₂ | CH₃ | OCH₃ | CH | |
| H | CH₃ | H | P(S)(CH₃)₂ | OCH₃ | OCH₃ | CH | |
| H | CH₃ | H | P(S)(CH₃)₂ | CH₃ | CH₃ | N | |
| H | CH₃ | H | P(S)(CH₃)₂ | CH₃ | OCH₃ | N | |
| H | CH₃ | H | P(S)(CH₃)₂ | OCH₃ | OCH₃ | N | |
| H | CH₃ | H | P(S)(OCH₃)₂ | OCH₃ | Cl | CH | |
| H | CH₃ | H | P(S)(OCH₃)₂ | CH₃ | CH₃ | CH | |
| CH₃ | CH₃ | H | P(S)(OCH₃)₂ | CH₃ | OCH₃ | CH | |
| H | CH₃ | H | P(S)OCH₃)₂ | OCH₃ | OCH₃ | CH | |
| H | CH₃ | H | P(S)(OCH₃)₂ | CH₃ | CH₃ | N | |
| H | CH₃ | H | P(S)(OCH₃)₂ | CH₃ | OCH₃ | N | |
| H | CH₃ | H | P(S)(OCH₃)SCH₃ | OCH₃ | OCH₃ | N | |
| H | CH₃ | H | P(S)(OCH₃)SCH₃ | OCH₃ | Cl | CH | |
| H | CH₃ | H | NO₂ | CH₃ | CH₃ | CH | |
| H | CH₃ | H | NO₂ | CH₃ | OCH₃ | CH | |
| H | CH₃ | H | NO₂ | OCH₃ | OCH₃ | CH | |
| H | CH₃ | H | NO₂ | CH₃ | CH₃ | N | |
| H | CH₃ | H | NO₂ | CH₃ | OCH₃ | N | |
| H | CH₃ | H | NO₂ | OCH₃ | OCH₃ | N | |
| H | CH₃ | H | CH₂C(O)CH(CH₂CH₂) (cyclopropyl) | CH₃ | CH₃ | N | |
| H | CH₃ | H | CH₂C(O)CH(CH₂CH₂) (cyclopropyl) | CH₃ | OCH₃ | N | |
| H | CH₃ | H | CH₂C(O)CH(CH₂CH₂) (cyclopropyl) | OCH₃ | OCH₃ | N | |
| H | CH₃ | H | CH₂C(O)CH(CH₂CH₂) (cyclopropyl) | OCH₃ | Cl | CH | |
| H | CH₃ | H | CH₂C(O)CH(CH₂CH₂) (cyclopropyl) | CH₃ | CH₃ | CH | |
| H | CH₃ | H | CH₂C(O)CH(CH₂CH₂) (cyclopropyl) | CH₃ | OCH₃ | CH | |
| H | CH₃ | H | CH₂C(O)Ph | OCH₃ | OCH₃ | CH | |
| H | CH₃ | H | CH₂C(O)Ph | CH₃ | CH₃ | N | |
| H | CH₃ | H | CH₂C(O)Ph | CH₃ | OCH₃ | N | |
| H | CH₃ | CH₃ | CH₂C(O)Ph | OCH₃ | OCH₃ | N | |
| H | CH₃ | H | CH₂C(O)Ph | OCH₃ | Cl | CH | |
| H | CH₃ | H | CH₂C(O)Ph | CH₃ | CH₃ | CH | |
| H | CH₃ | H | CH₂C(O)Ph | CH₃ | OCH₃ | CH | |
| H | CH₃ | H | CH(CH)₃C(O)CH₃ | OCH₃ | OCH₃ | CH | |
| H | CH₃ | H | CH(CH)₃C(O)CH₃ | CH₃ | CH₃ | N | |
| H | CH₃ | H | CH(CH)₃C(O)CH₃ | CH₃ | OCH₃ | N | |
| H | CH₃ | H | CH(CH)₃C(O)CH₃ | OCH₃ | OCH₃ | N | |
| H | CH₃ | H | CH₂CF₂—C(O)CH₃ | OCH₃ | Cl | CH | |
| H | CH₃ | H | CH₂CF₂—C(O)CH₃ | CH₃ | CH₃ | CH | |
| CH₃ | CH₃ | H | CH₂CF₂—C(O)CH₃ | CH₃ | OCH₃ | CH | |
| H | CH₃ | H | CH₂CF₂—C(O)CH₃ | OCH₃ | OCH₃ | CH | |
| H | CH₃ | H | CH₂C(O)CH₂OCH₃ | CH₃ | CH₃ | N | |
| H | CH₃ | H | CH₂C(O)CH₂OCH₃ | CH₃ | OCH₃ | N | |
| H | CH₃ | H | CH₂C(O)CH₂OCH₃ | OCH₃ | OCH₃ | N | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂C(O)CH₂OCH₃ | OCH₃ | Cl | CH | |
| H | CH₃ | H | CH₂CO₂CH₃ | CH₃ | CH₃ | CH | |
| H | CH₃ | H | CH₂CO₂CH₃ | CH₃ | OCH₃ | CH | |
| H | CH₃ | H | CH₂CO₂CH₃ | OCH₃ | OCH₃ | CH | |
| H | CH₃ | H | CH₂CO₂CH₃ | CH₃ | CH₃ | N | |
| H | CH₃ | H | CH₂CO₂CH₃ | CH₃ | OCH₃ | N | |
| H | CH₃ | H | CH₂CO₂CH₃ | OCH₃ | OCH₃ | N | |
| H | CH₃ | H | CH₂CO₂CH₃ | OCH₃ | Cl | CH | |
| H | CH₃ | H | CH₂CO₂CH₂CH₃ | CH₃ | CH₃ | CH | |
| H | CH₃ | H | CH₂CO₂CH₂CH₃ | CH₃ | OCH₃ | CH | |
| H | CH₃ | H | CH₂CO₂CH₂CH₃ | OCH₃ | OCH₃ | CH | |
| H | CH₃ | H | CH₂CO₂CH₂CH₃ | CH₃ | CH₃ | N | |
| H | CH₃ | H | CH₂CO₂CH₂CH₃ | CH₃ | OCH₃ | N | |
| H | CH₃ | H | CH₂CO₂CH₂CH₃ | OCH₃ | OCH₃ | N | |
| H | CH₃ | H | CH₂CO₂CH₂CH₃ | OCH₃ | Cl | CH | |
| H | CH₃ | H | CH₂CH₂CO₂CH₃ | CH₃ | CH₃ | CH | |
| H | CH₃ | H | CH₂CH₂CO₂CH₃ | CH₃ | OCH₃ | CH | |
| H | CH₃ | H | CH₂CH₂CO₂CH₃ | OCH₃ | OCH₃ | CH | |
| H | CH₃ | H | CH₂CH₂CO₂CH₃ | CH₃ | CH₃ | N | |
| H | CH₃ | H | CH₂CH₂CO₂CH₃ | OCH₃ | OCH₃ | N | |
| H | CH₃ | H | CH₂CH₂CO₂CH₃ | OCH₃ | Cl | CH | |
| H | CH₃ | H | CH₂—CO₂CH₂CH=CH₂ | CH₃ | CH₃ | CH | |
| H | CH₃ | H | CH₂—CO₂CH₂CH=CH₂ | CH₃ | OCH₃ | CH | |
| H | CH₃ | H | CH₂—CO₂CH₂CH=CH₂ | OCH₃ | OCH₃ | CH | |
| H | CH₃ | H | CH₂—CO₂CH₂CH=CH₂ | CH₃ | CH₃ | N | |
| H | CH₃ | H | CH₂—CO₂CH₂CH=CH₂ | CH₃ | OCH₃ | N | |
| H | CH₃ | H | CH₂—CO₂CH₂CH=CH₂ | OCH₃ | OCH₃ | N | |
| H | CH₃ | H | CH₂—CO₂CH₂CH=CH₂ | OCH₃ | Cl | CH | |
| H | CH₃ | H | CH₂(CH₂)₄CO₂CH₃ | CH₃ | CH₃ | CH | |
| H | CH₃ | H | CH₂(CH₂)₄CO₂CH₃ | CH₃ | OCH₃ | CH | |
| H | CH₃ | H | CH₂(CH₂)₄CO₂CH₃ | OCH₃ | OCH₃ | CH | |
| H | CH₃ | H | CH₂(CH₂)₄CO₂CH₃ | CH₃ | CH₃ | N | |
| H | CH₃ | H | CH₂(CH₂)₄CO₂CH₃ | CH₃ | OCH₃ | N | |
| H | CH₃ | CH₃ | CH₂(CH₂)₄CO₂CH₃ | OCH₃ | OCH₃ | N | |
| H | CH₃ | H | CH₂(CH₂)₄CO₂CH₃ | OCH₃ | Cl | CH | |
| H | CH₃ | H | CH₂CO₂CH₂C≡CH | CH₃ | CH₃ | CH | |
| H | CH₃ | H | CH₂CO₂CH₂C≡CH | CH₃ | OCH₃ | CH | |
| H | CH₃ | H | CH₂CO₂CH₂C≡CH | OCH₃ | OCH₃ | CH | |
| H | CH₃ | H | CH₂CO₂CH₂C≡CH | CH₃ | CH₃ | N | |
| H | CH₃ | H | CH₂CO₂CH₂C≡CH | CH₃ | OCH₃ | N | |
| H | CH₃ | H | CH₂CO₂CH₂C≡CH | OCH₃ | OCH₃ | N | |
| H | CH₃ | H | CH₂CO₂CH₂C≡CH | OCH₃ | Cl | CH | |
| H | CH₃ | H | CH₂CO₂CF₃ | CH₃ | CH₃ | CH | |
| CH₃ | CH₃ | H | CH₂CO₂CO₂CF₃ | CH₃ | OCH₃ | CH | |
| H | CH₃ | H | CH₂CO₂CF₃ | OCH₃ | OCH₃ | CH | |
| H | CH₃ | H | CH₂CO₂CF₃ | CH₃ | CH₃ | N | |
| H | CH₃ | H | CH₂CO₂CF₃ | CH₃ | OCH₃ | N | |
| H | CH₃ | H | CH₂CO₂CF₃ | OCH₃ | OCH₃ | N | |
| H | CH₃ | H | CH₂CO₂CF₃ | OCH₃ | Cl | CH | |
| H | CH₃ | H | CH₂C(O)N(CH₃)₂ | CH₃ | CH₃ | CH | |
| H | CH₃ | H | CH₂C(O)N(CH₃)₂ | CH₃ | OCH₃ | CH | |
| H | CH₃ | H | CH₂C(O)N(CH₃)₂ | OCH₃ | OCH₃ | CH | |
| H | CH₃ | H | CH₂C(O)N(CH₃)₂ | CH₃ | CH₃ | N | |
| H | CH₃ | H | CH₂C(O)N(CH₃)₂ | CH₃ | OCH₃ | N | |
| H | CH₃ | H | CH₂C(O)N(CH₃)₂ | OCH₃ | OCH₃ | N | |
| H | CH₃ | H | CH₂C(O)N(CH₃)₂ | OCH₃ | Cl | CH | |
| H | CH₃ | H | SeCH₃ | CH₃ | CH₃ | CH | |
| H | CH₃ | H | SeCH₃ | CH₃ | OCH₃ | CH | |
| H | CH₃ | H | SeCH₃ | OCH₃ | OCH₃ | CH | |
| H | CH₃ | H | SeCH₃ | CH₃ | CH₃ | N | |
| H | CH₃ | H | SeCH₃ | CH₃ | OCH₃ | N | |
| H | CH₃ | H | SeCH₃ | OCH₃ | OCH₃ | N | |
| H | CH₃ | H | SeCH₃ | OCH₃ | Cl | CH | |
| H | CH₃ | H | CH₂Ph | CH₃ | CH₃ | CH | |
| H | CH₃ | H | CH₂Ph | CH₃ | OCH₃ | CH | |
| H | CH₃ | H | CH₂Ph | OCH₃ | OCH₃ | CH | |
| H | CH₃ | H | CH₂Ph | CH₃ | CH₃ | N | |
| H | CH₃ | H | CH₂Ph | OCH₃ | OCH₃ | N | |
| H | CH₃ | H | CH₂Ph | OCH₃ | Cl | CH | |
| H | CH₃ | H | CH₂—(1,3-dioxolan-2-yl) | CH₃ | CH₃ | CH | |
| H | CH₃ | H | CH₂—(1,3-dioxolan-2-yl) | CH₃ | OCH₃ | CH | |
| H | CH₃ | H | CH₂—(1,3-dioxolan-2-yl) | OCH₃ | OCH₃ | CH | |
| H | CH₃ | H | CH₂—(1,3-dioxolan-2-yl) | CH₃ | CH₃ | N | |
| H | CH₃ | H | CH₂—(1,3-dioxolan-2-yl) | CH₃ | OCH₃ | N | |
| H | CH₃ | H | CH₂—(1,3-dioxolan-2-yl) | OCH₃ | OCH₃ | N | |
| H | CH₃ | H | CH₂—OTHP | OCH₃ | Cl | CH | |
| H | CH₃ | H | CH₂—OTHP | CH₃ | CH₃ | CH | |
| H | CH₃ | H | CH₂—OTHP | CH₃ | OCH₃ | CH | |
| H | CH₃ | H | CH₂—OTHP | OCH₃ | OCH₃ | CH | |
| H | CH₃ | H | CH₂—OTHP | CH₃ | CH₃ | N | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂—OTHP | CH₃ | OCH₃ | N | |
| H | CH₃ | CH₃ | CH₂—OTHP | OCH₃ | OCH₃ | N | |
| H | CH₃ | H | Si(CH₃)₃ | CH₃ | CH₃ | CH | |
| H | CH₃ | H | Si(CH₃)₃ | CH₃ | OCH₃ | CH | |
| H | CH₃ | H | Si(CH₃)₃ | OCH₃ | OCH₃ | CH | |
| H | CH₃ | H | Si(CH₃)₃ | CH₃ | CH₃ | N | |
| H | CH₃ | H | Si(CH₃)₃ | CH₃ | OCH₃ | N | |
| H | CH₃ | H | Si(CH₃)₃ | OCH₃ | OCH₃ | N | |
| H | CH₃ | H | Si(CH₃)₃ | OCH₃ | Cl | CH | |
| H | CH₃ | H | Si(CH₃)₂Ph | CH₃ | CH₃ | CH | |
| H | CH₃ | H | Si(CH₃)₂Ph | CH₃ | OCH₃ | CH | |
| H | CH₃ | H | Si(CH₃)₂Ph | OCH₃ | OCH₃ | CH | |
| H | CH₃ | H | Si(CH₃)₂Ph | CH₃ | CH₃ | N | |
| H | CH₃ | H | Si(CH₃)₂Ph | CH₃ | OCH₃ | N | |
| H | CH₃ | H | Si(CH₃)₂Ph | OCH₃ | OCH₃ | N | |
| H | CH₃ | H | Si(CH₃)₂Ph | OCH₃ | Cl | CH | |
| H | CH₃ | H | Si(CH₃)₂CH₂CH₃ | CH₃ | CH₃ | CH | |
| H | CH₃ | H | Si(CH₃)₂CH₂CH₃ | CH₃ | OCH₃ | CH | |
| H | CH₃ | H | Si(CH₃)₂CH₂CH₃ | OCH₃ | OCH₃ | CH | |
| H | CH₃ | H | Si(CH₃)₂CH₂CH₃ | CH₃ | CH₃ | N | |
| H | CH₃ | H | Si(CH₃)₂CH₂CH₃ | OCH₃ | OCH₃ | N | |
| H | CH₃ | H | Si(CH₃)₂CH₂CH₃ | OCH₃ | Cl | CH | |
| H | CH₃ | H | A-HET | CH₃ | CH₃ | CH | |
| H | CH₃ | H | A-HET | CH₃ | OCH₃ | CH | |
| H | CH₃ | H | A-HET | OCH₃ | OCH₃ | CH | |
| H | CH₃ | H | A-HET | CH₃ | CH₃ | N | |
| H | CH₃ | H | A-HET | CH₃ | OCH₃ | N | |
| H | CH₃ | H | A-HET | OCH₃ | OCH₃ | N | |
| H | CH₃ | H | A-HET | OCH₃ | Cl | CH | |
| H | CH₃ | H | B-HET | CH₃ | CH₃ | CH | |
| H | CH₃ | H | B-HET | CH₃ | OCH₃ | CH | |
| H | CH₃ | H | B-HET | OCH₃ | OCH₃ | CH | |
| H | CH₃ | H | B-HET | CH₃ | CH₃ | N | |
| H | CH₃ | H | B-HET | CH₃ | OCH₃ | N | |
| H | CH₃ | CH₃ | B-HET | OCH₃ | OCH₃ | N | |
| H | CH₃ | H | B-HET | OCH₃ | Cl | CH | |
| H | CH₃ | H | C-HET | CH₃ | CH₃ | CH | |
| H | CH₃ | H | C-HET | CH₃ | OCH₃ | CH | |
| H | CH₃ | H | C-HET | OCH₃ | OCH₃ | CH | |
| H | CH₃ | H | C-HET | CH₃ | CH₃ | N | |
| H | CH₃ | H | C-HET | CH₃ | OCH₃ | N | |
| H | CH₃ | H | C-HET | OCH₃ | OCH₃ | N | |
| H | CH₃ | H | C-HET | OCH₃ | Cl | CH | |
| H | CH₃ | H | D-HET | CH₃ | CH₃ | CH | |
| CH₃ | CH₃ | H | D-HET | CH₃ | OCH₃ | CH | |
| H | CH₃ | H | D-HET | OCH₃ | OCH₃ | CH | |
| H | CH₃ | H | D-HET | CH₃ | CH₃ | N | |
| H | CH₃ | H | D-HET | CH₃ | OCH₃ | N | |
| H | CH₃ | H | D-HET | OCH₃ | OCH₃ | N | |
| H | CH₃ | H | D-HET | OCH₃ | Cl | CH | |
| H | CH₃ | H | C(O)A-HET | CH₃ | CH₃ | CH | |
| H | CH₃ | H | C(O)A-HET | CH₃ | OCH₃ | CH | |
| H | CH₃ | H | C(O)A-HET | OCH₃ | OCH₃ | CH | |
| H | CH₃ | H | C(O)A-HET | CH₃ | CH₃ | N | |
| H | CH₃ | H | C(O)A-HET | CH₃ | OCH₃ | N | |
| H | CH₃ | H | C(O)A-HET | OCH₃ | OCH₃ | N | |
| H | CH₃ | H | C(O)A-HET | OCH₃ | Cl | CH | |
| H | CH₃ | H | C(O)B-HET | CH₃ | CH₃ | CH | |
| H | CH₃ | H | C(O)B-HET | CH₃ | OCH₃ | CH | |
| H | CH₃ | H | C(O)B-HET | OCH₃ | OCH₃ | CH | |
| H | CH₃ | H | C(O)B-HET | CH₃ | CH₃ | N | |
| H | CH₃ | H | C(O)B-HET | CH₃ | OCH₃ | N | |
| H | CH₃ | H | C(O)B-HET | OCH₃ | OCH₃ | N | |
| H | CH₃ | H | C(O)B-HET | OCH₃ | Cl | CH | |
| H | CH₃ | H | C(O)C-HET | CH₃ | CH₃ | CH | |
| H | CH₃ | H | C(O)C-HET | CH₃ | OCH₃ | CH | |
| H | CH₃ | H | C(O)C-HET | OCH₃ | OCH₃ | CH | |
| H | CH₃ | H | C(O)C-HET | CH₃ | CH₃ | N | |
| H | CH₃ | H | C(O)C-HET | OCH₃ | OCH₃ | N | |
| H | CH₃ | H | C(O)C-HET | OCH₃ | Cl | CH | |
| H | CH₃ | H | C(O)D-HET | CH₃ | CH₃ | CH | |
| H | CH₃ | H | C(O)D-HET | CH₃ | OCH₃ | CH | |
| H | CH₃ | H | C(O)D-HET | OCH₃ | OCH₃ | CH | |
| H | CH₃ | H | C(O)D-HET | CH₃ | CH₃ | N | |
| H | CH₃ | H | C(O)D-HET | CH₃ | OCH₃ | N | |
| H | CH₃ | H | C(O)D-HET | OCH₃ | OCH₃ | N | |

TABLE Ia-continued

General Structure Ia

| R | R₁ | R₂ | R₃ | X | Y | Z | m.p. (°C.) |
|---|---|---|---|---|---|---|---|
| H | CH₃ | H | C(O)D-HET | OCH₃ | Cl | CH | | wherein

A-HET is 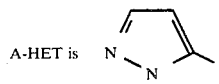

B-HET is 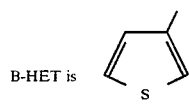

C-HET is 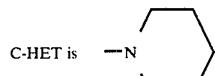

D-HET is 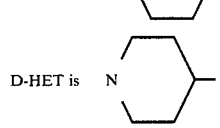

TABLE II

General Structure II

| R | R₁ | R₂ | R₃ | X | Y | Z | m.p. (°C.) |
|---|---|---|---|---|---|---|---|
| H | CH₃ | H | CH₂F | CH₃ | CH₃ | CH | |
| H | CH₃ | H | CH₂F | CH₃ | OCH₃ | CH | |
| H | CH₃ | H | CH₂F | OCH₃ | OCH₃ | CH | |
| H | CH₃ | H | CH₂F | CH₃ | CH₃ | N | |
| H | CH₃ | H | CH₂F | CH₃ | OCH₃ | N | |
| H | CH₃ | H | CH₂F | OCH₃ | OCH₃ | N | |
| H | CH₃ | H | CH₂F | OCH₃ | Cl | CH | |
| H | CH₃ | H | CH₂CH₂F | CH₃ | CH₃ | CH | |
| H | CH₃ | H | CH₂CH₂F | CH₃ | OCH₃ | CH | |
| H | CH₃ | H | CH₂CH₂F | OCH₃ | OCH₃ | CH | |
| H | CH₃ | H | CH₂CH₂F | CH₃ | CH₃ | N | |
| H | CH₃ | H | CH₂CH₂F | CH₃ | OCH₃ | N | |
| H | CH₃ | H | CH₂CH₂F | OCH₃ | OCH₃ | N | |
| H | CH₃ | H | CH₂CH₂F | OCH₃ | Cl | CH | |
| H | CH₃ | H | CHFCH₂F | CH₃ | CH₃ | CH | |
| H | CH₃ | H | CHFCH₂F | CH₃ | OCH₃ | CH | |
| H | CH₃ | H | CHFCH₂F | OCH₃ | OCH₃ | CH | |
| H | CH₃ | H | CHFCH₂F | CH₃ | CH₃ | N | |
| H | CH₃ | H | CHFCH₂F | OCH₃ | OCH₃ | N | |
| H | CH₃ | H | CHFCH₂F | OCH₃ | Cl | CH | |
| H | CH₃ | H | CH₂CHF₂ | CH₃ | CH₃ | CH | |
| H | CH₃ | H | CH₂CHF₂ | CH₃ | OCH₃ | CH | |
| H | CH₃ | H | CH₂CHF₂ | OCH₃ | OCH₃ | CH | |
| H | CH₃ | H | CH₂CHF₂ | CH₃ | CH₃ | N | |
| H | CH₃ | H | CH₂CHF₂ | CH₃ | OCH₃ | N | |
| H | CH₃ | H | CH₂CHF₂ | OCH₃ | OCH₃ | N | |
| H | CH₃ | H | CH₂CHF₂ | OCH₃ | Cl | CH | |
| H | CH₃ | H | CH(CH₂F)₂ | CH₃ | CH₃ | CH | |
| H | CH₃ | H | CH(CH₂F)₂ | CH₃ | OCH₃ | CH | |
| H | CH₃ | H | CH(CH₂F)₂ | OCH₃ | OCH₃ | CH | |
| H | CH₃ | H | CH₂CH₂CH₂F | CH₃ | CH₃ | N | |
| H | CH₃ | H | CH₂CH₂CH₂F | CH₃ | OCH₃ | N | |
| H | CH₃ | CH₃ | CH₂CH₂CH₂F | OCH₃ | OCH₃ | N | |
| H | CH₃ | H | CH₂CH₂CH₂F | OCH₃ | Cl | CH | |
| H | CH₃ | H | CH₂CH₂CH₂F | CH₃ | CH₃ | CH | |
| H | CH₃ | H | CH₂CH₂CH₂F | CH₃ | OCH₃ | CH | |
| H | CH₃ | H | CH₂CH₂CH₂F | OCH₃ | OCH₃ | CH | |
| H | CH₃ | H | CH₂(CH₂)₂CH₂F | CH₃ | CH₃ | N | |
| H | CH₃ | H | CH₂(CH₂)₂CH₂F | CH₃ | OCH₃ | N | |
| H | CH₃ | H | CH₂(CH₂)₂CH₂F | OCH₃ | OCH₃ | N | |
| H | CH₃ | H | CH₂(CH₂)₂CH₂F | OCH₃ | Cl | CH | |
| H | CH₃ | H | CH₂(CH₂)₂CH₂F | CH₃ | CH₃ | CH | |
| CH₃ | CH₃ | H | CH₂(CH₂)₂CH₂F | CH₃ | OCH₃ | CH | |
| H | CH₃ | H | CH₂(CH₂)₂CH₂F | OCH₃ | OCH₃ | CH | |
| H | CH₃ | H | CH(CH₃)CH₂F | CH₃ | CH₃ | N | |
| H | CH₃ | H | CH(CH₃)CH₂F | CH₃ | OCH₃ | N | |
| H | CH₃ | H | CH(CH₃)CH₂F | OCH₃ | OCH₃ | N | |
| H | CH₃ | H | CH(CH₃)CH₂F | OCH₃ | Cl | CH | |
| H | CH₃ | H | CH₂Br | CH₃ | CH₃ | CH | |
| H | CH₃ | H | CH₂Br | CH₃ | OCH₃ | CH | |
| H | CH₃ | H | CH₂Br | OCH₃ | OCH₃ | CH | |
| H | CH₃ | H | CH₂Br | CH₃ | CH₃ | N | |

TABLE II-continued

General Structure II

| R | R₁ | R₂ | R₃ | X | Y | Z | m.p. (°C.) |
|---|----|----|----|---|---|---|------------|
| H | CH₃ | H | CH₂Br | CH₃ | OCH₃ | N | |
| H | CH₃ | H | CH₂Br | OCH₃ | OCH₃ | N | |
| H | CH₃ | H | CH₂Br | OCH₃ | Cl | CH | |
| H | CH₃ | H | CH₂CH₂Br | CH₃ | CH₃ | CH | |
| H | CH₃ | H | CH₂CH₂Br | CH₃ | OCH₃ | CH | |
| H | CH₃ | H | CH₂CH₂Br | OCH₃ | OCH₃ | CH | |
| H | CH₃ | H | CH₂CH₂Br | CH₃ | CH₃ | N | |
| H | CH₃ | H | CH₂CH₂Br | CH₃ | OCH₃ | N | |
| H | CH₃ | H | CH₂CH₂Br | OCH₃ | OCH₃ | N | |
| H | CH₃ | H | CH₂CH₂Br | OCH₃ | Cl | CH | |
| H | CH₃ | H | CHBr—CH₃ | CH₃ | CH₃ | CH | |
| H | CH₃ | H | CHBrCH₃ | CH₃ | OCH₃ | CH | |
| H | CH₃ | H | CHBrCH₃ | OCH₃ | OCH₃ | CH | |
| H | CH₃ | H | CHBrCH₃ | CH₃ | CH₃ | N | |
| H | CH₃ | H | CHBrCH₃ | OCH₃ | OCH₃ | N | |
| H | CH₃ | H | CHBrCH₃ | OCH₃ | Cl | CH | |
| H | CH₃ | H | CH₂CHBr₂ | CH₃ | CH₃ | CH | |
| H | CH₃ | H | CH₂CHBr₂ | CH₃ | OCH₃ | CH | |
| H | CH₃ | H | CH₂CHBr₂ | OCH₃ | OCH₃ | CH | |
| H | CH₃ | H | CH₂CHBr₂ | CH₃ | CH₃ | N | |
| H | CH₃ | H | CH₂CHBr₂ | CH₃ | OCH₃ | N | |
| H | CH₃ | H | CH₂CHBr₂ | OCH₃ | OCH₃ | N | |
| H | CH₃ | H | CH₂CHBr₂ | OCH₃ | Cl | CH | |
| H | CH₃ | H | CH(CH₂Br)₂ | CH₃ | CH₃ | CH | |
| H | CH₃ | H | CH(CH₂Br)₂ | CH₃ | OCH₃ | CH | |
| H | CH₃ | H | CH(CH₂Br)₂ | OCH₃ | OCH₃ | CH | |
| H | CH₃ | H | CH(CH₂Br)₂ | CH₃ | CH₃ | N | |
| H | CH₃ | H | CH₂CHBrCH₃ | CH₃ | OCH₃ | N | |
| H | CH₃ | CH₃ | CH₂CHBrCH₃ | OCH₃ | OCH₃ | N | |
| H | CH₃ | H | CH₂CHBrCH₃ | OCH₃ | Cl | CH | |
| H | CH₃ | H | CH₂CHBrCH₃ | CH₃ | CH₃ | CH | |
| H | CH₃ | H | CH₂CHBrCH₃ | CH₃ | OCH₃ | CH | |
| H | CH₃ | H | CH₂(CH₂)₂CH₂Br | OCH₃ | OCH₃ | CH | |
| H | CH₃ | H | CH₂(CH₂)₂CH₂Br | CH₃ | CH₃ | N | |
| H | CH₃ | H | CH₂(CH₂)₂CH₂Br | CH₃ | OCH₃ | N | |
| H | CH₃ | H | CH₂(CH₂)₂CH₂Br | OCH₃ | OCH₃ | N | |
| H | CH₃ | H | CH₂(CH₂)₂CH₂Br | OCH₃ | Cl | CH | |
| H | CH₃ | H | CH₂(CH₂)₂CH₂Br | CH₃ | CH₃ | CH | |
| CH₃ | CH₃ | H | CH₂(CH₂)₂CH₂Br | CH₃ | OCH₃ | CH | |
| H | CH₃ | H | C(CH₃)(CH₂Br)CH₃ | OCH₃ | OCH₃ | CH | |
| H | CH₃ | H | CH₂CHBrCH₂CH₃ | CH₃ | CH₃ | N | |
| H | CH₃ | H | CH₂CHBrCH₂CH₃ | CH₃ | OCH₃ | N | |
| H | CH₃ | H | CH₂CHBrCH₂CH₃ | OCH₃ | OCH₃ | N | |
| H | CH₃ | H | CH₂CHBrCH₂CH₃ | OCH₃ | Cl | CH | |
| H | CH₃ | H | CH₂Cl | CH₃ | CH₃ | CH | |
| H | CH₃ | H | CH₂Cl | CH₃ | OCH₃ | CH | |
| H | CH₃ | H | CH₂Cl | OCH₃ | OCH₃ | CH | |
| H | CH₃ | H | CH₂Cl | CH₃ | CH₃ | N | |
| H | CH₃ | H | CH₂Cl | CH₃ | OCH₃ | N | |
| H | CH₃ | H | CH₂Cl | OCH₃ | OCH₃ | N | |
| H | CH₃ | H | CH₂Cl | OCH₃ | Cl | CH | |
| H | CH₃ | H | CH₂CH₂Cl | CH₃ | CH₃ | CH | |
| H | CH₃ | H | CH₂CH₂Cl | CH₃ | OCH₃ | CH | |
| H | CH₃ | H | CH₂CH₂Cl | OCH₃ | OCH₃ | CH | |
| H | CH₃ | H | CH₂CH₂Cl | CH₃ | CH₃ | N | |
| H | CH₃ | H | CH₂CH₂Cl | CH₃ | OCH₃ | N | |
| H | CH₃ | H | CH₂CH₂Cl | OCH₃ | OCH₃ | N | |
| H | CH₃ | H | CH₂CH₂Cl | OCH₃ | Cl | CH | |
| H | CH₃ | H | CHClCH₂Cl | CH₃ | CH₃ | CH | |
| H | CH₃ | H | CHClCH₂Cl | CH₃ | OCH₃ | CH | |
| H | CH₃ | H | CHClCH₂Cl | OCH₃ | OCH₃ | CH | |
| H | CH₃ | H | CHClCH₂Cl | CH₃ | CH₃ | N | |
| H | CH₃ | H | CHClCH₂Cl | OCH₃ | OCH₃ | N | |
| H | CH₃ | H | CHClCH₂Cl | OCH₃ | Cl | CH | |
| H | CH₃ | H | CH₂CCl₂CH₃ | CH₃ | CH₃ | CH | |
| H | CH₃ | H | CH₂CCl₂CH₃ | CH₃ | OCH₃ | CH | |
| H | CH₃ | H | CH₂CCl₂CH₃ | OCH₃ | OCH₃ | CH | |
| H | CH₃ | H | CH(CH₂Cl)₂ | CH₃ | CH₃ | N | |
| H | CH₃ | H | CH(CH₂Cl)₂ | CH₃ | OCH₃ | N | |
| H | CH₃ | H | CH(CH₂Cl)₂ | OCH₃ | OCH₃ | N | |
| H | CH₃ | H | CH(CH₂Cl)₂ | OCH₃ | Cl | CH | |
| H | CH₃ | H | CH(CH₂Cl)₂ | CH₃ | CH₃ | CH | |
| H | CH₃ | H | CH₂CH₂CH₂Cl | CH₃ | OCH₃ | CH | |
| H | CH₃ | H | CH₂CH₂CH₂Cl | OCH₃ | OCH₃ | CH | |
| H | CH₃ | H | CH₂CH₂CH₂Cl | CH₃ | CH₃ | N | |
| H | CH₃ | H | CH₂CH₂CH₂Cl | CH₃ | OCH₃ | N | |
| H | CH₃ | CH₃ | CH₂CH₂CH₂Cl | OCH₃ | OCH₃ | N | |
| H | CH₃ | H | CH₂CH₂CH₂Cl | OCH₃ | Cl | CH | |
| H | CH₃ | H | CH₂CH₂CH₂Cl | CH₃ | CH₃ | CH | |
| H | CH₃ | H | CH₂(CH₂)₂CH₂Cl | CH₃ | OCH₃ | CH | |

TABLE II-continued

General Structure II

| R | $R_1$ | $R_2$ | $R_3$ | X | Y | Z | m.p. (°C.) |
|---|---|---|---|---|---|---|---|
| H | $CH_3$ | H | $CH_2(CH_2)_2CH_2Cl$ | $OCH_3$ | $OCH_3$ | CH | |
| H | $CH_3$ | H | $CH_2(CH_2)_2CH_2Cl$ | $CH_3$ | $CH_3$ | N | |
| H | $CH_3$ | H | $CH_2(CH_2)_2CH_2Cl$ | $CH_3$ | $OCH_3$ | N | |
| H | $CH_3$ | H | $CH_2(CH_2)_2CH_2Cl$ | $OCH_3$ | $OCH_3$ | N | |
| H | $CH_3$ | H | $CH_2(CH_2)_2CH_2Cl$ | $OCH_3$ | Cl | CH | |
| H | $CH_3$ | H | $CH_2(CH_2)_2CH_2Cl$ | $CH_3$ | $CH_3$ | CH | |
| $CH_3$ | $CH_3$ | H | $CH(CH_3)CH_2Cl$ | $CH_3$ | $OCH_3$ | CH | |
| H | $CH_3$ | H | $CH(CH_3)CH_2Cl$ | $OCH_3$ | $OCH_3$ | CH | |
| H | $CH_3$ | H | $CH(CH_3)CH_2Cl$ | $CH_3$ | $CH_3$ | N | |
| H | $CH_3$ | H | $CHClCHClCH_3$ | $CH_3$ | $OCH_3$ | N | |
| H | $CH_3$ | H | $CHClCHClCH_3$ | $OCH_3$ | $OCH_3$ | N | |
| H | $CH_3$ | H | $CHClCHClCH_3$ | $OCH_3$ | Cl | CH | |
| H | $CH_3$ | H | $CH_2I$ | $CH_3$ | $CH_3$ | CH | |
| H | $CH_3$ | H | $CH_2I$ | $CH_3$ | $OCH_3$ | CH | |
| H | $CH_3$ | H | $CH_2I$ | $OCH_3$ | $OCH_3$ | CH | |
| H | $CH_3$ | H | $CH_2I$ | $CH_3$ | $CH_3$ | N | |
| H | $CH_3$ | H | $CH_2I$ | $CH_3$ | $OCH_3$ | N | |
| H | $CH_3$ | H | $CH_2I$ | $OCH_3$ | $OCH_3$ | N | |
| H | $CH_3$ | H | $CH_2I$ | $OCH_3$ | Cl | CH | |
| H | $CH_3$ | H | $CH_2CF_3$ | $CH_3$ | $CH_3$ | CH | |
| H | $CH_3$ | H | $CH_2CF_3$ | $CH_3$ | $OCH_3$ | CH | |
| H | $CH_3$ | H | $CH_2CF_3$ | $OCH_3$ | $OCH_3$ | CH | |
| H | $CH_3$ | H | $CH_2CF_3$ | $CH_3$ | $CH_3$ | N | |
| H | $CH_3$ | H | $CH_2CF_3$ | $CH_3$ | $OCH_3$ | N | |
| H | $CH_3$ | H | $CH_2CF_3$ | $OCH_3$ | $OCH_3$ | N | |
| H | $CH_3$ | H | $CH_2CF_3$ | $OCH_3$ | Cl | CH | |
| H | $CH_3$ | H | $CH_2CH_2CF_3$ | $CH_3$ | $CH_3$ | CH | |
| H | $CH_3$ | H | $CH_2CH_2CF_3$ | $CH_3$ | $OCH_3$ | CH | |
| H | $CH_3$ | H | $CH_2CH_2CF_3$ | $OCH_3$ | $OCH_3$ | CH | |
| H | $CH_3$ | H | $CH_2CH_2CF_3$ | $CH_3$ | $CH_3$ | N | |
| H | $CH_3$ | H | $CH_2CH_2CF_3$ | $OCH_3$ | $OCH_3$ | N | |
| H | $CH_3$ | H | $CH_2CH_2CF_3$ | $OCH_3$ | Cl | CH | |
| H | $CH_3$ | H | $CH_2(CH_2)_2CF_3$ | $CH_3$ | $CH_3$ | CH | |
| H | $CH_3$ | H | $CH_2(CH_2)_2CF_3$ | $CH_3$ | $OCH_3$ | CH | |
| H | $CH_3$ | H | $CH_2(CH_2)_2CF_3$ | $OCH_3$ | $OCH_3$ | CH | |
| H | $CH_3$ | H | $CH_2(CH_2)_2CF_3$ | $CH_3$ | $CH_3$ | N | |
| H | $CH_3$ | H | $CH_2(CH_2)_2CF_3$ | $CH_3$ | $OCH_3$ | N | |
| H | $CH_3$ | H | $CH_2(CH_2)_2CF_3$ | $OCH_3$ | $OCH_3$ | N | |
| H | $CH_3$ | H | $CH_2(CH_2)_3CF_3$ | $OCH_3$ | Cl | CH | |
| H | $CH_3$ | H | $CH_2(CH_2)_3CF_3$ | $CH_3$ | $CH_3$ | CH | |
| H | $CH_3$ | H | $CH_2(CH_2)_3CF_3$ | $CH_3$ | $OCH_3$ | CH | |
| H | $CH_3$ | H | $CH_2(CH_2)_3CF_3$ | $OCH_3$ | $OCH_3$ | CH | |
| H | $CH_3$ | H | $CH_2(CH_2)_3CF_3$ | $CH_3$ | $CH_3$ | N | |
| H | $CH_3$ | H | $CH_2(CH_2)_3CF_3$ | $CH_3$ | $OCH_3$ | N | |
| H | $CH_3$ | $CH_3$ | $CH_2(CH_2)_3CF_3$ | $OCH_3$ | $OCH_3$ | N | |
| H | $CH_3$ | H | $CH(CF_3)_2$ | $OCH_3$ | Cl | CH | |
| H | $CH_3$ | H | $CH(CF_3)_2$ | $CH_3$ | $CH_3$ | CH | |
| H | $CH_3$ | H | $CH(CF_3)_2$ | $CH_3$ | $OCH_3$ | CH | |
| H | $CH_3$ | H | $CH(CF_3)_2$ | $OCH_3$ | $OCH_3$ | CH | |
| H | $CH_3$ | H | $CH(CF_3)_2$ | $CH_3$ | $CH_3$ | N | |
| H | $CH_3$ | H | $CH(CF_3)_2$ | $CH_3$ | $OCH_3$ | N | |
| H | $CH_3$ | H | $CH(CF_3)_2$ | $OCH_3$ | $OCH_3$ | N | |
| H | $CH_3$ | H | $CH_2(CH_2)_4CF_3$ | $OCH_3$ | Cl | CH | |
| H | $CH_3$ | H | $CH_2(CH_2)_5CF_3$ | $CH_3$ | $CH_3$ | CH | |
| $CH_3$ | $CH_3$ | H | $CH_2(CH_2)_6CF_3$ | $CH_3$ | $OCH_3$ | CH | |
| H | $CH_3$ | H | $CH_2(CH_2)_7CF_3$ | $OCH_3$ | $OCH_3$ | CH | |
| H | $CH_3$ | H | $CH_2(CH_2)_8CF_3$ | $CH_3$ | $CH_3$ | N | |
| H | $CH_3$ | H | $CHF(CH_2)_8CF_3$ | $CH_3$ | $OCH_3$ | N | |
| H | $CH_3$ | H | $CH(CHF)_8CF_3$ | $OCH_3$ | $OCH_3$ | N | |
| H | $CH_3$ | H | $CH(CHF)_8CF_3$ | $OCH_3$ | Cl | CH | |
| H | $CH_3$ | H | $CH_2OCH_3$ | $CH_3$ | $CH_3$ | CH | |
| H | $CH_3$ | H | $CH_2OCH_3$ | $CH_3$ | $OCH_3$ | CH | |
| H | $CH_3$ | H | $CH_2OCH_3$ | $OCH_3$ | $OCH_3$ | CH | |
| H | $CH_3$ | H | $CH_2OCH_3$ | $CH_3$ | $CH_3$ | N | |
| H | $CH_3$ | H | $CH_2OCH_3$ | $CH_3$ | $OCH_3$ | N | |
| H | $CH_3$ | H | $CH_2OCH_3$ | $OCH_3$ | $OCH_3$ | N | |
| H | $CH_3$ | H | $CH_2OCH_3$ | $OCH_3$ | Cl | CH | |
| H | $CH_3$ | H | $CH_2OCH_2CH_3$ | $CH_3$ | $CH_3$ | CH | |
| H | $CH_3$ | H | $CH_2OCH_2CH_3$ | $CH_3$ | $OCH_3$ | CH | |
| H | $CH_3$ | H | $CH_2OCH_2CH_3$ | $OCH_3$ | $OCH_3$ | CH | |
| H | $CH_3$ | H | $CH_2-OCH_2F$ | $CH_3$ | $CH_3$ | N | |
| H | $CH_3$ | H | $CH_2-OCH_2F$ | $CH_3$ | $OCH_3$ | N | |
| H | $CH_3$ | H | $CH_2-OCH_2F$ | $OCH_3$ | $OCH_3$ | N | |
| H | $CH_3$ | H | $CH_2-OCH_2F$ | $OCH_3$ | Cl | CH | |
| H | $CH_3$ | H | $CH_2-CH_2OCH_3$ | $CH_3$ | $CH_3$ | CH | |
| H | $CH_3$ | H | $CH_2-CH_2OCH_3$ | $CH_3$ | $OCH_3$ | CH | |
| H | $CH_3$ | H | $CH_2-CH_2OCH_3$ | $OCH_3$ | $OCH_3$ | CH | |
| H | $CH_3$ | H | $CH_2-CH_2OCH_3$ | $CH_3$ | $CH_3$ | N | |
| H | $CH_3$ | H | $CH(OCH_3)_2$ | $OCH_3$ | $OCH_3$ | N | |
| H | $CH_3$ | H | $CH(OCH_3)_2$ | $OCH_3$ | Cl | CH | |

TABLE II-continued

General Structure II

| R | R₁ | R₂ | R₃ | X | Y | Z | m.p. (°C.) |
|---|---|---|---|---|---|---|---|
| H | CH₃ | H | CH₂(CH₂)₂OCH₃ | CH₃ | CH₃ | CH | |
| H | CH₃ | H | CH₂(CH₂)₂OCH₃ | CH₃ | OCH₃ | CH | |
| H | CH₃ | H | CH₂(CH₂)₂OCH₃ | OCH₃ | OCH₃ | CH | |
| H | CH₃ | H | CH₂(CH₂)₂OCH₃ | CH₃ | CH₃ | N | |
| H | CH₃ | H | CH₂(CH₂)₂OCH₃ | CH₃ | OCH₃ | N | |
| H | CH₃ | H | CH₂(CH₂)₃OCH₃ | OCH₃ | OCH₃ | N | |
| H | CH₃ | H | CH₂(CH₂)₃OCH₃ | OCH₃ | Cl | CH | |
| H | CH₃ | H | CH₂(CH₂)₃OCH₃ | CH₃ | CH₃ | CH | |
| H | CH₃ | H | CH₂(CH₂)₃OCH₃ | CH₃ | OCH₃ | CH | |
| H | CH₃ | H | CH₂(CH₂)₃OCH₃ | OCH₃ | OCH₃ | CH | |
| H | CH₃ | H | CH(OCH₃)CH₃ | CH₃ | CH₃ | N | |
| H | CH₃ | H | CH(OCH₃)CH₃ | CH₃ | OCH₃ | N | |
| H | CH₃ | CH₃ | CH(OCH₃)CH₃ | OCH₃ | OCH₃ | N | |
| H | CH₃ | H | CH₂OCH₂C=CH₂ | OCH₃ | Cl | CH | |
| H | CH₃ | H | CH₂OCH₂C=CH₂ | CH₃ | CH₃ | CH | |
| H | CH₃ | H | CH₂OCH₂C=CH₂ | CH₃ | OCH₃ | CH | |
| H | CH₃ | H | CH₂OCH₂C=CH₂ | OCH₃ | OCH₃ | CH | |
| H | CH₃ | H | CH₂OCH₂C=CH₂ | CH₃ | CH₃ | N | |
| H | CH₃ | H | CH₂OCH₂C=CH₂ | CH₃ | OCH₃ | N | |
| H | CH₃ | H | CH₂CH(OCH₃)₂ | OCH₃ | OCH₃ | N | |
| H | CH₃ | H | CH₂CH(OCH₃)₂ | OCH₃ | Cl | CH | |
| H | CH₃ | H | CH₂CH₂CH(OCH₃)₂ | CH₃ | CH₃ | CH | |
| CH₃ | CH₃ | H | CH₂CH(OCH₃)₂ | CH₃ | OCH₃ | CH | |
| H | CH₃ | H | CH₂C(OCH₃)₂CH₃ | OCH₃ | OCH₃ | CH | |
| H | CH₃ | H | CH₂C(OCH₃)₂CH₃ | CH₃ | CH₃ | N | |
| H | CH₃ | H | CH₂C(OCH₃)₂CH₃ | CH₃ | OCH₃ | N | |
| H | CH₃ | H | CH₂(CH₂)₆OCH₃ | OCH₃ | OCH₃ | N | |
| H | CH₃ | H | CH₂(CH₂)₆OCH₃ | OCH₃ | Cl | CH | |
| H | CH₃ | H | CH₂OC(O)CH₃ | CH₃ | CH₃ | CH | |
| H | CH₃ | H | CH₂OC(O)CH₃ | CH₃ | OCH₃ | CH | |
| H | CH₃ | H | CH₂OC(O)CH₃ | OCH₃ | OCH₃ | CH | |
| H | CH₃ | H | CH₂OC(O)CH₃ | CH₃ | CH₃ | N | |
| H | CH₃ | H | CH₂OC(O)CH₃ | CH₃ | OCH₃ | N | |
| H | CH₃ | H | CH₂OC(O)CH₃ | OCH₃ | OCH₃ | N | |
| H | CH₃ | H | CH₂OC(O)CH₃ | OCH₃ | Cl | CH | |
| H | CH₃ | H | CH₂CH₂OC(O)CH₃ | CH₃ | CH₃ | CH | |
| H | CH₃ | H | CH₂CH₂OC(O)CH₃ | CH₃ | OCH₃ | CH | |
| H | CH₃ | H | CH₂CH₂OC(O)CH₃ | OCH₃ | OCH₃ | CH | |
| H | CH₃ | H | CH₂CH₂OC(O)CH₃ | CH₃ | CH₃ | N | |
| H | CH₃ | H | CH₂CH₂OC(O)CH₃ | CH₃ | OCH₃ | N | |
| H | CH₃ | H | CH₂CH₂OC(O)CH₃ | OCH₃ | OCH₃ | N | |
| H | CH₃ | H | CH₂CH₂OC(O)CH₃ | OCH₃ | Cl | CH | |
| H | CH₃ | H | CH₂(CH₂)₂OC(O)CH₃ | CH₃ | CH₃ | CH | |
| H | CH₃ | H | CH₂(CH₂)₂OC(O)CH₃ | CH₃ | OCH₃ | CH | |
| H | CH₃ | H | CH₂(CH₂)₂OC(O)CH₃ | OCH₃ | OCH₃ | CH | |
| H | CH₃ | H | CH₂(CH₂)₃OC(O)CH₃ | CH₃ | CH₃ | N | |
| H | CH₃ | H | CH₂(CH₂)₃OC(O)CH₃ | OCH₃ | OCH₃ | N | |
| H | CH₃ | H | CH₂(CH₂)₃OC(O)CH₃ | OCH₃ | Cl | CH | |
| H | CH₃ | H | CH₂(CH₂)₃OC(O)CH₃ | CH₃ | CH₃ | CH | |
| H | CH₃ | H | CH₂P(CH₃)(Br)(CH₃) | CH₃ | OCH₃ | CH | |
| H | CH₃ | H | CH₂P(C₆H₅)₃ | OCH₃ | OCH₃ | CH | |
| H | CH₃ | H | CH₂OC(O)N(CH₃)₂ | CH₃ | CH₃ | N | |
| H | CH₃ | H | CH₂OC(O)N(CH₃)₂ | CH₃ | OCH₃ | N | |
| H | CH₃ | H | CH₂OC(O)N(CH₃)₂ | OCH₃ | OCH₃ | N | |
| H | CH₃ | H | CH₂OC(O)N(CH₃)₂ | OCH₃ | Cl | CH | |
| H | CH₃ | H | CH₂OC(O)N(CH₃)₂ | CH₃ | CH₃ | CH | |
| H | CH₃ | H | CH₂OC(O)N(CH₃)₂ | CH₃ | OCH₃ | CH | |
| H | CH₃ | H | CH₂OC(O)N(CH₃)₂ | OCH₃ | OCH₃ | CH | |
| H | CH₃ | H | CH₂CH₂OC(O)N(CH₃)₂ | CH₃ | CH₃ | N | |
| H | CH₃ | H | CH₂CH₂OC(O)N(CH₃)₂ | CH₃ | OCH₃ | N | |
| H | CH₃ | CH₃ | CH₂CH₂OC(O)N(CH₃)₂ | OCH₃ | OCH₃ | N | |
| H | CH₃ | H | CH₂CH₂OC(O)N(CH₃)₂ | OCH₃ | Cl | CH | |
| H | CH₃ | H | CH₂CH₂OC(O)N(CH₃)₂ | CH₃ | CH₃ | CH | |
| H | CH₃ | H | CH₂CH₂OC(O)N(CH₃)₂ | CH₃ | OCH₃ | CH | |
| H | CH₃ | H | CH₂OSO₂CH₃ | OCH₃ | OCH₃ | CH | |
| H | CH₃ | H | CH₂OSO₂CH₃ | CH₃ | CH₃ | N | |
| H | CH₃ | H | CH₂OSO₂CH₃ | CH₃ | OCH₃ | N | |
| H | CH₃ | H | CH₂OSO₂CH₃ | OCH₃ | OCH₃ | N | |
| H | CH₃ | H | CH₂OSO₂CH₂CH₃ | OCH₃ | Cl | CH | |
| H | CH₃ | H | CH₂OSO₂CH₂CH₃ | CH₃ | CH₃ | CH | |
| CH₃ | CH₃ | H | CH₂OSO₂CH₂CH₃ | CH₃ | OCH₃ | CH | |
| H | CH₃ | H | CH₂(CH₂)₂OSO₂CH₃ | OCH₃ | OCH₃ | CH | |
| H | CH₃ | H | CH₂(CH₂)₂OSO₂CH₃ | CH₃ | CH₃ | N | |
| H | CH₃ | H | CH₂(CH₂)₂OSO₂CH₃ | CH₃ | OCH₃ | N | |
| H | CH₃ | H | CH₂(CH₂)₂OSO₂CH₃ | OCH₃ | OCH₃ | N | |
| H | CH₃ | H | CH₂(CH₂)₂OSO₂CH₃ | OCH₃ | Cl | CH | |
| H | CH₃ | H | CH₂OP(O)(CH₃)₂ | CH₃ | CH₃ | CH | |
| H | CH₃ | H | CH₂OP(O)(CH₃)₂ | CH₃ | OCH₃ | CH | |
| H | CH₃ | H | CH₂OP(O)(CH₃)₂ | OCH₃ | OCH₃ | CH | |
| H | CH₃ | H | CH₂OP(O)(CH₃)₂ | CH₃ | CH₃ | N | |

TABLE II-continued

General Structure II

| R | $R_1$ | $R_2$ | $R_3$ | X | Y | Z | m.p. (°C.) |
|---|---|---|---|---|---|---|---|
| H | $CH_3$ | H | $CH_2OP(O)(CH_3)_2$ | $CH_3$ | $OCH_3$ | N | |
| H | $CH_3$ | H | $CH_2OP(O)(CH_3)_2$ | $OCH_3$ | $OCH_3$ | N | |
| H | $CH_3$ | H | $CH_2OP(O)(CH_3)_2$ | $OCH_3$ | Cl | CH | |
| H | $CH_3$ | H | $CH_2OP(O)(CH_3)Ph$ | $CH_3$ | $CH_3$ | CH | |
| H | $CH_3$ | H | $CH_2OP(O)(CH_3)Ph$ | $CH_3$ | $OCH_3$ | CH | |
| H | $CH_3$ | H | $CH_2OP(O)(CH_3)Ph$ | $OCH_3$ | $OCH_3$ | CH | |
| H | $CH_3$ | H | $CH_2OP(O)(CH_3)Ph$ | $CH_3$ | $CH_3$ | N | |
| H | $CH_3$ | H | $CH_2OP(O)(Ph)_2$ | $CH_3$ | $OCH_3$ | N | |
| H | $CH_3$ | H | $CH_2OP(O)(Ph)_2$ | $OCH_3$ | $OCH_3$ | N | |
| H | $CH_3$ | H | $CH_2OP(O)(Ph)_2$ | $OCH_3$ | Cl | CH | |
| H | $CH_3$ | H | $CH_2OP(O)(Ph)_2$ | $CH_3$ | $CH_3$ | CH | |
| H | $CH_3$ | H | $CH_2OP(O)(Ph)_2$ | $CH_3$ | $OCH_3$ | CH | |
| H | $CH_3$ | H | $CH_2OP(O)(Ph)_2$ | $OCH_3$ | $OCH_3$ | CH | |
| H | $CH_3$ | H | $CH_2CH_2OP(O)(CH_3)_2$ | $CH_3$ | $CH_3$ | N | |
| H | $CH_3$ | H | $CH_2CH_2OP(O)(CH_3)_2$ | $OCH_3$ | $OCH_3$ | N | |
| H | $CH_3$ | H | $CH_2CH_2OP(O)(CH_3)_2$ | $OCH_3$ | Cl | CH | |
| H | $CH_3$ | H | $CH_2CH_2OP(O)(CH_3)_2$ | $CH_3$ | $CH_3$ | CH | |
| H | $CH_3$ | H | $CH_2CH_2OP(O)(CH_3)_2$ | $CH_3$ | $OCH_3$ | CH | |
| H | $CH_3$ | H | $CH_2(CH_2)_2OP(O)(CH_3)_2$ | $OCH_3$ | $OCH_3$ | CH | |
| H | $CH_3$ | H | $CH_2(CH_2)_2OP(O)(CH_3)_2$ | $CH_3$ | $CH_3$ | N | |
| H | $CH_3$ | H | $CH_2(CH_2)_2OP(O)(CH_3)_2$ | $CH_3$ | $OCH_3$ | N | |
| H | $CH_3$ | H | $CH_2(CH_2)_2OP(O)(CH_3)_2$ | $OCH_3$ | $OCH_3$ | N | |
| H | $CH_3$ | H | $CH_2(CH_2)_2OP(O)(CH_3)_2$ | $OCH_3$ | Cl | CH | |
| H | $CH_3$ | H | $CH_2(CH_2)_2OP(O)(CH_3)_2$ | $CH_3$ | $CH_3$ | CH | |
| H | $CH_3$ | H | $CH_2P(O)(CH_3)_2$ | $CH_3$ | $OCH_3$ | CH | |
| H | $CH_3$ | H | $CH_2P(O)(CH_3)_2$ | $OCH_3$ | $OCH_3$ | CH | |
| H | $CH_3$ | H | $CH_2P(O)(CH_3)_2$ | $CH_3$ | $CH_3$ | N | |
| H | $CH_3$ | H | $CH_2P(O)(CH_3)_2$ | $CH_3$ | $OCH_3$ | N | |
| H | $CH_3$ | $CH_3$ | $CH_2P(O)(CH_3)_2$ | $OCH_3$ | $OCH_3$ | N | |
| H | $CH_3$ | H | $CH_2P(O)(CH_3)_2$ | $OCH_3$ | Cl | CH | |
| H | $CH_3$ | H | $CH_2P(O)(CH_3)_2$ | $CH_3$ | $CH_3$ | CH | |
| H | $CH_3$ | H | $CH_2P(O)(OCH_3)_2$ | $CH_3$ | $OCH_3$ | CH | |
| H | $CH_3$ | H | $CH_2P(O)(OCH_3)_2$ | $OCH_3$ | $OCH_3$ | CH | |
| H | $CH_3$ | H | $CH_2P(O)(OCH_3)_2$ | $CH_3$ | $CH_3$ | N | |
| H | $CH_3$ | H | $CH_2P(O)(OCH_3)_2$ | $CH_3$ | $OCH_3$ | N | |
| H | $CH_3$ | H | $CH_2P(O)(OCH_3)_2$ | $OCH_3$ | $OCH_3$ | N | |
| H | $CH_3$ | H | $CH_2P(O)(OCH_3)_2$ | $OCH_3$ | Cl | CH | |
| H | $CH_3$ | H | $CH_2P(O)(OCH_3)_2$ | $CH_3$ | $CH_3$ | CH | |
| $CH_3$ | $CH_3$ | H | $CH_2CH_2P(O)(OCH_2CH_3)_2$ | $CH_3$ | $OCH_3$ | CH | |
| H | $CH_3$ | H | $CH_2CH_2P(O)(OCH_2CH_3)_2$ | $OCH_3$ | $OCH_3$ | CH | |
| H | $CH_3$ | H | $CH_2(CH_2)_3P(O)(OCH_3)_2$ | $CH_3$ | $CH_3$ | N | |
| H | $CH_3$ | H | $CH_2(CH_2)_3P(O)(OCH_3)_2$ | $CH_3$ | $OCH_3$ | N | |
| H | $CH_3$ | H | $CH_2(CH_2)_3P(O)(OCH_3)_2$ | $OCH_3$ | $OCH_3$ | N | |
| H | $CH_3$ | H | $CH_2(CH_2)_3P(O)(OCH_3)_2$ | $OCH_3$ | Cl | CH | |
| H | $CH_3$ | H | $CH_2OP(S)(CH_3)_2$ | $CH_3$ | $CH_3$ | CH | |
| H | $CH_3$ | H | $CH_2OP(S)(CH_3)_2$ | $CH_3$ | $OCH_3$ | CH | |
| H | $CH_3$ | H | $CH_2OP(S)(CH_3)_2$ | $OCH_3$ | $OCH_3$ | CH | |
| H | $CH_3$ | H | $CH_2OP(S)(CH_3)_2$ | $CH_3$ | $CH_3$ | N | |
| H | $CH_3$ | H | $CH_2OP(S)(CH_3)_2$ | $CH_3$ | $OCH_3$ | N | |
| H | $CH_3$ | H | $CH_2OP(S)(CH_3)_2$ | $OCH_3$ | $OCH_3$ | N | |
| H | $CH_3$ | H | $CH_2OP(S)(CH_3)_2$ | $OCH_3$ | Cl | CH | |
| H | $CH_3$ | H | $CH_2OP(S)(OCH_3)_2$ | $CH_3$ | $CH_3$ | CH | |
| H | $CH_3$ | H | $CH_2OP(S)(OCH_3)_2$ | $CH_3$ | $OCH_3$ | CH | |
| H | $CH_3$ | H | $CH_2OP(S)(OCH_3)_2$ | $OCH_3$ | $OCH_3$ | CH | |
| H | $CH_3$ | H | $CH_2OP(S)(OCH_3)_2$ | $CH_3$ | $CH_3$ | N | |
| H | $CH_3$ | H | $CH_2OP(S)(OCH_3)_2$ | $CH_3$ | $OCH_3$ | N | |
| H | $CH_3$ | H | $CH_2OP(S)(OCH_3)_2$ | $OCH_3$ | $OCH_3$ | N | |
| H | $CH_3$ | H | $CH_2OP(S)(OCH_3)_2$ | $OCH_3$ | Cl | CH | |
| H | $CH_3$ | H | $CH_2P(S)(CH_3)_2$ | $CH_3$ | $CH_3$ | CH | |
| H | $CH_3$ | H | $CH_2P(S)(CH_3)_2$ | $CH_3$ | $OCH_3$ | CH | |
| H | $CH_3$ | H | $CH_2P(S)(CH_3)_2$ | $OCH_3$ | $OCH_3$ | CH | |
| H | $CH_3$ | H | $CH_2P(S)(CH_3)_2$ | $CH_3$ | $CH_3$ | N | |
| H | $CH_3$ | H | $CH_2P(S)(CH_3)_2$ | $OCH_3$ | $OCH_3$ | N | |
| H | $CH_3$ | H | $CH_2P(S)(CH_3)_2$ | $OCH_3$ | Cl | CH | |
| H | $CH_3$ | H | $CH_2P(S)(OCH_3)_2$ | $CH_3$ | $CH_3$ | CH | |
| H | $CH_3$ | H | $CH_2P(S)(OCH_3)_2$ | $CH_3$ | $OCH_3$ | CH | |
| H | $CH_3$ | H | $CH_2P(S)(OCH_3)_2$ | $OCH_3$ | $OCH_3$ | CH | |
| H | $CH_3$ | H | $CH_2P(S)(OCH_3)_2$ | $CH_3$ | $CH_3$ | N | |
| H | $CH_3$ | H | $CH_2P(S)(OCH_3)_2$ | $CH_3$ | $OCH_3$ | N | |
| H | $CH_3$ | H | $CH_2P(S)(OCH_3)_2$ | $OCH_3$ | $OCH_3$ | N | |
| H | $CH_3$ | H | $CH_2P(S)(OCH_3)_2$ | $OCH_3$ | Cl | CH | |
| H | $CH_3$ | H | $CH_2CH_2OP(S)(CH_3)_2$ | $CH_3$ | $CH_3$ | CH | |
| H | $CH_3$ | H | $CH_2CH_2OP(S)(CH_3)_2$ | $CH_3$ | $OCH_3$ | CH | |
| H | $CH_3$ | H | $CH_2CH_2OP(S)(CH_3)_2$ | $OCH_3$ | $OCH_3$ | CH | |
| H | $CH_3$ | H | $CH_2CH_2OP(S)(CH_3)_2$ | $CH_3$ | $CH_3$ | N | |
| H | $CH_3$ | H | $CH_2CH_2OP(S)(CH_3)_2$ | $CH_3$ | $OCH_3$ | N | |
| H | $CH_3$ | $CH_3$ | $CH_2CH_2OP(S)(CH_3)_2$ | $OCH_3$ | $OCH_3$ | N | |
| H | $CH_3$ | H | $CH_2CH_2OP(S)(CH_3)_2$ | $OCH_3$ | Cl | CH | |
| H | $CH_3$ | H | $CH_2CH_2P(S)(OCH_3)_2$ | $CH_3$ | $CH_3$ | CH | |
| H | $CH_3$ | H | $CH_2CH_2P(S)(OCH_3)_2$ | $CH_3$ | $OCH_3$ | CH | |

TABLE II-continued

General Structure II

| R | R₁ | R₂ | R₃ | X | Y | Z | m.p. (°C.) |
|---|---|---|---|---|---|---|---|
| H | CH₃ | H | CH₂CH₂P(S)(OCH₃)₂ | OCH₃ | OCH₃ | CH | |
| H | CH₃ | H | CH₂CH₂P(S)(OCH₃)₂ | CH₃ | CH₃ | N | |
| H | CH₃ | H | CH₂CH₂P(S)(OCH₃)₂ | CH₃ | OCH₃ | N | |
| H | CH₃ | H | CH₂CH₂P(S)(OCH₃)₂ | OCH₃ | OCH₃ | N | |
| H | CH₃ | H | CH₂CH₂P(S)(OCH₃)₂ | OCH₃ | Cl | CH | |
| H | CH₃ | H | CH₂(CH₂)₃OP(S)(CH₃)₂ | CH₃ | CH₃ | CH | |
| CH₃ | CH₃ | H | CH₂(CH₂)₃OP(S)(CH₃)₂ | CH₃ | OCH₃ | CH | |
| H | CH₃ | H | CH₂(CH₂)₃OP(S)(CH₃)₂ | OCH₃ | OCH₃ | CH | |
| H | CH₃ | H | CH₂(CH₂)₃OP(S)(CH₃)₂ | CH₃ | CH₃ | N | |
| H | CH₃ | H | CH₂(CH₂)₃OP(S)(CH₃)₂ | CH₃ | OCH₃ | N | |
| H | CH₃ | H | CH₂(CH₂)₃OP(S)(CH₃)₂ | OCH₃ | OCH₃ | N | |
| H | CH₃ | H | CH₂(CH₂)₃OP(S)(CH₃)₂ | OCH₃ | Cl | CH | |
| H | CH₃ | H | CH₂OSi(CH₃)₃ | CH₃ | CH₃ | CH | |
| H | CH₃ | H | CH₂OSi(CH₃)₃ | CH₃ | OCH₃ | CH | |
| H | CH₃ | H | CH₂OSi(CH₃)₃ | OCH₃ | OCH₃ | CH | |
| H | CH₃ | H | CH₂OSi(CH₃)₃ | CH₃ | CH₃ | N | |
| H | CH₃ | H | CH₂OSi(CH₃)₃ | CH₃ | OCH₃ | N | |
| H | CH₃ | H | CH₂OSi(CH₃)₃ | OCH₃ | OCH₃ | N | |
| H | CH₃ | H | CH₂OSi(CH₃)₃ | OCH₃ | Cl | CH | |
| H | CH₃ | H | CH₂CH₂OSi(CH₃)₃ | CH₃ | CH₃ | CH | |
| H | CH₃ | H | CH₂CH₂OSi(CH₃)₃ | CH₃ | OCH₃ | CH | |
| H | CH₃ | H | CH₂CH₂OSi(CH₃)₃ | OCH₃ | OCH₃ | CH | |
| H | CH₃ | H | CH₂CH₂OSi(CH₃)₃ | CH₃ | CH₃ | N | |
| H | CH₃ | H | CH₂CH₂OSi(CH₃)₃ | CH₃ | OCH₃ | N | |
| H | CH₃ | H | CH₂CH₂OSi(CH₃)₃ | OCH₃ | OCH₃ | N | |
| H | CH₃ | H | CH₂CH₂OSi(CH₃)₃ | OCH₃ | Cl | CH | |
| H | CH₃ | H | CH₂(CH₂)₂OSi(CH₃)₃ | CH₃ | CH₃ | CH | |
| H | CH₃ | H | CH₂(CH₂)₂OSi(CH₃)₃ | CH₃ | OCH₃ | CH | |
| H | CH₃ | H | CH₂(CH₂)₂OSi(CH₃)₃ | OCH₃ | OCH₃ | CH | |
| H | CH₃ | H | CH₂(CH₂)₂OSi(CH₃)₃ | CH₃ | CH₃ | N | |
| H | CH₃ | H | CH₂(CH₂)₂OSi(CH₃)₃ | OCH₃ | OCH₃ | N | |
| H | CH₃ | H | CH₂(CH₂)₂OSi(CH₃)₃ | OCH₃ | Cl | CH | |
| H | CH₃ | H | CH₂(CH₂)₃OSi(CH₃)₃ | CH₃ | CH₃ | CH | |
| H | CH₃ | H | CH₂(CH₂)₃OSi(CH₃)₃ | CH₃ | OCH₃ | CH | |
| H | CH₃ | H | CH₂(CH₂)₃OSi(CH₃)₃ | OCH₃ | OCH₃ | CH | |
| H | CH₃ | H | CH₂(CH₂)₃OSi(CH₃)₃ | CH₃ | CH₃ | N | |
| H | CH₃ | H | CH₂(CH₂)₃OSi(CH₃)₃ | CH₃ | OCH₃ | N | |
| H | CH₃ | H | CH₂(CH₂)₃OSi(CH₃)₃ | OCH₃ | OCH₃ | N | |
| H | CH₃ | H | CH₂(CH₂)₃OSi(CH₃)₃ | OCH₃ | Cl | CH | |
| H | CH₃ | H | CH₂(CH₂)₄OSi(CH₃)₃ | CH₃ | CH₃ | CH | |
| H | CH₃ | H | CH₂(CH₂)₅OSi(CH₃)₃ | CH₃ | OCH₃ | CH | |
| H | CH₃ | H | CH₂(CH₂)₆OSi(CH₃)₃ | OCH₃ | OCH₃ | CH | |
| H | CH₃ | H | CH₂(CH₂)₇OSi(CH₃)₃ | CH₃ | CH₃ | N | |
| H | CH₃ | H | CH₂OSi(CH₂CH₃)₃ | CH₃ | OCH₃ | N | |
| H | CH₃ | CH₃ | CH₂OSi(CH₃)₂(Ph) | OCH₃ | OCH₃ | N | |
| H | CH₃ | H | CH(CH₃)OSi(CH₃)₃ | OCH₃ | Cl | CH | |
| H | CH₃ | H | CH(CH₃)OSi(CH₃)₃ | CH₃ | CH₃ | CH | |
| H | CH₃ | H | CH(CH₃)OSi(CH₃)₃ | CH₃ | OCH₃ | CH | |
| H | CH₃ | H | CH(CH₃)OSi(CH₃)₃ | OCH₃ | OCH₃ | CH | |
| H | CH₃ | H | CH(CH₃)OSi(CH₃)₃ | CH₃ | CH₃ | N | |
| H | CH₃ | H | CH₂Si(CH₃)₃ | CH₃ | OCH₃ | N | |
| H | CH₃ | H | CH₂Si(CH₃)₃ | OCH₃ | OCH₃ | N | |
| H | CH₃ | H | CH₂Si(CH₃)₃ | OCH₃ | Cl | CH | |
| H | CH₃ | H | CH₂Si(CH₃)₃ | CH₃ | CH₃ | CH | |
| CH₃ | CH₃ | H | CH₂Si(CH₃)₃ | CH₃ | OCH₃ | CH | |
| H | CH₃ | H | CH₂Si(CH₃)₃ | OCH₃ | OCH₃ | CH | |
| H | CH₃ | H | CH₂Si(CH₃)₃ | CH₃ | CH₃ | N | |
| H | CH₃ | H | CH₂CH₂Si(CH₃)₃ | CH₃ | OCH₃ | N | |
| H | CH₃ | H | CH₂CH₂Si(CH₃)₃ | OCH₃ | OCH₃ | N | |
| H | CH₃ | H | CH₂CH₂Si(CH₃)₃ | OCH₃ | Cl | CH | |
| H | CH₃ | H | CH₂(CH₂)₂Si(CH₃)₃ | CH₃ | CH₃ | CH | |
| H | CH₃ | H | CH₂(CH₂)₂Si(CH₃)₃ | CH₃ | OCH₃ | CH | |
| H | CH₃ | H | CH₂(CH₂)₂Si(CH₃)₃ | OCH₃ | OCH₃ | CH | |
| H | CH₃ | H | CH₂(CH₂)₂Si(CH₃)₃ | CH₃ | CH₃ | N | |
| H | CH₃ | H | CH₂(CH₂)₂Si(CH₃)₃ | CH₃ | OCH₃ | N | |
| H | CH₃ | H | CH₂(CH₂)₂Si(CH₃)₃ | OCH₃ | OCH₃ | N | |
| H | CH₃ | H | CH₂(CH₂)₂Si(CH₃)₃ | OCH₃ | Cl | CH | |
| H | CH₃ | H | C(Si(CH₃)₃)(CH₃)₂ | CH₃ | CH₃ | CH | |
| H | CH₃ | H | C(Si(CH₃)₃)(CH₃)₂ | CH₃ | OCH₃ | CH | |
| H | CH₃ | H | C(Si(CH₃)₃)(CH₃)₂ | OCH₃ | OCH₃ | CH | |
| H | CH₃ | H | C(Si(CH₃)₃)(CH₃)₂ | CH₃ | CH₃ | N | |
| H | CH₃ | H | C(Si(CH₃)₃)(CH₃)₂ | CH₃ | OCH₃ | N | |
| H | CH₃ | H | C(Si(CH₃)₃)(CH₃)₂ | OCH₃ | OCH₃ | N | |
| H | CH₃ | H | C(Si(CH₃)₃)(CH₃)₂ | OCH₃ | Cl | CH | |
| H | CH₃ | H | CH₂SCH₃ | CH₃ | CH₃ | CH | |
| H | CH₃ | H | CH₂SCH₃ | CH₃ | OCH₃ | CH | |
| H | CH₃ | H | CH₂SCH₃ | OCH₃ | OCH₃ | CH | |
| H | CH₃ | H | CH₂SCH₃ | CH₃ | CH₃ | N | |
| H | CH₃ | H | CH₂SCH₃ | OCH₃ | OCH₃ | N | |
| H | CH₃ | H | CH₂SCH₃ | OCH₃ | Cl | CH | |

TABLE II-continued

General Structure II

| R | R₁ | R₂ | R₃ | X | Y | Z | m.p. (°C.) |
|---|----|----|----|---|---|---|-----------|
| H | CH₃ | H | CH₂SCH₂CH₃ | CH₃ | CH₃ | CH | |
| H | CH₃ | H | CH₂CH₂SCH₃ | CH₃ | OCH₃ | CH | |
| H | CH₃ | H | CH₂CH₂SCH₃ | OCH₃ | OCH₃ | CH | |
| H | CH₃ | H | CH₂CH₂SCH₃ | CH₃ | CH₃ | N | |
| H | CH₃ | H | CH₂CH₂SCH₃ | CH₃ | OCH₃ | N | |
| H | CH₃ | H | CH₂CH₂SCH₃ | OCH₃ | OCH₃ | N | |
| H | CH₃ | H | CH₂CH₂SCH₃ | OCH₃ | Cl | CH | |
| H | CH₃ | H | CH₂CH₂SCH₃ | CH₃ | CH₃ | CH | |
| H | CH₃ | H | CH₂(CH₂)₂SCH₃ | CH₃ | OCH₃ | CH | |
| H | CH₃ | H | CH₂(CH₂)₂SCH₃ | OCH₃ | OCH₃ | CH | |
| H | CH₃ | H | CH₂(CH₂)₂SCH₃ | CH₃ | CH₃ | N | |
| H | CH₃ | H | CH₂(CH₂)₂SCH₃ | CH₃ | OCH₃ | N | |
| H | CH₃ | CH₃ | CH₂(CH₂)₂SCH₃ | OCH₃ | OCH₃ | N | |
| H | CH₃ | H | CH₂(CH₂)₃SCH₃ | OCH₃ | Cl | CH | |
| H | CH₃ | H | CH₂(CH₂)₃SCH₃ | CH₃ | CH₃ | CH | |
| H | CH₃ | H | CH₂(CH₂)₃SCH₃ | CH₃ | OCH₃ | CH | |
| H | CH₃ | H | CH₂(CH₂)₃SCH₃ | OCH₃ | OCH₃ | CH | |
| H | CH₃ | H | CH₂(CH₂)₃SCH₃ | CH₃ | CH₃ | N | |
| H | CH₃ | H | CH₂(CH₂)₃SCH₃ | CH₃ | OCH₃ | N | |
| H | CH₃ | H | CH₂(CH₂)₃SCH₃ | OCH₃ | OCH₃ | N | |
| H | CH₃ | H | CH(CH₃)SCH₃ | OCH₃ | Cl | CH | |
| H | CH₃ | H | CH(CH₃)SCH₃ | CH₃ | CH₃ | CH | |
| CH₃ | CH₃ | H | CH(CH₃)SCH₃ | CH₃ | OCH₃ | CH | |
| H | CH₃ | H | CH(SCH₃)₂ | OCH₃ | OCH₃ | CH | |
| H | CH₃ | H | CH₂CH(CH₃)SCH₃ | CH₃ | CH₃ | N | |
| H | CH₃ | H | CH₂CH(CH₃)SCH₃ | CH₃ | OCH₃ | N | |
| H | CH₃ | H | CH₂(CH₂)₈SCH₃ | OCH₃ | OCH₃ | N | |
| H | CH₃ | H | CH₂(CH₂)₈SCH₃ | OCH₃ | Cl | CH | |
| H | CH₃ | H | CH₂SOCH₃ | CH₃ | CH₃ | CH | |
| H | CH₃ | H | CH₂SOCH₃ | CH₃ | OCH₃ | CH | |
| H | CH₃ | H | CH₂SOCH₃ | OCH₃ | OCH₃ | CH | |
| H | CH₃ | H | CH₂SOCH₃ | CH₃ | CH₃ | N | |
| H | CH₃ | H | CH₂SOCH₃ | CH₃ | OCH₃ | N | |
| H | CH₃ | H | CH₂SOCH₃ | OCH₃ | OCH₃ | N | |
| H | CH₃ | H | CH₂SOCH₃ | OCH₃ | Cl | CH | |
| H | CH₃ | H | CH₂CH₂SOCH₃ | CH₃ | CH₃ | CH | |
| H | CH₃ | H | CH₂CH₂SOCH₃ | CH₃ | OCH₃ | CH | |
| H | CH₃ | H | CH₂CH₂SOCH₃ | OCH₃ | OCH₃ | CH | |
| H | CH₃ | H | CH₂CH₂SOCH₃ | CH₃ | CH₃ | N | |
| H | CH₃ | H | CH₂CH₂SOCH₃ | CH₃ | OCH₃ | N | |
| H | CH₃ | H | CH₂CH₂SOCH₃ | OCH₃ | OCH₃ | N | |
| H | CH₃ | H | CH₂CH₂SOCH₃ | OCH₃ | Cl | CH | |
| H | CH₃ | H | CH₂(CH₂)₃SOCH₃ | CH₃ | CH₃ | CH | |
| H | CH₃ | H | CH₂(CH₂)₃SOCH₃ | CH₃ | OCH₃ | CH | |
| H | CH₃ | H | CH₂(CH₂)₃SOCH₃ | OCH₃ | OCH₃ | CH | |
| H | CH₃ | H | CH₂(CH₂)₃SOCH₃ | CH₃ | CH₃ | N | |
| H | CH₃ | H | CH₂(CH₂)₃SOCH₃ | OCH₃ | OCH₃ | N | |
| H | CH₃ | H | CH₂(CH₂)₃SOCH₃ | OCH₃ | Cl | CH | |
| H | CH₃ | H | CH₂SO₂CH₃ | CH₃ | CH₃ | CH | |
| H | CH₃ | H | CH₂SO₂CH₃ | CH₃ | OCH₃ | CH | |
| H | CH₃ | H | CH₂SO₂CH₃ | OCH₃ | OCH₃ | CH | |
| H | CH₃ | H | CH₂SO₂CH₃ | CH₃ | CH₃ | N | |
| H | CH₃ | H | CH₂SO₂CH₃ | CH₃ | OCH₃ | N | |
| H | CH₃ | H | CH₂SO₂CH₃ | OCH₃ | OCH₃ | N | |
| H | CH₃ | H | CH₂SO₂CH₃ | OCH₃ | Cl | CH | |
| H | CH₃ | H | CH₂CH₂SO₂CH₃ | CH₃ | CH₃ | CH | |
| H | CH₃ | H | CH₂CH₂SO₂CH₃ | CH₃ | OCH₃ | CH | |
| H | CH₃ | H | CH₂CH₂SO₂CH₃ | OCH₃ | OCH₃ | CH | |
| H | CH₃ | H | CH₂CH₂SO₂CH₃ | CH₃ | CH₃ | N | |
| H | CH₃ | H | CH₂CH₂SO₂CH₃ | CH₃ | OCH₃ | N | |
| H | CH₃ | CH₃ | CH₂CH₂SO₂CH₃ | OCH₃ | OCH₃ | N | |
| H | CH₃ | H | CH₂CH₂SO₂CH₃ | OCH₃ | Cl | CH | |
| H | CH₃ | H | CH₂(CH₂)₃SO₂CH₃ | CH₃ | CH₃ | CH | |
| H | CH₃ | H | CH₂(CH₂)₃SO₂CH₃ | CH₃ | OCH₃ | CH | |
| H | CH₃ | H | CH₂(CH₂)₃SO₂CH₃ | OCH₃ | OCH₃ | CH | |
| H | CH₃ | H | CH₂(CH₂)₃SO₂CH₃ | CH₃ | CH₃ | N | |
| H | CH₃ | CH₃ | CH₂(CH₂)₃SO₂CH₃ | OCH₃ | OCH₃ | N | |
| H | CH₃ | H | CH₂(CH₂)₃SO₂CH₃ | OCH₃ | Cl | CH | |
| H | CH₃ | H | CH₂SOCH₂CH₃ | CH₃ | CH₃ | CH | |
| CH₃ | CH₃ | H | CH₂SOCH₂CH₃ | CH₃ | OCH₃ | CH | |
| H | CH₃ | H | CH₂SO₂CH₂CH₃ | OCH₃ | OCH₃ | CH | |
| H | CH₃ | H | CH₂(CH₂)₆SOCH₃ | CH₃ | CH₃ | N | |
| H | CH₃ | H | CH₂(CH₂)₆SOCH₃ | CH₃ | OCH₃ | N | |
| H | CH₃ | H | CH₂(CH₂)₄SO₂CH₃ | OCH₃ | OCH₃ | N | |
| H | CH₃ | H | CH₂(CH₂)₄SO₂CH₃ | OCH₃ | Cl | CH | |
| H | CH₃ | H | CH₂SCN | CH₃ | CH₃ | CH | |
| H | CH₃ | H | CH₂SCN | CH₃ | OCH₃ | CH | |
| H | CH₃ | H | CH₂SCN | OCH₃ | OCH₃ | CH | |
| H | CH₃ | H | CH₂SCN | CH₃ | CH₃ | N | |
| H | CH₃ | H | CH₂SCN | CH₃ | OCH₃ | N | |

TABLE II-continued

General Structure II

| R | R₁ | R₂ | R₃ | X | Y | Z | m.p. (°C.) |
|---|---|---|---|---|---|---|---|
| H | CH₃ | H | CH₂SCN | OCH₃ | OCH₃ | N | |
| H | CH₃ | H | CH₂SCN | OCH₃ | Cl | CH | |
| H | CH₃ | H | CH₂CH₂SCN | CH₃ | CH₃ | CH | |
| H | CH₃ | H | CH₂CH₂SCN | CH₃ | OCH₃ | CH | |
| H | CH₃ | H | CH₂CH₂SCN | OCH₃ | OCH₃ | CH | |
| H | CH₃ | H | CH₂CH₂SCN | CH₃ | CH₃ | N | |
| H | CH₃ | H | CH₂CH₂SCN | CH₃ | OCH₃ | N | |
| H | CH₃ | H | CH₂CH₂SCN | OCH₃ | OCH₃ | N | |
| H | CH₃ | H | CH₂CH₂SCN | OCH₃ | Cl | CH | |
| H | CH₃ | H | CH₂(CH₂)₂SCN | CH₃ | CH₃ | CH | |
| H | CH₃ | H | CH₂(CH₂)₂SCN | CH₃ | CH₃ | CH | |
| H | CH₃ | H | CH₂(CH₂)₃SO₂CH₃ | CH₃ | OCH₃ | N | |
| H | CH₃ | H | CH₂(CH₂)₂SCN | OCH₃ | OCH₃ | CH | |
| H | CH₃ | H | CH₂(CH₂)₂SCN | CH₃ | CH₃ | N | |
| H | CH₃ | H | CH₂(CH₂)₂SCN | OCH₃ | OCH₃ | N | |
| H | CH₃ | H | CH₂(CH₂)₂SCN | OCH₃ | Cl | CH | |
| H | CH₃ | H | CH₂(CH₂)₃SCN | CH₃ | CH₃ | CH | |
| H | CH₃ | H | CH₂(CH₂)₃SCN | CH₃ | OCH₃ | CH | |
| H | CH₃ | H | CH₂(CH₂)₃SCN | OCH₃ | OCH₃ | CH | |
| H | CH₃ | H | CH₂(CH₂)₃SCN | CH₃ | CH₃ | N | |
| H | CH₃ | H | CH₂(CH₂)₃SCN | CH₃ | OCH₃ | N | |
| H | CH₃ | H | CH₂(CH₂)₃SCN | OCH₃ | OCH₃ | N | |
| H | CH₃ | H | CH₂(CH₂)₃SCN | OCH₃ | Cl | CH | |
| H | CH₃ | H | CH₂CHFSCN | CH₃ | CH₃ | CH | |
| H | CH₃ | H | CH(CF₃)SCN | CH₃ | OCH₃ | CH | |
| H | CH₃ | H | CH₂(CH₂)₅SCN | OCH₃ | OCH₃ | CH | |
| H | CH₃ | H | CH₂CN | CH₃ | CH₃ | N | |
| H | CH₃ | H | CH₂CN | CH₃ | OCH₃ | N | |
| H | CH₃ | CH₃ | CH₂CN | OCH₃ | OCH₃ | N | |
| H | CH₃ | H | CH₂CN | OCH₃ | Cl | CH | |
| H | CH₃ | H | CH₂CN | CH₃ | CH₃ | CH | |
| H | CH₃ | H | CH₂CN | CH₃ | OCH₃ | CH | |
| H | CH₃ | H | CH₂CH₂CN | OCH₃ | OCH₃ | CH | |
| H | CH₃ | H | CH₂CH₂CN | CH₃ | CH₃ | N | |
| H | CH₃ | H | CH₂CH₂CN | CH₃ | OCH₃ | N | |
| H | CH₃ | H | CH₂CH₂CN | OCH₃ | OCH₃ | N | |
| H | CH₃ | H | CH₂CH₂CN | OCH₃ | Cl | CH | |
| H | CH₃ | H | CH₂CH₂CN | CH₃ | CH₃ | CH | |
| CH₃ | CH₃ | H | CH₂CH₂CN | CH₃ | OCH₃ | CH | |
| H | CH₃ | H | CH₂CH₂CN | OCH₃ | OCH₃ | CH | |
| H | CH₃ | H | CH₂(CH₂)₃CN | CH₃ | CH₃ | N | |
| H | CH₃ | H | CH₂(CH₂)₃CN | CH₃ | OCH₃ | N | |
| H | CH₃ | H | CH₂(CH₂)₃CN | OCH₃ | OCH₃ | N | |
| H | CH₃ | H | CH₂(CH₂)₃CN | OCH₃ | Cl | CH | |
| H | CH₃ | H | CH₂(CH₂)₄CN | CH₃ | CH₃ | CH | |
| H | CH₃ | H | CH₂(CH₂)₂CH(CN)₂ | CH₃ | OCH₃ | CH | |
| H | CH₃ | H | CH(CH₃)CH₂CN | OCH₃ | OCH₃ | CH | |
| H | CH₃ | H | CH(CH₃)CH₂CN | CH₃ | CH₃ | N | |
| H | CH₃ | H | CH(CH₃)CH₂CN | CH₃ | OCH₃ | N | |
| H | CH₃ | H | CH(CH₃)CH₂CN | OCH₃ | OCH₃ | N | |
| H | CH₃ | H | CH(CH₃)CH₂CN | OCH₃ | Cl | CH | |
| H | CH₃ | H | CH₂SP(O)(CH₃)₂ | CH₃ | CH₃ | CH | |
| H | CH₃ | H | CH₂SP(O)(CH₃)₂ | CH₃ | OCH₃ | CH | |
| H | CH₃ | H | CH₂SP(O)(CH₃)₂ | OCH₃ | OCH₃ | CH | |
| H | CH₃ | H | CH₂CH₂SP(O)(CH₃)₂ | CH₃ | CH₃ | N | |
| H | CH₃ | H | CH₂CH₂SP(O)(CH₃)₂ | CH₃ | OCH₃ | N | |
| H | CH₃ | H | CH₂CH₂SP(O)(CH₃)₂ | OCH₃ | OCH₃ | N | |
| H | CH₃ | H | CH₂P(S)(CH₃)₂ | OCH₃ | Cl | CH | |
| H | CH₃ | H | CH₂P(S)(CH₃)₂ | CH₃ | CH₃ | CH | |
| H | CH₃ | H | CH₂P(S)(CH₃)₂ | CH₃ | OCH₃ | CH | |
| H | CH₃ | H | CH₂—CH₂P(S)(CH₃)₂ | OCH₃ | OCH₃ | CH | |
| H | CH₃ | H | CH₂—CH₂P(S)(CH₃)₂ | CH₃ | CH₃ | N | |
| H | CH₃ | H | CH₂—CH₂P(S)(CH₃)₂ | OCH₃ | OCH₃ | N | |
| H | CH₃ | H | CH₂—CH₂P(S)(CH₃)₂ | OCH₃ | Cl | CH | |
| H | CH₃ | H | CH₂—CH₂P(S)(CH₃)₂ | CH₃ | CH₃ | CH | |
| H | CH₃ | H | CH₂N(CH₃)₂ | CH₃ | OCH₃ | CH | |
| H | CH₃ | H | CH₂N(CH₃)₂ | OCH₃ | OCH₃ | CH | |
| H | CH₃ | H | CH₂N(CH₃)₂ | CH₃ | CH₃ | N | |
| H | CH₃ | H | CH₂N(CH₃)₂ | CH₃ | OCH₃ | N | |
| H | CH₃ | H | CH₂N(CH₃)₂ | OCH₃ | OCH₃ | N | |
| H | CH₃ | H | CH₂N(CH₃)₂ | OCH₃ | Cl | CH | |
| H | CH₃ | H | CH₂N(CH₃)₂ | CH₃ | CH₃ | CH | |
| H | CH₃ | H | CH₂(CH₂)₃N(CH₃)₂ | CH₃ | OCH₃ | CH | |
| H | CH₃ | H | CH₂(CH₂)₃N(CH₃)₂ | OCH₃ | OCH₃ | CH | |
| H | CH₃ | H | CH₂(CH₂)₃N(CH₃)₂ | CH₃ | CH₃ | N | |
| H | CH₃ | H | CH₂(CH₂)₃N(CH₃)₂ | CH₃ | OCH₃ | N | |
| H | CH₃ | CH₃ | CH₂(CH₂)₃N(CH₃)₂ | OCH₃ | OCH₃ | N | |
| H | CH₃ | H | CH₂(CH₂)₃N(CH₃)₂ | OCH₃ | Cl | CH | |
| H | CH₃ | H | CH₂(CH₂)₃N(CH₃)₂ | CH₃ | CH₃ | CH | |
| H | CH₃ | H | CH₂N(CH₃)₂Ph | CH₃ | OCH₃ | CH | |

TABLE II-continued

General Structure II

| R | R$_1$ | R$_2$ | R$_3$ | X | Y | Z | m.p. (°C.) |
|---|---|---|---|---|---|---|---|
| H | CH$_3$ | H | CH$_2$N(CH$_3$)$_2$Ph | OCH$_3$ | OCH$_3$ | CH | |
| H | CH$_3$ | H | CH$_2$N(CH$_3$)$_2$Ph | CH$_3$ | CH$_3$ | N | |
| H | CH$_3$ | H | CH$_2$N(CH$_3$)$_2$Ph | CH$_3$ | OCH$_3$ | N | |
| H | CH$_3$ | H | CH$_2$—CH(CH$_3$)N(CH$_3$)$_2$ | OCH$_3$ | OCH$_3$ | N | |
| H | CH$_3$ | H | CH$_2$—CH(CH$_3$)N(CH$_3$)$_2$ | OCH$_3$ | Cl | CH | |
| H | CH$_3$ | H | CH$_2$—CH(CH$_3$)N(CH$_3$)$_2$ | CH$_3$ | CH$_3$ | CH | |
| CH$_3$ | CH$_3$ | H | CH$_2$—CH(CH$_3$)N(CH$_3$)$_2$ | CH$_3$ | OCH$_3$ | CH | |
| H | CH$_3$ | H | CH$_2$—CH(CH$_3$)N(CH$_3$)$_2$ | OCH$_3$ | OCH$_3$ | CH | |
| H | CH$_3$ | H | CH$_2$CH$_2$CH(CH$_3$)$_2$ | CH$_3$ | CH$_3$ | N | |
| H | CH$_3$ | H | CH$_2$CH$_2$CH(CH$_3$)$_2$ | CH$_3$ | OCH$_3$ | N | |
| H | CH$_3$ | H | CH$_2$CH$_2$CH(CH$_3$)$_2$ | OCH$_3$ | OCH$_3$ | N | |
| H | CH$_3$ | H | CH$_2$CH$_2$CH(CH$_3$)$_2$ | OCH$_3$ | Cl | CH | |
| H | CH$_3$ | H | CH$_2$NHC(O)CH$_3$ | CH$_3$ | CH$_3$ | CH | |
| H | CH$_3$ | H | CH$_2$NHC(O)CH$_3$ | CH$_3$ | OCH$_3$ | CH | |
| H | CH$_3$ | H | CH$_2$NHC(O)CH$_3$ | OCH$_3$ | OCH$_3$ | CH | |
| H | CH$_3$ | H | CH$_2$NHC(O)CH$_3$ | CH$_3$ | CH$_3$ | N | |
| H | CH$_3$ | H | CH$_2$NHC(O)CH$_3$ | CH$_3$ | OCH$_3$ | N | |
| H | CH$_3$ | H | CH$_2$NHC(O)CH$_3$ | OCH$_3$ | OCH$_3$ | N | |
| H | CH$_3$ | H | CH$_2$NHC(O)CH$_3$ | OCH$_3$ | Cl | CH | |
| H | CH$_3$ | H | CH$_2$CH$_2$N(CH$_3$)C(O)CH$_3$ | CH$_3$ | CH$_3$ | CH | |
| H | CH$_3$ | H | CH$_2$CH$_2$N(CH$_3$)C(O)CH$_3$ | CH$_3$ | OCH$_3$ | CH | |
| H | CH$_3$ | H | CH$_2$CH$_2$N(CH$_3$)C(O)CH$_3$ | OCH$_3$ | OCH$_3$ | CH | |
| H | CH$_3$ | H | CH$_2$CH$_2$N(CH$_3$)C(O)CH$_3$ | CH$_3$ | CH$_3$ | N | |
| H | CH$_3$ | H | CH$_2$(CH$_2$)$_3$NHC(O)CH$_3$ | CH$_3$ | OCH$_3$ | N | |
| H | CH$_3$ | H | CH$_2$(CH$_2$)$_3$NHC(O)CH$_3$ | OCH$_3$ | OCH$_3$ | N | |
| H | CH$_3$ | H | CH$_2$N(CH$_3$)C(O)OCH$_3$ | OCH$_3$ | Cl | CH | |
| H | CH$_3$ | H | CH$_2$N(CH$_3$)C(O)OCH$_3$ | CH$_3$ | CH$_3$ | CH | |
| H | CH$_3$ | H | CH$_2$NHC(O)OCH$_3$ | CH$_3$ | OCH$_3$ | CH | |
| H | CH$_3$ | H | CH$_2$NHC(O)OCH$_3$ | OCH$_3$ | OCH$_3$ | CH | |
| H | CH$_3$ | H | CH$_2$NHC(O)OCH$_3$ | CH$_3$ | CH$_3$ | N | |
| H | CH$_3$ | H | CH$_2$NHC(O)OCH$_3$ | OCH$_3$ | OCH$_3$ | N | |
| H | CH$_3$ | H | CH$_2$NHC(O)OCH$_3$ | OCH$_3$ | Cl | CH | |
| H | CH$_3$ | H | CH$_2$NHC(O)OCH$_3$ | CH$_3$ | CH$_3$ | CH | |
| H | CH$_3$ | H | CH$_2$(CH$_2$)$_3$NHC(O)OCH$_3$ | CH$_3$ | OCH$_3$ | CH | |
| H | CH$_3$ | H | CH$_2$(CH$_2$)$_3$NHC(O)OCH$_3$ | OCH$_3$ | OCH$_3$ | CH | |
| H | CH$_3$ | H | CH$_2$(CH$_2$)$_3$NHC(O)OCH$_3$ | CH$_3$ | CH$_3$ | N | |
| H | CH$_3$ | H | CH$_2$N(CH$_3$)C(O)OCH$_2$CH$_3$ | CH$_3$ | OCH$_3$ | N | |
| H | CH$_3$ | H | CH(CH$_3$)NHC(O)OCH$_3$ | OCH$_3$ | OCH$_3$ | N | |
| H | CH$_3$ | H | CH(CH$_3$)NHC(O)OCH$_3$ | OCH$_3$ | Cl | CH | |
| H | CH$_3$ | H | CH(CH$_3$)NHC(O)OCH$_3$ | CH$_3$ | CH$_3$ | CH | |
| H | CH$_3$ | H | CH$_2$NHSO$_2$CH$_3$ | CH$_3$ | CH$_3$ | CH | |
| H | CH$_3$ | H | CH$_2$NHSO$_2$CH$_3$ | OCH$_3$ | OCH$_3$ | CH | |
| H | CH$_3$ | H | CH$_2$NHSO$_2$CH$_3$ | CH$_3$ | CH$_3$ | N | |
| H | CH$_3$ | H | CH$_2$NHSO$_2$CH$_3$ | CH$_3$ | OCH$_3$ | N | |
| H | CH$_3$ | CH$_3$ | CH$_2$NHSO$_2$CH$_3$ | OCH$_3$ | OCH$_3$ | N | |
| H | CH$_3$ | H | CH$_2$CH$_2$NHSO$_2$CH$_3$ | OCH$_3$ | Cl | CH | |
| H | CH$_3$ | H | CH$_2$CH$_2$NHSO$_2$CH$_3$ | CH$_3$ | CH$_3$ | CH | |
| H | CH$_3$ | H | CH$_2$CH$_2$NHSO$_2$CH$_3$ | CH$_3$ | OCH$_3$ | CH | |
| H | CH$_3$ | H | CH$_2$CH$_2$NHSO$_2$CH$_3$ | OCH$_3$ | OCH$_3$ | CH | |
| H | CH$_3$ | H | CH$_2$CH$_2$NHSO$_2$CH$_3$ | CH$_3$ | CH$_3$ | N | |
| H | CH$_3$ | H | CH$_2$CH$_2$NHSO$_2$CH$_3$ | CH$_3$ | OCH$_3$ | N | |
| H | CH$_3$ | H | CH$_2$(CH$_2$)$_3$NHSO$_2$CH$_3$ | OCH$_3$ | OCH$_3$ | N | |
| H | CH$_3$ | H | CH$_2$(CH$_2$)$_3$NHSO$_2$CH$_3$ | OCH$_3$ | Cl | CH | |
| H | CH$_3$ | H | CH$_2$(CH$_2$)$_3$NHSO$_2$CH$_3$ | CH$_3$ | CH$_3$ | CH | |
| CH$_3$ | CH$_3$ | H | CH$_2$NHP(O)(CH$_3$)$_2$ | CH$_3$ | OCH$_3$ | CH | |
| H | CH$_3$ | H | CH$_2$NHP(O)(CH$_3$)$_2$ | OCH$_3$ | OCH$_3$ | CH | |
| H | CH$_3$ | H | CH$_2$NHP(O)(CH$_3$)$_2$ | CH$_3$ | CH$_3$ | N | |
| H | CH$_3$ | H | CH$_2$NHP(O)(OCH$_3$)$_2$ | CH$_3$ | OCH$_3$ | N | |
| H | CH$_3$ | H | CH$_2$NHP(O)(OCH$_3$)$_2$ | OCH$_3$ | OCH$_3$ | N | |
| H | CH$_3$ | H | CH$_2$NHP(O)(OCH$_3$)$_2$ | OCH$_3$ | Cl | CH | |
| H | CH$_3$ | H | CH=CH$_2$ | CH$_3$ | CH$_3$ | CH | |
| H | CH$_3$ | H | CH=CH$_2$ | CH$_3$ | OCH$_3$ | CH | |
| H | CH$_3$ | H | CH$_2$NO$_2$ | CH$_3$ | CH$_3$ | CH | |
| H | CH$_3$ | H | CH$_2$NO$_2$ | CH$_3$ | OCH$_3$ | CH | |
| H | CH$_3$ | H | CH$_2$NO$_2$ | OCH$_3$ | OCH$_3$ | CH | |
| H | CH$_3$ | H | CH$_2$NO$_2$ | CH$_3$ | CH$_3$ | N | |
| H | CH$_3$ | H | CH$_2$NO$_2$ | CH$_3$ | OCH$_3$ | N | |
| H | CH$_3$ | H | CH$_2$NO$_2$ | OCH$_3$ | OCH$_3$ | N | |
| H | CH$_3$ | H | CH$_2$NO$_2$ | OCH$_3$ | Cl | CH | |
| H | CH$_3$ | H | CH$_2$CH$_2$NO$_2$ | CH$_3$ | CH$_3$ | CH | |
| H | CH$_3$ | H | CH$_2$CH$_2$NO$_2$ | CH$_3$ | OCH$_3$ | CH | |
| H | CH$_3$ | H | CH$_2$CH$_2$NO$_2$ | OCH$_3$ | OCH$_3$ | CH | |
| H | CH$_3$ | H | CH$_2$CH$_2$NO$_2$ | CH$_3$ | CH$_3$ | N | |
| H | CH$_3$ | H | CH$_2$CH$_2$NO$_2$ | CH$_3$ | OCH$_3$ | N | |
| H | CH$_3$ | H | CH$_2$CH$_2$NO$_2$ | OCH$_3$ | OCH$_3$ | N | |
| H | CH$_3$ | H | CH$_2$CH$_2$NO$_2$ | OCH$_3$ | Cl | CH | |
| H | CH$_3$ | H | CH$_2$C(O)CH$_3$ | CH$_3$ | CH$_3$ | CH | |
| H | CH$_3$ | H | CH$_2$C(O)CH$_3$ | CH$_3$ | OCH$_3$ | CH | |
| H | CH$_3$ | H | CH$_2$C(O)CH$_3$ | OCH$_3$ | OCH$_3$ | N | |
| H | CH$_3$ | H | CH$_2$C(O)CH$_3$ | CH$_3$ | CH$_3$ | N | |

TABLE II-continued

General Structure II

| R | R$_1$ | R$_2$ | R$_3$ | X | Y | Z | m.p. (°C.) |
|---|---|---|---|---|---|---|---|
| H | CH$_3$ | H | CH$_2$C(O)CH$_3$ | OCH$_3$ | OCH$_3$ | N | |
| H | CH$_3$ | H | CH$_2$C(O)CH$_3$ | OCH$_3$ | Cl | CH | |
| H | CH$_3$ | H | CH$_2$C(O)CH$_2$CH$_3$ | CH$_3$ | CH$_3$ | CH | |
| H | CH$_3$ | H | CH$_2$C(O)CH$_2$CH$_3$ | CH$_3$ | OCH$_3$ | CH | |
| H | CH$_3$ | H | CH$_2$C(O)CH$_2$CH$_3$ | OCH$_3$ | OCH$_3$ | CH | |
| H | CH$_3$ | H | CH$_2$C(O)CH$_2$CH$_3$ | CH$_3$ | CH$_3$ | N | |
| H | CH$_3$ | H | CH$_2$C(O)CH$_2$CH$_3$ | CH$_3$ | OCH$_3$ | N | |
| H | CH$_3$ | H | CH$_2$C(O)CH$_2$CH$_3$ | OCH$_3$ | OCH$_3$ | N | |
| H | CH$_3$ | H | CH$_2$C(O)CH$_2$CH$_3$ | OCH$_3$ | Cl | CH | |
| H | CH$_3$ | H | CH$_2$(CH$_2$)$_3$C(O)CH$_3$ | CH$_3$ | CH$_3$ | CH | |
| H | CH$_3$ | H | CH$_2$(CH$_2$)$_3$C(O)CH$_3$ | CH$_3$ | OCH$_3$ | CH | |
| H | CH$_3$ | H | CH$_2$(CH$_2$)$_3$C(O)CH$_3$ | OCH$_3$ | OCH$_3$ | CH | |
| H | CH$_3$ | H | CH$_2$(CH$_2$)$_3$C(O)CH$_3$ | CH$_3$ | CH$_3$ | N | |
| H | CH$_3$ | H | CH$_2$(CH$_2$)$_3$C(O)CH$_3$ | CH$_3$ | OCH$_3$ | N | |
| H | CH$_3$ | CH$_3$ | CH$_2$(CH$_2$)$_3$C(O)CH$_3$ | OCH$_3$ | OCH$_3$ | N | |
| H | CH$_3$ | H | CH$_2$(CH$_2$)$_3$C(O)CH$_3$ | OCH$_3$ | Cl | CH | |
| H | CH$_3$ | H | CH$_2$CH$_2$C(O)CH$_3$ | CH$_3$ | CH$_3$ | CH | |
| H | CH$_3$ | H | CH$_2$CH$_2$C(O)CH$_3$ | CH$_3$ | OCH$_3$ | CH | |
| H | CH$_3$ | H | CH$_2$CH$_2$C(O)CH$_3$ | OCH$_3$ | OCH$_3$ | CH | |
| H | CH$_3$ | H | CH$_2$CH$_2$C(O)CH$_3$ | CH$_3$ | CH$_3$ | N | |
| H | CH$_3$ | H | CH$_2$—CH(CH$_3$)C(O)CH$_3$ | CH$_3$ | OCH$_3$ | N | |
| H | CH$_3$ | CH$_3$ | CH$_2$—CH(CH$_2$)C(O)CH$_3$ | OCH$_3$ | OCH$_3$ | N | |
| H | CH$_3$ | H | CH$_2$—CH(CH$_2$)C(O)CH$_3$ | OCH$_3$ | Cl | CH | |
| H | CH$_3$ | H | CH$_2$—CH(CH$_3$)C(O)CH$_3$ | CH$_3$ | CH$_3$ | CH | |
| CH$_3$ | CH$_3$ | CH$_3$ | CH$_2$—CH(CH$_2$)C(O)CH$_3$ | CH$_3$ | OCH$_3$ | CH | |
| H | CH$_3$ | H | CH$_2$(CH$_2$)$_6$C(O)CH$_2$CH$_3$ | OCH$_3$ | OCH$_3$ | CH | |
| H | CH$_3$ | H | CH$_2$(CH$_2$)$_6$C(O)CH$_2$CH$_3$ | CH$_3$ | CH$_3$ | N | |
| H | CH$_3$ | H | CH$_2$(CH$_2$)$_6$C(O)CH$_2$CH$_3$ | CH$_3$ | OCH$_3$ | N | |
| H | CH$_3$ | H | CH$_2$(CH$_2$)$_6$C(O)CH$_2$CH$_3$ | OCH$_3$ | OCH$_3$ | N | |
| H | CH$_3$ | H | CH$_2$(CH$_2$)$_6$C(O)CH$_2$CH$_3$ | OCH$_3$ | Cl | CH | |
| H | CH$_3$ | H | CH$_2$C(O)OCH$_3$ | CH$_3$ | CH$_3$ | CH | |
| H | CH$_3$ | H | CH$_2$C(O)OCH$_3$ | CH$_3$ | OCH$_3$ | CH | |
| H | CH$_3$ | H | CH$_2$C(O)OCH$_3$ | OCH$_3$ | OCH$_3$ | CH | |
| H | CH$_3$ | H | CH$_2$C(O)OCH$_3$ | CH$_3$ | CH$_3$ | N | |
| H | CH$_3$ | H | CH$_2$C(O)OCH$_3$ | CH$_3$ | OCH$_3$ | N | |
| H | CH$_3$ | H | CH$_2$C(O)OCH$_3$ | OCH$_3$ | OCH$_3$ | N | |
| H | CH$_3$ | H | CH$_2$C(O)OCH$_3$ | OCH$_3$ | Cl | CH | |
| H | CH$_3$ | H | CH$_2$C(O)OCH$_2$CH$_3$ | CH$_3$ | CH$_3$ | CH | |
| H | CH$_3$ | H | CH$_2$C(O)OCH$_2$CH$_3$ | CH$_3$ | OCH$_3$ | CH | |
| H | CH$_3$ | H | CH$_2$C(O)OCH$_2$CH$_3$ | OCH$_3$ | OCH$_3$ | CH | |
| H | CH$_3$ | H | CH$_2$C(O)OCH$_2$CH$_3$ | CH$_3$ | CH$_3$ | N | |
| H | CH$_3$ | H | CH$_2$C(O)OCH$_2$CH$_3$ | CH$_3$ | OCH$_3$ | N | |
| H | CH$_3$ | H | CH$_2$C(O)OCH$_2$CH$_3$ | OCH$_3$ | OCH$_3$ | N | |
| H | CH$_3$ | H | CH$_2$C(O)OCH$_2$CH$_3$ | OCH$_3$ | Cl | CH | |
| H | CH$_3$ | H | CH$_2$CH$_2$C(O)CH$_3$ | CH$_3$ | CH$_3$ | CH | |
| H | CH$_3$ | H | CH$_2$CH$_2$C(O)CH$_3$ | CH$_3$ | OCH$_3$ | CH | |
| H | CH$_3$ | H | CH$_2$CH$_2$C(O)CH$_3$ | OCH$_3$ | OCH$_3$ | N | |
| H | CH$_3$ | H | CH$_2$CH$_2$C(O)CH$_3$ | CH$_3$ | CH$_3$ | N | |
| H | CH$_3$ | H | CH$_2$CH$_2$C(O)CH$_3$ | OCH$_3$ | OCH$_3$ | N | |
| H | CH$_3$ | H | CH$_2$CH$_2$C(O)CH$_3$ | OCH$_3$ | Cl | CH | |
| H | CH$_3$ | H | CH$_2$C(O)N(CH$_3$)$_2$ | CH$_3$ | CH$_3$ | CH | |
| H | CH$_3$ | H | CH$_2$C(O)N(CH$_3$)$_2$ | CH$_3$ | OCH$_3$ | CH | |
| H | CH$_3$ | H | CH$_2$C(O)N(CH$_3$)$_2$ | OCH$_3$ | OCH$_3$ | CH | |
| H | CH$_3$ | H | CH$_2$C(O)N(CH$_3$)$_2$ | CH$_3$ | CH$_3$ | N | |
| H | CH$_3$ | H | CH$_2$C(O)N(CH$_3$)$_2$ | CH$_3$ | OCH$_3$ | N | |
| H | CH$_3$ | H | CH$_2$C(O)N(CH$_3$)$_2$ | OCH$_3$ | OCH$_3$ | N | |
| H | CH$_3$ | H | CH$_2$C(O)N(CH$_3$)$_2$ | OCH$_3$ | Cl | CH | |
| H | CH$_3$ | H | CH$_2$CH$_2$C(O)N(CH$_3$)$_2$ | CH$_3$ | CH$_3$ | CH | |
| H | CH$_3$ | H | CH$_2$CH$_2$C(O)N(CH$_3$)$_2$ | CH$_3$ | OCH$_3$ | CH | |
| H | CH$_3$ | H | CH$_2$CH$_2$C(O)N(CH$_3$)$_2$ | OCH$_3$ | OCH$_3$ | CH | |
| H | CH$_3$ | H | CH$_2$CH$_2$C(O)N(CH$_3$)$_2$ | CH$_3$ | CH$_3$ | N | |
| H | CH$_3$ | H | CH$_2$CH$_2$C(O)N(CH$_3$)$_2$ | CH$_3$ | OCH$_3$ | N | |
| H | CH$_3$ | CH$_3$ | CH$_2$CH$_2$C(O)N(CH$_3$)$_2$ | OCH$_3$ | OCH$_3$ | N | |
| H | CH$_3$ | H | CH$_2$CH$_2$C(O)N(CH$_3$)$_2$ | OCH$_3$ | Cl | CH | |
| H | CH$_3$ | H | CH$_2$C(O)N(CH$_3$)CH$_2$CH$_3$ | CH$_3$ | CH$_3$ | CH | |
| H | CH$_3$ | H | CH$_2$C(O)N(CH$_3$)CH$_2$CH$_3$ | CH$_3$ | OCH$_3$ | CH | |
| H | CH$_3$ | H | CH$_2$C(O)N(CH$_3$)CH$_2$CH$_3$ | OCH$_3$ | OCH$_3$ | CH | |
| H | CH$_3$ | H | CH$_2$C(O)N(CH$_3$)CH$_2$CH$_3$ | CH$_3$ | CH$_3$ | N | |
| H | CH$_3$ | H | CH$_2$C(O)N(CH$_3$)CH$_2$OCH$_3$ | CH$_3$ | OCH$_3$ | N | |
| H | CH$_3$ | H | CH$_2$C(O)N(CH$_3$)CH$_2$OCH$_3$ | OCH$_3$ | OCH$_3$ | N | |
| H | CH$_3$ | H | CH$_2$C(O)N(CH$_3$)CH$_2$OCH$_3$ | OCH$_3$ | Cl | CH | |
| H | CH$_3$ | H | CH$_2$SeCH$_3$ | CH$_3$ | CH$_3$ | CH | |
| CH$_3$ | CH$_3$ | H | CH$_2$SeCH$_3$ | CH$_3$ | OCH$_3$ | CH | |
| H | CH$_3$ | H | CH$_2$SeCH$_3$ | OCH$_3$ | OCH$_3$ | CH | |
| H | CH$_3$ | H | CH$_2$SePh | CH$_3$ | CH$_3$ | N | |
| H | CH$_3$ | H | CH$_2$SePh | CH$_3$ | OCH$_3$ | N | |
| H | CH$_3$ | H | CH$_2$—CH$_2$SeCH$_3$ | OCH$_3$ | OCH$_3$ | N | |
| H | CH$_3$ | H | CH$_2$—CH$_2$SeCH$_3$ | OCH$_3$ | Cl | CH | |
| H | CH$_3$ | H | CH=CH$_2$ | OCH$_3$ | OCH$_3$ | CH | |
| H | CH$_3$ | H | CH=CH$_2$ | CH$_3$ | CH$_3$ | N | |

TABLE II-continued

General Structure II

| R | R$_1$ | R$_2$ | R$_3$ | X | Y | Z | m.p. (°C.) |
|---|---|---|---|---|---|---|---|
| H | CH$_3$ | H | CH=CH$_2$ | CH$_3$ | OCH$_3$ | N | |
| H | CH$_3$ | H | CH=CH$_2$ | OCH$_3$ | OCH$_3$ | N | |
| H | CH$_3$ | H | CH=CH$_2$ | OCH$_3$ | Cl | CH | |
| H | CH$_3$ | H | CH=CH—CH$_3$ | CH$_3$ | CH$_3$ | CH | |
| H | CH$_3$ | H | CH=CH—CH$_3$ | CH$_3$ | OCH$_3$ | CH | |
| H | CH$_3$ | H | CH=CH—CH$_3$ | OCH$_3$ | OCH$_3$ | CH | |
| H | CH$_3$ | H | CH=CH—CH$_3$ | CH$_3$ | CH$_3$ | N | |
| H | CH$_3$ | H | CH=CH—CH$_3$ | CH$_3$ | OCH$_3$ | N | |
| H | CH$_3$ | H | CH=CH—CH$_3$ | OCH$_3$ | OCH$_3$ | N | |
| H | CH$_3$ | H | CH=CH—CH$_3$ | OCH$_3$ | Cl | CH | |
| H | CH$_3$ | H | CH=CH—CH$_2$—CH$_3$ | CH$_3$ | CH$_3$ | CH | |
| H | CH$_3$ | H | CH=CH—CH$_2$—CH$_3$ | CH$_3$ | OCH$_3$ | CH | |
| H | CH$_3$ | H | CH=CH—CH$_2$—CH$_3$ | OCH$_3$ | OCH$_3$ | CH | |
| H | CH$_3$ | H | CH=CH—CH$_2$—CH$_3$ | CH$_3$ | CH$_3$ | N | |
| H | CH$_3$ | H | CH=CH—CH$_2$—CH$_3$ | OCH$_3$ | OCH$_3$ | N | |
| H | CH$_3$ | H | CH=CH—CH$_2$—CH$_3$ | OCH$_3$ | Cl | CH | |
| H | CH$_3$ | H | CH=C(CH$_3$)$_2$ | CH$_3$ | CH$_3$ | CH | |
| H | CH$_3$ | H | CH=C(CH$_3$)$_2$ | CH$_3$ | OCH$_3$ | CH | |
| H | CH$_3$ | H | CH=C(CH$_3$)$_2$ | OCH$_3$ | OCH$_3$ | CH | |
| H | CH$_3$ | H | CH=C(CH$_3$)$_2$ | CH$_3$ | CH$_3$ | N | |
| H | CH$_3$ | H | CH=C(CH$_3$)$_2$ | CH$_3$ | OCH$_3$ | N | |
| H | CH$_3$ | H | CH=C(CH$_3$)$_2$ | OCH$_3$ | OCH$_3$ | N | |
| H | CH$_3$ | H | CH=C(CH$_3$)$_2$ | OCH$_3$ | Cl | CH | |
| H | CH$_3$ | H | CH=CH(CH$_2$)$_3$CH$_3$ | CH$_3$ | CH$_3$ | CH | |
| H | CH$_3$ | H | CH=CH(CH$_2$)$_3$CH$_3$ | CH$_3$ | OCH$_3$ | CH | |
| H | CH$_3$ | H | CH=CH(CH$_2$)$_3$CH$_3$ | OCH$_3$ | OCH$_3$ | CH | |
| H | CH$_3$ | H | CH=CH(CH$_2$)$_3$CH$_3$ | CH$_3$ | CH$_3$ | N | |
| H | CH$_3$ | H | CH=CH(CH$_2$)$_3$CH$_3$ | CH$_3$ | OCH$_3$ | N | |
| H | CH$_3$ | CH$_3$ | CH=CH(CH$_2$)$_3$CH$_3$ | OCH$_3$ | OCH$_3$ | N | |
| H | CH$_3$ | H | CH=CH(CH$_2$)$_3$CH$_3$ | OCH$_3$ | Cl | CH | |
| H | CH$_3$ | H | CH=C(CH$_3$)CH$_2$CH$_3$ | CH$_3$ | CH$_3$ | CH | |
| H | CH$_3$ | H | CH=C(CH$_3$)CH$_2$CH$_3$ | CH$_3$ | OCH$_3$ | CH | |
| H | CH$_3$ | H | CH=C(CH$_3$)CH$_2$CH$_3$ | OCH$_3$ | OCH$_3$ | CH | |
| H | CH$_3$ | H | CH=CH—CH(CH$_3$)$_2$ | CH$_3$ | CH$_3$ | N | |
| H | CH$_3$ | H | CH=CH—CH(CH$_3$)$_2$ | CH$_3$ | OCH$_3$ | N | |
| H | CH$_3$ | H | CH=CH—CH(CH$_3$)$_2$ | OCH$_3$ | OCH$_3$ | N | |
| H | CH$_3$ | H | CH=CH—CH(CH$_3$)$_2$ | OCH$_3$ | Cl | CH | |
| H | CH$_3$ | H | CH=CH (CH$_2$)$_4$CH$_3$ | CH$_3$ | CH$_3$ | CH | |
| CH$_3$ | CH$_3$ | H | CH=CH(CH$_2$)$_4$CH$_3$ | CH$_3$ | OCH$_3$ | CH | |
| H | CH$_3$ | H | CH=CH(CH$_2$)$_6$CH$_3$ | OCH$_3$ | OCH$_3$ | CH | |
| H | CH$_3$ | H | CH=CH(CH$_2$)$_6$CH$_3$ | CH$_3$ | CH$_3$ | N | |
| H | CH$_3$ | H | CH=CH(CH$_2$)$_6$CH$_3$ | CH$_3$ | OCH$_3$ | N | |
| H | CH$_3$ | H | CH=C(CH$_3$)(CH$_2$)$_3$CH$_3$ | OCH$_3$ | OCH$_3$ | N | |
| H | CH$_3$ | H | CH=C(CH$_3$)(CH$_2$)$_3$CH$_3$ | OCH$_3$ | Cl | CH | |
| H | CH$_3$ | H | CH$_2$CH=CH$_2$ | CH$_3$ | CH$_3$ | CH | |
| H | CH$_3$ | H | CH$_2$CH=CH$_2$ | CH$_3$ | OCH$_3$ | CH | |
| H | CH$_3$ | H | CH$_2$CH=CH$_2$ | OCH$_3$ | OCH$_3$ | CH | |
| H | CH$_3$ | H | CH$_2$CH=CH$_2$ | CH$_3$ | CH$_3$ | N | |
| H | CH$_3$ | H | CH$_2$CH=CH$_2$ | CH$_3$ | OCH$_3$ | N | |
| H | CH$_3$ | H | CH$_2$CH=CH$_2$ | OCH$_3$ | OCH$_3$ | N | |
| H | CH$_3$ | H | CH$_2$CH=CH$_2$ | OCH$_3$ | Cl | CH | |
| H | CH$_3$ | H | CH$_2$CH$_2$CH=CH$_2$ | CH$_3$ | CH$_3$ | CH | |
| H | CH$_3$ | H | CH$_2$CH$_2$CH=CH$_2$ | CH$_3$ | OCH$_3$ | CH | |
| H | CH$_3$ | H | CH$_2$CH$_2$CH=CH$_2$ | OCH$_3$ | OCH$_3$ | CH | |
| H | CH$_3$ | H | CH$_2$CH$_2$CH=CH$_2$ | CH$_3$ | CH$_3$ | N | |
| H | CH$_3$ | H | CH$_2$CH$_2$CH=CH$_2$ | CH$_3$ | OCH$_3$ | N | |
| H | CH$_3$ | H | CH$_2$CH$_2$CH=CH$_2$ | OCH$_3$ | OCH$_3$ | N | |
| H | CH$_3$ | H | CH$_2$CH$_2$CH=CH$_2$ | OCH$_3$ | Cl | CH | |
| H | CH$_3$ | H | CH$_2$CH=CHCH$_3$ | CH$_3$ | CH$_3$ | CH | |
| H | CH$_3$ | H | CH$_2$CH=CHCH$_3$ | CH$_3$ | OCH$_3$ | CH | |
| H | CH$_3$ | H | CH$_2$CH=CHCH$_3$ | OCH$_3$ | OCH$_3$ | CH | |
| H | CH$_3$ | H | CH$_2$CH=CHCH$_3$ | CH$_3$ | CH$_3$ | N | |
| H | CH$_3$ | H | CH$_2$—CH=CH—CH$_3$ | OCH$_3$ | OCH$_3$ | N | |
| H | CH$_3$ | H | CH$_2$—CH=CH—CH$_3$ | OCH$_3$ | Cl | CH | |
| H | CH$_3$ | H | CH$_2$—CH=C(CH$_3$)$_2$ | CH$_3$ | CH$_3$ | CH | |
| H | CH$_3$ | H | CH$_2$—CH=C(CH$_3$)$_2$ | CH$_3$ | OCH$_3$ | CH | |
| H | CH$_3$ | H | CH$_2$—CH=C(CH$_3$)$_2$ | OCH$_3$ | OCH$_3$ | CH | |
| H | CH$_3$ | H | CH$_2$—CH=C(CH$_3$)$_2$ | CH$_3$ | CH$_3$ | N | |
| H | CH$_3$ | H | CH$_2$—CH=C(CH$_3$)$_2$ | CH$_3$ | OCH$_3$ | N | |
| H | CH$_3$ | H | CH$_2$—CH=C(CH$_3$)$_2$ | OCH$_3$ | OCH$_3$ | N | |
| H | CH$_3$ | H | CH$_2$—CH=CH(CH$_2$)$_3$CH$_3$ | OCH$_3$ | Cl | CH | |
| H | CH$_3$ | H | CH$_2$—CH=CH(CH$_2$)$_3$CH$_3$ | CH$_3$ | CH$_3$ | CH | |
| H | CH$_3$ | H | CH$_2$—CH=CH(CH$_2$)$_3$CH$_3$ | CH$_3$ | OCH$_3$ | CH | |
| H | CH$_3$ | H | CH$_2$—CH=CH(CH$_2$)$_3$CH$_3$ | OCH$_3$ | OCH$_3$ | CH | |
| H | CH$_3$ | H | CH$_2$—CH=CH(CH$_2$)$_3$CH$_3$ | CH$_3$ | CH$_3$ | N | |
| H | CH$_3$ | H | CH$_2$—CH=CH(CH$_2$)$_3$CH$_3$ | CH$_3$ | OCH$_3$ | N | |
| H | CH$_3$ | CH$_3$ | CH$_2$—CH=CH(CH$_2$)$_3$CH$_3$ | OCH$_3$ | OCH$_3$ | N | |
| H | CH$_3$ | H | CH$_2$—CH$_2$—CH=CH$_2$ | OCH$_3$ | Cl | CH | |
| H | CH$_3$ | H | CH$_2$—CH$_2$—CH=CH$_2$ | CH$_3$ | CH$_3$ | CH | |
| H | CH$_3$ | H | CH$_2$—CH$_2$—CH=CH$_2$ | CH$_3$ | OCH$_3$ | CH | |

TABLE II-continued

General Structure II

| R | R₁ | R₂ | R₃ | X | Y | Z | m.p. (°C.) |
|---|----|----|----|----|----|----|----|
| H | CH₃ | H | CH₂—CH₂—CH=CH₂ | OCH₃ | OCH₃ | CH | |
| H | CH₃ | H | CH₂—CH₂—CH=CH₂ | CH₃ | CH₃ | N | |
| H | CH₃ | H | CH₂—(CH₂)₄CH=CH₂ | CH₃ | OCH₃ | N | |
| H | CH₃ | H | CH₂—CH=CH—CH(CH₃)₂ | OCH₃ | OCH₃ | N | |
| H | CH₃ | H | CH₂—CH=CH—CH(CH₃)₂ | OCH₃ | Cl | CH | |
| H | CH₃ | H | CH₂—CH=CH—CH(CH₃)₂ | CH₃ | CH₃ | CH | |
| CH₃ | CH₃ | H | CH₂—CH=CH—CH(CH₃)₂ | CH₃ | OCH₃ | CH | |
| H | CH₃ | H | CH₂—CH=CH—CH(CH₃)₂ | OCH₃ | OCH₃ | CH | |
| H | CH₃ | H | CH₂—CH=CH—CH=CH₂ | CH₃ | CH₃ | N | |
| H | CH₃ | H | CH₂—CH=CH—CH=CH₂ | CH₃ | OCH₃ | N | |
| H | CH₃ | H | CH₂—CH=CH—CH=CH₂ | OCH₃ | OCH₃ | N | |
| H | CH₃ | H | CH₂—CH=CH—CH=CH₂ | OCH₃ | Cl | CH | |
| H | CH₃ | H | C≡CH | CH₃ | CH₃ | CH | |
| H | CH₃ | H | C≡CH | CH₃ | OCH₃ | CH | |
| H | CH₃ | H | C≡CH | OCH₃ | OCH₃ | CH | |
| H | CH₃ | H | C≡CH | CH₃ | CH₃ | N | |
| H | CH₃ | H | C≡CH | CH₃ | OCH₃ | N | |
| H | CH₃ | H | C≡CH | OCH₃ | OCH₃ | N | |
| H | CH₃ | H | C≡CH | OCH₃ | Cl | CH | |
| H | CH₃ | H | C≡C—CH₃ | CH₃ | CH₃ | CH | |
| H | CH₃ | H | C≡C—CH₃ | CH₃ | OCH₃ | CH | |
| H | CH₃ | H | C≡C—CH₃ | OCH₃ | OCH₃ | CH | |
| H | CH₃ | H | C≡C—CH₃ | CH₃ | CH₃ | N | |
| H | CH₃ | H | C≡C—CH₃ | CH₃ | OCH₃ | N | |
| H | CH₃ | H | C≡C—CH₃ | OCH₃ | OCH₃ | N | |
| H | CH₃ | H | C≡C—CH₃ | OCH₃ | Cl | CH | |
| H | CH₃ | H | C≡C(CH₂)₂CH₃ | CH₃ | CH₃ | CH | |
| H | CH₃ | H | C≡C(CH₂)₂CH₃ | CH₃ | OCH₃ | CH | |
| H | CH₃ | H | C≡C(CH₂)₂CH₃ | OCH₃ | OCH₃ | CH | |
| H | CH₃ | H | C≡C(CH₂)₂CH₃ | CH₃ | CH₃ | N | |
| H | CH₃ | H | C≡C(CH₂)₂CH₃ | OCH₃ | OCH₃ | N | |
| H | CH₃ | H | CH₂—C≡CH | OCH₃ | Cl | CH | |
| H | CH₃ | H | CH₂—C≡CH | CH₃ | CH₃ | CH | |
| H | CH₃ | H | CH₂—C≡CH | CH₃ | OCH₃ | CH | |
| H | CH₃ | H | CH₂—C≡CH | OCH₃ | OCH₃ | CH | |
| H | CH₃ | H | CH₂—C≡CH | CH₃ | CH₃ | N | |
| H | CH₃ | H | CH₂—C≡CH | CH₃ | OCH₃ | N | |
| H | CH₃ | H | CH₂—C≡CH | OCH₃ | OCH₃ | N | |
| H | CH₃ | H | CH₂—C≡CH | OCH₃ | Cl | CH | |
| H | CH₃ | H | CH₂—C≡C—CH₃ | CH₃ | CH₃ | CH | |
| H | CH₃ | H | CH₂—C≡C—CH₃ | CH₃ | OCH₃ | CH | |
| H | CH₃ | H | CH₂—C≡C—CH₃ | OCH₃ | OCH₃ | CH | |
| H | CH₃ | H | CH₂—C≡C—CH₃ | CH₃ | CH₃ | N | |
| H | CH₃ | H | CH₂—C≡C—CH₃ | CH₃ | OCH₃ | N | |
| H | CH₃ | CH₃ | CH₂—C≡C—CH₃ | OCH₃ | OCH₃ | N | |
| H | CH₃ | H | CH₂—CH₂—C≡CH | OCH₃ | Cl | CH | |
| H | CH₃ | H | CH₂—CH₂—C≡CH | CH₃ | CH₃ | CH | |
| H | CH₃ | H | CH₂—CH₂—C≡CH | CH₃ | OCH₃ | CH | |
| H | CH₃ | H | CH₂—CH₂—C≡CH | OCH₃ | OCH₃ | CH | |
| H | CH₃ | H | CH₂—CH₂—C≡CH | CH₃ | CH₃ | N | |
| H | CH₃ | H | CH₂—CH₂—C≡CH | CH₃ | OCH₃ | N | |
| H | CH₃ | H | CH₂—CH₂—C≡CH | OCH₃ | OCH₃ | N | |
| H | CH₃ | H | CH₂—C≡C—CH(CH₃)₂ | OCH₃ | Cl | CH | |
| H | CH₃ | H | CH₂—C≡C—CH(CH₃)₂ | CH₃ | CH₃ | CH | |
| CH₃ | CH₃ | H | CH₂—C≡C—CH(CH₃)₂ | CH₃ | OCH₃ | CH | |
| H | CH₃ | H | C≡C—(CH₂)₆CH₃ | OCH₃ | OCH₃ | CH | |
| H | CH₃ | H | C≡C—(CH₂)₆CH₃ | CH₃ | CH₃ | N | |
| H | CH₃ | H | C≡C—(CH₂)₆CH₃ | CH₃ | OCH₃ | N | |
| H | CH₃ | H | CH₂(CH₂)₇C≡CH | OCH₃ | OCH₃ | N | |
| H | CH₃ | H | CH₂(CH₂)₇C≡CH | OCH₃ | Cl | CH | |
| H | CH₃ | H | CH₂—CH(O)CH₂ (epoxide) | CH₃ | CH₃ | CH | |
| H | CH₃ | H | CH₂—CH(O)CH₂ (epoxide) | CH₃ | OCH₃ | CH | |
| H | CH₃ | H | CH₂—CH(O)CH₂ (epoxide) | OCH₃ | OCH₃ | CH | |
| H | CH₃ | H | CH₂—CH(O)CH₂ (epoxide) | CH₃ | CH₃ | N | |
| H | CH₃ | H | CH₂—CH(O)CH₂ (epoxide) | CH₃ | OCH₃ | N | |
| H | CH₃ | H | CH₂—CH(O)CH₂ (epoxide) | OCH₃ | OCH₃ | N | |

TABLE II-continued

General Structure II

| R | R₁ | R₂ | R₃ | X | Y | Z | m.p. (°C.) |
|---|---|---|---|---|---|---|---|
| H | CH₃ | H | CH₂—CH(—O—)CH₂ | OCH₃ | Cl | CH | |
| H | CH₃ | H | CH₂—CH(—O—)CH—CH₃ | CH₃ | CH₃ | CH | |
| H | CH₃ | H | CH₂—CH(—O—)CH—CH₂ | CH₃ | OCH₃ | CH | |
| H | CH₃ | H | CH₂—CH—O—CH—CH₃ | OCH₃ | OCH₃ | CH | |
| H | CH₃ | H | CH₂—CH—O—CH—CH₃ | CH₃ | CH₃ | N | |
| H | CH₃ | H | CH₂—CH—O—CH—CH₃ | CH₃ | OCH₃ | N | |
| H | CH₃ | H | CH₂—CH—O—CH—CH₃ | OCH₃ | OCH₃ | N | |
| H | CH₃ | H | CH₂—CH—O—CH—CH₃ | OCH₃ | Cl | CH | |
| H | CH₃ | H | CH₂—CH₂—CH—O—CH₂ | CH₃ | CH₃ | CH | |
| H | CH₃ | H | CH₂—CH₂—CH—O—CH₂ | CH₃ | OCH₃ | CH | |
| H | CH₃ | H | CH₂—CH₂—CH—O—CH₂ | OCH₃ | OCH₃ | CH | |
| H | CH₃ | H | CH₂—CH₂—CH—O—CH₂ | CH₃ | CH₃ | N | |
| H | CH₃ | H | CH₂—CH₂—CH—O—CH₂ | OCH₃ | OCH₃ | N | |
| H | CH₃ | H | CH₂—CH₂—CH—O—CH₂ | OCH₃ | Cl | CH | |
| H | CH₃ | H | cyclobutyl | CH₃ | CH₃ | CH | |
| H | CH₃ | H | cyclobutyl | CH₃ | OCH₃ | CH | |
| H | CH₃ | H | cyclobutyl | OCH₃ | OCH₃ | CH | |
| H | CH₃ | H | cyclobutyl | CH₃ | CH₃ | N | |
| H | CH₃ | H | cyclobutyl | CH₃ | OCH₃ | N | |
| H | CH₃ | H | cyclobutyl | OCH₃ | OCH₃ | N | |
| H | CH₃ | H | cyclobutyl | OCH₃ | Cl | CH | |
| H | CH₃ | H | cyclopentyl | CH₃ | CH₃ | CH | |
| H | CH₃ | H | cyclopentyl | CH₃ | OCH₃ | CH | |
| H | CH₃ | H | cyclopentyl | OCH₃ | OCH₃ | CH | |
| H | CH₃ | H | cyclopentyl | CH₃ | CH₃ | N | |
| H | CH₃ | H | cyclopentyl | CH₃ | OCH₃ | N | |
| H | CH₃ | CH₃ | cyclopentyl | OCH₃ | OCH₃ | N | |
| H | CH₃ | H | cyclopentyl | OCH₃ | Cl | CH | |
| H | CH₃ | H | cyclohexyl | CH₃ | CH₃ | CH | |
| H | CH₃ | H | cyclohexyl | CH₃ | OCH₃ | CH | |
| H | CH₃ | H | cyclohexyl | OCH₃ | OCH₃ | CH | |
| H | CH₃ | H | cyclohexyl | CH₃ | CH₃ | N | |
| H | CH₃ | H | cyclohexyl | CH₃ | OCH₃ | N | |
| H | CH₃ | CH₃ | cyclohexyl | OCH₃ | OCH₃ | N | |
| H | CH₃ | H | cyclohexyl | OCH₃ | Cl | CH | |
| H | CH₃ | H | cyclopropyl | CH₃ | CH₃ | CH | |
| CH₃ | CH₃ | H | cyclopropyl | CH₃ | OCH₃ | CH | |
| H | CH₃ | H | cyclopropyl | OCH₃ | OCH₃ | CH | |
| H | CH₃ | H | cyclopropyl | CH₃ | CH₃ | N | |
| H | CH₃ | H | cyclopropyl | CH₃ | OCH₃ | N | |
| H | CH₃ | H | cyclopropyl | OCH₃ | OCH₃ | N | |
| H | CH₃ | H | cyclopropyl | OCH₃ | Cl | CH | |
| H | CH₃ | H | CH₂—cyclopropyl | CH₃ | CH₃ | CH | |
| H | CH₃ | H | CH₂—cyclopropyl | CH₃ | OCH₃ | CH | |
| H | CH₃ | H | CH₂—cyclopropyl | OCH₃ | OCH₃ | CH | |
| H | CH₃ | H | CH₂—cyclopropyl | CH₃ | CH₃ | N | |
| H | CH₃ | H | CH₂—cyclopropyl | CH₃ | OCH₃ | N | |
| H | CH₃ | H | CH₂—cyclopropyl | OCH₃ | OCH₃ | N | |
| H | CH₃ | H | CH₂—cyclopropyl | OCH₃ | Cl | CH | |
| H | CH₃ | H | CH₂—cyclopentyl | CH₃ | CH₃ | CH | |
| H | CH₃ | H | CH₂—cyclopentyl | CH₃ | OCH₃ | CH | |
| H | CH₃ | H | CH₂—cyclopentyl | OCH₃ | OCH₃ | CH | |
| H | CH₃ | H | CH₂—cyclopentyl | CH₃ | CH₃ | N | |
| H | CH₃ | H | CH₂—cyclopentyl | CH₃ | OCH₃ | N | |
| H | CH₃ | H | CH₂—cyclopentyl | OCH₃ | OCH₃ | N | |
| H | CH₃ | H | CH₂—cyclopentyl | OCH₃ | Cl | CH | |
| H | CH₃ | H | C₆H₅ | CH₃ | CH₃ | CH | |
| H | CH₃ | H | C₆H₅ | CH₃ | OCH₃ | CH | |
| H | CH₃ | H | C₆H₅ | OCH₃ | OCH₃ | CH | |

TABLE II-continued

General Structure II

| R | R₁ | R₂ | R₃ | X | Y | Z | m.p. (°C.) |
|---|----|----|----|---|---|---|-----------|
| H | CH₃ | H | C₆H₅ | CH₃ | CH₃ | N | |
| H | CH₃ | H | C₆H₅ | OCH₃ | OCH₃ | N | |
| H | CH₃ | H | C₆H₅ | OCH₃ | Cl | CH | |
| H | CH₃ | H | CH=CH—CF₃ | CH₃ | CH₃ | CH | |
| H | CH₃ | H | CH=CH—CF₃ | CH₃ | OCH₃ | CH | |
| H | CH₃ | H | CH=CH—CF₃ | OCH₃ | OCH₃ | CH | |
| H | CH₃ | H | CH=CH—CF₃ | CH₃ | CH₃ | N | |
| H | CH₃ | H | CH=CH—CF₃ | CH₃ | OCH₃ | N | |
| H | CH₃ | H | CH=CH—CF₃ | OCH₃ | OCH₃ | N | |
| H | CH₃ | H | CH=CH—CF₃ | OCH₃ | Cl | CH | |
| H | CH₃ | H | CH₂—C≡C—CF₃ | CH₃ | CH₃ | CH | |
| H | CH₃ | H | CH₂—C≡C—CF₃ | CH₃ | OCH₃ | CH | |
| H | CH₃ | H | CH₂—C≡C—CF₃ | OCH₃ | OCH₃ | CH | |
| H | CH₃ | H | CH₂—C≡C—CF₃ | CH₃ | CH₃ | N | |
| H | CH₃ | H | CH₂—C≡C—CF₃ | CH₃ | OCH₃ | N | |
| H | CH₃ | CH₃ | CH₂—C≡C—CF₃ | OCH₃ | OCH₃ | N | |
| H | CH₃ | H | CH₂—CH=CF₂ | OCH₃ | Cl | CH | |
| H | CH₃ | H | CH=CH—CH₂Cl | CH₃ | CH₃ | CH | |
| H | CH₃ | H | CH=CH—CH₂Cl | CH₃ | OCH₃ | CH | |
| H | CH₃ | H | CH=CH—CH₂Cl | OCH₃ | OCH₃ | CH | |
| H | CH₃ | H | CH=CH—CH₂Cl | CH₃ | CH₃ | N | |
| H | CH₃ | H | CH=CH—CH₂Cl | CH₃ | OCH₃ | N | |
| H | CH₃ | H | CH=CH—CH₂Cl | OCH₃ | OCH₃ | N | |
| H | CH₃ | H | CH₂—C(CHF)(CH₂) (cyclopropyl) | OCH₃ | Cl | CH | |
| H | CH₃ | H | CH₂—C(CHF)(CH₂) (cyclopropyl) | CH₃ | CH₃ | CH | |
| CH₃ | CH₃ | H | CH₂—C(CHF)(CH₂) (cyclopropyl) | CH₃ | OCH₃ | CH | |
| H | CH₃ | H | CH₂—C(CHF)(CH₂) (cyclopropyl) | OCH₃ | OCH₃ | CH | |
| H | CH₃ | H | CH₂—C(CHF)(CH₂) (cyclopropyl) | CH₃ | CH₃ | N | |
| H | CH₃ | H | CH₂—C(CHF)(CH₂) (cyclopropyl) | CH₃ | OCH₃ | N | |
| H | CH₃ | H | CH₂—C≡C—CH₂Br | OCH₃ | OCH₃ | N | |
| H | CH₃ | H | CH₂—C≡C—CH₂Br | OCH₃ | Cl | CH | |
| H | CH₃ | H | CH₂—CH=CHOCH₃ | CH₃ | CH₃ | CH | |
| H | CH₃ | H | CH₂—CH=CHOCH₃ | CH₃ | OCH₃ | CH | |
| H | CH₃ | H | CH₂—CH=CHOCH₃ | OCH₃ | OCH₃ | CH | |
| H | CH₃ | H | CH₂—CH=CHOCH₃ | CH₃ | CH₃ | N | |
| H | CH₃ | H | CH₂—C≡CHOCH₃ | CH₃ | OCH₃ | N | |
| H | CH₃ | H | CH₂—C≡C—OCH₃ | OCH₃ | OCH₃ | N | |
| H | CH₃ | H | CH₂—CH₂—CH=CHCN | OCH₃ | Cl | CH | |
| H | CH₃ | H | CH₂—CH₂—CH=CHCN | CH₃ | CH₃ | CH | |
| H | CH₃ | H | CH₂—CH₂—CH=CHCN | CH₃ | OCH₃ | CH | |
| H | CH₃ | H | CH(OSO₂CH₃)C≡CH | OCH₃ | OCH₃ | CH | |
| H | CH₃ | H | CH(OSO₂CH₃)C≡CH | CH₃ | CH₃ | N | |
| H | CH₃ | H | CH(OSO₂CH₃)C≡CH | CH₃ | OCH₃ | N | |
| H | CH₃ | H | CH(OSO₂CH₃)C≡CH | OCH₃ | OCH₃ | N | |
| H | CH₃ | H | CH(OSO₂CH₃)C≡CH | OCH₃ | Cl | CH | |
| H | CH₃ | H | C≡C—Si(CH₃)₃ | CH₃ | CH₃ | CH | |
| H | CH₃ | H | C≡C—Si(CH₃)₃ | CH₃ | OCH₃ | CH | |
| H | CH₃ | H | C≡C—Si(CH₃)₃ | OCH₃ | OCH₃ | CH | |
| H | CH₃ | H | CH₂—CH=CHP(O)(CH₃)₂ | CH₃ | CH₃ | N | |
| H | CH₃ | H | CH₂—CH=CHP(O)(CH₃)₂ | OCH₃ | OCH₃ | N | |
| H | CH₃ | H | CH₂—CH=CHP(O)(CH₃)₂ | OCH₃ | Cl | CH | |
| H | CH₃ | H | CH₂—CH=CHP(O)(CH₃)₂ | CH₃ | CH₃ | CH | |
| H | CH₃ | H | CH₂—CH=CHP(O)(CH₃)₂ | CH₃ | OCH₃ | CH | |
| H | CH₃ | H | CH=CH—OSi(CH₃)₃ | OCH₃ | OCH₃ | CH | |
| H | CH₃ | H | CH=CH—OSi(CH₃)₃ | CH₃ | CH₃ | N | |
| H | CH₃ | H | CH=CH—OSi(CH₃)₃ | CH₃ | OCH₃ | N | |

TABLE II-continued

General Structure II

| R | $R_1$ | $R_2$ | $R_3$ | X | Y | Z | m.p. (°C.) |
|---|---|---|---|---|---|---|---|
| H | $CH_3$ | H | $CH=CH-OSi(CH_3)_3$ | $OCH_3$ | $OCH_3$ | N | |
| H | $CH_3$ | H | $CH_2(CH_2)_5CH=CH-CN$ | $OCH_3$ | Cl | CH | |
| H | $CH_3$ | H | $CH_2(CH_2)_5CH=CH-CN$ | $CH_3$ | $CH_3$ | CH | |
| H | $CH_3$ | H | $CH_2(CH_2)_5CH=CH-CN$ | $CH_3$ | $OCH_3$ | CH | |
| H | $CH_3$ | H | $CH_2(CH_2)_5CH=CH-CN$ | $OCH_3$ | $OCH_3$ | CH | |
| H | $CH_3$ | H | $CH_2(CH_2)_5CH=CH-CN$ | $CH_3$ | $CH_3$ | N | |
| H | $CH_3$ | H | $CH=CH-CH_2SCN$ | $CH_3$ | $OCH_3$ | N | |
| H | $CH_3$ | $CH_3$ | $CH=CH-CH_2SCN$ | $OCH_3$ | $OCH_3$ | N | |
| H | $CH_3$ | H | $CH=CH-CH_2SCN$ | $OCH_3$ | Cl | CH | |
| H | $CH_3$ | H | $C{\equiv}C-C{\equiv}C-CH_2OCH_3$ | $CH_3$ | $CH_3$ | CH | |
| H | $CH_3$ | H | $C{\equiv}C-C{\equiv}C-CH_2OCH_3$ | $CH_3$ | $OCH_3$ | CH | |
| H | $CH_3$ | H | $C{\equiv}C-C{\equiv}C-CH_2OCH_3$ | $OCH_3$ | $OCH_3$ | CH | |
| H | $CH_3$ | H | $CH_2-CH=CH-CH_2SCH_3$ | $CH_3$ | $CH_3$ | N | |
| H | $CH_3$ | H | $CH_2-CH=CH-CH_2SCH_3$ | $CH_3$ | $OCH_3$ | N | |
| H | $CH_3$ | H | $CH_2-CH=CH-CH_2SCH_3$ | $OCH_3$ | $OCH_3$ | N | |
| H | $CH_3$ | H | $CH_2-CH=CH-CH_2SCH_3$ | $OCH_3$ | Cl | CH | |
| H | $CH_3$ | H | $CH=CH-CH_2N(CH_3)_2$ | $CH_3$ | $CH_3$ | CH | |
| $CH_3$ | $CH_3$ | H | $CH=CH-CH_2N(CH_3)_2$ | $CH_3$ | $OCH_3$ | CH | |
| H | $CH_3$ | H | $CH=CH-CH_2N(CH_3)_2$ | $OCH_3$ | $OCH_3$ | CH | |
| H | $CH_3$ | H | $CH_2-CH=CH-P(O)(OCH_3)_2$ | $CH_3$ | $CH_3$ | N | |
| H | $CH_3$ | H | $CH_2-CH=CH-P(O)(OCH_3)_2$ | $CH_3$ | $OCH_3$ | N | |
| H | $CH_3$ | H | $CH_2-CH=CH-P(O)(OCH_3)_2$ | $OCH_3$ | $OCH_3$ | N | |
| H | $CH_3$ | H | $CH_2-CH=CH-P(O)(OCH_3)_2$ | $OCH_3$ | Cl | CH | |
| H | $CH_3$ | H | $SCH_3$ | $CH_3$ | $CH_3$ | CH | |
| H | $CH_3$ | H | $SCH_3$ | $CH_3$ | $OCH_3$ | CH | |
| H | $CH_3$ | H | $SCH_3$ | $OCH_3$ | $OCH_3$ | CH | |
| H | $CH_3$ | H | $SCH_3$ | $CH_3$ | $CH_3$ | N | |
| H | $CH_3$ | H | $SCH_3$ | $CH_3$ | $OCH_3$ | N | |
| H | $CH_3$ | H | $SCH_3$ | $OCH_3$ | $OCH_3$ | N | |
| H | $CH_3$ | H | $SCH_3$ | $OCH_3$ | Cl | CH | |
| H | $CH_3$ | H | $SCH_2CF_3$ | $CH_3$ | $CH_3$ | CH | |
| H | $CH_3$ | H | $SCH_2CH_3$ | $CH_3$ | $OCH_3$ | CH | |
| H | $CH_3$ | H | $SCH_2CH_3$ | $OCH_3$ | $OCH_3$ | CH | |
| H | $CH_3$ | H | $SCH_2CH_3$ | $CH_3$ | $CH_3$ | N | |
| H | $CH_3$ | H | $SCH_2CH_3$ | $CH_3$ | $OCH_3$ | N | |
| H | $CH_3$ | H | $SCH_2CH_3$ | $OCH_3$ | $OCH_3$ | N | |
| H | $CH_3$ | H | $SCH_2CH_3$ | $OCH_3$ | Cl | CH | |
| H | $CH_3$ | H | $SO_2CH_3$ | $CH_3$ | $CH_3$ | CH | |
| H | $CH_3$ | H | $SO_2CH_3$ | $CH_3$ | $OCH_3$ | CH | |
| H | $CH_3$ | H | $SO_2CH_3$ | $OCH_3$ | $OCH_3$ | CH | |
| H | $CH_3$ | H | $SO_2CH_3$ | $CH_3$ | $CH_3$ | N | |
| H | $CH_3$ | H | $SO_2CH_3$ | $OCH_3$ | $OCH_3$ | N | |
| H | $CH_3$ | H | $SO_2CH_3$ | $OCH_3$ | Cl | CH | |
| H | $CH_3$ | H | $SO_2CH_2CH_3$ | $CH_3$ | $CH_3$ | CH | |
| H | $CH_3$ | H | $SO_2CH_2CH_3$ | $CH_3$ | $OCH_3$ | CH | |
| H | $CH_3$ | H | $SO_2CH_2CH_3$ | $OCH_3$ | $OCH_3$ | CH | |
| H | $CH_3$ | H | $SO_2CH_2CH_3$ | $CH_3$ | $CH_3$ | N | |
| H | $CH_3$ | H | $SO_2CH_2CH_3$ | $CH_3$ | $OCH_3$ | N | |
| H | $CH_3$ | H | $SO_2CH_2CH_3$ | $OCH_3$ | $OCH_3$ | N | |
| H | $CH_3$ | H | $SO_2CH_2CH_3$ | $OCH_3$ | Cl | CH | |
| H | $CH_3$ | H | $OCH_3$ | $CH_3$ | $CH_3$ | CH | |
| H | $CH_3$ | H | $OCH_3$ | $CH_3$ | $OCH_3$ | CH | |
| H | $CH_3$ | H | $OCH_3$ | $OCH_3$ | $OCH_3$ | CH | |
| H | $CH_3$ | H | $OCH_3$ | $CH_3$ | $CH_3$ | N | |
| H | $CH_3$ | H | $OCH_3$ | $CH_3$ | $OCH_3$ | N | |
| H | $CH_3$ | $CH_3$ | $OCH_3$ | $OCH_3$ | $OCH_3$ | N | |
| H | $CH_3$ | H | $OCH_3$ | $OCH_3$ | Cl | CH | |
| H | $CH_3$ | H | $OCH_2CH_3$ | $CH_3$ | $CH_3$ | CH | |
| H | $CH_3$ | H | $OCH_2CH_3$ | $CH_3$ | $OCH_3$ | CH | |
| H | $CH_3$ | H | $OCH_2CH_3$ | $OCH_3$ | $OCH_3$ | CH | |
| H | $CH_3$ | H | $OCH_2CH_3$ | $CH_3$ | $CH_3$ | N | |
| H | $CH_3$ | H | $OCH_2CH_3$ | $CH_3$ | $OCH_3$ | N | |
| H | $CH_3$ | H | $OCH_2CH_3$ | $OCH_3$ | $OCH_3$ | N | |
| H | $CH_3$ | H | $OCH_2CH_3$ | $OCH_3$ | Cl | CH | |
| H | $CH_3$ | H | $OCH_2(CH_3)_2$ | $CH_3$ | $CH_3$ | CH | |
| $CH_3$ | $CH_3$ | H | $OCH(CH_3)_2$ | $CH_3$ | $OCH_3$ | CH | |
| H | $CH_3$ | H | $OCH(CH_3)_2$ | $OCH_3$ | $OCH_3$ | CH | |
| H | $CH_3$ | H | $OCH(CH_3)_2$ | $CH_3$ | $CH_3$ | N | |
| H | $CH_3$ | H | $OCH(CH_3)_2$ | $CH_3$ | $OCH_3$ | N | |
| H | $CH_3$ | H | $OCH(CH_3)_2$ | $OCH_3$ | $OCH_3$ | N | |
| H | $CH_3$ | H | $OCH(CH_3)_2$ | $OCH_3$ | Cl | CH | |
| H | $CH_3$ | H | $C(O)CH_3$ | $CH_3$ | $CH_3$ | CH | |
| H | $CH_3$ | H | $C(O)CH_3$ | $CH_3$ | $OCH_3$ | CH | |
| H | $CH_3$ | H | $C(O)CH_3$ | $OCH_3$ | $OCH_3$ | CH | |
| H | $CH_3$ | H | $C(O)CH_3$ | $CH_3$ | $CH_3$ | N | |
| H | $CH_3$ | H | $C(O)CH_3$ | $CH_3$ | $OCH_3$ | N | |
| H | $CH_3$ | H | $C(O)CH_3$ | $OCH_3$ | $OCH_3$ | N | |
| H | $CH_3$ | H | $C(O)CH_3$ | $OCH_3$ | Cl | CH | |
| H | $CH_3$ | H | $C(O)CH_2CH_3$ | $CH_3$ | $CH_3$ | CH | |
| H | $CH_3$ | H | $C(O)CH_2CH_3$ | $CH_3$ | $OCH_3$ | CH | |

TABLE II-continued

General Structure II

| R | R$_1$ | R$_2$ | R$_3$ | X | Y | Z | m.p. (°C.) |
|---|---|---|---|---|---|---|---|
| H | CH$_3$ | H | C(O)CH$_2$CH$_3$ | OCH$_3$ | OCH$_3$ | CH | |
| H | CH$_3$ | H | C(O)CH$_2$CH$_3$ | CH$_3$ | CH$_3$ | N | |
| H | CH$_3$ | H | C(O)CH$_2$CH$_3$ | CH$_3$ | OCH$_3$ | N | |
| H | CH$_3$ | H | C(O)CH$_2$CH$_3$ | OCH$_3$ | OCH$_3$ | N | |
| H | CH$_3$ | H | C(O)CH$_2$CH$_3$ | OCH$_3$ | Cl | CH | |
| H | CH$_3$ | H | C(O)(CH)(CH$_3$)$_2$ | CH$_3$ | CH$_3$ | CH | |
| H | CH$_3$ | H | C(O)(CH)(CH$_3$)$_2$ | CH$_3$ | OCH$_3$ | CH | |
| H | CH$_3$ | H | C(O)(CH)(CH$_3$)$_2$ | OCH$_3$ | OCH$_3$ | CH | |
| H | CH$_3$ | H | C(O)(CH)(CH$_3$)$_2$ | CH$_3$ | CH$_3$ | N | |
| H | CH$_3$ | H | C(O)(CH)(CH$_3$)$_2$ | OCH$_3$ | OCH$_3$ | N | |
| H | CH$_3$ | H | C(O)(CH)(CH$_3$)$_2$ | OCH$_3$ | Cl | CH | |
| H | CH$_3$ | H | C(O)CHF$_2$ | CH$_3$ | CH$_3$ | CH | |
| H | CH$_3$ | H | C(O)CHF$_2$ | CH$_3$ | OCH$_3$ | CH | |
| H | CH$_3$ | H | C(O)CHF$_2$ | OCH$_3$ | OCH$_3$ | CH | |
| H | CH$_3$ | H | C(O)CF$_3$ | CH$_3$ | CH$_3$ | N | |
| H | CH$_3$ | H | C(O)CF$_3$ | CH$_3$ | OCH$_3$ | N | |
| H | CH$_3$ | H | C(O)CF$_3$ | OCH$_3$ | OCH$_3$ | N | |
| H | CH$_3$ | H | C(O)CF$_3$ | OCH$_3$ | Cl | CH | |
| H | CH$_3$ | H | C(O)CH$_2$CH$_2$CH$_3$ | CH$_3$ | CH$_3$ | CH | |
| H | CH$_3$ | H | C(O)CH$_2$CH$_2$CH$_3$ | CH$_3$ | OCH$_3$ | CH | |
| H | CH$_3$ | H | C(O)CH$_2$CH$_2$CH$_3$ | OCH$_3$ | OCH$_3$ | CH | |
| H | CH$_3$ | H | C(O)CH$_2$CH$_2$CH$_3$ | CH$_3$ | CH$_3$ | N | |
| H | CH$_3$ | H | C(O)CH$_2$CH$_2$CH$_3$ | CH$_3$ | OCH$_3$ | N | |
| H | CH$_3$ | H | C(O)CH$_2$CH$_2$CH$_3$ | OCH$_3$ | OCH$_3$ | N | |
| H | CH$_3$ | H | C(O)CH$_2$CH$_2$CH$_3$ | OCH$_3$ | Cl | CH | |
| H | CH$_3$ | H | C(O)CH$_2$OCH$_3$ | CH$_3$ | CH$_3$ | CH | |
| H | CH$_3$ | H | C(O)CH$_2$OCH$_3$ | CH$_3$ | OCH$_3$ | CH | |
| H | CH$_3$ | H | C(O)CH$_2$OCH$_3$ | OCH$_3$ | OCH$_3$ | CH | |
| H | CH$_3$ | H | C(O)CH$_2$OCH$_3$ | CH$_3$ | CH$_3$ | N | |
| H | CH$_3$ | H | C(O)CH$_2$Cl | CH$_3$ | OCH$_3$ | N | |
| H | CH$_3$ | H | C(O)CH$_2$Cl | OCH$_3$ | OCH$_3$ | N | |
| H | CH$_3$ | H | C(O)CH$_2$Cl | OCH$_3$ | Cl | CH | |
| H | CH$_3$ | H | C(O)CH$_2$CH(CH$_3$)CN | CH$_3$ | CH$_3$ | CH | |
| CH$_3$ | CH$_3$ | H | C(O)CH$_2$CH(CH$_3$)CN | CH$_3$ | OCH$_3$ | CH | |
| H | CH$_3$ | H | C(O)CH$_2$N(CH$_3$)$_2$ | OCH$_3$ | OCH$_3$ | CH | |
| H | CH$_3$ | H | C(O)CH$_2$N(CH$_3$)$_2$ | CH$_3$ | CH$_3$ | N | |
| H | CH$_3$ | H | C(O)CH$_2$CH=CH$_2$ | CH$_3$ | OCH$_3$ | N | |
| H | CH$_3$ | H | C(O)CH$_2$CH=CH$_2$ | OCH$_3$ | OCH$_3$ | N | |
| H | CH$_3$ | H | C(O)CH$_2$C≡CH | OCH$_3$ | Cl | CH | |
| H | CH$_3$ | H | CO$_2$CH$_3$ | CH$_3$ | CH$_3$ | CH | |
| H | CH$_3$ | H | CO$_2$CH$_3$ | CH$_3$ | OCH$_3$ | CH | |
| H | CH$_3$ | H | CO$_2$CH$_3$ | OCH$_3$ | OCH$_3$ | CH | |
| H | CH$_3$ | H | CO$_2$CH$_3$ | CH$_3$ | CH$_3$ | N | |
| H | CH$_3$ | H | CO$_2$CH$_3$ | CH$_3$ | OCH$_3$ | N | |
| H | CH$_3$ | H | CO$_2$CH$_3$ | OCH$_3$ | OCH$_3$ | N | |
| H | CH$_3$ | H | CO$_2$CH$_3$ | OCH$_3$ | Cl | CH | |
| H | CH$_3$ | H | CO$_2$CH$_2$CH$_3$ | CH$_3$ | CH$_3$ | CH | |
| H | CH$_3$ | H | CO$_2$CH$_2$CH$_3$ | CH$_3$ | OCH$_3$ | CH | |
| H | CH$_3$ | H | CO$_2$CH$_2$CH$_3$ | OCH$_3$ | OCH$_3$ | CH | |
| H | CH$_3$ | H | CO$_2$CH$_2$CH$_3$ | CH$_3$ | CH$_3$ | N | |
| H | CH$_3$ | H | CO$_2$CH$_2$CH$_3$ | CH$_3$ | OCH$_3$ | N | |
| H | CH$_3$ | H | CO$_2$CH$_2$CH$_3$ | OCH$_3$ | OCH$_3$ | N | |
| H | CH$_3$ | H | CO$_2$CH$_2$CH$_3$ | OCH$_3$ | Cl | CH | |
| H | CH$_3$ | H | CO$_2$CH$_2$CF$_3$ | CH$_3$ | CH$_3$ | CH | |
| H | CH$_3$ | H | CO$_2$CH$_2$CF$_3$ | CH$_3$ | OCH$_3$ | CH | |
| H | CH$_3$ | H | CO$_2$CH$_2$CF$_3$ | OCH$_3$ | OCH$_3$ | CH | |
| H | CH$_3$ | H | CO$_2$CH$_2$CF$_3$ | CH$_3$ | CH$_3$ | N | |
| H | CH$_3$ | H | CO$_2$CF$_3$ | OCH$_3$ | OCH$_3$ | N | |
| H | CH$_3$ | H | CO$_2$CF$_3$ | OCH$_3$ | Cl | CH | |
| H | CH$_3$ | H | CO$_2$CF$_3$ | CH$_3$ | CH$_3$ | CH | |
| H | CH$_3$ | H | CO$_2$CH$_2$C≡CH | CH$_3$ | OCH$_3$ | CH | |
| H | CH$_3$ | H | CO$_2$CH$_2$C≡CH | OCH$_3$ | OCH$_3$ | CH | |
| H | CH$_3$ | H | CO$_2$CH$_2$C≡CH | CH$_3$ | CH$_3$ | N | |
| H | CH$_3$ | H | CO$_2$CH$_2$C≡CH | CH$_3$ | OCH$_3$ | N | |
| H | CH$_3$ | H | CO$_2$CH$_2$C≡CH | OCH$_3$ | OCH$_3$ | N | |
| H | CH$_3$ | H | CO$_2$CH$_2$CH=CH$_2$ | OCH$_3$ | Cl | CH | |
| H | CH$_3$ | H | CO$_2$CH$_2$CH=CH$_2$ | CH$_3$ | CH$_3$ | CH | |
| H | CH$_3$ | H | CO$_2$CH$_2$CH=CH$_2$ | CH$_3$ | OCH$_3$ | CH | |
| H | CH$_3$ | H | CO$_2$CH$_2$CH=CH$_2$ | OCH$_3$ | OCH$_3$ | CH | |
| H | CH$_3$ | H | CO$_2$CH$_2$CH=CH$_2$ | CH$_3$ | CH$_3$ | N | |
| H | CH$_3$ | H | CO$_2$CH$_2$CH=CH$_2$ | CH$_3$ | OCH$_3$ | N | |
| H | CH$_3$ | CH$_3$ | CO$_2$CH$_3$ | OCH$_3$ | OCH$_3$ | N | |
| H | CH$_3$ | H | CO$_2$CF$_3$ | OCH$_3$ | Cl | CH | |
| H | CH$_3$ | H | CO$_2$CF$_3$ | CH$_3$ | CH$_3$ | CH | |
| H | CH$_3$ | H | CO$_2$CF$_3$ | CH$_3$ | OCH$_3$ | CH | |
| H | CH$_3$ | H | CO$_2$CF$_3$ | OCH$_3$ | OCH$_3$ | CH | |
| H | CH$_3$ | H | CO$_2$CH$_2$CH$_2$Cl | CH$_3$ | CH$_3$ | N | |
| H | CH$_3$ | H | CO$_2$CH$_2$CH$_2$Cl | CH$_3$ | OCH$_3$ | N | |
| H | CH$_3$ | H | CO$_2$CH$_2$CH$_2$Cl | OCH$_3$ | OCH$_3$ | N | |
| H | CH$_3$ | H | CO$_2$CH$_2$CH$_2$P(O)(CH$_3$)$_2$ | OCH$_3$ | Cl | CH | |

TABLE II-continued

General Structure II

| R | R₁ | R₂ | R₃ | X | Y | Z | m.p. (°C.) |
|---|----|----|----|---|---|---|------------|
| H | CH₃ | H | CO₂CH₂CH₂P(O)(CH₃)₂ | CH₃ | CH₃ | CH | |
| CH₃ | CH₃ | H | CO₂C(CH₃)₃ | CH₃ | OCH₃ | CH | |
| H | CH₃ | H | CO₂C(CH₃)₃ | OCH₃ | OCH₃ | CH | |
| H | CH₃ | H | CO₂CH₂(CH₂)₄CH₃ | CH₃ | CH₃ | N | |
| H | CH₃ | H | CO₂CH₂(CH₂)₄CH₃ | CH₃ | OCH₃ | N | |
| H | CH₃ | H | CO₂CH₂OCH₃ | OCH₃ | OCH₃ | N | |
| H | CH₃ | H | CO₂CH₂OCH₃ | OCH₃ | Cl | CH | |
| H | CH₃ | H | (C(O))₂OCH₃ | CH₃ | CH₃ | CH | |
| H | CH₃ | H | (C(O))₂OCH₃ | CH₃ | OCH₃ | CH | |
| H | CH₃ | H | (C(O))₂OCH₃ | OCH₃ | OCH₃ | CH | |
| H | CH₃ | H | (C(O))₂OCH₃ | CH₃ | CH₃ | N | |
| H | CH₃ | H | (C(O))₂OCH₃ | CH₃ | OCH₃ | N | |
| H | CH₃ | H | (C(O))₂OCH₃ | OCH₃ | OCH₃ | N | |
| H | CH₃ | H | (C(O))₂OCH₃ | OCH₃ | Cl | CH | |
| H | CH₃ | H | (CO)₂CH₃ | CH₃ | CH₃ | CH | |
| H | CH₃ | H | (CO)₂CH₃ | CH₃ | OCH₃ | CH | |
| H | CH₃ | H | (CO)₂CH₃ | OCH₃ | OCH₃ | CH | |
| H | CH₃ | H | (CO)₂CH₃ | CH₃ | CH₃ | N | |
| H | CH₃ | H | (CO)₂CH₃ | CH₃ | OCH₃ | N | |
| H | CH₃ | H | (CO)₂CH₃ | OCH₃ | OCH₃ | N | |
| H | CH₃ | H | (CO)₂CH₃ | OCH₃ | Cl | CH | |
| H | CH₃ | H | C(O)N(CH₃)₂ | CH₃ | CH₃ | CH | |
| H | CH₃ | H | C(O)N(CH₃)₂ | CH₃ | OCH₃ | CH | |
| H | CH₃ | H | C(O)N(CH₃)₂ | OCH₃ | OCH₃ | CH | |
| H | CH₃ | H | C(O)N(CH₃)₂ | CH₃ | CH₃ | N | |
| H | CH₃ | H | C(O)N(CH₃)₂ | OCH₃ | OCH₃ | N | |
| H | CH₃ | H | C(O)N(CH₃)₂ | OCH₃ | Cl | CH | |
| H | CH₃ | H | C(O)N(CH₂CH₃)₂ | CH₃ | CH₃ | CH | |
| H | CH₃ | H | C(O)N(CH₂CH₃)₂ | CH₃ | OCH₃ | CH | |
| H | CH₃ | H | C(O)N(CH₂CH₃)₂ | OCH₃ | OCH₃ | CH | |
| H | CH₃ | H | C(O)N(CH₂CH₃)₂ | CH₃ | CH₃ | N | |
| H | CH₃ | H | C(O)N(CH₂CH₃)₂ | CH₃ | OCH₃ | N | |
| H | CH₃ | H | C(O)N(CH₂CH₃)₂ | OCH₃ | OCH₃ | N | |
| H | CH₃ | H | C(O)N(CH₃)CH₂CH₃ | OCH₃ | Cl | CH | |
| H | CH₃ | H | C(O)N(CH₃)CH₂CH₃ | CH₃ | CH₃ | CH | |
| H | CH₃ | H | C(O)N(CH₃)CH₂CH₃ | CH₃ | OCH₃ | CH | |
| H | CH₃ | H | C(O)N(CH₃)CH₂CH₃ | OCH₃ | OCH₃ | CH | |
| H | CH₃ | H | C(O)N(CH₃)CH₂CH₃ | CH₃ | CH₃ | N | |
| H | CH₃ | H | C(O)N(CF₃)CH₃ | CH₃ | OCH₃ | N | |
| H | CH₃ | CH₃ | C(O)N(CF₃)CH₃ | OCH₃ | OCH₃ | N | |
| H | CH₃ | H | C(O)N(CF₃)CH₃ | OCH₃ | Cl | CH | |
| H | CH₃ | H | C(O)N(CH₃)OCH₃ | CH₃ | CH₃ | CH | |
| H | CH₃ | H | C(O)N(CH₃)OCH₃ | CH₃ | OCH₃ | CH | |
| H | CH₃ | H | C(O)N(CH₃)OCH₃ | OCH₃ | OCH₃ | CH | |
| H | CH₃ | H | C(O)N(CH₃)OCH₃ | CH₃ | CH₃ | N | |
| H | CH₃ | H | C(O)N(CH=CH₂)CH₃ | CH₃ | OCH₃ | N | |
| H | CH₃ | H | C(O)N(CH=CH₂)CH₃ | OCH₃ | OCH₃ | N | |
| H | CH₃ | H | C(O)N(CH=CH₂)CH₃ | OCH₃ | Cl | CH | |
| H | CH₃ | H | C(O)N(CH=CH₂)CH₃ | CH₃ | CH₃ | CH | |
| CH₃ | CH₃ | H | C(O)N(CH=CH₂)CH₃ | CH₃ | OCH₃ | CH | |
| H | CH₃ | H | C(O)N(CH₃)Ph | OCH₃ | OCH₃ | CH | |
| H | CH₃ | H | C(O)N(CH₃)Ph | CH₃ | CH₃ | N | |
| H | CH₃ | H | C(O)N(CH₃)Ph | CH₃ | OCH₃ | N | |
| H | CH₃ | H | C(O)N(OCH₃)₂ | OCH₃ | OCH₃ | N | |
| H | CH₃ | H | C(O)N(OCH₃)₂ | OCH₃ | Cl | CH | |
| H | CH₃ | H | CS₂CH₃ | CH₃ | CH₃ | CH | |
| H | CH₃ | H | CS₂CH₃ | CH₃ | OCH₃ | CH | |
| H | CH₃ | H | CS₂CH₃ | OCH₃ | OCH₃ | CH | |
| H | CH₃ | H | CS₂CH₃ | CH₃ | CH₃ | N | |
| H | CH₃ | H | CS₂CH₃ | CH₃ | OCH₃ | N | |
| H | CH₃ | H | CS₂CH₃ | OCH₃ | OCH₃ | N | |
| H | CH₃ | H | CS₂CH₃ | OCH₃ | Cl | CH | |
| H | CH₃ | H | CS₂CH₂CH₃ | CH₃ | CH₃ | CH | |
| H | CH₃ | H | CS₂CH₂CH₃ | CH₃ | OCH₃ | CH | |
| H | CH₃ | H | CS₂CH₂CH₃ | OCH₃ | OCH₃ | CH | |
| H | CH₃ | H | CS₂CH₂CH₃ | CH₃ | CH₃ | N | |
| H | CH₃ | H | CS₂CH₂CH₃ | CH₃ | OCH₃ | N | |
| H | CH₃ | H | CS₂CH₂CH=CH₂ | OCH₃ | OCH₃ | N | |
| H | CH₃ | H | CS₂CH₂CH=CH₂ | OCH₃ | Cl | CH | |
| H | CH₃ | H | CS₂CH₂CH=CH₂ | CH₃ | CH₃ | CH | |
| H | CH₃ | H | NH₂ | CH₃ | CH₃ | CH | |
| H | CH₃ | H | NH₂ | CH₃ | OCH₃ | CH | |
| H | CH₃ | H | NH₂ | OCH₃ | OCH₃ | CH | |
| H | CH₃ | H | NH₂ | CH₃ | CH₃ | N | |
| H | CH₃ | H | NH₂ | CH₃ | OCH₃ | N | |
| H | CH₃ | H | NH₂ | OCH₃ | OCH₃ | N | |
| H | CH₃ | H | NH₂ | OCH₃ | Cl | CH | |
| H | CH₃ | H | N(CH₃)₂ | CH₃ | CH₃ | CH | |
| H | CH₃ | H | N(CH₃)₂ | CH₃ | OCH₃ | CH | |
| H | CH₃ | H | N(CH₃)₂ | OCH₃ | OCH₃ | CH | |

TABLE II-continued

General Structure II

| R | R₁ | R₂ | R₃ | X | Y | Z | m.p. (°C.) |
|---|----|----|----|---|---|---|---|
| H | CH₃ | H | N(CH₃)₂ | CH₃ | CH₃ | N | |
| H | CH₃ | H | N(CH₃)₂ | CH₃ | OCH₃ | N | |
| H | CH₃ | CH₃ | N(CH₃)₂ | OCH₃ | OCH₃ | N | |
| H | CH₃ | H | N(CH₃)₂ | OCH₃ | Cl | CH | |
| H | CH₃ | H | N(CH₃)(CH₂CH₃) | CH₃ | CH₃ | CH | |
| H | CH₃ | H | N(CH₃)(CH₂CH₃) | CH₃ | OCH₃ | CH | |
| H | CH₃ | H | N(CH₃)(CH₂CH₃) | OCH₃ | OCH₃ | CH | |
| H | CH₃ | H | N(CH₃)OCH₃ | CH₃ | CH₃ | N | |
| H | CH₃ | H | N(CH₃)OCH₃ | CH₃ | OCH₃ | N | |
| H | CH₃ | H | N(CH₃)OCH₃ | OCH₃ | OCH₃ | N | |
| H | CH₃ | H | N(CH₃)CH=CH₂ | OCH₃ | Cl | CH | |
| H | CH₃ | H | N(CH₃)CH=CH₂ | CH₃ | CH₃ | CH | |
| CH₃ | CH₃ | H | N(CH₃)CH=CH₂ | CH₃ | OCH₃ | CH | |
| H | CH₃ | H | N(CH₃)CH=CH₂ | OCH₃ | OCH₃ | CH | |
| H | CH₃ | H | N(CH₂CH₃)₂ | CH₃ | CH₃ | N | |
| H | CH₃ | H | N(CH₂CH₃)₂ | CH₃ | OCH₃ | N | |
| H | CH₃ | H | N(CH₂CH₃)₂ | OCH₃ | OCH₃ | N | |
| H | CH₃ | H | N(CH₂CH₃)₂ | OCH₃ | Cl | CH | |
| H | CH₃ | H | OH | CH₃ | CH₃ | CH | |
| H | CH₃ | H | OH | CH₃ | OCH₃ | CH | |
| H | CH₃ | H | OH | OCH₃ | OCH₃ | CH | |
| H | CH₃ | H | OH | CH₃ | CH₃ | N | |
| H | CH₃ | H | OH | CH₃ | OCH₃ | N | |
| H | CH₃ | H | OH | OCH₃ | OCH₃ | N | |
| H | CH₃ | H | OH | OCH₃ | Cl | CH | |
| H | CH₃ | H | CN | CH₃ | CH₃ | CH | |
| H | CH₃ | H | CN | CH₃ | OCH₃ | CH | |
| H | CH₃ | H | CN | OCH₃ | OCH₃ | CH | |
| H | CH₃ | H | CN | CH₃ | CH₃ | N | |
| H | CH₃ | H | CN | CH₃ | OCH₃ | N | |
| H | CH₃ | H | CN | OCH₃ | OCH₃ | N | |
| H | CH₃ | H | CN | OCH₃ | Cl | CH | |
| H | CH₃ | H | P(O)(CH₃)₂ | CH₃ | CH₃ | CH | |
| H | CH₃ | H | P(O)(CH₃)₂ | CH₃ | OCH₃ | CH | |
| H | CH₃ | H | P(O)(CH₃)₂ | OCH₃ | OCH₃ | CH | |
| H | CH₃ | H | P(O)(CH₃)₂ | CH₃ | CH₃ | N | |
| H | CH₃ | H | P(O)(CH₃)₂ | OCH₃ | OCH₃ | N | |
| H | CH₃ | H | P(O)(OCH₃)₂ | OCH₃ | Cl | CH | |
| H | CH₃ | H | P(O)(OCH₃)₂ | CH₃ | CH₃ | CH | |
| H | CH₃ | H | P(O)(OCH₃)₂ | CH₃ | OCH₃ | CH | |
| H | CH₃ | H | P(O)(OCH₃)₂ | OCH₃ | OCH₃ | CH | |
| H | CH₃ | H | P(O)(OCH₃)SCH₃ | CH₃ | CH₃ | N | |
| H | CH₃ | H | P(O)(OCH₃)SCH₃ | CH₃ | OCH₃ | N | |
| H | CH₃ | H | P(O)(OCH₃)SCH₃ | OCH₃ | OCH₃ | N | |
| H | CH₃ | H | P(O)(OCH₃)SCH₃ | OCH₃ | Cl | CH | |
| H | CH₃ | H | P(O)(OCH₃)SCH₂CH₂CH₃ | CH₃ | CH₃ | CH | |
| H | CH₃ | H | P(O)(OCH₃)SCH₂CH₂CH₃ | CH₃ | OCH₃ | CH | |
| H | CH₃ | H | P(O)(OCH₃)SCH₂CH₂CH₃ | OCH₃ | OCH₃ | CH | |
| H | CH₃ | H | P(O)(OCH₃)SCH₂CH₂CH₃ | CH₃ | CH₃ | N | |
| H | CH₃ | H | P(O)(OCH₃)SCH₂CH₂CH₃ | CH₃ | OCH₃ | N | |
| H | CH₃ | CH₃ | OH | OCH₃ | OCH₃ | N | |
| H | CH₃ | H | P(S)(CH₃)₂ | OCH₃ | Cl | CH | |
| H | CH₃ | H | P(S)(CH₃)₂ | CH₃ | CH₃ | CH | |
| H | CH₃ | H | P(S)(CH₃)₂ | CH₃ | OCH₃ | CH | |
| H | CH₃ | H | P(S)(CH₃)₂ | OCH₃ | OCH₃ | CH | |
| H | CH₃ | H | P(S)(CH₃)₂ | CH₃ | CH₃ | N | |
| H | CH₃ | H | P(S)(CH₃)₂ | CH₃ | OCH₃ | N | |
| H | CH₃ | H | P(S)(CH₃)₂ | OCH₃ | OCH₃ | N | |
| H | CH₃ | H | P(S)(OCH₃)₂ | OCH₃ | Cl | CH | |
| H | CH₃ | H | P(S)(OCH₃)₂ | CH₃ | CH₃ | CH | |
| CH₃ | CH₃ | H | P(S)(OCH₃)₂ | CH₃ | OCH₃ | CH | |
| H | CH₃ | H | P(S)(OCH₃)₂ | OCH₃ | OCH₃ | CH | |
| H | CH₃ | H | P(S)(OCH₃)₂ | CH₃ | CH₃ | N | |
| H | CH₃ | H | P(S)(OCH₃)₂ | CH₃ | OCH₃ | N | |
| H | CH₃ | H | P(S)(OCH₃)SCH₃ | OCH₃ | OCH₃ | N | |
| H | CH₃ | H | P(S)(OCH₃)SCH₃ | OCH₃ | Cl | CH | |
| H | CH₃ | H | NO₂ | CH₃ | CH₃ | CH | |
| H | CH₃ | H | NO₂ | CH₃ | OCH₃ | CH | |
| H | CH₃ | H | NO₂ | OCH₃ | OCH₃ | CH | |
| H | CH₃ | H | NO₂ | CH₃ | CH₃ | N | |
| H | CH₃ | H | NO₂ | CH₃ | OCH₃ | N | |
| H | CH₃ | H | NO₂ | OCH₃ | OCH₃ | N | |
| H | CH₃ | H | CH₂C(O)CH₂CH₃ | CH₃ | CH₃ | N | |
| H | CH₃ | H | CH₂C(O)CH₂CH₃ | OCH₃ | OCH₃ | N | |
| H | CH₃ | H | CH₂C(O)CH₂CH₃ | OCH₃ | Cl | CH | |
| H | CH₃ | H | CH₂C(O)CH₂CH₃ | CH₃ | CH₃ | CH | |
| H | CH₃ | H | CH₂C(O)CH₂CH₃ | CH₃ | OCH₃ | CH | |
| H | CH₃ | H | CH₂C(O)CH₂CH₃ | OCH₃ | OCH₃ | CH | |

TABLE II-continued

General Structure II

| R | R₁ | R₂ | R₃ | X | Y | Z | m.p. (°C.) |
|---|---|---|---|---|---|---|---|
| H | CH₃ | H | CH₂C(O)CH(CH₂)(CH₂) (ring) | CH₃ | CH₃ | N | |
| H | CH₃ | H | CH₂C(O)CH(CH₂)(CH₂) (ring) | CH₃ | OCH₃ | N | |
| H | CH₃ | H | CH₂C(O)CH(CH₂)(CH₂) (ring) | OCH₃ | OCH₃ | N | |
| H | CH₃ | H | CH₂C(O)CH(CH₂)(CH₂) (ring) | OCH₃ | Cl | CH | |
| H | CH₃ | H | CH₂C(O)CH(CH₂)(CH₂) (ring) | CH₃ | CH₃ | CH | |
| H | CH₃ | H | CH₂C(O)CH(CH₂)(CH₂) (ring) | CH₃ | OCH₃ | CH | |
| H | CH₃ | H | CH₂C(O)Ph | OCH₃ | OCH₃ | CH | |
| H | CH₃ | H | CH₂C(O)Ph | CH₃ | CH₃ | N | |
| H | CH₃ | H | CH₂C(O)Ph | CH₃ | OCH₃ | N | |
| H | CH₃ | CH₃ | CH₂C(O)Ph | OCH₃ | OCH₃ | N | |
| H | CH₃ | H | CH₂C(O)Ph | OCH₃ | Cl | CH | |
| H | CH₃ | H | CH₂C(O)Ph | CH₃ | CH₃ | CH | |
| H | CH₃ | H | CH₂C(O)Ph | CH₃ | OCH₃ | CH | |
| H | CH₃ | H | CH(CH₃)₃C(O)CH₃ | OCH₃ | OCH₃ | CH | |
| H | CH₃ | H | CH(CH₃)₃C(O)CH₃ | CH₃ | CH₃ | N | |
| H | CH₃ | H | CH(CH₃)₃C(O)CH₃ | CH₃ | OCH₃ | N | |
| H | CH₃ | H | CH(CH₃)₃C(O)CH₃ | OCH₃ | OCH₃ | N | |
| H | CH₃ | H | CH₂CF₂—C(O)CH₃ | OCH₃ | Cl | CH | |
| H | CH₃ | H | CH₂CF₂—C(O)CH₃ | CH₃ | CH₃ | CH | |
| CH₃ | CH₃ | H | CH₂CF₂—C(O)CH₃ | CH₃ | OCH₃ | CH | |
| H | CH₃ | H | CH₂CF₂—C(O)CH₃ | OCH₃ | OCH₃ | CH | |
| H | CH₃ | H | CH₂C(O)CH₂OCH₃ | CH₃ | CH₃ | N | |
| H | CH₃ | H | CH₂C(O)CH₂OCH₃ | CH₃ | OCH₃ | N | |
| H | CH₃ | H | CH₂C(O)CH₂OCH₃ | OCH₃ | OCH₃ | N | |
| H | CH₃ | H | CH₂C(O)CH₂OCH₃ | OCH₃ | Cl | CH | |
| H | CH₃ | H | CH₂CO₂CH₃ | CH₃ | CH₃ | CH | |
| H | CH₃ | H | CH₂CO₂CH₃ | CH₃ | OCH₃ | CH | |
| H | CH₃ | H | CH₂CO₂CH₃ | OCH₃ | OCH₃ | CH | |
| H | CH₃ | H | CH₂CO₂CH₃ | CH₃ | CH₃ | N | |
| H | CH₃ | H | CH₂CO₂CH₃ | CH₃ | OCH₃ | N | |
| H | CH₃ | H | CH₂CO₂CH₃ | OCH₃ | OCH₃ | N | |
| H | CH₃ | H | CH₂CO₂CH₃ | OCH₃ | Cl | CH | |
| H | CH₃ | H | CH₂CO₂CH₂CH₃ | CH₃ | CH₃ | CH | |
| H | CH₃ | H | CH₂CO₂CH₂CH₃ | CH₃ | OCH₃ | CH | |
| H | CH₃ | H | CH₂CO₂CH₂CH₃ | OCH₃ | OCH₃ | CH | |
| H | CH₃ | H | CH₂CO₂CH₂CH₃ | CH₃ | CH₃ | N | |
| H | CH₃ | H | CH₂CO₂CH₂CH₃ | CH₃ | OCH₃ | N | |
| H | CH₃ | H | CH₂CO₂CH₂CH₃ | OCH₃ | OCH₃ | N | |
| H | CH₃ | H | CH₂CO₂CH₂CH₃ | OCH₃ | Cl | CH | |
| H | CH₃ | H | CH₂CO₂CH₂CH₃ | CH₃ | CH₃ | CH | |
| H | CH₃ | H | CH₂CH₂CO₂CH₃ | CH₃ | OCH₃ | CH | |
| H | CH₃ | H | CH₂CH₂CO₂CH₃ | OCH₃ | OCH₃ | CH | |
| H | CH₃ | H | CH₂CH₂CO₂CH₃ | CH₃ | CH₃ | N | |
| H | CH₃ | H | CH₂CH₂CO₂CH₃ | OCH₃ | OCH₃ | N | |
| H | CH₃ | H | CH₂CH₂CO₂CH₃ | OCH₃ | Cl | CH | |
| H | CH₃ | H | CH₂—CO₂CH₂CH=CH₂ | CH₃ | CH₃ | CH | |
| H | CH₃ | H | CH₂—CO₂CH₂CH=CH₂ | CH₃ | OCH₃ | CH | |
| H | CH₃ | H | CH₂—CO₂CH₂CH=CH₂ | OCH₃ | OCH₃ | CH | |
| H | CH₃ | H | CH₂—CO₂CH₂CH=CH₂ | CH₃ | CH₃ | N | |
| H | CH₃ | H | CH₂—CO₂CH₂CH=CH₂ | CH₃ | OCH₃ | N | |
| H | CH₃ | H | CH₂—CO₂CH₂CH=CH₂ | OCH₃ | OCH₃ | N | |
| H | CH₃ | H | CH₂—CO₂CH₂CH=CH₂ | OCH₃ | Cl | CH | |
| H | CH₃ | H | CH₂(CH₂)₄CO₂CH₃ | CH₃ | CH₃ | CH | |
| H | CH₃ | H | CH₂(CH₂)₄CO₂CH₃ | CH₃ | OCH₃ | CH | |
| H | CH₃ | H | CH₂(CH₂)₄CO₂CH₃ | OCH₃ | OCH₃ | CH | |
| H | CH₃ | H | CH₂(CH₂)₄CO₂CH₃ | CH₃ | CH₃ | N | |

TABLE II-continued

General Structure II

| R | R₁ | R₂ | R₃ | X | Y | Z | m.p. (°C.) |
|---|----|----|----|----|----|----|------------|
| H | CH₃ | H | CH₂(CH₂)₄CO₂CH₃ | CH₃ | OCH₃ | N | |
| H | CH₃ | CH₃ | CH₂(CH₂)₄CO₂CH₃ | OCH₃ | OCH₃ | N | |
| H | CH₃ | H | CH₂(CH₂)₄CO₂CH₃ | OCH₃ | Cl | CH | |
| H | CH₃ | H | CH₂CO₂CH₂C≡CH | CH₃ | CH₃ | CH | |
| H | CH₃ | H | CH₂CO₂CH₂C≡CH | CH₃ | OCH₃ | CH | |
| H | CH₃ | H | CH₂CO₂CH₂C≡CH | OCH₃ | OCH₃ | CH | |
| H | CH₃ | H | CH₂CO₂CH₂C≡CH | CH₃ | CH₃ | N | |
| H | CH₃ | H | CH₂CO₂CH₂C≡CH | CH₃ | OCH₃ | N | |
| H | CH₃ | H | CH₂CO₂CH₂C≡CH | OCH₃ | OCH₃ | N | |
| H | CH₃ | H | CH₂CO₂CH₂C≡CH | OCH₃ | Cl | CH | |
| H | CH₃ | H | CH₂CO₂CF₃ | CH₃ | CH₃ | CH | |
| CH₃ | CH₃ | H | CH₂CO₂CF₃ | CH₃ | OCH₃ | CH | |
| H | CH₃ | H | CH₂CO₂CF₃ | OCH₃ | OCH₃ | CH | |
| H | CH₃ | H | CH₂CO₂CF₃ | CH₃ | CH₃ | N | |
| H | CH₃ | H | CH₂CO₂CF₃ | CH₃ | OCH₃ | N | |
| H | CH₃ | H | CH₂CO₂CF₃ | OCH₃ | OCH₃ | N | |
| H | CH₃ | H | CH₂CO₂CF₃ | OCH₃ | Cl | CH | |
| H | CH₃ | H | CH₂C(O)N(CH₃)₂ | CH₃ | CH₃ | CH | |
| H | CH₃ | H | CH₂C(O)N(CH₃)₂ | CH₃ | OCH₃ | CH | |
| H | CH₃ | H | CH₂C(O)N(CH₃)₂ | OCH₃ | OCH₃ | CH | |
| H | CH₃ | H | CH₂C(O)N(CH₃)₂ | CH₃ | CH₃ | N | |
| H | CH₃ | H | CH₂C(O)N(CH₃)₂ | CH₃ | OCH₃ | N | |
| H | CH₃ | H | CH₂C(O)N(CH₃)₂ | OCH₃ | OCH₃ | N | |
| H | CH₃ | H | CH₂C(O)N(CH₃)₂ | OCH₃ | Cl | CH | |
| H | CH₃ | H | SeCH₃ | CH₃ | CH₃ | CH | |
| H | CH₃ | H | SeCH₃ | CH₃ | OCH₃ | CH | |
| H | CH₃ | H | SeCH₃ | OCH₃ | OCH₃ | CH | |
| H | CH₃ | H | SeCH₃ | CH₃ | CH₃ | N | |
| H | CH₃ | H | SeCH₃ | CH₃ | OCH₃ | N | |
| H | CH₃ | H | SeCH₃ | OCH₃ | OCH₃ | N | |
| H | CH₃ | H | SeCH₃ | OCH₃ | Cl | CH | |
| H | CH₃ | H | CH₂Ph | CH₃ | CH₃ | CH | |
| H | CH₃ | H | CH₂Ph | CH₃ | OCH₃ | CH | |
| H | CH₃ | H | CH₂Ph | OCH₃ | OCH₃ | CH | |
| H | CH₃ | H | CH₂Ph | CH₃ | CH₃ | N | |
| H | CH₃ | H | CH₂Ph | CH₃ | OCH₃ | N | |
| H | CH₃ | H | CH₂Ph | OCH₃ | OCH₃ | N | |
| H | CH₃ | H | CH₂Ph | OCH₃ | Cl | CH | |
| H | CH₃ | H | CH₂—(1,3-dioxolan-2-yl) | CH₃ | CH₃ | CH | |
| H | CH₃ | H | CH₂—(1,3-dioxolan-2-yl) | CH₃ | OCH₃ | CH | |
| H | CH₃ | H | CH₂—(1,3-dioxolan-2-yl) | OCH₃ | OCH₃ | CH | |
| H | CH₃ | H | CH₂—(1,3-dioxolan-2-yl) | CH₃ | CH₃ | N | |
| H | CH₃ | H | CH₂—(1,3-dioxolan-2-yl) | CH₃ | OCH₃ | N | |
| H | CH₃ | H | CH₂—(1,3-dioxolan-2-yl) | OCH₃ | OCH₃ | N | |
| H | CH₃ | H | CH₂—OTHP | OCH₃ | Cl | CH | |
| H | CH₃ | H | CH₂—OTHP | CH₃ | CH₃ | CH | |
| H | CH₃ | H | CH₂—OTHP | CH₃ | OCH₃ | CH | |
| H | CH₃ | H | CH₂—OTHP | OCH₃ | OCH₃ | CH | |
| H | CH₃ | H | CH₂—OTHP | CH₃ | CH₃ | N | |
| H | CH₃ | H | CH₂—OTHP | CH₃ | OCH₃ | N | |
| H | CH₃ | CH₃ | CH₂—OTHP | OCH₃ | OCH₃ | N | |
| H | CH₃ | H | Si(CH₃)₃ | CH₃ | CH₃ | CH | |
| H | CH₃ | H | Si(CH₃)₃ | CH₃ | OCH₃ | CH | |
| H | CH₃ | H | Si(CH₃)₃ | OCH₃ | OCH₃ | CH | |
| H | CH₃ | H | Si(CH₃)₃ | CH₃ | CH₃ | N | |
| H | CH₃ | H | Si(CH₃)₃ | CH₃ | OCH₃ | N | |
| H | CH₃ | H | Si(CH₃)₃ | OCH₃ | OCH₃ | N | |
| H | CH₃ | H | Si(CH₃)₃ | OCH₃ | Cl | CH | |
| H | CH₃ | H | Si(CH₃)₂Ph | CH₃ | CH₃ | CH | |
| H | CH₃ | H | Si(CH₃)₂Ph | CH₃ | OCH₃ | CH | |
| H | CH₃ | H | Si(CH₃)₂Ph | OCH₃ | OCH₃ | CH | |
| H | CH₃ | H | Si(CH₃)₂Ph | CH₃ | CH₃ | N | |
| H | CH₃ | H | Si(CH₃)₂Ph | CH₃ | OCH₃ | N | |
| H | CH₃ | H | Si(CH₃)₂Ph | OCH₃ | OCH₃ | N | |
| H | CH₃ | H | Si(CH₃)₂Ph | OCH₃ | Cl | CH | |
| H | CH₃ | H | Si(CH₃)₂CH₂CH₃ | CH₃ | CH₃ | CH | |
| H | CH₃ | H | Si(CH₃)₂CH₂CH₃ | CH₃ | OCH₃ | CH | |
| H | CH₃ | H | Si(CH₃)₂CH₂CH₃ | OCH₃ | OCH₃ | CH | |
| H | CH₃ | H | Si(CH₃)₂CH₂CH₃ | CH₃ | CH₃ | N | |
| H | CH₃ | H | Si(CH₃)₂CH₂CH₃ | OCH₃ | OCH₃ | N | |
| H | CH₃ | H | Si(CH₃)₂CH₂CH₃ | OCH₃ | Cl | CH | |
| H | CH₃ | H | A-HET | CH₃ | CH₃ | CH | |
| H | CH₃ | H | A-HET | CH₃ | OCH₃ | CH | |
| H | CH₃ | H | A-HET | OCH₃ | OCH₃ | CH | |
| H | CH₃ | H | A-HET | CH₃ | CH₃ | N | |
| H | CH₃ | H | A-HET | CH₃ | OCH₃ | N | |
| H | CH₃ | H | A-HET | OCH₃ | OCH₃ | N | |
| H | CH₃ | H | A-HET | OCH₃ | Cl | CH | |
| H | CH₃ | H | B-HET | CH₃ | CH₃ | CH | |
| H | CH₃ | H | B-HET | CH₃ | OCH₃ | CH | |
| H | CH₃ | H | B-HET | OCH₃ | OCH₃ | CH | |

TABLE II-continued

General Structure II

| R | R₁ | R₂ | R₃ | X | Y | Z | m.p. (°C.) |
|---|-----|-----|-----|---|---|---|---|
| H | CH₃ | H | B-HET | CH₃ | CH₃ | N | |
| H | CH₃ | H | B-HET | CH₃ | OCH₃ | N | |
| H | CH₃ | CH₃ | B-HET | OCH₃ | OCH₃ | N | |
| H | CH₃ | H | B-HET | OCH₃ | Cl | CH | |
| H | CH₃ | H | C-HET | CH₃ | CH₃ | CH | |
| H | CH₃ | H | C-HET | CH₃ | OCH₃ | CH | |
| H | CH₃ | H | C-HET | OCH₃ | OCH₃ | CH | |
| H | CH₃ | H | C-HET | CH₃ | CH₃ | N | |
| H | CH₃ | H | C-HET | CH₃ | OCH₃ | N | |
| H | CH₃ | H | C-HET | OCH₃ | OCH₃ | N | |
| H | CH₃ | H | C-HET | OCH₃ | Cl | CH | |
| H | CH₃ | H | D-HET | CH₃ | CH₃ | CH | |
| CH₃ | CH₃ | H | D-HET | CH₃ | OCH₃ | CH | |
| H | CH₃ | H | D-HET | OCH₃ | OCH₃ | CH | |
| H | CH₃ | H | D-HET | CH₃ | CH₃ | N | |
| H | CH₃ | H | D-HET | CH₃ | OCH₃ | N | |
| H | CH₃ | H | D-HET | OCH₃ | OCH₃ | N | |
| H | CH₃ | H | D-HET | OCH₃ | Cl | CH | |
| H | CH₃ | H | C(O)A-HET | CH₃ | CH₃ | CH | |
| H | CH₃ | H | C(O)A-HET | CH₃ | OCH₃ | CH | |
| H | CH₃ | H | C(O)A-HET | OCH₃ | OCH₃ | CH | |
| H | CH₃ | H | C(O)A-HET | CH₃ | CH₃ | N | |
| H | CH₃ | H | C(O)A-HET | CH₃ | OCH₃ | N | |
| H | CH₃ | H | C(O)A-HET | OCH₃ | OCH₃ | N | |
| H | CH₃ | H | C(O)A-HET | OCH₃ | Cl | CH | |
| H | CH₃ | H | C(O)B-HET | CH₃ | CH₃ | CH | |
| H | CH₃ | H | C(O)B-HET | CH₃ | OCH₃ | CH | |
| H | CH₃ | H | C(O)B-HET | OCH₃ | OCH₃ | CH | |
| H | CH₃ | H | C(O)B-HET | CH₃ | CH₃ | N | |
| H | CH₃ | H | C(O)B-HET | CH₃ | OCH₃ | N | |
| H | CH₃ | H | C(O)B-HET | OCH₃ | OCH₃ | N | |
| H | CH₃ | H | C(O)B-HET | OCH₃ | Cl | CH | |
| H | CH₃ | H | C(O)C-HET | CH₃ | CH₃ | CH | |
| H | CH₃ | H | C(O)C-HET | CH₃ | OCH₃ | CH | |
| H | CH₃ | H | C(O)C-HET | OCH₃ | OCH₃ | CH | |
| H | CH₃ | H | C(O)C-HET | CH₃ | CH₃ | N | |
| H | CH₃ | H | C(O)C-HET | OCH₃ | OCH₃ | N | |
| H | CH₃ | H | C(O)C-HET | OCH₃ | Cl | CH | |
| H | CH₃ | H | C(O)D-HET | CH₃ | CH₃ | CH | |
| H | CH₃ | H | C(O)D-HET | CH₃ | OCH₃ | CH | |
| H | CH₃ | H | C(O)D-HET | OCH₃ | OCH₃ | CH | |
| H | CH₃ | H | C(O)D-HET | CH₃ | CH₃ | N | |
| H | CH₃ | H | C(O)D-HET | CH₃ | OCH₃ | N | |
| H | CH₃ | H | C(O)D-HET | OCH₃ | OCH₃ | N | |
| H | CH₃ | H | C(O)D-HET | OCH₃ | Cl | CH | | wherein

A-HET is 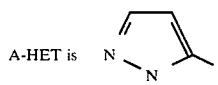

B-HET is 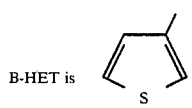

C-HET is 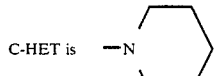

D-HET is 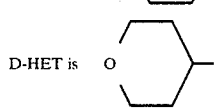

TABLE IIa

General Structure IIa

| R | R₁ | R₂ | R₃ | X | Y | Z | m.p. (°C.) |
|---|-----|-----|-----|---|---|---|---|
| H | CH₃ | H | CH₂F | CH₃ | CH₃ | CH | |
| H | CH₃ | H | CH₂F | CH₃ | OCH₃ | CH | |
| H | CH₃ | H | CH₂F | OCH₃ | OCH₃ | CH | |
| H | CH₃ | H | CH₂F | CH₃ | CH₃ | N | |
| H | CH₃ | H | CH₂F | CH₃ | OCH₃ | N | |
| H | CH₃ | H | CH₂F | OCH₃ | OCH₃ | N | |
| H | CH₃ | H | CH₂F | OCH₃ | Cl | CH | |
| H | CH₃ | H | CH₂CH₂F | CH₃ | CH₃ | CH | |

TABLE IIa-continued

General Structure IIa

| R | R$_1$ | R$_2$ | R$_3$ | X | Y | Z | m.p. (°C.) |
|---|---|---|---|---|---|---|---|
| H | CH$_3$ | H | CH$_2$CH$_2$F | CH$_3$ | OCH$_3$ | CH | |
| H | CH$_3$ | H | CH$_2$CH$_2$F | OCH$_3$ | OCH$_3$ | CH | |
| H | CH$_3$ | H | CH$_2$CH$_2$F | CH$_3$ | CH$_3$ | N | |
| H | CH$_3$ | H | CH$_2$CH$_2$F | CH$_3$ | OCH$_3$ | N | |
| H | CH$_3$ | H | CH$_2$CH$_2$F | OCH$_3$ | OCH$_3$ | N | |
| H | CH$_3$ | H | CH$_2$CH$_2$F | OCH$_3$ | Cl | CH | |
| H | CH$_3$ | H | CHFCH$_2$F | CH$_3$ | CH$_3$ | CH | |
| H | CH$_3$ | H | CHFCH$_2$F | CH$_3$ | OCH$_3$ | CH | |
| H | CH$_3$ | H | CHFCH$_2$F | OCH$_3$ | OCH$_3$ | CH | |
| H | CH$_3$ | H | CHFCH$_2$F | CH$_3$ | CH$_3$ | N | |
| H | CH$_3$ | H | CHFCH$_2$F | OCH$_3$ | OCH$_3$ | N | |
| H | CH$_3$ | H | CHFCH$_2$F | OCH$_3$ | Cl | CH | |
| H | CH$_3$ | H | CH$_2$CHF$_2$ | CH$_3$ | CH$_3$ | CH | |
| H | CH$_3$ | H | CH$_2$CHF$_2$ | CH$_3$ | OCH$_3$ | CH | |
| H | CH$_3$ | H | CH$_2$CHF$_2$ | OCH$_3$ | OCH$_3$ | CH | |
| H | CH$_3$ | H | CH$_2$CHF$_2$ | CH$_3$ | CH$_3$ | N | |
| H | CH$_3$ | H | CH$_2$CHF$_2$ | CH$_3$ | OCH$_3$ | N | |
| H | CH$_3$ | H | CH$_2$CHF$_2$ | OCH$_3$ | OCH$_3$ | N | |
| H | CH$_3$ | H | CH$_2$CHF$_2$ | OCH$_3$ | Cl | CH | |
| H | CH$_3$ | H | CH(CH$_2$F)$_2$ | CH$_3$ | CH$_3$ | CH | |
| H | CH$_3$ | H | CH(CH$_2$F)$_2$ | CH$_3$ | OCH$_3$ | CH | |
| H | CH$_3$ | H | CH(CH$_2$F)$_2$ | OCH$_3$ | OCH$_3$ | CH | |
| H | CH$_3$ | H | CH$_2$CH$_2$CH$_2$F | CH$_3$ | CH$_3$ | N | |
| H | CH$_3$ | H | CH$_2$CH$_2$CH$_2$F | CH$_3$ | OCH$_3$ | N | |
| H | CH$_3$ | CH$_3$ | CH$_2$CH$_2$CH$_2$F | OCH$_3$ | OCH$_3$ | N | |
| H | CH$_3$ | H | CH$_2$CH$_2$CH$_2$F | OCH$_3$ | Cl | CH | |
| H | CH$_3$ | H | CH$_2$CH$_2$CH$_2$F | CH$_3$ | CH$_3$ | CH | |
| H | CH$_3$ | H | CH$_2$CH$_2$CH$_2$F | CH$_3$ | OCH$_3$ | CH | |
| H | CH$_3$ | H | CH$_2$CH$_2$CH$_2$F | OCH$_3$ | OCH$_3$ | CH | |
| H | CH$_3$ | H | CH$_2$(CH$_2$)$_2$CH$_2$F | CH$_3$ | CH$_3$ | N | |
| H | CH$_3$ | H | CH$_2$(CH$_2$)$_2$CH$_2$F | CH$_3$ | OCH$_3$ | N | |
| H | CH$_3$ | H | CH$_2$(CH$_2$)$_2$CH$_2$F | OCH$_3$ | OCH$_3$ | N | |
| H | CH$_3$ | H | CH$_2$(CH$_2$)$_2$CH$_2$F | OCH$_3$ | Cl | CH | |
| H | CH$_3$ | H | CH$_2$(CH$_2$)$_2$CH$_2$F | CH$_3$ | CH$_3$ | CH | |
| CH$_3$ | CH$_3$ | H | CH$_2$(CH$_2$)$_2$CH$_2$F | CH$_3$ | OCH$_3$ | CH | |
| H | CH$_3$ | H | CH$_2$(CH$_2$)$_2$CH$_2$F | OCH$_3$ | OCH$_3$ | CH | |
| H | CH$_3$ | H | CH(CH$_3$)CH$_2$F | CH$_3$ | CH$_3$ | N | |
| H | CH$_3$ | H | CH(CH$_3$)CH$_2$F | CH$_3$ | OCH$_3$ | N | |
| H | CH$_3$ | H | CH(CH$_3$)CH$_2$F | OCH$_3$ | OCH$_3$ | N | |
| H | CH$_3$ | H | CH(CH$_3$)CH$_2$F | OCH$_3$ | Cl | CH | |
| H | CH$_3$ | H | CH$_2$Br | CH$_3$ | CH$_3$ | CH | |
| H | CH$_3$ | H | CH$_2$Br | CH$_3$ | OCH$_3$ | CH | |
| H | CH$_3$ | H | CH$_2$Br | OCH$_3$ | OCH$_3$ | CH | |
| H | CH$_3$ | H | CH$_2$Br | CH$_3$ | CH$_3$ | N | |
| H | CH$_3$ | H | CH$_2$Br | CH$_3$ | OCH$_3$ | N | |
| H | CH$_3$ | H | CH$_2$Br | OCH$_3$ | OCH$_3$ | N | |
| H | CH$_3$ | H | CH$_2$Br | OCH$_3$ | Cl | CH | |
| H | CH$_3$ | H | CH$_2$CH$_2$Br | CH$_3$ | CH$_3$ | CH | |
| H | CH$_3$ | H | CH$_2$CH$_2$Br | CH$_3$ | OCH$_3$ | CH | |
| H | CH$_3$ | H | CH$_2$CH$_2$Br | OCH$_3$ | OCH$_3$ | CH | |
| H | CH$_3$ | H | CH$_2$CH$_2$Br | CH$_3$ | CH$_3$ | N | |
| H | CH$_3$ | H | CH$_2$CH$_2$Br | CH$_3$ | OCH$_3$ | N | |
| H | CH$_3$ | H | CH$_2$CH$_2$Br | OCH$_3$ | OCH$_3$ | N | |
| H | CH$_3$ | H | CH$_2$CH$_2$Br | OCH$_3$ | Cl | CH | |
| H | CH$_3$ | H | CHBrCH$_3$ | CH$_3$ | CH$_3$ | CH | |
| H | CH$_3$ | H | CHBrCH$_3$ | CH$_3$ | OCH$_3$ | CH | |
| H | CH$_3$ | H | CHBrCH$_3$ | OCH$_3$ | OCH$_3$ | CH | |
| H | CH$_3$ | H | CHBrCH$_3$ | CH$_3$ | CH$_3$ | N | |
| H | CH$_3$ | H | CHBrCH$_3$ | OCH$_3$ | OCH$_3$ | N | |
| H | CH$_3$ | H | CHBrCH$_3$ | OCH$_3$ | Cl | CH | |
| H | CH$_3$ | H | CH$_2$CHBr$_2$ | CH$_3$ | CH$_3$ | CH | |
| H | CH$_3$ | H | CH$_2$CHBr$_2$ | CH$_3$ | OCH$_3$ | CH | |
| H | CH$_3$ | H | CH$_2$CHBr$_2$ | OCH$_3$ | OCH$_3$ | CH | |
| H | CH$_3$ | H | CH$_2$CHBr$_2$ | CH$_3$ | CH$_3$ | N | |
| H | CH$_3$ | H | CH$_2$CHBr$_2$ | CH$_3$ | OCH$_3$ | N | |
| H | CH$_3$ | H | CH$_2$CHBr$_2$ | OCH$_3$ | OCH$_3$ | N | |
| H | CH$_3$ | H | CH$_2$CHBr$_2$ | OCH$_3$ | Cl | CH | |
| H | CH$_3$ | H | CH(CH$_2$Br)$_2$ | CH$_3$ | CH$_3$ | CH | |
| H | CH$_3$ | H | CH(CH$_2$Br)$_2$ | CH$_3$ | OCH$_3$ | CH | |
| H | CH$_3$ | H | CH(CH$_2$Br)$_2$ | OCH$_3$ | OCH$_3$ | CH | |
| H | CH$_3$ | H | CH$_2$CHBrCH$_3$ | CH$_3$ | CH$_3$ | N | |
| H | CH$_3$ | H | CH$_2$CHBrCH$_3$ | CH$_3$ | OCH$_3$ | N | |
| H | CH$_3$ | CH$_3$ | CH$_2$CHBrCH$_3$ | OCH$_3$ | OCH$_3$ | N | |
| H | CH$_3$ | H | CH$_2$CHBrCH$_3$ | OCH$_3$ | Cl | CH | |
| H | CH$_3$ | H | CH$_2$CHBrCH$_3$ | CH$_3$ | CH$_3$ | CH | |
| H | CH$_3$ | H | CH$_2$CHBrCH$_3$ | CH$_3$ | OCH$_3$ | CH | |
| H | CH$_3$ | H | CH$_2$(CH$_2$)$_2$CH$_2$Br | OCH$_3$ | OCH$_3$ | CH | |
| H | CH$_3$ | H | CH$_2$(CH$_2$)$_2$CH$_2$Br | CH$_3$ | CH$_3$ | N | |
| H | CH$_3$ | H | CH$_2$(CH$_2$)$_2$CH$_2$Br | CH$_3$ | OCH$_3$ | N | |
| H | CH$_3$ | H | CH$_2$(CH$_2$)$_2$CH$_2$Br | OCH$_3$ | OCH$_3$ | N | |

TABLE IIa-continued

General Structure IIa

| R | R₁ | R₂ | R₃ | X | Y | Z | m.p. (°C.) |
|---|---|---|---|---|---|---|---|
| H | CH₃ | H | CH₂(CH₂)₂CH₂Br | OCH₃ | Cl | CH | |
| H | CH₃ | H | CH₂(CH₂)₂CH₂Br | CH₃ | CH₃ | CH | |
| CH₃ | CH₃ | H | CH₂(CH₂)₂CH₂Br | CH₃ | OCH₃ | CH | |
| H | CH₃ | H | C(CH₃)(CH₂Br)CH₃ | OCH₃ | OCH₃ | CH | |
| H | CH₃ | H | CH₂CHBrCH₂CH₃ | CH₃ | CH₃ | N | |
| H | CH₃ | H | CH₂CHBrCH₂CH₃ | CH₃ | OCH₃ | N | |
| H | CH₃ | H | CH₂CHBrCH₂CH₃ | OCH₃ | OCH₃ | N | |
| H | CH₃ | H | CH₂CHBrCH₂CH₃ | OCH₃ | Cl | CH | |
| H | CH₃ | H | CH₂Cl | CH₃ | CH₃ | CH | |
| H | CH₃ | H | CH₂Cl | CH₃ | OCH₃ | CH | |
| H | CH₃ | H | CH₂Cl | OCH₃ | OCH₃ | CH | |
| H | CH₃ | H | CH₂Cl | CH₃ | CH₃ | N | |
| H | CH₃ | H | CH₂Cl | CH₃ | OCH₃ | N | |
| H | CH₃ | H | CH₂Cl | OCH₃ | OCH₃ | N | |
| H | CH₃ | H | CH₂Cl | OCH₃ | Cl | CH | |
| H | CH₃ | H | CH₂CH₂Cl | CH₃ | CH₃ | CH | |
| H | CH₃ | H | CH₂CH₂Cl | CH₃ | OCH₃ | CH | |
| H | CH₃ | H | CH₂CH₂Cl | OCH₃ | OCH₃ | CH | |
| H | CH₃ | H | CH₂CH₂Cl | CH₃ | CH₃ | N | |
| H | CH₃ | H | CH₂CH₂Cl | CH₃ | OCH₃ | N | |
| H | CH₃ | H | CH₂CH₂Cl | OCH₃ | OCH₃ | N | |
| H | CH₃ | H | CH₂CH₂Cl | OCH₃ | Cl | CH | |
| H | CH₃ | H | CHClCH₂Cl | CH₃ | CH₃ | CH | |
| H | CH₃ | H | CHClCH₂Cl | CH₃ | OCH₃ | CH | |
| H | CH₃ | H | CHClCH₂Cl | OCH₃ | OCH₃ | CH | |
| H | CH₃ | H | CHClCH₂Cl | CH₃ | CH₃ | N | |
| H | CH₃ | H | CHClCH₂Cl | OCH₃ | OCH₃ | N | |
| H | CH₃ | H | CHClCH₂Cl | OCH₃ | Cl | CH | |
| H | CH₃ | H | CH₂CCl₂CH₃ | CH₃ | CH₃ | CH | |
| H | CH₃ | H | CH₂CCl₂CH₃ | CH₃ | OCH₃ | CH | |
| H | CH₃ | H | CH₂CCl₂CH₃ | OCH₃ | OCH₃ | CH | |
| H | CH₃ | H | CH(CH₂Cl)₂ | CH₃ | CH₃ | N | |
| H | CH₃ | H | CH(CH₂Cl)₂ | CH₃ | OCH₃ | N | |
| H | CH₃ | H | CH(CH₂Cl)₂ | OCH₃ | OCH₃ | N | |
| H | CH₃ | H | CH(CH₂Cl)₂ | OCH₃ | Cl | CH | |
| H | CH₃ | H | CH(CH₂Cl)₂ | CH₃ | CH₃ | CH | |
| H | CH₃ | H | CH₂CH₂CH₂Cl | CH₃ | OCH₃ | CH | |
| H | CH₃ | H | CH₂CH₂CH₂Cl | OCH₃ | OCH₃ | CH | |
| H | CH₃ | H | CH₂CH₂CH₂Cl | CH₃ | CH₃ | N | |
| H | CH₃ | H | CH₂CH₂CH₂Cl | CH₃ | OCH₃ | N | |
| H | CH₃ | CH₃ | CH₂CH₂CH₂Cl | OCH₃ | OCH₃ | N | |
| H | CH₃ | H | CH₂CH₂CH₂Cl | OCH₃ | Cl | CH | |
| H | CH₃ | H | CH₂CH₂CH₂Cl | CH₃ | CH₃ | CH | |
| H | CH₃ | H | CH₂(CH₂)₂CH₂Cl | CH₃ | OCH₃ | CH | |
| H | CH₃ | H | CH₂(CH₂)₂CH₂Cl | OCH₃ | OCH₃ | CH | |
| H | CH₃ | H | CH₂(CH₂)₂CH₂Cl | CH₃ | CH₃ | N | |
| H | CH₃ | H | CH₂(CH₂)₂CH₂Cl | CH₃ | OCH₃ | N | |
| H | CH₃ | H | CH₂(CH₂)₂CH₂Cl | OCH₃ | OCH₃ | N | |
| H | CH₃ | H | CH₂(CH₂)₂CH₂Cl | OCH₃ | Cl | CH | |
| H | CH₃ | H | CH₂(CH₂)₂CH₂Cl | CH₃ | CH₃ | CH | |
| CH₃ | CH₃ | H | CH(CH₃)CH₂Cl | CH₃ | OCH₃ | CH | |
| H | CH₃ | H | CH(CH₃)CH₂Cl | OCH₃ | OCH₃ | CH | |
| H | CH₃ | H | CH(CH₃)CH₂Cl | CH₃ | CH₃ | N | |
| H | CH₃ | H | CHClCHClCH₃ | CH₃ | OCH₃ | N | |
| H | CH₃ | H | CHClCHClCH₃ | OCH₃ | OCH₃ | N | |
| H | CH₃ | H | CHClCHClCH₃ | OCH₃ | Cl | CH | |
| H | CH₃ | H | CH₂I | CH₃ | CH₃ | CH | |
| H | CH₃ | H | CH₂I | CH₃ | OCH₃ | CH | |
| H | CH₃ | H | CH₂I | OCH₃ | OCH₃ | CH | |
| H | CH₃ | H | CH₂I | CH₃ | CH₃ | N | |
| H | CH₃ | H | CH₂I | CH₃ | OCH₃ | N | |
| H | CH₃ | H | CH₂I | OCH₃ | OCH₃ | N | |
| H | CH₃ | H | CH₂I | OCH₃ | Cl | CH | |
| H | CH₃ | H | CH₂CF₃ | CH₃ | CH₃ | CH | |
| H | CH₃ | H | CH₂CF₃ | CH₃ | OCH₃ | CH | |
| H | CH₃ | H | CH₂CF₃ | OCH₃ | OCH₃ | CH | |
| H | CH₃ | H | CH₂CF₃ | CH₃ | CH₃ | N | |
| H | CH₃ | H | CH₂CF₃ | CH₃ | OCH₃ | N | |
| H | CH₃ | H | CH₂CF₃ | OCH₃ | OCH₃ | N | |
| H | CH₃ | H | CH₂CF₃ | OCH₃ | Cl | CH | |
| H | CH₃ | H | CH₂CH₂CF₃ | CH₃ | CH₃ | CH | |
| H | CH₃ | H | CH₂CH₂CF₃ | CH₃ | OCH₃ | CH | |
| H | CH₃ | H | CH₂CH₂CF₃ | OCH₃ | OCH₃ | CH | |
| H | CH₃ | H | CH₂CH₂CF₃ | CH₃ | CH₃ | N | |
| H | CH₃ | H | CH₂CH₂CF₃ | OCH₃ | OCH₃ | N | |
| H | CH₃ | H | CH₂CH₂CF₃ | OCH₃ | Cl | CH | |
| H | CH₃ | H | CH₂(CH₂)₂CF₃ | CH₃ | CH₃ | CH | |
| H | CH₃ | H | CH₂(CH₂)₂CF₃ | CH₃ | OCH₃ | CH | |
| H | CH₃ | H | CH₂(CH₂)₂CF₃ | OCH₃ | OCH₃ | CH | |
| H | CH₃ | H | CH₂(CH₂)₂CF₃ | CH₃ | CH₃ | N | |

TABLE IIa-continued

General Structure IIa

| R | $R_1$ | $R_2$ | $R_3$ | X | Y | Z | m.p. (°C.) |
|---|---|---|---|---|---|---|---|
| H | $CH_3$ | H | $CH_2(CH_2)_2CF_3$ | $CH_3$ | $OCH_3$ | N | |
| H | $CH_3$ | H | $CH_2(CH_2)_2CF_3$ | $OCH_3$ | $OCH_3$ | N | |
| H | $CH_3$ | H | $CH_2(CH_2)_3CF_3$ | $OCH_3$ | Cl | CH | |
| H | $CH_3$ | H | $CH_2(CH_2)_3CF_3$ | $CH_3$ | $CH_3$ | CH | |
| H | $CH_3$ | H | $CH_2(CH_2)_3CF_3$ | $CH_3$ | $OCH_3$ | CH | |
| H | $CH_3$ | H | $CH_2(CH_2)_3CF_3$ | $OCH_3$ | $OCH_3$ | CH | |
| H | $CH_3$ | H | $CH_2(CH_2)_3CF_3$ | $CH_3$ | $CH_3$ | N | |
| H | $CH_3$ | H | $CH_2(CH_2)_3CF_3$ | $CH_3$ | $OCH_3$ | N | |
| H | $CH_3$ | $CH_3$ | $CH_2(CH_2)_3CF_3$ | $OCH_3$ | $OCH_3$ | N | |
| H | $CH_3$ | H | $CH(CF_3)_2$ | $OCH_3$ | Cl | CH | |
| H | $CH_3$ | H | $CH(CF_3)_2$ | $CH_3$ | $CH_3$ | CH | |
| H | $CH_3$ | H | $CH(CF_3)_2$ | $CH_3$ | $OCH_3$ | CH | |
| H | $CH_3$ | H | $CH(CF_3)_2$ | $OCH_3$ | $OCH_3$ | CH | |
| H | $CH_3$ | H | $CH(CF_3)_2$ | $CH_3$ | $CH_3$ | N | |
| H | $CH_3$ | H | $CH(CF_3)_2$ | $CH_3$ | $OCH_3$ | N | |
| H | $CH_3$ | H | $CH(CF_3)_2$ | $OCH_3$ | $OCH_3$ | N | |
| H | $CH_3$ | H | $CH_2(CH_2)_4CF_3$ | $OCH_3$ | Cl | CH | |
| H | $CH_3$ | H | $CH_2(CH_2)_5CF_3$ | $CH_3$ | $CH_3$ | CH | |
| $CH_3$ | $CH_3$ | H | $CH_2(CH_2)_6CF_3$ | $CH_3$ | $OCH_3$ | CH | |
| H | $CH_3$ | H | $CH_2(CH_2)_7CF_3$ | $OCH_3$ | $OCH_3$ | CH | |
| H | $CH_3$ | H | $CH_2(CH_2)_8CF_3$ | $CH_3$ | $CH_3$ | N | |
| H | $CH_3$ | H | $CHF(CH_2)_8CF_3$ | $CH_3$ | $OCH_3$ | N | |
| H | $CH_3$ | H | $CH(CHF)_8CF_3$ | $OCH_3$ | $OCH_3$ | N | |
| H | $CH_3$ | H | $CH(CHF)_8CF_3$ | $OCH_3$ | Cl | CH | |
| H | $CH_3$ | H | $CH_2OCH_3$ | $CH_3$ | $CH_3$ | CH | |
| H | $CH_3$ | H | $CH_2OCH_3$ | $CH_3$ | $OCH_3$ | CH | |
| H | $CH_3$ | H | $CH_2OCH_3$ | $OCH_3$ | $OCH_3$ | CH | |
| H | $CH_3$ | H | $CH_2OCH_3$ | $CH_3$ | $CH_3$ | N | |
| H | $CH_3$ | H | $CH_2OCH_3$ | $CH_3$ | $OCH_3$ | N | |
| H | $CH_3$ | H | $CH_2OCH_3$ | $OCH_3$ | $OCH_3$ | N | |
| H | $CH_3$ | H | $CH_2OCH_3$ | $OCH_3$ | Cl | CH | |
| H | $CH_3$ | H | $CH_2OCH_2CH_3$ | $CH_3$ | $CH_3$ | CH | |
| H | $CH_3$ | H | $CH_2OCH_2CH_3$ | $CH_3$ | $OCH_3$ | CH | |
| H | $CH_3$ | H | $CH_2OCH_2CH_3$ | $OCH_3$ | $OCH_3$ | CH | |
| H | $CH_3$ | H | $CH_2-OCH_2F$ | $CH_3$ | $CH_3$ | N | |
| H | $CH_3$ | H | $CH_2-OCH_2F$ | $CH_3$ | $OCH_3$ | N | |
| H | $CH_3$ | H | $CH_2-OCH_2F$ | $OCH_3$ | $OCH_3$ | N | |
| H | $CH_3$ | H | $CH_2-OCH_2F$ | $OCH_3$ | Cl | CH | |
| H | $CH_3$ | H | $CH_2-CH_2OCH_3$ | $CH_3$ | $CH_3$ | CH | |
| H | $CH_3$ | H | $CH_2-CH_2OCH_3$ | $CH_3$ | $OCH_3$ | CH | |
| H | $CH_3$ | H | $CH_2-CH_2OCH_3$ | $OCH_3$ | $OCH_3$ | CH | |
| H | $CH_3$ | H | $CH_2-CH_2OCH_3$ | $CH_3$ | $CH_3$ | N | |
| H | $CH_3$ | H | $CH(OCH_3)_2$ | $OCH_3$ | $OCH_3$ | N | |
| H | $CH_3$ | H | $CH(OCH_3)_2$ | $OCH_3$ | Cl | CH | |
| H | $CH_3$ | H | $CH_2(CH_2)_2OCH_3$ | $CH_3$ | $CH_3$ | CH | |
| H | $CH_3$ | H | $CH_2(CH_2)_2OCH_3$ | $CH_3$ | $OCH_3$ | CH | |
| H | $CH_3$ | H | $CH_2(CH_2)_2OCH_3$ | $OCH_3$ | $OCH_3$ | CH | |
| H | $CH_3$ | H | $CH_2(CH_2)_2OCH_3$ | $CH_3$ | $CH_3$ | N | |
| H | $CH_3$ | H | $CH_2(CH_2)_2OCH_3$ | $CH_3$ | $OCH_3$ | N | |
| H | $CH_3$ | H | $CH_2(CH_2)_3OCH_3$ | $OCH_3$ | $OCH_3$ | N | |
| H | $CH_3$ | H | $CH_2(CH_2)_3OCH_3$ | $OCH_3$ | Cl | CH | |
| H | $CH_3$ | H | $CH_2(CH_2)_3OCH_3$ | $CH_3$ | $CH_3$ | CH | |
| H | $CH_3$ | H | $CH_2(CH_2)_3OCH_3$ | $CH_3$ | $OCH_3$ | CH | |
| H | $CH_3$ | H | $CH_2(CH_2)_3OCH_3$ | $OCH_3$ | $OCH_3$ | CH | |
| H | $CH_3$ | H | $CH(OCH_3)CH_3$ | $CH_3$ | $CH_3$ | N | |
| H | $CH_3$ | H | $CH(OCH_3)CH_3$ | $CH_3$ | $OCH_3$ | N | |
| H | $CH_3$ | $CH_3$ | $CH(OCH_3)CH_3$ | $OCH_3$ | $OCH_3$ | N | |
| H | $CH_3$ | H | $CH_2OCH_2C=CH_2$ | $OCH_3$ | Cl | CH | |
| H | $CH_3$ | H | $CH_2OCH_2C=CH_2$ | $CH_3$ | $CH_3$ | CH | |
| H | $CH_3$ | H | $CH_2OCH_2C=CH_2$ | $CH_3$ | $OCH_3$ | CH | |
| H | $CH_3$ | H | $CH_2OCH_2C=CH_2$ | $OCH_3$ | $OCH_3$ | CH | |
| H | $CH_3$ | H | $CH_2OCH_2C=CH_2$ | $CH_3$ | $CH_3$ | N | |
| H | $CH_3$ | H | $CH_2OCH_2C=CH_2$ | $CH_3$ | $OCH_3$ | N | |
| H | $CH_3$ | H | $CH_2CH(OCH_3)_2$ | $OCH_3$ | $OCH_3$ | N | |
| H | $CH_3$ | H | $CH_2CH(OCH_3)_2$ | $OCH_3$ | Cl | CH | |
| H | $CH_3$ | H | $CH_2CH(OCH_3)_2$ | $CH_3$ | $CH_3$ | CH | |
| $CH_3$ | $CH_3$ | H | $CH_2CH(OCH_3)_2$ | $CH_3$ | $OCH_3$ | CH | |
| H | $CH_3$ | H | $CH_2C(OCH_3)_2CH_3$ | $OCH_3$ | $OCH_3$ | CH | |
| H | $CH_3$ | H | $CH_2C(OCH_3)_2CH_3$ | $CH_3$ | $CH_3$ | N | |
| H | $CH_3$ | H | $CH_2C(OCH_3)_2CH_3$ | $CH_3$ | $OCH_3$ | N | |
| H | $CH_3$ | H | $CH_2(CH_2)_6OCH_3$ | $OCH_3$ | $OCH_3$ | N | |
| H | $CH_3$ | H | $CH_2(CH_2)_6OCH_3$ | $OCH_3$ | Cl | CH | |
| H | $CH_3$ | H | $CH_2OC(O)CH_3$ | $CH_3$ | $CH_3$ | CH | |
| H | $CH_3$ | H | $CH_2OC(O)CH_3$ | $CH_3$ | $OCH_3$ | CH | |
| H | $CH_3$ | H | $CH_2OC(O)CH_3$ | $OCH_3$ | $OCH_3$ | CH | |
| H | $CH_3$ | H | $CH_2OC(O)CH_3$ | $CH_3$ | $CH_3$ | N | |
| H | $CH_3$ | H | $CH_2OC(O)CH_3$ | $CH_3$ | $OCH_3$ | N | |
| H | $CH_3$ | H | $CH_2OC(O)CH_3$ | $OCH_3$ | $OCH_3$ | N | |
| H | $CH_3$ | H | $CH_2OC(O)CH_3$ | $OCH_3$ | Cl | CH | |
| H | $CH_3$ | H | $CH_2CH_2OC(O)CH_3$ | $CH_3$ | $CH_3$ | CH | |

TABLE IIa-continued

General Structure IIa

| R | R$_1$ | R$_2$ | R$_3$ | X | Y | Z | m.p. (°C.) |
|---|---|---|---|---|---|---|---|
| H | CH$_3$ | H | CH$_2$CH$_2$OC(O)CH$_3$ | CH$_3$ | OCH$_3$ | CH | |
| H | CH$_3$ | H | CH$_2$CH$_2$OC(O)CH$_3$ | OCH$_3$ | OCH$_3$ | CH | |
| H | CH$_3$ | H | CH$_2$CH$_2$OC(O)CH$_3$ | CH$_3$ | CH$_3$ | N | |
| H | CH$_3$ | H | CH$_2$CH$_2$OC(O)CH$_3$ | CH$_3$ | OCH$_3$ | N | |
| H | CH$_3$ | H | CH$_2$CH$_2$OC(O)CH$_3$ | OCH$_3$ | OCH$_3$ | N | |
| H | CH$_3$ | H | CH$_2$CH$_2$OC(O)CH$_3$ | OCH$_3$ | Cl | CH | |
| H | CH$_3$ | H | CH$_2$(CH$_2$)$_2$OC(O)CH$_3$ | CH$_3$ | CH$_3$ | CH | |
| H | CH$_3$ | H | CH$_2$(CH$_2$)$_2$OC(O)CH$_3$ | CH$_3$ | OCH$_3$ | CH | |
| H | CH$_3$ | H | CH$_2$(CH$_2$)$_2$OC(O)CH$_3$ | OCH$_3$ | OCH$_3$ | CH | |
| H | CH$_3$ | H | CH$_2$(CH$_2$)$_3$OC(O)CH$_3$ | CH$_3$ | CH$_3$ | N | |
| H | CH$_3$ | H | CH$_2$(CH$_2$)$_3$OC(O)CH$_3$ | OCH$_3$ | OCH$_3$ | N | |
| H | CH$_3$ | H | CH$_2$(CH$_2$)$_3$OC(O)CH$_3$ | OCH$_3$ | Cl | CH | |
| H | CH$_3$ | H | CH$_2$(CH$_2$)$_3$OC(O)CH$_3$ | CH$_3$ | CH$_3$ | CH | |
| H | CH$_3$ | H | CH$_2$P(CH$_3$)(Br)(CH$_3$) | CH$_3$ | OCH$_3$ | CH | |
| H | CH$_3$ | H | CH$_2$P(C$_6$H$_5$)$_3$ | OCH$_3$ | OCH$_3$ | CH | |
| H | CH$_3$ | H | CH$_2$OC(O)N(CH$_3$)$_2$ | CH$_3$ | CH$_3$ | N | |
| H | CH$_3$ | H | CH$_2$OC(O)N(CH$_3$)$_2$ | CH$_3$ | OCH$_3$ | N | |
| H | CH$_3$ | H | CH$_2$OC(O)N(CH$_3$)$_2$ | OCH$_3$ | OCH$_3$ | N | |
| H | CH$_3$ | H | CH$_2$OC(O)N(CH$_3$)$_2$ | OCH$_3$ | Cl | CH | |
| H | CH$_3$ | H | CH$_2$OC(O)N(CH$_3$)$_2$ | CH$_3$ | CH$_3$ | CH | |
| H | CH$_3$ | H | CH$_2$OC(O)N(CH$_3$)$_2$ | CH$_3$ | OCH$_3$ | CH | |
| H | CH$_3$ | H | CH$_2$OC(O)N(CH$_3$)$_2$ | OCH$_3$ | OCH$_3$ | CH | |
| H | CH$_3$ | H | CH$_2$CH$_2$OC(O)N(CH$_3$)$_2$ | CH$_3$ | CH$_3$ | N | |
| H | CH$_3$ | H | CH$_2$CH$_2$OC(O)N(CH$_3$)$_2$ | CH$_3$ | OCH$_3$ | N | |
| H | CH$_3$ | CH$_3$ | CH$_2$CH$_2$OC(O)N(CH$_3$)$_2$ | OCH$_3$ | OCH$_3$ | N | |
| H | CH$_3$ | H | CH$_2$CH$_2$OC(O)N(CH$_3$)$_2$ | OCH$_3$ | Cl | CH | |
| H | CH$_3$ | H | CH$_2$CH$_2$OC(O)N(CH$_3$)$_2$ | CH$_3$ | CH$_3$ | CH | |
| H | CH$_3$ | H | CH$_2$CH$_2$OC(O)N(CH$_3$)$_2$ | CH$_3$ | OCH$_3$ | CH | |
| H | CH$_3$ | H | CH$_2$OSO$_2$CH$_3$ | OCH$_3$ | OCH$_3$ | CH | |
| H | CH$_3$ | H | CH$_2$OSO$_2$CH$_3$ | CH$_3$ | CH$_3$ | N | |
| H | CH$_3$ | H | CH$_2$OSO$_2$CH$_3$ | CH$_3$ | OCH$_3$ | N | |
| H | CH$_3$ | H | CH$_2$OSO$_2$CH$_3$ | OCH$_3$ | OCH$_3$ | N | |
| H | CH$_3$ | H | CH$_2$OSO$_2$CH$_2$CH$_3$ | OCH$_3$ | Cl | CH | |
| H | CH$_3$ | H | CH$_2$OSO$_2$CH$_2$CH$_3$ | CH$_3$ | CH$_3$ | CH | |
| CH$_3$ | CH$_3$ | H | CH$_2$OSO$_2$CH$_2$CH$_3$ | CH$_3$ | OCH$_3$ | CH | |
| H | CH$_3$ | H | CH$_2$(CH$_2$)$_2$OSO$_2$CH$_3$ | OCH$_3$ | OCH$_3$ | CH | |
| H | CH$_3$ | H | CH$_2$(CH$_2$)$_2$OSO$_2$CH$_3$ | CH$_3$ | CH$_3$ | N | |
| H | CH$_3$ | H | CH$_2$(CH$_2$)$_2$OSO$_2$CH$_3$ | CH$_3$ | OCH$_3$ | N | |
| H | CH$_3$ | H | CH$_2$(CH$_2$)$_2$OSO$_2$CH$_3$ | OCH$_3$ | OCH$_3$ | N | |
| H | CH$_3$ | H | CH$_2$(CH$_2$)$_2$OSO$_2$CH$_3$ | OCH$_3$ | Cl | CH | |
| H | CH$_3$ | H | CH$_2$OP(O)(CH$_3$)$_2$ | CH$_3$ | CH$_3$ | CH | |
| H | CH$_3$ | H | CH$_2$OP(O)(CH$_3$)$_2$ | CH$_3$ | OCH$_3$ | CH | |
| H | CH$_3$ | H | CH$_2$OP(O)(CH$_3$)$_2$ | OCH$_3$ | OCH$_3$ | CH | |
| H | CH$_3$ | H | CH$_2$OP(O)(CH$_3$)$_2$ | CH$_3$ | CH$_3$ | N | |
| H | CH$_3$ | H | CH$_2$OP(O)(CH$_3$)$_2$ | CH$_3$ | OCH$_3$ | N | |
| H | CH$_3$ | H | CH$_2$OP(O)(CH$_3$)$_2$ | OCH$_3$ | OCH$_3$ | N | |
| H | CH$_3$ | H | CH$_2$OP(O)(CH$_3$)$_2$ | OCH$_3$ | Cl | CH | |
| H | CH$_3$ | H | CH$_2$OP(O)(CH$_3$)Ph | CH$_3$ | CH$_3$ | CH | |
| H | CH$_3$ | H | CH$_2$OP(O)(CH$_3$)Ph | CH$_3$ | OCH$_3$ | CH | |
| H | CH$_3$ | H | CH$_2$OP(O)(CH$_3$)Ph | OCH$_3$ | OCH$_3$ | CH | |
| H | CH$_3$ | H | CH$_2$OP(O)(CH$_3$)Ph | CH$_3$ | CH$_3$ | N | |
| H | CH$_3$ | H | CH$_2$OP(O)(Ph)$_2$ | CH$_3$ | OCH$_3$ | N | |
| H | CH$_3$ | H | CH$_2$OP(O)(Ph)$_2$ | OCH$_3$ | OCH$_3$ | N | |
| H | CH$_3$ | H | CH$_2$OP(O)(Ph)$_2$ | OCH$_3$ | Cl | CH | |
| H | CH$_3$ | H | CH$_2$OP(O)(Ph)$_2$ | CH$_3$ | CH$_3$ | CH | |
| H | CH$_3$ | H | CH$_2$OP(O)(Ph)$_2$ | CH$_3$ | OCH$_3$ | CH | |
| H | CH$_3$ | H | CH$_2$OP(O)(Ph)$_2$ | OCH$_3$ | OCH$_3$ | CH | |
| H | CH$_3$ | H | CH$_2$CH$_2$OP(O)(CH$_3$)$_2$ | CH$_3$ | CH$_3$ | N | |
| H | CH$_3$ | H | CH$_2$CH$_2$OP(O)(CH$_2$)$_2$ | OCH$_3$ | OCH$_3$ | N | |
| H | CH$_3$ | H | CH$_2$CH$_2$OP(O)(CH$_3$)$_2$ | OCH$_3$ | Cl | CH | |
| H | CH$_3$ | H | CH$_2$CH$_2$OP(O)(CH$_3$)$_2$ | CH$_3$ | CH$_3$ | CH | |
| H | CH$_3$ | H | CH$_2$CH$_2$OP(O)(CH$_3$)$_2$ | CH$_3$ | OCH$_3$ | CH | |
| H | CH$_3$ | H | CH$_2$(CH$_2$)$_2$OP(O)(CH$_3$)$_2$ | OCH$_3$ | OCH$_3$ | CH | |
| H | CH$_3$ | H | CH$_2$(CH$_2$)$_2$OP(O)(CH$_3$)$_2$ | CH$_3$ | CH$_3$ | N | |
| H | CH$_3$ | H | CH$_2$(CH$_2$)$_2$OP(O)(CH$_3$)$_2$ | CH$_3$ | OCH$_3$ | N | |
| H | CH$_3$ | H | CH$_2$(CH$_2$)$_2$OP(O)(CH$_3$)$_2$ | OCH$_3$ | OCH$_3$ | N | |
| H | CH$_3$ | H | CH$_2$(CH$_2$)$_2$OP(O)(CH$_3$)$_2$ | OCH$_3$ | Cl | CH | |
| H | CH$_3$ | H | CH$_2$(CH$_2$)$_2$OP(O)(CH$_3$)$_2$ | CH$_3$ | CH$_3$ | CH | |
| H | CH$_3$ | H | CH$_2$P(O)(CH$_3$)$_2$ | CH$_3$ | OCH$_3$ | CH | |
| H | CH$_3$ | H | CH$_2$P(O)(CH$_3$)$_2$ | OCH$_3$ | OCH$_3$ | CH | |
| H | CH$_3$ | H | CH$_2$P(O)(CH$_3$)$_2$ | CH$_3$ | CH$_3$ | N | |
| H | CH$_3$ | H | CH$_2$P(O)(CH$_3$)$_2$ | CH$_3$ | OCH$_3$ | N | |
| H | CH$_3$ | CH$_3$ | CH$_2$P(O)(CH$_3$)$_2$ | OCH$_3$ | OCH$_3$ | N | |
| H | CH$_3$ | H | CH$_2$P(O)(CH$_3$)$_2$ | OCH$_3$ | Cl | CH | |
| H | CH$_3$ | H | CH$_2$P(O)(CH$_3$)$_2$ | CH$_3$ | CH$_3$ | CH | |
| H | CH$_3$ | H | CH$_2$P(O)(OCH$_3$)$_2$ | CH$_3$ | OCH$_3$ | CH | |
| H | CH$_3$ | H | CH$_2$P(O)(OCH$_3$)$_2$ | OCH$_3$ | OCH$_3$ | CH | |
| H | CH$_3$ | H | CH$_2$P(O)(OCH$_3$)$_2$ | CH$_3$ | CH$_3$ | N | |
| H | CH$_3$ | H | CH$_2$P(O)(OCH$_3$)$_2$ | CH$_3$ | OCH$_3$ | N | |
| H | CH$_3$ | H | CH$_2$P(O)(OCH$_3$)$_2$ | OCH$_3$ | OCH$_3$ | N | |

TABLE IIa-continued

General Structure IIa

| R | R₁ | R₂ | R₃ | X | Y | Z | m.p. (°C.) |
|---|---|---|---|---|---|---|---|
| H | CH₃ | H | CH₂P(O)(OCH₃)₂ | OCH₃ | Cl | CH | |
| H | CH₃ | H | CH₂P(O)(OCH₃)₂ | CH₃ | CH₃ | CH | |
| CH₃ | CH₃ | H | CH₂CH₂P(O)(OCH₂CH₃)₂ | CH₃ | OCH₃ | CH | |
| H | CH₃ | H | CH₂CH₂P(O)(OCH₃CH₃)₂ | OCH₃ | OCH₃ | CH | |
| H | CH₃ | H | CH₂(CH₂)₃P(O)(OCH₃)₂ | CH₃ | CH₃ | N | |
| H | CH₃ | H | CH₂(CH₂)₃P(O)(OCH₃)₂ | CH₃ | OCH₃ | N | |
| H | CH₃ | H | CH₂(CH₂)₃P(O)(OCH₃)₂ | OCH₃ | OCH₃ | N | |
| H | CH₃ | H | CH₂(CH₂)₃P(O)(OCH₃)₂ | OCH₃ | Cl | CH | |
| H | CH₃ | H | CH₂OP(S)(CH₃)₂ | CH₃ | CH₃ | CH | |
| H | CH₃ | H | CH₂OP(S)(CH₃)₂ | CH₃ | OCH₃ | CH | |
| H | CH₃ | H | CH₂OP(S)(CH₃)₂ | OCH₃ | OCH₃ | CH | |
| H | CH₃ | H | CH₂OP(S)(CH₃)₂ | CH₃ | CH₃ | N | |
| H | CH₃ | H | CH₂OP(S)(CH₃)₂ | CH₃ | OCH₃ | N | |
| H | CH₃ | H | CH₂OP(S)(CH₃)₂ | OCH₃ | OCH₃ | N | |
| H | CH₃ | H | CH₂OP(S)(CH₃)₂ | OCH₃ | Cl | CH | |
| H | CH₃ | H | CH₂OP(S)(OCH₃)₂ | CH₃ | CH₃ | CH | |
| H | CH₃ | H | CH₂OP(S)(OCH₃)₂ | CH₃ | OCH₃ | CH | |
| H | CH₃ | H | CH₂OP(S)OCH₃)₂ | OCH₃ | OCH₃ | CH | |
| H | CH₃ | H | CH₂OP(S)(OCH₃)₂ | CH₃ | CH₃ | N | |
| H | CH₃ | H | CH₂OP(S)(OCH₃)₂ | CH₃ | OCH₃ | N | |
| H | CH₃ | H | CH₂OP(S)(OCH₃)₂ | OCH₃ | OCH₃ | N | |
| H | CH₃ | H | CH₂OP(S)(OCH₃)₂ | OCH₃ | Cl | CH | |
| H | CH₃ | H | CH₂P(S)(CH₃)₂ | CH₃ | CH₃ | CH | |
| H | CH₃ | H | CH₂P(S)(CH₃)₂ | CH₃ | OCH₃ | CH | |
| H | CH₃ | H | CH₂P(S)(CH₃)₂ | OCH₃ | OCH₃ | CH | |
| H | CH₃ | H | CH₂P(S)(CH₃)₂ | CH₃ | CH₃ | N | |
| H | CH₃ | H | CH₂P(S)(CH₃)₂ | OCH₃ | OCH₃ | N | |
| H | CH₃ | H | CH₂P(S)(CH₃)₂ | OCH₃ | Cl | CH | |
| H | CH₃ | H | CH₂P(S)(OCH₃)₂ | CH₃ | CH₃ | CH | |
| H | CH₃ | H | CH₂P(S)(OCH₃)₂ | CH₃ | OCH₃ | CH | |
| H | CH₃ | H | CH₂P(S)(OCH₃)₂ | OCH₃ | OCH₃ | CH | |
| H | CH₃ | H | CH₂P(S)(OCH₃)₂ | CH₃ | CH₃ | N | |
| H | CH₃ | H | CH₂P(S)(OCH₃)₂ | CH₃ | OCH₃ | N | |
| H | CH₃ | H | CH₂P(S)(OCH₃)₂ | OCH₃ | OCH₃ | N | |
| H | CH₃ | H | CH₂P(S)(OCH₃)₂ | OCH₃ | Cl | CH | |
| H | CH₃ | H | CH₂CH₂OP(S)(CH₃)₂ | CH₃ | CH₃ | CH | |
| H | CH₃ | H | CH₂CH₂OP(S)(CH₃)₂ | CH₃ | OCH₃ | CH | |
| H | CH₃ | H | CH₂CH₂OP(S)(CH₃)₂ | OCH₃ | OCH₃ | CH | |
| H | CH₃ | H | CH₂CH₂OP(S)(CH₃)₂ | CH₃ | CH₃ | N | |
| H | CH₃ | H | CH₂CH₂OP(S)(CH₃)₂ | CH₃ | OCH₃ | N | |
| H | CH₃ | CH₃ | CH₂CH₂OP(S)(CH₃)₂ | OCH₃ | OCH₃ | N | |
| H | CH₃ | H | CH₂CH₂OP(S)(CH₃)₂ | OCH₃ | Cl | CH | |
| H | CH₃ | H | CH₂CH₂P(S)(OCH₃)₂ | CH₃ | CH₃ | CH | |
| H | CH₃ | H | CH₂CH₂P(S)(OCH₃)₂ | CH₃ | OCH₃ | CH | |
| H | CH₃ | H | CH₂CH₂P(S)(OCH₃)₂ | OCH₃ | OCH₃ | CH | |
| H | CH₃ | H | CH₂CH₂P(S)(OCH₃)₂ | CH₃ | CH₃ | N | |
| H | CH₃ | H | CH₂CH₂P(S)(OCH₃)₂ | CH₃ | OCH₃ | N | |
| H | CH₃ | H | CH₂CH₂P(S)(OCH₃)₂ | OCH₃ | OCH₃ | N | |
| H | CH₃ | H | CH₂CH₂P(S)(OCH₃)₂ | OCH₃ | Cl | CH | |
| H | CH₃ | H | CH₂(CH₂)₃OP(S)(CH₃)₂ | CH₃ | CH₃ | CH | |
| CH₃ | CH₃ | H | CH₂(CH₂)₃OP(S)(CH₃)₂ | CH₃ | OCH₃ | CH | |
| H | CH₃ | H | CH₂(CH₂)₃OP(S)(CH₃)₂ | OCH₃ | OCH₃ | CH | |
| H | CH₃ | H | CH₂(CH₂)₃OP(S)(CH₃)₂ | CH₃ | CH₃ | N | |
| H | CH₃ | H | CH₂(CH₂)₃OP(S)(CH₃)₂ | CH₃ | OCH₃ | N | |
| H | CH₃ | H | CH₂(CH₂)₃OP(S)(CH₃)₂ | OCH₃ | OCH₃ | N | |
| H | CH₃ | H | CH₂(CH₂)₃OP(S)(CH₃)₂ | OCH₃ | Cl | CH | |
| H | CH₃ | H | CH₂OSi(CH₃)₃ | CH₃ | CH₃ | CH | |
| H | CH₃ | H | CH₂OSi(CH₃)₃ | CH₃ | OCH₃ | CH | |
| H | CH₃ | H | CH₂OSi(CH₃)₃ | OCH₃ | OCH₃ | CH | |
| H | CH₃ | H | CH₂OSi(CH₃)₃ | CH₃ | CH₃ | N | |
| H | CH₃ | H | CH₂OSi(CH₃)₃ | CH₃ | OCH₃ | N | |
| H | CH₃ | H | CH₂OSi(CH₃)₃ | OCH₃ | OCH₃ | N | |
| H | CH₃ | H | CH₂OSi(CH₃)₃ | OCH₃ | Cl | CH | |
| H | CH₃ | H | CH₂CH₂OSi(CH₃)₃ | CH₃ | CH₃ | CH | |
| H | CH₃ | H | CH₂CH₂OSi(CH₃)₃ | CH₃ | OCH₃ | CH | |
| H | CH₃ | H | CH₂CH₂OSi(CH₃)₃ | OCH₃ | OCH₃ | CH | |
| H | CH₃ | H | CH₂CH₂OSi(CH₃)₃ | CH₃ | CH₃ | N | |
| H | CH₃ | H | CH₂CH₂OSi(CH₃)₃ | CH₃ | OCH₃ | N | |
| H | CH₃ | H | CH₂CH₂OSi(CH₃)₃ | OCH₃ | OCH₃ | N | |
| H | CH₃ | H | CH₂CH₂OSi(CH₃)₃ | OCH₃ | Cl | CH | |
| H | CH₃ | H | CH₂(CH₂)₂OSi(CH₃)₃ | CH₃ | CH₃ | CH | |
| H | CH₃ | H | CH₂(CH₂)₂OSi(CH₃)₃ | CH₃ | OCH₃ | CH | |
| H | CH₃ | H | CH₂(CH₂)₂OSi(CH₃)₃ | OCH₃ | OCH₃ | CH | |
| H | CH₃ | H | CH₂(CH₂)₂OSi(CH₃)₃ | CH₃ | CH₃ | N | |
| H | CH₃ | H | CH₂(CH₂)₂OSi(CH₃)₃ | OCH₃ | OCH₃ | N | |
| H | CH₃ | H | CH₂(CH₂)₂OSi(CH₃)₃ | OCH₃ | Cl | CH | |
| H | CH₃ | H | CH₂(CH₂)₃OSi(CH₃)₃ | CH₃ | CH₃ | CH | |
| H | CH₃ | H | CH₂(CH₂)₃OSi(CH₃)₃ | CH₃ | OCH₃ | CH | |
| H | CH₃ | H | CH₂(CH₂)₃OSi(CH₃)₃ | OCH₃ | OCH₃ | CH | |
| H | CH₃ | H | CH₂(CH₂)₃OSi(CH₃)₃ | CH₃ | CH₃ | N | |

TABLE IIa-continued

General Structure IIa

| R | R₁ | R₂ | R₃ | X | Y | Z | m.p. (°C.) |
|---|---|---|---|---|---|---|---|
| H | CH₃ | H | CH₂(CH₂)₃OSi(CH₃)₃ | CH₃ | OCH₃ | N | |
| H | CH₃ | H | CH₂(CH₂)₃OSi(CH₃)₃ | OCH₃ | OCH₃ | N | |
| H | CH₃ | H | CH₂(CH₂)₃OSi(CH₃)₃ | OCH₃ | Cl | CH | |
| H | CH₃ | H | CH₂(CH₂)₄OSi(CH₃)₃ | CH₃ | CH₃ | CH | |
| H | CH₃ | H | CH₂(CH₂)₅OSi(CH₃)₃ | CH₃ | OCH₃ | CH | |
| H | CH₃ | H | CH₂(CH₂)₆OSi(CH₃)₃ | OCH₃ | OCH₃ | CH | |
| H | CH₃ | H | CH₂(CH₂)₇OSi(CH₃)₃ | CH₃ | CH₃ | N | |
| H | CH₃ | H | CH₂OSi(CH₂CH₃)₃ | CH₃ | OCH₃ | N | |
| H | CH₃ | CH₃ | CH₂OSi(CH₃)₂(Ph) | OCH₃ | OCH₃ | N | |
| H | CH₃ | H | CH(CH₃)OSi(CH₃)₃ | OCH₃ | Cl | CH | |
| H | CH₃ | H | CH(CH₃)OSi(CH₃)₃ | CH₃ | CH₃ | CH | |
| H | CH₃ | H | CH(CH₃)OSi(CH₃)₃ | CH₃ | OCH₃ | CH | |
| H | CH₃ | H | CH(CH₃)OSi(CH₃)₃ | OCH₃ | OCH₃ | CH | |
| H | CH₃ | H | CH(CH₃)OSi(CH₃)₃ | CH₃ | CH₃ | N | |
| H | CH₃ | H | CH₂Si(CH₃)₃ | CH₃ | OCH₃ | N | |
| H | CH₃ | H | CH₂Si(CH₃)₃ | OCH₃ | OCH₃ | N | |
| H | CH₃ | H | CH₂Si(CH₃)₃ | OCH₃ | Cl | CH | |
| H | CH₃ | H | CH₂Si(CH₃)₃ | CH₃ | CH₃ | CH | |
| CH₃ | CH₃ | H | CH₂Si(CH₃)₃ | CH₃ | OCH₃ | CH | |
| H | CH₃ | H | CH₂Si(CH₃)₃ | OCH₃ | OCH₃ | CH | |
| H | CH₃ | H | CH₂Si(CH₃)₃ | CH₃ | CH₃ | N | |
| H | CH₃ | H | CH₂CH₂Si(CH₃)₃ | CH₃ | OCH₃ | N | |
| H | CH₃ | H | CH₂CH₂Si(CH₃)₃ | OCH₃ | OCH₃ | N | |
| H | CH₃ | H | CH₂CH₂Si(CH₃)₃ | OCH₃ | Cl | CH | |
| H | CH₃ | H | CH₂(CH₂)₂Si(CH₃)₃ | CH₃ | CH₃ | CH | |
| H | CH₃ | H | CH₂(CH₂)₂Si(CH₃)₃ | CH₃ | OCH₃ | CH | |
| H | CH₃ | H | CH₂(CH₂)₂Si(CH₃)₃ | OCH₃ | OCH₃ | CH | |
| H | CH₃ | H | CH₂(CH₂)₂Si(CH₃)₃ | CH₃ | CH₃ | N | |
| H | CH₃ | H | CH₂(CH₂)₂Si(CH₃)₃ | CH₃ | OCH₃ | N | |
| H | CH₃ | H | CH₂(CH₂)₂Si(CH₃)₃ | OCH₃ | OCH₃ | N | |
| H | CH₃ | H | CH₂(CH₂)₂Si(CH₃)₃ | OCH₃ | Cl | CH | |
| H | CH₃ | H | C(Si(CH₃)₃)(CH₃)₂ | CH₃ | CH₃ | CH | |
| H | CH₃ | H | C(Si(CH₃)₃)(CH₃)₂ | CH₃ | OCH₃ | CH | |
| H | CH₃ | H | C(Si(CH₃)₃)(CH₃)₂ | OCH₃ | OCH₃ | CN | |
| H | CH₃ | H | C(Si(CH₃)₃)(CH₃)₂ | CH₃ | CH₃ | N | |
| H | CH₃ | H | C(Si(CH₃)₃)(CH₃)₂ | CH₃ | OCH₃ | N | |
| H | CH₃ | H | C(Si(CH₃)₃)(CH₃)₂ | OCH₃ | OCH₃ | N | |
| H | CH₃ | H | C(Si(CH₃)₃)(CH₃)₂ | OCH₃ | Cl | CH | |
| H | CH₃ | H | CH₂SCH₃ | CH₃ | CH₃ | CH | |
| H | CH₃ | H | CH₃SCH₃ | CH₃ | OCH₃ | CH | |
| H | CH₃ | H | CH₂SCH₃ | OCH₃ | OCH₃ | CH | |
| H | CH₃ | H | CH₂SCH₃ | CH₃ | CH₃ | N | |
| H | CH₃ | H | CH₂SCH₃ | OCH₃ | OCH₃ | N | |
| H | CH₃ | H | CH₂SCH₃ | OCH₃ | Cl | CH | |
| H | CH₃ | H | CH₂SCH₂CH₃ | CH₃ | CH₃ | CH | |
| H | CH₃ | H | CH₂CH₂SCH₃ | CH₃ | CH₃ | CH | |
| H | CH₃ | H | CH₂CH₂SCH₃ | OCH₃ | OCH₃ | CH | |
| H | CH₃ | H | CH₂CH₂SCH₃ | CH₃ | CH₃ | N | |
| H | CH₃ | H | CH₂CH₂SCH₃ | OCH₃ | OCH₃ | N | |
| H | CH₃ | H | CH₂CH₂SCH₃ | OCH₃ | Cl | CH | |
| H | CH₃ | H | CH₂CH₂SCH₃ | CH₃ | CH₃ | CH | |
| H | CH₃ | H | CH₂(CH₂)₂SCH₃ | CH₃ | OCH₃ | CH | |
| H | CH₃ | H | CH₂(CH₂)₂SCH₃ | OCH₃ | OCH₃ | CH | |
| H | CH₃ | H | CH₂(CH₂)₂SCH₃ | CH₃ | CH₃ | N | |
| H | CH₃ | H | CH₂(CH₂)₂SCH₃ | CH₃ | OCH₃ | N | |
| H | CH₃ | CH₃ | CH₂(CH₂)₂SCH₃ | OCH₃ | OCH₃ | N | |
| H | CH₃ | H | CH₂(CH₂)₃SCH₃ | OCH₃ | Cl | CH | |
| H | CH₃ | H | CH₂(CH₂)₃SCH₃ | CH₃ | CH₃ | CH | |
| H | CH₃ | H | CH₂(CH₂)₃SCH₃ | CH₃ | OCH₃ | CH | |
| H | CH₃ | H | CH₂(CH₂)₃SCH₃ | OCH₃ | OCH₃ | CH | |
| H | CH₃ | H | CH₂(CH₂)₃SCH₃ | CH₃ | CH₃ | N | |
| H | CH₃ | H | CH₂(CH₂)₃SCH₃ | CH₃ | OCH₃ | N | |
| H | CH₃ | H | CH₂(CH₂)₃SCH₃ | OCH₃ | OCH₃ | N | |
| H | CH₃ | H | CH(CH₃)SCH₃ | OCH₃ | Cl | CH | |
| H | CH₃ | H | CH(CH₃)SCH₃ | CH₃ | CH₃ | CH | |
| CH₃ | CH₃ | H | CH(CH₃)SCH₃ | CH₃ | OCH₃ | CH | |
| H | CH₃ | H | CH(SCH₃)₂ | OCH₃ | OCH₃ | CH | |
| H | CH₃ | H | CH₂CH(CH₃)SCH₃ | CH₃ | CH₃ | N | |
| H | CH₃ | H | CH₂CH(CH₃)SCH₃ | CH₃ | OCH₃ | N | |
| H | CH₃ | H | CH₂(CH₂)₈SCH₃ | OCH₃ | OCH₃ | N | |
| H | CH₃ | H | CH₂(CH₂)₈SCH₃ | OCH₃ | Cl | CH | |
| H | CH₃ | H | CH₂SOCH₃ | CH₃ | CH₃ | CH | |
| H | CH₃ | H | CH₂SOCH₃ | CH₃ | OCH₃ | CH | |
| H | CH₃ | H | CH₂SOCH₃ | OCH₃ | OCH₃ | CH | |
| H | CH₃ | H | CH₂SOCH₃ | CH₃ | CH₃ | N | |
| H | CH₃ | H | CH₂SOCH₃ | CH₃ | OCH₃ | N | |
| H | CH₃ | H | CH₂SOCH₃ | OCH₃ | OCH₃ | N | |
| H | CH₃ | H | CH₂SOCH₃ | OCH₃ | Cl | CH | |
| H | CH₃ | H | CH₂CH₂SOCH₃ | CH₃ | CH₃ | CH | |

TABLE IIa-continued

General Structure IIa

| R | R₁ | R₂ | R₃ | X | Y | Z | m.p. (°C.) |
|---|---|---|---|---|---|---|---|
| H | CH₃ | H | CH₂CH₂SOCH₃ | CH₃ | OCH₃ | CH | |
| H | CH₃ | H | CH₂CH₂SOCH₃ | OCH₃ | OCH₃ | CH | |
| H | CH₃ | H | CH₂CH₂SOCH₃ | CH₃ | CH₃ | N | |
| H | CH₃ | H | CH₂CH₂SOCH₃ | CH₃ | OCH₃ | N | |
| H | CH₃ | H | CH₂CH₂SOCH₃ | OCH₃ | OCH₃ | N | |
| H | CH₃ | H | CH₂CH₂SOCH₃ | OCH₃ | Cl | CH | |
| H | CH₃ | H | CH₂(CH₂)₃SOCH₃ | CH₃ | CH₃ | CH | |
| H | CH₃ | H | CH₂(CH₂)₃SOCH₃ | CH₃ | OCH₃ | CH | |
| H | CH₃ | H | CH₂(CH₂)₃SOCH₃ | OCH₃ | OCH₃ | CH | |
| H | CH₃ | H | CH₂(CH₂)₃SOCH₃ | CH₃ | CH₃ | N | |
| H | CH₃ | H | CH₂(CH₂)₃SOCH₃ | OCH₃ | OCH₃ | N | |
| H | CH₃ | H | CH₂(CH₂)₃SOCH₃ | OCH₃ | Cl | CH | |
| H | CH₃ | H | CH₂SO₂CH₃ | CH₃ | CH₃ | CH | |
| H | CH₃ | H | CH₂SO₂CH₃ | CH₃ | OCH₃ | CH | |
| H | CH₃ | H | CH₂SO₂CH₃ | OCH₃ | OCH₃ | CH | |
| H | CH₃ | H | CH₂SO₂CH₃ | CH₃ | CH₃ | N | |
| H | CH₃ | H | CH₂SO₂CH₃ | CH₃ | OCH₃ | N | |
| H | CH₃ | H | CH₂SO₂CH₃ | OCH₃ | OCH₃ | N | |
| H | CH₃ | H | CH₂SO₂CH₃ | OCH₃ | Cl | CH | |
| H | CH₃ | H | CH₂CH₂SO₂CH₃ | CH₃ | CH₃ | CH | |
| H | CH₃ | H | CH₂CH₂SO₂CH₃ | CH₃ | OCH₃ | CH | |
| H | CH₃ | H | CH₂CH₂SO₂CH₃ | OCH₃ | OCH₃ | CH | |
| H | CH₃ | H | CH₂CH₂SO₂CH₃ | CH₃ | CH₃ | N | |
| H | CH₃ | H | CH₂CH₂SO₂CH₃ | CH₃ | OCH₃ | N | |
| H | CH₃ | CH₃ | CH₂CH₂SO₂CH₃ | OCH₃ | OCH₃ | N | |
| H | CH₃ | H | CH₂CH₂SO₂CH₃ | OCH₃ | Cl | CH | |
| H | CH₃ | H | CH₂(CH₂)₃SO₂CH₃ | CH₃ | CH₃ | CH | |
| H | CH₃ | H | CH₂(CH₂)₃SO₂CH₃ | CH₃ | OCH₃ | CH | |
| H | CH₃ | H | CH₂(CH₂)₃SO₂CH₃ | OCH₃ | OCH₃ | CH | |
| H | CH₃ | H | CH₂(CH₂)₃SO₂CH₃ | CH₃ | CH₃ | N | |
| H | CH₃ | H | CH₂(CH₂)₃SO₂CH₃ | CH₃ | OCH₃ | N | |
| H | CH₃ | CH₃ | CH₂(CH₂)₃SO₂CH₃ | OCH₃ | OCH₃ | N | |
| H | CH₃ | H | CH₂(CH₂)₃SO₂CH₃ | OCH₃ | Cl | CH | |
| H | CH₃ | H | CH₂SOCH₂CH₃ | CH₃ | CH₃ | CH | |
| CH₃ | CH₃ | H | CH₂SOCH₂CH₃ | CH₃ | OCH₃ | CH | |
| H | CH₃ | H | CH₂SO₂CH₂CH₃ | OCH₃ | OCH₃ | CH | |
| H | CH₃ | H | CH₂(CH₂)₆SOCH₃ | CH₃ | CH₃ | N | |
| H | CH₃ | H | CH₂(CH₂)₆SOCH₃ | CH₃ | OCH₃ | N | |
| H | CH₃ | H | CH₂(CH₂)₄SO₂CH₃ | OCH₃ | OCH₃ | N | |
| H | CH₃ | H | CH₂(CH₂)₄SO₂CH₃ | OCH₃ | Cl | CH | |
| H | CH₃ | H | CH₂SCN | CH₃ | CH₃ | CH | |
| H | CH₃ | H | CH₂SCN | CH₃ | OCH₃ | CH | |
| H | CH₃ | H | CH₂SCN | OCH₃ | OCH₃ | CH | |
| H | CH₃ | H | CH₂SCN | CH₃ | CH₃ | N | |
| H | CH₃ | H | CH₂SCN | CH₃ | OCH₃ | N | |
| H | CH₃ | H | CH₂SCN | OCH₃ | OCH₃ | N | |
| H | CH₃ | H | CH₂SCN | OCH₃ | Cl | CH | |
| H | CH₃ | H | CH₂CH₂SCN | CH₃ | CH₃ | CH | |
| H | CH₃ | H | CH₂CH₂SCN | OCH₃ | OCH₃ | CH | |
| H | CH₃ | H | CH₂CH₂SCN | CH₃ | CH₃ | N | |
| H | CH₃ | H | CH₂CH₂SCN | CH₃ | OCH₃ | N | |
| H | CH₃ | H | CH₂CH₂SCN | OCH₃ | OCH₃ | N | |
| H | CH₃ | H | CH₂CH₂SCN | OCH₃ | Cl | CH | |
| H | CH₃ | H | CH₂(CH₂)₂SCN | CH₃ | CH₃ | CH | |
| H | CH₃ | H | CH₂(CH₂)₂SCN | CH₃ | OCH₃ | CH | |
| H | CH₃ | H | CH₂(CH₂)₂SCN | OCH₃ | OCH₃ | CH | |
| H | CH₃ | H | CH₂(CH₂)₂SCN | CH₃ | CH₃ | N | |
| H | CH₃ | H | CH₂(CH₂)₂SCN | OCH₃ | OCH₃ | N | |
| H | CH₃ | H | CH₂(CH₂)₂SCN | OCH₃ | Cl | CH | |
| H | CH₃ | H | CH₂(CH₂)₃SCN | CH₃ | CH₃ | CH | |
| H | CH₃ | H | CH₂(CH₂)₃SCN | CH₃ | OCH₃ | CH | |
| H | CH₃ | H | CH₂(CH₂)₃SCN | OCH₃ | OCH₃ | CH | |
| H | CH₃ | H | CH₂(CH₂)₃SCN | CH₃ | CH₃ | N | |
| H | CH₃ | H | CH₂(CH₂)₃SCN | CH₃ | OCH₃ | N | |
| H | CH₃ | H | CH₂(CH₂)₃SCN | OCH₃ | OCH₃ | N | |
| H | CH₃ | H | CH₂(CH₂)₃SCN | OCH₃ | Cl | CH | |
| H | CH₃ | H | CH₂CHFSCN | CH₃ | CH₃ | CH | |
| H | CH₃ | H | CH(CF₃)SCN | CH₃ | OCH₃ | CH | |
| H | CH₃ | H | CH₂(CH₂)₅SCN | OCH₃ | OCH₃ | CH | |
| H | CH₃ | H | CH₂CN | CH₃ | CH₃ | N | |
| H | CH₃ | H | CH₂CN | CH₃ | OCH₃ | N | |
| H | CH₃ | CH₃ | CH₂CN | OCH₃ | OCH₃ | N | |
| H | CH₃ | H | CH₂CN | OCH₃ | Cl | CH | |
| H | CH₃ | H | CH₂CN | CH₃ | CH₃ | CH | |
| H | CH₃ | H | CH₂CN | CH₃ | OCH₃ | CH | |
| H | CH₃ | H | CH₂CH₂CN | OCH₃ | OCH₃ | CH | |
| H | CH₃ | H | CH₂CH₂CN | CH₃ | CH₃ | N | |
| H | CH₃ | H | CH₂CH₂CN | CH₃ | OCH₃ | N | |
| H | CH₃ | H | CH₂CH₂CN | OCH₃ | OCH₃ | N | |

TABLE IIa-continued

General Structure IIa

| R | R₁ | R₂ | R₃ | X | Y | Z | m.p. (°C.) |
|---|---|---|---|---|---|---|---|
| H | CH₃ | H | CH₂CH₂CN | OCH₃ | Cl | CH | |
| H | CH₃ | H | CH₂CH₂CN | CH₃ | CH₃ | CH | |
| CH₃ | CH₃ | H | CH₂CH₂CN | CH₃ | OCH₃ | CH | |
| H | CH₃ | H | CH₂CH₂CN | OCH₃ | OCH₃ | CH | |
| H | CH₃ | H | CH₂(CH₂)₃CN | CH₃ | CH₃ | N | |
| H | CH₃ | H | CH₂(CH₂)₃CN | CH₃ | OCH₃ | N | |
| H | CH₃ | H | CH₂(CH₂)₃CN | OCH₃ | OCH₃ | N | |
| H | CH₃ | H | CH₂(CH₂)₃CN | OCH₃ | Cl | CH | |
| H | CH₃ | H | CH₂(CH₂)₄CN | CH₃ | CH₃ | CH | |
| H | CH₃ | H | CH₂(CH₂)₂CH(CN)₂ | CH₃ | OCH₃ | CH | |
| H | CH₃ | H | CH(CH₃)CH₂CN | OCH₃ | OCH₃ | CH | |
| H | CH₃ | H | CH(CH₃)CH₂CN | CH₃ | CH₃ | N | |
| H | CH₃ | H | CH(CH₃)CH₂CN | CH₃ | OCH₃ | N | |
| H | CH₃ | H | CH(CH₃)CH₂CN | OCH₃ | OCH₃ | N | |
| H | CH₃ | H | CH(CH₃)CH₂CN | OCH₃ | Cl | CH | |
| H | CH₃ | H | CH₂SP(O)(CH₃)₂ | CH₃ | CH₃ | CH | |
| H | CH₃ | H | CH₂SP(O)(CH₃)₂ | CH₃ | OCH₃ | CH | |
| H | CH₃ | H | CH₂SP(O)(CH₃)₂ | OCH₃ | OCH₃ | CH | |
| H | CH₃ | H | CH₂CH₂SP(O)(CH₃)₂ | CH₃ | CH₃ | N | |
| H | CH₃ | H | CH₂CH₂SP(O)(CH₃)₂ | CH₃ | OCH₃ | N | |
| H | CH₃ | H | CH₂CH₂SP(O)(CH₃)₂ | OCH₃ | OCH₃ | N | |
| H | CH₃ | H | CH₂P(S)(CH₃)₂ | OCH₃ | Cl | CH | |
| H | CH₃ | H | CH₂P(S)(CH₃)₂ | CH₃ | CH₃ | CH | |
| H | CH₃ | H | CH₂P(S)(CH₃)₂ | CH₃ | OCH₃ | CH | |
| H | CH₃ | H | CH₂—CH₂P(S)(CH₃)₂ | OCH₃ | OCH₃ | CH | |
| H | CH₃ | H | CH₂—CH₂P(S)(CH₃)₂ | CH₃ | CH₃ | N | |
| H | CH₃ | H | CH₂—CH₂P(S)(CH₃)₂ | OCH₃ | OCH₃ | N | |
| H | CH₃ | H | CH₂—CH₂P(S)(CH₃)₂ | OCH₃ | Cl | CH | |
| H | CH₃ | H | CH₂—CH₂P(S)(CH₃)₂ | CH₃ | CH₃ | CH | |
| H | CH₃ | H | CH₂N(CH₃)₂ | CH₃ | OCH₃ | CH | |
| H | CH₃ | H | CH₂N(CH₃)₂ | OCH₃ | OCH₃ | CH | |
| H | CH₃ | H | CH₂N(CH₃)₂ | CH₃ | CH₃ | N | |
| H | CH₃ | H | CH₂N(CH₃)₂ | CH₃ | OCH₃ | N | |
| H | CH₃ | H | CH₂N(CH₃)₂ | OCH₃ | OCH₃ | N | |
| H | CH₃ | H | CH₂N(CH₃)₂ | OCH₃ | Cl | CH | |
| H | CH₃ | H | CH₂N(CH₃)₂ | CH₃ | CH₃ | CH | |
| H | CH₃ | H | CH₂(CH₂)₃N(CH₃)₂ | CH₃ | OCH₃ | CH | |
| H | CH₃ | H | CH₂(CH₂)₃N(CH₃)₂ | OCH₃ | OCH₃ | CH | |
| H | CH₃ | H | CH₂(CH₂)₃N(CH₃)₂ | CH₃ | CH₃ | N | |
| H | CH₃ | H | CH₂(CH₂)₃N(CH₃)₂ | CH₃ | OCH₃ | N | |
| H | CH₃ | CH₃ | CH₂(CH₂)₃N(CH₃)₂ | OCH₃ | OCH₃ | N | |
| H | CH₃ | H | CH₂(CH₂)₃N(CH₃)₂ | OCH₃ | Cl | CH | |
| H | CH₃ | H | CH₂(CH₂)₃N(CH₃)₂ | CH₃ | CH₃ | CH | |
| H | CH₃ | H | CH₂N(CH₃)₂Ph | CH₃ | OCH₃ | CH | |
| H | CH₃ | H | CH₂N(CH₃)₂Ph | OCH₃ | OCH₃ | CH | |
| H | CH₃ | H | CH₂N(CH₃)₂Ph | CH₃ | CH₃ | N | |
| H | CH₃ | H | CH₂N(CH₃)₂Ph | CH₃ | OCH₃ | N | |
| H | CH₃ | H | CH₂—CH(CH₃)N(CH₃)₂ | OCH₃ | OCH₃ | N | |
| H | CH₃ | H | CH₂—CH(CH₃)N(CH₃)₂ | OCH₃ | Cl | CH | |
| H | CH₃ | H | CH₂—CH(CH₃)N(CH₃)₂ | CH₃ | CH₃ | CH | |
| CH₃ | CH₃ | H | CH₂—CH(CH₃)N(CH₃)₂ | CH₃ | OCH₃ | CH | |
| H | CH₃ | H | CH₂—CH(CH₃)N(CH₃)₂ | OCH₃ | OCH₃ | CH | |
| H | CH₃ | H | CH₂CH₂CH(CH₃)₂ | CH₃ | CH₃ | N | |
| H | CH₃ | H | CH₂CH₂CH(CH₃)₂ | CH₃ | OCH₃ | N | |
| H | CH₃ | H | CH₂CH₂CH(CH₃)₂ | OCH₃ | OCH₃ | N | |
| H | CH₃ | H | CH₂CH₂CH(CH₃)₂ | OCH₃ | Cl | CH | |
| H | CH₃ | H | CH₂NHC(O)CH₃ | CH₃ | CH₃ | CH | |
| H | CH₃ | H | CH₂NHC(O)CH₃ | CH₃ | OCH₃ | CH | |
| H | CH₃ | H | CH₂NHC(O)CH₃ | OCH₃ | OCH₃ | CH | |
| H | CH₃ | H | CH₂NHC(O)CH₃ | CH₃ | CH₃ | N | |
| H | CH₃ | H | CH₂NHC(O)CH₃ | OCH₃ | OCH₃ | N | |
| H | CH₃ | H | CH₂NHC(O)CH₃ | OCH₃ | Cl | CH | |
| H | CH₃ | H | CH₂CH₂N(CH₃)C(O)CH₃ | CH₃ | CH₃ | CH | |
| H | CH₃ | H | CH₂CH₂N(CH₃)C(O)CH₃ | CH₃ | OCH₃ | CH | |
| H | CH₃ | H | CH₂CH₂N(CH₃)C(O)CH₃ | OCH₃ | OCH₃ | CH | |
| H | CH₃ | H | CH₂CH₂N(CH₃)C(O)CH₃ | CH₃ | CH₃ | N | |
| H | CH₃ | H | CH₂(CH₂)₃NHC(O)CH₃ | CH₃ | OCH₃ | N | |
| H | CH₃ | H | CH₂(CH₂)₃NHC(O)CH₃ | OCH₃ | OCH₃ | N | |
| H | CH₃ | H | CH₂N(CH₃)C(O)OCH₃ | OCH₃ | Cl | CH | |
| H | CH₃ | H | CH₂N(CH₃)C(O)OCH₃ | CH₃ | CH₃ | CH | |
| H | CH₃ | H | CH₂NHC(O)OCH₃ | CH₃ | OCH₃ | CH | |
| H | CH₃ | H | CH₂NHC(O)OCH₃ | OCH₃ | OCH₃ | CH | |
| H | CH₃ | H | CH₂NHC(O)OCH₃ | CH₃ | CH₃ | N | |
| H | CH₃ | H | CH₂NHC(O)OCH₃ | OCH₃ | OCH₃ | N | |
| H | CH₃ | H | CH₂NHC(O)OCH₃ | OCH₃ | Cl | CH | |
| H | CH₃ | H | CH₂NHC(O)OCH₃ | CH₃ | CH₃ | CH | |
| H | CH₃ | H | CH₂(CH₂)₃NHC(O)OCH₃ | CH₃ | OCH₃ | CH | |
| H | CH₃ | H | CH₂(CH₂)₃NHC(O)OCH₃ | OCH₃ | OCH₃ | CH | |
| H | CH₃ | H | CH₂(CH₂)₃NHC(O)OCH₃ | CH₃ | CH₃ | N | |

TABLE IIa-continued

General Structure IIa

| R | R₁ | R₂ | R₃ | X | Y | Z | m.p. (°C.) |
|---|---|---|---|---|---|---|---|
| H | CH₃ | H | CH₂N(CH₃)C(O)OCH₂CH₃ | CH₃ | OCH₃ | N | |
| H | CH₃ | H | CH(CH₃)NHC(O)OCH₃ | OCH₃ | OCH₃ | N | |
| H | CH₃ | H | CH(CH₃)NHC(O)OCH₃ | OCH₃ | Cl | CH | |
| H | CH₃ | H | CH(CH₃)NHC(O)OCH₃ | CH₃ | CH₃ | CH | |
| H | CH₃ | H | CH₂NHSO₂CH₃ | CH₃ | OCH₃ | CH | |
| H | CH₃ | H | CH₂NHSO₂CH₃ | OCH₃ | OCH₃ | CH | |
| H | CH₃ | H | CH₂NHSO₂CH₃ | CH₃ | CH₃ | N | |
| H | CH₃ | H | CH₂NHSO₂CH₃ | CH₃ | OCH₃ | N | |
| H | CH₃ | CH₃ | CH₂NHSO₂CH₃ | OCH₃ | OCH₃ | N | |
| H | CH₃ | H | CH₂CH₂NHSO₂CH₃ | OCH₃ | Cl | CH | |
| H | CH₃ | H | CH₂CH₂NHSO₂CH₃ | CH₃ | CH₃ | CH | |
| H | CH₃ | H | CH₂CH₂NHSO₂CH₃ | CH₃ | OCH₃ | CH | |
| H | CH₃ | H | CH₂CH₂NHSO₂CH₃ | OCH₃ | OCH₃ | CH | |
| H | CH₃ | H | CH₂CH₂NHSO₂CH₃ | CH₃ | CH₃ | N | |
| H | CH₃ | H | CH₂CH₂NHSO₂CH₃ | CH₃ | OCH₃ | N | |
| H | CH₃ | H | CH₂(CH₂)₃NHSO₂CH₃ | OCH₃ | OCH₃ | N | |
| H | CH₃ | H | CH₂(CH₂)₃NHSO₂CH₃ | OCH₃ | Cl | CH | |
| H | CH₃ | H | CH₂(CH₂)₃NHSO₂CH₃ | CH₃ | CH₃ | CH | |
| CH₃ | CH₃ | H | CH₂NHP(O)(CH₃)₂ | CH₃ | OCH₃ | CH | |
| H | CH₃ | H | CH₂NHP(O)(CH₃)₂ | OCH₃ | OCH₃ | CH | |
| H | CH₃ | H | CH₂NHP(O)(CH₃)₂ | CH₃ | CH₃ | N | |
| H | CH₃ | H | CH₂NHP(O)(OCH₃)₂ | CH₃ | OCH₃ | N | |
| H | CH₃ | H | CH₂NHP(O)(OCH₃)₂ | OCH₃ | OCH₃ | N | |
| H | CH₃ | H | CH₂NHP(O)(OCH₃)₂ | OCH₃ | Cl | CH | |
| H | CH₃ | H | CH═CH₂ | CH₃ | CH₃ | CH | |
| H | CH₃ | H | CH═CH₂ | CH₃ | OCH₃ | CH | |
| H | CH₃ | H | CH₂NO₂ | CH₃ | CH₃ | CH | |
| H | CH₃ | H | CH₂NO₂ | CH₃ | OCH₃ | CH | |
| H | CH₃ | H | CH₂NO₂ | OCH₃ | OCH₃ | CH | |
| H | CH₃ | H | CH₂NO₂ | CH₃ | CH₃ | N | |
| H | CH₃ | H | CH₂NO₂ | CH₃ | OCH₃ | N | |
| H | CH₃ | H | CH₂NO₂ | OCH₃ | OCH₃ | N | |
| H | CH₃ | H | CH₂NO₂ | OCH₃ | Cl | CH | |
| H | CH₃ | H | CH₂CH₂NO₂ | CH₃ | CH₃ | CH | |
| H | CH₃ | H | CH₂CH₂NO₂ | CH₃ | OCH₃ | CH | |
| H | CH₃ | H | CH₂CH₂NO₂ | OCH₃ | OCH₃ | CH | |
| H | CH₃ | H | CH₂CH₂NO₂ | CH₃ | CH₃ | N | |
| H | CH₃ | H | CH₂CH₂NO₂ | CH₃ | OCH₃ | N | |
| H | CH₃ | H | CH₂CH₂NO₂ | OCH₃ | OCH₃ | N | |
| H | CH₃ | H | CH₂CH₂NO₂ | OCH₃ | Cl | CH | |
| H | CH₃ | H | CH₂C(O)CH₃ | CH₃ | CH₃ | CH | |
| H | CH₃ | H | CH₂C(O)CH₃ | CH₃ | OCH₃ | CH | |
| H | CH₃ | H | CH₂C(O)CH₃ | OCH₃ | OCH₃ | N | |
| H | CH₃ | H | CH₂C(O)CH₃ | CH₃ | CH₃ | N | |
| H | CH₃ | H | CH₂C(O)CH₃ | OCH₃ | OCH₃ | N | |
| H | CH₃ | H | CH₂C(O)CH₃ | OCH₃ | Cl | CH | |
| H | CH₃ | H | CH₂C(O)CH₂CH₃ | CH₃ | CH₃ | CH | |
| H | CH₃ | H | CH₂C(O)CH₂CH₃ | CH₃ | OCH₃ | CH | |
| H | CH₃ | H | CH₂C(O)CH₂CH₃ | OCH₃ | OCH₃ | CH | |
| H | CH₃ | H | CH₂C(O)CH₂CH₃ | CH₃ | CH₃ | N | |
| H | CH₃ | H | CH₂C(O)CH₂CH₃ | CH₃ | OCH₃ | N | |
| H | CH₃ | H | CH₂C(O)CH₂CH₃ | OCH₃ | OCH₃ | N | |
| H | CH₃ | H | CH₂C(O)CH₂CH₃ | OCH₃ | Cl | CH | |
| H | CH₃ | H | CH₂(CH₂)₃C(O)CH₃ | CH₃ | CH₃ | CH | |
| H | CH₃ | H | CH₂(CH₂)₃C(O)CH₃ | CH₃ | OCH₃ | CH | |
| H | CH₃ | H | CH₂(CH₂)₃C(O)CH₃ | OCH₃ | OCH₃ | CH | |
| H | CH₃ | H | CH₂(CH₂)₃C(O)CH₃ | CH₃ | CH₃ | N | |
| H | CH₃ | H | CH₂(CH₂)₃C(O)CH₃ | CH₃ | OCH₃ | N | |
| H | CH₃ | CH₃ | CH₂(CH₂)₃C(O)CH₃ | OCH₃ | OCH₃ | N | |
| H | CH₃ | H | CH₂(CH₂)₃C(O)CH₃ | OCH₃ | Cl | CH | |
| H | CH₃ | H | CH₂CH₂C(O)CH₃ | CH₃ | CH₃ | CH | |
| H | CH₃ | H | CH₂CH₂C(O)CH₃ | CH₃ | OCH₃ | CH | |
| H | CH₃ | H | CH₂CH₂C(O)CH₃ | OCH₃ | OCH₃ | CH | |
| H | CH₃ | H | CH₂CH₂C(O)CH₃ | CH₃ | CH₃ | N | |
| H | CH₃ | H | CH₂CH₂C(O)CH₃ | CH₃ | OCH₃ | N | |
| H | CH₃ | CH₃ | CH₂—CH(CH₂)C(O)CH₃ | OCH₃ | OCH₃ | N | |
| H | CH₃ | H | CH₂—CH(CH₂)C(O)CH₃ | OCH₃ | Cl | CH | |
| H | CH₃ | H | CH₂—CH(CH₃)C(O)CH₃ | CH₃ | CH₃ | CH | |
| CH₃ | CH₃ | CH₃ | CH₂—CH(CH₂)C(O)CH₃ | CH₃ | OCH₃ | CH | |
| H | CH₃ | H | CH₂(CH₂)₆C(O)CH₂CH₃ | OCH₃ | OCH₃ | CH | |
| H | CH₃ | H | CH₂(CH₂)₆C(O)CH₂CH₃ | CH₃ | CH₃ | N | |
| H | CH₃ | H | CH₂(CH₂)₆C(O)CH₂CH₃ | CH₃ | OCH₃ | N | |
| H | CH₃ | H | CH₂(CH₂)₆C(O)CH₂CH₃ | OCH₃ | OCH₃ | N | |
| H | CH₃ | H | CH₂(CH₂)₆C(O)CH₂CH₃ | OCH₃ | Cl | CH | |
| H | CH₃ | H | CH₂C(O)OCH₃ | CH₃ | CH₃ | CH | |
| H | CH₃ | H | CH₂C(O)OCH₃ | CH₃ | OCH₃ | CH | |
| H | CH₃ | H | CH₂C(O)OCH₃ | OCH₃ | OCH₃ | CH | |
| H | CH₃ | H | CH₂C(O)OCH₃ | CH₃ | CH₃ | N | |
| H | CH₃ | H | CH₂C(O)OCH₃ | CH₃ | OCH₃ | N | |
| H | CH₃ | H | CH₂C(O)OCH₃ | OCH₃ | OCH₃ | N | |

TABLE IIa-continued

General Structure IIa

| R | $R_1$ | $R_2$ | $R_3$ | X | Y | Z | m.p. (°C.) |
|---|---|---|---|---|---|---|---|
| H | $CH_3$ | H | $CH_2C(O)OCH_3$ | $OCH_3$ | Cl | CH | |
| H | $CH_3$ | H | $CH_2C(O)OCH_2CH_3$ | $CH_3$ | $CH_3$ | CH | |
| H | $CH_3$ | H | $CH_2C(O)OCH_2CH_3$ | $CH_3$ | $OCH_3$ | CH | |
| H | $CH_3$ | H | $CH_2C(O)OCH_2CH_3$ | $OCH_3$ | $OCH_3$ | CH | |
| H | $CH_3$ | H | $CH_2C(O)OCH_2CH_3$ | $CH_3$ | $CH_3$ | N | |
| H | $CH_3$ | H | $CH_2C(O)OCH_2CH_3$ | $CH_3$ | $OCH_3$ | N | |
| H | $CH_3$ | H | $CH_2C(O)OCH_2CH_3$ | $OCH_3$ | $OCH_3$ | N | |
| H | $CH_3$ | H | $CH_2C(O)OCH_2CH_3$ | $OCH_3$ | Cl | CH | |
| H | $CH_3$ | H | $CH_2CH_2C(O)CH_3$ | $CH_3$ | $CH_3$ | CH | |
| H | $CH_3$ | H | $CH_2CH_2C(O)CH_3$ | $CH_3$ | $OCH_3$ | CH | |
| H | $CH_3$ | H | $CH_2CH_2C(O)CH_3$ | $OCH_3$ | $OCH_3$ | N | |
| H | $CH_3$ | H | $CH_2CH_2C(O)CH_3$ | $CH_3$ | $CH_3$ | N | |
| H | $CH_3$ | H | $CH_2CH_2C(O)CH_3$ | $OCH_3$ | $OCH_3$ | N | |
| H | $CH_3$ | H | $CH_2CH_2C(O)CH_3$ | $OCH_3$ | Cl | CH | |
| H | $CH_3$ | H | $CH_2C(O)N(CH_3)_2$ | $CH_3$ | $CH_3$ | CH | |
| H | $CH_3$ | H | $CH_2C(O)N(CH_3)_2$ | $CH_3$ | $OCH_3$ | CH | |
| H | $CH_3$ | H | $CH_2C(O)N(CH_3)_2$ | $OCH_3$ | $OCH_3$ | CH | |
| H | $CH_3$ | H | $CH_2C(O)N(CH_3)_2$ | $CH_3$ | $CH_3$ | N | |
| H | $CH_3$ | H | $CH_2C(O)N(CH_3)_2$ | $CH_3$ | $OCH_3$ | N | |
| H | $CH_3$ | H | $CH_2C(O)N(CH_3)_2$ | $OCH_3$ | $OCH_3$ | N | |
| H | $CH_3$ | H | $CH_2C(O)N(CH_3)_2$ | $OCH_3$ | Cl | CH | |
| H | $CH_3$ | H | $CH_2CH_2C(O)N(CH_3)_2$ | $CH_3$ | $CH_3$ | CH | |
| H | $CH_3$ | H | $CH_2CH_2C(O)N(CH_3)_2$ | $CH_3$ | $OCH_3$ | CH | |
| H | $CH_3$ | H | $CH_2CH_2C(O)N(CH_3)_2$ | $OCH_3$ | $OCH_3$ | CH | |
| H | $CH_3$ | H | $CH_2CH_2C(O)N(CH_3)_2$ | $CH_3$ | $CH_3$ | N | |
| H | $CH_3$ | H | $CH_2CH_2C(O)N(CH_3)_2$ | $CH_3$ | $OCH_3$ | N | |
| H | $CH_3$ | $CH_3$ | $CH_2CH_2C(O)N(CH_3)_2$ | $OCH_3$ | $OCH_3$ | N | |
| H | $CH_3$ | H | $CH_2CH_2C(O)N(CH_3)_2$ | $OCH_3$ | Cl | CH | |
| H | $CH_3$ | H | $CH_2C(O)N(CH_3)CH_2CH_3$ | $CH_3$ | $CH_3$ | CH | |
| H | $CH_3$ | H | $CH_2C(O)N(CH_3)CH_2CH_3$ | $CH_3$ | $OCH_3$ | CH | |
| H | $CH_3$ | H | $CH_2C(O)N(CH_3)CH_2CH_3$ | $OCH_3$ | $OCH_3$ | CH | |
| H | $CH_3$ | H | $CH_2C(O)N(CH_3)CH_2CH_3$ | $CH_3$ | $CH_3$ | N | |
| H | $CH_3$ | H | $CH_2C(O)N(CH_3)CH_2OCH_3$ | $CH_3$ | $OCH_3$ | N | |
| H | $CH_3$ | H | $CH_2C(O)N(CH_3)CH_2OCH_3$ | $OCH_3$ | $OCH_3$ | N | |
| H | $CH_3$ | H | $CH_2C(O)N(CH_3)CH_2OCH_3$ | $OCH_3$ | Cl | CH | |
| H | $CH_3$ | H | $CH_2SeCH_3$ | $CH_3$ | $CH_3$ | CH | |
| $CH_3$ | $CH_3$ | H | $CH_2SeCH_3$ | $CH_3$ | $OCH_3$ | CH | |
| H | $CH_3$ | H | $CH_2SeCH_3$ | $OCH_3$ | $OCH_3$ | CH | |
| H | $CH_3$ | H | $CH_2SePh$ | $CH_3$ | $CH_3$ | N | |
| H | $CH_3$ | H | $CH_2SePh$ | $CH_3$ | $OCH_3$ | N | |
| H | $CH_3$ | H | $CH_2-CH_2SeCH_3$ | $OCH_3$ | $OCH_3$ | N | |
| H | $CH_3$ | H | $CH_2-CH_2SeCH_3$ | $OCH_3$ | Cl | CH | |
| H | $CH_3$ | H | $CH=CH_2$ | $OCH_3$ | $OCH_3$ | CH | |
| H | $CH_3$ | H | $CH=CH_2$ | $CH_3$ | $CH_3$ | N | |
| H | $CH_3$ | H | $CH=CH_2$ | $CH_3$ | $OCH_3$ | N | |
| H | $CH_3$ | H | $CH=CH_2$ | $OCH_3$ | $OCH_3$ | N | |
| H | $CH_3$ | H | $CH=CH_2$ | $OCH_3$ | Cl | CH | |
| H | $CH_3$ | H | $CH=CH-CH_3$ | $CH_3$ | $CH_3$ | CH | |
| H | $CH_3$ | H | $CH=CH-CH_3$ | $CH_3$ | $OCH_3$ | CH | |
| H | $CH_3$ | H | $CH=CH-CH_3$ | $OCH_3$ | $OCH_3$ | CH | |
| H | $CH_3$ | H | $CH=CH-CH_3$ | $CH_3$ | $CH_3$ | N | |
| H | $CH_3$ | H | $CH=CH-CH_3$ | $CH_3$ | $OCH_3$ | N | |
| H | $CH_3$ | H | $CH=CH-CH_3$ | $OCH_3$ | $OCH_3$ | N | |
| H | $CH_3$ | H | $CH=CH-CH_3$ | $OCH_3$ | Cl | CH | |
| H | $CH_3$ | H | $CH=CH-CH_2-CH_3$ | $CH_3$ | $CH_3$ | CH | |
| H | $CH_3$ | H | $CH=CH-CH_2-CH_3$ | $CH_3$ | $OCH_3$ | CH | |
| H | $CH_3$ | H | $CH=CH-CH_2-CH_3$ | $OCH_3$ | $OCH_3$ | CH | |
| H | $CH_3$ | H | $CH=CH-CH_2-CH_3$ | $CH_3$ | $CH_3$ | N | |
| H | $CH_3$ | H | $CH=CH-CH_2-CH_3$ | $OCH_3$ | $OCH_3$ | N | |
| H | $CH_3$ | H | $CH=CH-CH_2-CH_3$ | $OCH_3$ | Cl | CH | |
| H | $CH_3$ | H | $CH=C(CH_3)_2$ | $CH_3$ | $CH_3$ | CH | |
| H | $CH_3$ | H | $CH=C(CH_3)_2$ | $CH_3$ | $OCH_3$ | CH | |
| H | $CH_3$ | H | $CH=C(CH_3)_2$ | $OCH_3$ | $OCH_3$ | CH | |
| H | $CH_3$ | H | $CH=C(CH_3)_2$ | $CH_3$ | $CH_3$ | N | |
| H | $CH_3$ | H | $CH=C(CH_3)_2$ | $CH_3$ | $OCH_3$ | N | |
| H | $CH_3$ | H | $CH=C(CH_3)_2$ | $OCH_3$ | $OCH_3$ | N | |
| H | $CH_3$ | H | $CH=C(CH_3)_2$ | $OCH_3$ | Cl | CH | |
| H | $CH_3$ | H | $CH=CH(CH_2)_3CH_3$ | $CH_3$ | $CH_3$ | CH | |
| H | $CH_3$ | H | $CH=CH(CH_2)_3CH_3$ | $CH_3$ | $OCH_3$ | CH | |
| H | $CH_3$ | H | $CH=CH(CH_2)_3CH_3$ | $OCH_3$ | $OCH_3$ | CH | |
| H | $CH_3$ | H | $CH=CH(CH_2)_3CH_3$ | $CH_3$ | $CH_3$ | N | |
| H | $CH_3$ | H | $CH=CH(CH_2)_3CH_3$ | $CH_3$ | $OCH_3$ | N | |
| H | $CH_3$ | $CH_3$ | $CH=CH(CH_2)_3CH_3$ | $OCH_3$ | $OCH_3$ | N | |
| H | $CH_3$ | H | $CH=CH(CH_2)_3CH_3$ | $OCH_3$ | Cl | CH | |
| H | $CH_3$ | H | $CH=C(CH_3)CH_2CH_3$ | $CH_3$ | $CH_3$ | CH | |
| H | $CH_3$ | H | $CH=C(CH_3)CH_2CH_3$ | $CH_3$ | $OCH_3$ | CH | |
| H | $CH_3$ | H | $CH=C(CH_3)CH_2CH_3$ | $OCH_3$ | $OCH_3$ | CH | |
| H | $CH_3$ | H | $CH=CH-CH(CH_3)_2$ | $CH_3$ | $CH_3$ | N | |
| H | $CH_3$ | H | $CH=CH-CH(CH_3)_2$ | $CH_3$ | $OCH_3$ | N | |
| H | $CH_3$ | H | $CH=CH-CH(CH_3)_2$ | $OCH_3$ | $OCH_3$ | N | |

TABLE IIa-continued

General Structure IIa

| R | R₁ | R₂ | R₃ | X | Y | Z | m.p. (°C.) |
|---|---|---|---|---|---|---|---|
| H | CH₃ | H | CH=CH—CH(CH₃)₂ | OCH₃ | Cl | CH | |
| H | CH₃ | H | CH=CH(CH₂)₄CH₃ | CH₃ | CH₃ | CH | |
| CH₃ | CH₃ | H | CH=CH(CH₂)₄CH₃ | CH₃ | OCH₃ | CH | |
| H | CH₃ | H | CH=CH(CH₂)₆CH₃ | OCH₃ | OCH₃ | CH | |
| H | CH₃ | H | CH=CH(CH₂)₆CH₃ | CH₃ | CH₃ | N | |
| H | CH₃ | H | CH=CH(CH₂)₆CH₃ | CH₃ | OCH₃ | N | |
| H | CH₃ | H | CH=C(CH₃)(CH₂)₃CH₃ | OCH₃ | OCH₃ | N | |
| H | CH₃ | H | CH=C(CH₃)(CH₂)₃CH₃ | OCH₃ | Cl | CH | |
| H | CH₃ | H | CH₂CH=CH₂ | CH₃ | CH₃ | CH | |
| H | CH₃ | H | CH₂CH=CH₂ | CH₃ | OCH₃ | CH | |
| H | CH₃ | H | CH₂CH=CH₂ | OCH₃ | OCH₃ | CH | |
| H | CH₃ | H | CH₂CH=CH₂ | CH₃ | CH₃ | N | |
| H | CH₃ | H | CH₂CH=CH₂ | CH₃ | OCH₃ | N | |
| H | CH₃ | H | CH₂CH=CH₂ | OCH₃ | OCH₃ | N | |
| H | CH₃ | H | CH₂CH=CH₂ | OCH₃ | Cl | CH | |
| H | CH₃ | H | CH₂CH₂CH=CH₂ | CH₃ | CH₃ | CH | |
| H | CH₃ | H | CH₂CH₂CH=CH₂ | CH₃ | OCH₃ | CH | |
| H | CH₃ | H | CH₂CH₂CH=CH₂ | OCH₃ | OCH₃ | CH | |
| H | CH₃ | H | CH₂CH₂CH=CH₂ | CH₃ | CH₃ | N | |
| H | CH₃ | H | CH₂CH₂CH=CH₂ | CH₃ | OCH₃ | N | |
| H | CH₃ | H | CH₂CH₂CH=CH₂ | OCH₃ | OCH₃ | N | |
| H | CH₃ | H | CH₂CH₂CH=CH₂ | OCH₃ | Cl | CH | |
| H | CH₃ | H | CH₂CH=CHCH₃ | CH₃ | CH₃ | CH | |
| H | CH₃ | H | CH₂CH=CHCH₃ | CH₃ | OCH₃ | CH | |
| H | CH₃ | H | CH₂CH=CHCH₃ | OCH₃ | OCH₃ | CH | |
| H | CH₃ | H | CH₂CH=CHCH₃ | CH₃ | CH₃ | N | |
| H | CH₃ | H | CH₂—CH=CH—CH₃ | OCH₃ | OCH₃ | N | |
| H | CH₃ | H | CH₂—CH=CH—CH₃ | OCH₃ | Cl | CH | |
| H | CH₃ | H | CH₂—CH=C(CH₃)₂ | CH₃ | CH₃ | CH | |
| H | CH₃ | H | CH₂—CH=C(CH₃)₂ | CH₃ | OCH₃ | CH | |
| H | CH₃ | H | CH₂—CH=C(CH₃)₂ | OCH₃ | OCH₃ | CH | |
| H | CH₃ | H | CH₂—CH=C(CH₃)₂ | CH₃ | CH₃ | N | |
| H | CH₃ | H | CH₂—CH=C(CH₃)₂ | CH₃ | OCH₃ | N | |
| H | CH₃ | H | CH₂—CH=C(CH₃)₂ | OCH₃ | OCH₃ | N | |
| H | CH₃ | H | CH₂—CH=CH(CH₂)₃CH₃ | OCH₃ | Cl | CH | |
| H | CH₃ | H | CH₂—CH=CH(CH₂)₃CH₃ | CH₃ | CH₃ | CH | |
| H | CH₃ | H | CH₂—CH=CH(CH₂)₃CH₃ | OCH₃ | CH | | |
| H | CH₃ | H | CH₂—CH=CH(CH₂)₃CH₃ | OCH₃ | OCH₃ | CH | |
| H | CH₃ | H | CH₂—CH=CH(CH₂)₃CH₃ | CH₃ | CH₃ | N | |
| H | CH₃ | H | CH₂—CH=CH(CH₂)₃CH₃ | CH₃ | OCH₃ | N | |
| H | CH₃ | CH₃ | CH₂—CH=CH(CH₂)₃CH₃ | OCH₃ | OCH₃ | N | |
| H | CH₃ | H | CH₂—CH₂—CH=CH₂ | OCH₃ | Cl | CH | |
| H | CH₃ | H | CH₂—CH₂—CH=CH₂ | CH₃ | CH₃ | CH | |
| H | CH₃ | H | CH₂—CH₂—CH=CH₂ | CH₃ | OCH₃ | CH | |
| H | CH₃ | H | CH₂—CH₂—CH=CH₂ | OCH₃ | OCH₃ | CH | |
| H | CH₃ | H | CH₂—CH₂—CH=CH₂ | CH₃ | CH₃ | N | |
| H | CH₃ | H | CH₂—(CH₂)₄CH=CH₂ | CH₃ | OCH₃ | N | |
| H | CH₃ | H | CH₂—CH=CH—CH(CH₃)₂ | OCH₃ | OCH₃ | N | |
| H | CH₃ | H | CH₂—CH=CH—CH(CH₃)₂ | OCH₃ | Cl | CH | |
| H | CH₃ | H | CH₂—CH=CH—CH(CH₃)₂ | CH₃ | CH₃ | CH | |
| CH₃ | CH₃ | H | CH₂—CH=CH—CH(CH₃)₂ | CH₃ | OCH₃ | CH | |
| H | CH₃ | H | CH₂—CH=CH—CH(CH₃)₂ | OCH₃ | OCH₃ | CH | |
| H | CH₃ | H | CH₂—CH=CH—CH=CH₂ | CH₃ | CH₃ | N | |
| H | CH₃ | H | CH₂—CH=CH—CH=CH₂ | CH₃ | OCH₃ | N | |
| H | CH₃ | H | CH₂—CH=CH—CH=CH₂ | OCH₃ | OCH₃ | N | |
| H | CH₃ | H | CH₂—CH=CH—CH=CH₂ | OCH₃ | Cl | CH | |
| H | CH₃ | H | C≡CH | CH₃ | CH₃ | CH | |
| H | CH₃ | H | C≡CH | CH₃ | OCH₃ | CH | |
| H | CH₃ | H | C≡CH | OCH₃ | OCH₃ | CH | |
| H | CH₃ | H | C≡CH | CH₃ | CH₃ | N | |
| H | CH₃ | H | C≡CH | CH₃ | OCH₃ | N | |
| H | CH₃ | H | C≡CH | OCH₃ | OCH₃ | N | |
| H | CH₃ | H | C≡CH | OCH₃ | Cl | CH | |
| H | CH₃ | H | C≡C—CH₃ | CH₃ | CH₃ | CH | |
| H | CH₃ | H | C≡C—CH₃ | CH₃ | OCH₃ | CH | |
| H | CH₃ | H | C≡C—CH₃ | OCH₃ | OCH₃ | CH | |
| H | CH₃ | H | C≡C—CH₃ | CH₃ | CH₃ | N | |
| H | CH₃ | H | C≡C—CH₃ | CH₃ | OCH₃ | N | |
| H | CH₃ | H | C≡C—CH₃ | OCH₃ | OCH₃ | N | |
| H | CH₃ | H | C≡C—CH₃ | OCH₃ | Cl | CH | |
| H | CH₃ | H | C≡C(CH₂)₂CH₃ | CH₃ | CH₃ | CH | |
| H | CH₃ | H | C≡C(CH₂)₂CH₃ | CH₃ | OCH₃ | CH | |
| H | CH₃ | H | C≡C(CH₂)₂CH₃ | OCH₃ | OCH₃ | CH | |
| H | CH₃ | H | C≡C(CH₂)₂CH₃ | CH₃ | CH₃ | N | |
| H | CH₃ | H | C≡C(CH₂)₂CH₃ | OCH₃ | OCH₃ | N | |
| H | CH₃ | H | CH₂—C≡CH | OCH₃ | Cl | CH | |
| H | CH₃ | H | CH₂—C≡CH | CH₃ | CH₃ | CH | |
| H | CH₃ | H | CH₂—C≡CH | CH₃ | OCH₃ | CH | |
| H | CH₃ | H | CH₂—C≡CH | OCH₃ | OCH₃ | CH | |
| H | CH₃ | H | CH₂—C≡CH | CH₃ | CH₃ | N | |

TABLE IIa-continued

General Structure IIa

| R | R₁ | R₂ | R₃ | X | Y | Z | m.p. (°C.) |
|---|---|---|---|---|---|---|---|
| H | CH₃ | H | CH₂—C≡CH | CH₃ | OCH₃ | N | |
| H | CH₃ | H | CH₂—C≡CH | OCH₃ | OCH₃ | N | |
| H | CH₃ | H | CH₂—C≡C—CH₃ | OCH₃ | Cl | CH | |
| H | CH₃ | H | CH₂—C≡C—CH₃ | CH₃ | CH₃ | CH | |
| H | CH₃ | H | CH₂—C≡C—CH₃ | CH₃ | OCH₃ | CH | |
| H | CH₃ | H | CH₂—C≡C—CH₃ | OCH₃ | OCH₃ | CH | |
| H | CH₃ | H | CH₂—C≡C—CH₃ | CH₃ | CH₃ | N | |
| H | CH₃ | H | CH₂—C≡C—CH₃ | CH₃ | OCH₃ | N | |
| H | CH₃ | CH₃ | CH₂—C≡C—CH₃ | OCH₃ | OCH₃ | N | |
| H | CH₃ | H | CH₂—CH₂—C≡CH | OCH₃ | Cl | CH | |
| H | CH₃ | H | CH₂—CH₂—C≡CH | CH₃ | CH₃ | CH | |
| H | CH₃ | H | CH₂—CH₂—C≡CH | CH₃ | OCH₃ | CH | |
| H | CH₃ | H | CH₂—CH₂—C≡CH | OCH₃ | OCH₃ | CH | |
| H | CH₃ | H | CH₂—CH₂—C≡CH | CH₃ | CH₃ | N | |
| H | CH₃ | H | CH₂—CH₂—C≡CH | CH₃ | OCH₃ | N | |
| H | CH₃ | H | CH₂—CH₂—C≡CH | OCH₃ | OCH₃ | N | |
| H | CH₃ | H | CH₂—C≡C—CH(CH₃)₂ | OCH₃ | Cl | CH | |
| H | CH₃ | H | CH₂—C≡C—CH(CH₃)₂ | CH₃ | CH₃ | CH | |
| CH₃ | CH₃ | H | CH₂—C≡C—CH(CH₃)₂ | CH₃ | OCH₃ | CH | |
| H | CH₃ | H | C≡C—(CH₂)₆CH₃ | OCH₃ | OCH₃ | CH | |
| H | CH₃ | H | C≡C—(CH₂)₆CH₃ | CH₃ | CH₃ | N | |
| H | CH₃ | H | C≡C—(CH₂)₆CH₃ | CH₃ | OCH₃ | N | |
| H | CH₃ | H | CH₂(CH₂)₇C≡CH | OCH₃ | OCH₃ | N | |
| H | CH₃ | H | CH₂(CH₂)₇C≡CH | OCH₃ | Cl | CH | |
| H | CH₃ | H | CH₂—CH(O)CH₂ (epoxide) | CH₃ | CH₃ | CH | |
| H | CH₃ | H | CH₂—CH(O)CH₂ (epoxide) | CH₃ | OCH₃ | CH | |
| H | CH₃ | H | CH₂—C(O)H—CH₂ (epoxide) | OCH₃ | OCH₃ | CH | |
| H | CH₃ | H | CH₂—CH(O)CH₂ (epoxide) | CH₃ | CH₃ | N | |
| H | CH₃ | H | CH₂—CH(O)CH₂ (epoxide) | CH₃ | OCH₃ | N | |
| H | CH₃ | H | CH₂—CH(O)CH₂ (epoxide) | OCH₃ | OCH₃ | N | |
| H | CH₃ | H | CH₂—CH(O)CH₂ (epoxide) | OCH₃ | Cl | CH | |
| H | CH₃ | H | CH₂—CH₂—CH(O)CH—CH₃ | CH₃ | CH₃ | CH | |
| H | CH₃ | H | CH₂—CH₂—CH(O)CH—CH₃ | CH₃ | OCH₃ | CH | |
| H | CH₃ | H | CH₂—CH₂—CH(O)CH—CH₃ | OCH₃ | OCH₃ | CH | |
| H | CH₃ | H | CH₂—CH₂—CH(O)CH—CH₃ | CH₃ | CH₃ | N | |
| H | CH₃ | H | CH₂—CH₂—CH(O)CH—CH₃ | CH₃ | OCH₃ | N | |
| H | CH₃ | H | CH₂—CH₂—CH(O)CH—CH₃ | OCH₃ | OCH₃ | N | |
| H | CH₃ | H | CH₂—CH₂—CH(O)CH—CH₃ | OCH₃ | Cl | CH | |
| H | CH₃ | H | CH₂—CH₂—CH(O)CH₂ | CH₃ | CH₃ | CH | |
| H | CH₃ | H | CH₂—CH₂—CH(O)CH₂ | CH₃ | OCH₃ | CH | |
| H | CH₃ | H | CH₂—CH₂—CH(O)CH₂ | OCH₃ | OCH₃ | CH | |
| H | CH₃ | H | CH₂—CH₂—CH(O)CH₂ | CH₃ | CH₃ | N | |
| H | CH₃ | H | CH₂—CH₂—CH(O)CH₂ | OCH₃ | OCH₃ | N | |

TABLE IIa-continued

General Structure IIa

| R | $R_1$ | $R_2$ | $R_3$ | X | Y | Z | m.p. (°C.) |
|---|---|---|---|---|---|---|---|
| H | $CH_3$ | H | $CH_2-CH_2-\overset{\displaystyle O}{\overset{|}{CH}}-CH_2$ | $OCH_3$ | Cl | CH | |
| H | $CH_3$ | H | cyclobutyl | $CH_3$ | $CH_3$ | CH | |
| H | $CH_3$ | H | cyclobutyl | $CH_3$ | $OCH_3$ | CH | |
| H | $CH_3$ | H | cyclobutyl | $OCH_3$ | $OCH_3$ | CH | |
| H | $CH_3$ | H | cyclobutyl | $CH_3$ | $CH_3$ | N | |
| H | $CH_3$ | H | cyclobutyl | $CH_3$ | $OCH_3$ | N | |
| H | $CH_3$ | H | cyclobutyl | $OCH_3$ | $OCH_3$ | N | |
| H | $CH_3$ | H | cyclobutyl | $OCH_3$ | Cl | CH | |
| H | $CH_3$ | H | cyclopentyl | $CH_3$ | $CH_3$ | CH | |
| H | $CH_3$ | H | cyclopentyl | $CH_3$ | $OCH_3$ | CH | |
| H | $CH_3$ | H | cyclopentyl | $OCH_3$ | $OCH_3$ | CH | |
| H | $CH_3$ | H | cyclopentyl | $CH_3$ | $CH_3$ | N | |
| H | $CH_3$ | H | cyclopentyl | $CH_3$ | $OCH_3$ | N | |
| H | $CH_3$ | $CH_3$ | cyclopentyl | $OCH_3$ | $OCH_3$ | N | |
| H | $CH_3$ | H | cyclopentyl | $OCH_3$ | Cl | CH | |
| H | $CH_3$ | H | cyclohexyl | $CH_3$ | $CH_3$ | CH | |
| H | $CH_3$ | H | cyclohexyl | $CH_3$ | $OCH_3$ | CH | |
| H | $CH_3$ | H | cyclohexyl | $OCH_3$ | $OCH_3$ | CH | |
| H | $CH_3$ | H | cyclohexyl | $CH_3$ | $CH_3$ | N | |
| H | $CH_3$ | H | cyclohexyl | $CH_3$ | $OCH_3$ | N | |
| H | $CH_3$ | $CH_3$ | cyclohexyl | $OCH_3$ | $OCH_3$ | N | |
| H | $CH_3$ | H | cyclohexyl | $OCH_3$ | Cl | CH | |
| H | $CH_3$ | H | cyclopropyl | $CH_3$ | $CH_3$ | CH | |
| $CH_3$ | $CH_3$ | H | cyclopropyl | $CH_3$ | $OCH_3$ | CH | |
| H | $CH_3$ | H | cyclopropyl | $OCH_3$ | $OCH_3$ | CH | |
| H | $CH_3$ | H | cyclopropyl | $CH_3$ | $CH_3$ | N | |
| H | $CH_3$ | H | cyclopropyl | $CH_3$ | $OCH_3$ | N | |
| H | $CH_3$ | H | cyclopropyl | $OCH_3$ | $OCH_3$ | N | |
| H | $CH_3$ | H | cyclopropyl | $OCH_3$ | Cl | CH | |
| H | $CH_3$ | H | $CH_2$—cyclopropyl | $CH_3$ | $CH_3$ | CH | |
| H | $CH_3$ | H | $CH_2$—cyclopropyl | $CH_3$ | $OCH_3$ | CH | |
| H | $CH_3$ | H | $CH_2$—cyclopropyl | $OCH_3$ | $OCH_3$ | CH | |
| H | $CH_3$ | H | $CH_2$—cyclopropyl | $CH_3$ | $CH_3$ | N | |
| H | $CH_3$ | H | $CH_2$—cyclopropyl | $CH_3$ | $OCH_3$ | N | |
| H | $CH_3$ | H | $CH_2$—cyclopropyl | $OCH_3$ | $OCH_3$ | N | |
| H | $CH_3$ | H | $CH_2$—cyclopropyl | $OCH_3$ | Cl | CH | |
| H | $CH_3$ | H | $CH_2$—cyclopentyl | $CH_3$ | $CH_3$ | CH | |
| H | $CH_3$ | H | $CH_2$—cyclopentyl | $CH_3$ | $OCH_3$ | CH | |
| H | $CH_3$ | H | $CH_2$—cyclopentyl | $OCH_3$ | $OCH_3$ | CH | |
| H | $CH_3$ | H | $CH_2$—cyclopentyl | $CH_3$ | $CH_3$ | N | |
| H | $CH_3$ | H | $CH_2$—cyclopentyl | $CH_3$ | $OCH_3$ | N | |
| H | $CH_3$ | H | $CH_2$—cyclopentyl | $OCH_3$ | $OCH_3$ | N | |
| H | $CH_3$ | H | $CH_2$—cyclopentyl | $OCH_3$ | Cl | CH | |
| H | $CH_3$ | H | $C_6H_5$ | $CH_3$ | $CH_3$ | CH | |
| H | $CH_3$ | H | $C_6H_5$ | $CH_3$ | $OCH_3$ | CH | |
| H | $CH_3$ | H | $C_6H_5$ | $OCH_3$ | $OCH_3$ | CH | |
| H | $CH_3$ | H | $C_6H_5$ | $CH_3$ | $CH_3$ | N | |
| H | $CH_3$ | H | $C_6H_5$ | $CH_3$ | $OCH_3$ | N | |
| H | $CH_3$ | H | $C_6H_5$ | $OCH_3$ | Cl | CH | |
| H | $CH_3$ | H | $CH=CH-CF_3$ | $CH_3$ | $CH_3$ | CH | |
| H | $CH_3$ | H | $CH=CH-CF_3$ | $CH_3$ | $OCH_3$ | CH | |
| H | $CH_3$ | H | $CH=CH-CF_3$ | $OCH_3$ | $OCH_3$ | CH | |
| H | $CH_3$ | H | $CH=CH-CF_3$ | $CH_3$ | $CH_3$ | N | |
| H | $CH_3$ | H | $CH=CH-CF_3$ | $CH_3$ | $OCH_3$ | N | |
| H | $CH_3$ | H | $CH=CH-CF_3$ | $OCH_3$ | $OCH_3$ | N | |
| H | $CH_3$ | H | $CH=CH-CF_3$ | $OCH_3$ | Cl | CH | |
| H | $CH_3$ | H | $CH_2-C{\equiv}C-CF_3$ | $CH_3$ | $CH_3$ | CH | |
| H | $CH_3$ | H | $CH_2-C{\equiv}C-CF_3$ | $CH_3$ | $OCH_3$ | CH | |
| H | $CH_3$ | H | $CH_2-C{\equiv}C-CF_3$ | $OCH_3$ | $OCH_3$ | CH | |
| H | $CH_3$ | H | $CH_2-C{\equiv}C-CF_3$ | $CH_3$ | $CH_3$ | N | |
| H | $CH_3$ | H | $CH_2-C{\equiv}C-CF_3$ | $CH_3$ | $OCH_3$ | N | |
| H | $CH_3$ | $CH_3$ | $CH_2-C{\equiv}C-CF_3$ | $OCH_3$ | $OCH_3$ | N | |
| H | $CH_3$ | H | $CH_2-CH=CF_2$ | $OCH_3$ | Cl | CH | |
| H | $CH_3$ | H | $CH=CH-CH_2Cl$ | $CH_3$ | $CH_3$ | CH | |
| H | $CH_3$ | H | $CH=CH-CH_2Cl$ | $CH_3$ | $OCH_3$ | CH | |
| H | $CH_3$ | H | $CH=CH-CH_2Cl$ | $OCH_3$ | $OCH_3$ | CH | |
| H | $CH_3$ | H | $CH=CH-CH_2Cl$ | $CH_3$ | $CH_3$ | N | |
| H | $CH_3$ | H | $CH=CH-CH_2Cl$ | $CH_3$ | $OCH_3$ | N | |
| H | $CH_3$ | H | $CH=CH-CH_2Cl$ | $OCH_3$ | $OCH_3$ | N | |
| H | $CH_3$ | H | $CH_2-C\!\!\begin{array}{c}\diagup CHF\\ \diagdown CH_2\end{array}$ | $OCH_3$ | Cl | CH | |

TABLE IIa-continued

General Structure IIa

| R | R₁ | R₂ | R₃ | X | Y | Z | m.p. (°C.) |
|---|---|---|---|---|---|---|---|
| H | CH₃ | H | CH₂—C(CHF)(CH₂) (cyclopropane with CHF) | CH₃ | CH₃ | CH | |
| CH₃ | CH₃ | H | CH₂—C(CHF)(CH₂) | CH₃ | OCH₃ | CH | |
| H | CH₃ | H | CH₂—C(CHF)(CH₂) | OCH₃ | OCH₃ | CH | |
| H | CH₃ | H | CH₂—C(CHF)(CH₂) | CH₃ | CH₃ | N | |
| H | CH₃ | H | CH₂—C(CHF)(CH₂) | CH₃ | OCH₃ | N | |
| H | CH₃ | H | CH₂—C≡C—CH₂Br | OCH₃ | OCH₃ | N | |
| H | CH₃ | H | CH₂—C≡C—CH₂Br | OCH₃ | Cl | CH | |
| H | CH₃ | H | CH₂—CH=CHOCH₃ | CH₃ | CH₃ | CH | |
| H | CH₃ | H | CH₂—CH=CHOCH₃ | CH₃ | OCH₃ | CH | |
| H | CH₃ | H | CH₂—CH=CHOCH₃ | OCH₃ | OCH₃ | CH | |
| H | CH₃ | H | CH₂—CH=CHOCH₃ | CH₃ | CH₃ | N | |
| H | CH₃ | H | CH₂—C≡C—OCH₃ | CH₃ | OCH₃ | N | |
| H | CH₃ | H | CH₂—C≡C—OCH₃ | OCH₃ | OCH₃ | N | |
| H | CH₃ | H | CH₂—CH₂—CH=CHCN | OCH₃ | Cl | CH | |
| H | CH₃ | H | CH₂—CH₂—CH=CHCN | CH₃ | CH₃ | CH | |
| H | CH₃ | H | CH₂—CH₂—CH=CHCN | CH₃ | OCH₃ | CH | |
| H | CH₃ | H | CH(OSO₂CH₃)C≡CH | OCH₃ | OCH₃ | CH | |
| H | CH₃ | H | CH(OSO₂CH₃)C≡CH | CH₃ | CH₃ | N | |
| H | CH₃ | H | CH(OSO₂CH₃)C≡CH | CH₃ | OCH₃ | N | |
| H | CH₃ | H | CH(OSO₂CH₃)C≡CH | OCH₃ | OCH₃ | N | |
| H | CH₃ | H | CH(OSO₂CH₃)C≡CH | OCH₃ | Cl | CH | |
| H | CH₃ | H | C≡C—Si(CH₃)₃ | CH₃ | CH₃ | CH | |
| H | CH₃ | H | C≡C—Si(CH₃)₃ | CH₃ | OCH₃ | CH | |
| H | CH₃ | H | C≡C—Si(CH₃)₃ | OCH₃ | OCH₃ | CH | |
| H | CH₃ | H | CH₂—CH=CHP(O)(CH₃)₂ | CH₃ | CH₃ | N | |
| H | CH₃ | H | CH₂—CH=CHP(O)(CH₃)₂ | OCH₃ | OCH₃ | N | |
| H | CH₃ | H | CH₂—CH=CHP(O)(CH₃)₂ | OCH₃ | Cl | CH | |
| H | CH₃ | H | CH₂—CH=CHP(O)(CH₃)₂ | CH₃ | CH₃ | CH | |
| H | CH₃ | H | CH₂—CH=CHP(O)(CH₃)₂ | CH₃ | OCH₃ | CH | |
| H | CH₃ | H | CH=CH—OSi(CH₃)₃ | OCH₃ | OCH₃ | CH | |
| H | CH₃ | H | CH=CH—OSi(CH₃)₃ | CH₃ | CH₃ | N | |
| H | CH₃ | H | CH=CH—OSi(CH₃)₃ | CH₃ | OCH₃ | N | |
| H | CH₃ | H | CH=CH—OSi(CH₃)₃ | OCH₃ | OCH₃ | N | |
| H | CH₃ | H | CH₂(CH₂)₅CH=CH—CN | OCH₃ | Cl | CH | |
| H | CH₃ | H | CH₂(CH₂)₅CH=CH—CN | CH₃ | CH₃ | CH | |
| H | CH₃ | H | CH₂(CH₂)₅CH=CH—CN | CH₃ | OCH₃ | CH | |
| H | CH₃ | H | CH₂(CH₂)₅CH=CH—CN | OCH₃ | OCH₃ | CH | |
| H | CH₃ | H | CH₂(CH₂)₅CH=CH—CN | CH₃ | CH₃ | N | |
| H | CH₃ | H | CH=CH—CH₂SCN | CH₃ | OCH₃ | N | |
| H | CH₃ | CH₃ | CH=CH—CH₂SCN | OCH₃ | OCH₃ | N | |
| H | CH₃ | H | CH=CH—CH₂SCN | OCH₃ | Cl | CH | |
| H | CH₃ | H | C≡C—CH₂OCH₃ | CH₃ | CH₃ | CH | |
| H | CH₃ | H | C≡C—C≡C—CH₂OCH₃ | CH₃ | OCH₃ | CH | |
| H | CH₃ | H | C≡C—CH₂OCH₃ | OCH₃ | OCH₃ | CH | |
| H | CH₃ | H | CH₂—CH=CH—CH₂SCH₃ | CH₃ | CH₃ | N | |
| H | CH₃ | H | CH₂—CH=CH—CH₂SCH₃ | CH₃ | OCH₃ | N | |
| H | CH₃ | H | CH₂—CH=CH—CH₂SCH₃ | OCH₃ | OCH₃ | N | |
| H | CH₃ | H | CH₂—CH=CH—CH₂SCH₃ | OCH₃ | Cl | CH | |
| H | CH₃ | H | CH=CH—CH₂N(CH₃)₂ | CH₃ | CH₃ | CH | |
| CH₃ | CH₃ | H | CH=CH—CH₂N(CH₃)₂ | CH₃ | OCH₃ | CH | |
| H | CH₃ | H | CH=CH—CH₂N(CH₃)₂ | OCH₃ | OCH₃ | CH | |
| H | CH₃ | H | CH₂—CH—P(O)(OCH₃)₂ | CH₃ | CH₃ | N | |
| H | CH₃ | H | CH₂—CH=CH—P(O)(OCH₃)₂ | CH₃ | OCH₃ | N | |
| H | CH₃ | H | CH₂—CH=CH—P(O)(OCH₃)₂ | OCH₃ | OCH₃ | N | |
| H | CH₃ | H | CH₂—CH=CH—P(O)(OCH₃)₂ | OCH₃ | Cl | CH | |
| H | CH₃ | H | SCH₃ | CH₃ | CH₃ | CH | |
| H | CH₃ | H | SCH₃ | CH₃ | OCH₃ | CH | |
| H | CH₃ | H | SCH₃ | OCH₃ | OCH₃ | CH | |
| H | CH₃ | H | SCH₃ | CH₃ | CH₃ | N | |
| H | CH₃ | H | SCH₃ | CH₃ | OCH₃ | N | |

TABLE IIa-continued

General Structure IIa

| R | $R_1$ | $R_2$ | $R_3$ | X | Y | Z | m.p. (°C.) |
|---|---|---|---|---|---|---|---|
| H | $CH_3$ | H | $SCH_3$ | $OCH_3$ | $OCH_3$ | N | |
| H | $CH_3$ | H | $SCH_3$ | $OCH_3$ | Cl | CH | |
| H | $CH_3$ | H | $SCH_2CF_3$ | $CH_3$ | $CH_3$ | CH | |
| H | $CH_3$ | H | $SCH_2CH_3$ | $CH_3$ | $OCH_3$ | CH | |
| H | $CH_3$ | H | $SCH_2CH_3$ | $OCH_3$ | $OCH_3$ | CH | |
| H | $CH_3$ | H | $SCH_2CH_3$ | $CH_3$ | $CH_3$ | N | |
| H | $CH_3$ | H | $SCH_2CH_3$ | $CH_3$ | $OCH_3$ | N | |
| H | $CH_3$ | H | $SCH_2CH_3$ | $OCH_3$ | $OCH_3$ | N | |
| H | $CH_3$ | H | $SCH_2CH_3$ | $OCH_3$ | Cl | CH | |
| H | $CH_3$ | H | $SO_2CH_3$ | $CH_3$ | $CH_3$ | CH | |
| H | $CH_3$ | H | $SO_2CH_3$ | $CH_3$ | $OCH_3$ | CH | |
| H | $CH_3$ | H | $SO_2CH_3$ | $OCH_3$ | $OCH_3$ | CH | |
| H | $CH_3$ | H | $SO_2CH_3$ | $CH_3$ | $CH_3$ | N | |
| H | $CH_3$ | H | $SO_2CH_3$ | $OCH_3$ | $OCH_3$ | N | |
| H | $CH_3$ | H | $SO_2CH_3$ | $OCH_3$ | Cl | CH | |
| H | $CH_3$ | H | $SO_2CH_2CH_3$ | $CH_3$ | $CH_3$ | $OCH_3$ | |
| H | $CH_3$ | H | $SO_2CH_2CH_3$ | $CH_3$ | $OCH_3$ | CH | |
| H | $CH_3$ | H | $SO_2CH_2CH_3$ | $OCH_3$ | $OCH_3$ | CH | |
| H | $CH_3$ | H | $SO_2CH_2CH_3$ | $CH_3$ | $CH_3$ | N | |
| H | $CH_3$ | H | $SO_2CH_2CH_3$ | $CH_3$ | $OCH_3$ | N | |
| H | $CH_3$ | H | $SO_2CH_2CH_3$ | $OCH_3$ | $OCH_3$ | N | |
| H | $CH_3$ | H | $SO_2CH_2CH_3$ | $OCH_3$ | Cl | CH | |
| H | $CH_3$ | H | $OCH_3$ | $CH_3$ | $CH_3$ | CH | |
| H | $CH_3$ | H | $OCH_3$ | $CH_3$ | $OCH_3$ | CH | |
| H | $CH_3$ | H | $OCH_3$ | $OCH_3$ | $OCH_3$ | CH | |
| H | $CH_3$ | H | $OCH_3$ | $CH_3$ | $CH_3$ | N | |
| H | $CH_3$ | H | $OCH_3$ | $CH_3$ | $OCH_3$ | N | |
| H | $CH_3$ | $CH_3$ | $OCH_3$ | $OCH_3$ | $OCH_3$ | N | |
| H | $CH_3$ | H | $OCH_3$ | $OCH_3$ | Cl | CH | |
| H | $CH_3$ | H | $OCH_2CH_3$ | $CH_3$ | $CH_3$ | CH | |
| H | $CH_3$ | H | $OCH_2CH_3$ | $CH_3$ | $OCH_3$ | CH | |
| H | $CH_3$ | H | $OCH_2CH_3$ | $OCH_3$ | | CH | |
| H | $CH_3$ | H | $OCH_2CH_3$ | $CH_3$ | $CH_3$ | N | |
| H | $CH_3$ | H | $OCH_2CH_3$ | $CH_3$ | $OCH_3$ | N | |
| H | $CH_3$ | H | $OCH_2CH_3$ | $OCH_3$ | $OCH_3$ | N | |
| H | $CH_3$ | H | $OCH_2CH_3$ | $OCH_3$ | Cl | CH | |
| H | $CH_3$ | H | $OCH(CH_3)_2$ | $CH_3$ | $CH_3$ | CH | |
| $CH_3$ | $CH_3$ | H | $OCH(CH_3)_2$ | $CH_3$ | $OCH_3$ | CH | |
| H | $CH_3$ | H | $OCH(CH_3)_2$ | $OCH_3$ | $OCH_3$ | CH | |
| H | $CH_3$ | H | $OCH(CH_3)_2$ | $CH_3$ | $CH_3$ | N | |
| H | $CH_3$ | H | $OCH(CH_3)_2$ | $CH_3$ | $OCH_3$ | N | |
| H | $CH_3$ | H | $OCH(CH_3)_2$ | $OCH_3$ | $OCH_3$ | N | |
| H | $CH_3$ | H | $OCH(CH_3)_2$ | $OCH_3$ | Cl | CH | |
| H | $CH_3$ | H | $C(O)CH_3$ | $CH_3$ | $CH_3$ | CH | |
| H | $CH_3$ | H | $C(O)CH_3$ | $CH_3$ | $OCH_3$ | CH | |
| H | $CH_3$ | H | $C(O)CH_3$ | $OCH_3$ | $OCH_3$ | CH | |
| H | $CH_3$ | H | $C(O)CH_3$ | $CH_3$ | $CH_3$ | N | |
| H | $CH_3$ | H | $C(O)CH_3$ | $CH_3$ | $OCH_3$ | N | |
| H | $CH_3$ | H | $C(O)CH_3$ | $OCH_3$ | $OCH_3$ | N | |
| H | $CH_3$ | H | $C(O)CH_3$ | $OCH_3$ | Cl | CH | |
| H | $CH_3$ | H | $C(O)CH_2CH_3$ | $CH_3$ | $CH_3$ | CH | |
| H | $CH_3$ | H | $C(O)CH_2CH_3$ | $CH_3$ | $OCH_3$ | CH | |
| H | $CH_3$ | H | $C(O)CH_2CH_3$ | $OCH_3$ | $OCH_3$ | CH | |
| H | $CH_3$ | H | $C(O)CH_2CH_3$ | $CH_3$ | $CH_3$ | N | |
| H | $CH_3$ | H | $C(O)CH_2CH_3$ | $CH_3$ | $OCH_3$ | N | |
| H | $CH_3$ | H | $C(O)CH_2CH_3$ | $OCH_3$ | $OCH_3$ | N | |
| H | $CH_3$ | H | $C(O)CH_2CH_3$ | $OCH_3$ | Cl | CH | |
| H | $CH_3$ | H | $C(O)(CH)(CH_3)_2$ | $CH_3$ | $CH_3$ | CH | |
| H | $CH_3$ | H | $C(O)(CH)(CH_3)_2$ | $CH_3$ | $OCH_3$ | CH | |
| H | $CH_3$ | H | $C(O)(CH)(CH_3)_2$ | $OCH_3$ | $OCH_3$ | CH | |
| H | $CH_3$ | H | $C(O)(CH)(CH_3)_2$ | $CH_3$ | $CH_3$ | N | |
| H | $CH_3$ | H | $C(O)(CH)(CH_3)_2$ | $OCH_3$ | $OCH_3$ | N | |
| H | $CH_3$ | H | $C(O)(CH)(CH_3)_2$ | $OCH_3$ | Cl | CH | |
| H | $CH_3$ | H | $C(O)CHF_2$ | $CH_3$ | $CH_3$ | CH | |
| H | $CH_3$ | H | $C(O)CHF_2$ | $CH_3$ | $OCH_3$ | CH | |
| H | $CH_3$ | H | $C(O)CHF_2$ | $OCH_3$ | $OCH_3$ | CH | |
| H | $CH_3$ | H | $C(O)CF_3$ | $CH_3$ | $CH_3$ | N | |
| H | $CH_3$ | H | $C(O)CF_3$ | $CH_3$ | $OCH_3$ | N | |
| H | $CH_3$ | H | $C(O)CF_3$ | $OCH_3$ | $OCH_3$ | N | |
| H | $CH_3$ | H | $C(O)CF_3$ | $OCH_3$ | Cl | CH | |
| H | $CH_3$ | H | $C(O)CH_2CH_2CH_3$ | $CH_3$ | $CH_3$ | CH | |
| H | $CH_3$ | H | $C(O)CH_2CH_2CH_3$ | $CH_3$ | $OCH_3$ | CH | |
| H | $CH_3$ | H | $C(O)CH_2CH_2CH_3$ | $OCH_3$ | $OCH_3$ | CH | |
| H | $CH_3$ | H | $C(O)CH_2CH_2CH_3$ | $CH_3$ | $CH_3$ | N | |
| H | $CH_3$ | H | $C(O)CH_2CH_2CH_3$ | $CH_3$ | $OCH_3$ | N | |
| H | $CH_3$ | $CH_3$ | $C(O)CH_2CH_2CH_3$ | $OCH_3$ | $OCH_3$ | N | |
| H | $CH_3$ | H | $C(O)CH_2CH_2CH_3$ | $OCH_3$ | Cl | CH | |
| H | $CH_3$ | H | $C(O)CH_2OCH_3$ | $CH_3$ | $CH_3$ | CH | |
| H | $CH_3$ | H | $C(O)CH_2OCH_3$ | $CH_3$ | $OCH_3$ | CH | |
| H | $CH_3$ | H | $C(O)CH_2OCH_3$ | $OCH_3$ | $OCH_3$ | CH | |

TABLE IIa-continued

General Structure IIa

| R | $R_1$ | $R_2$ | $R_3$ | X | Y | Z | m.p. (°C.) |
|---|---|---|---|---|---|---|---|
| H | $CH_3$ | H | $C(O)CH_2OCH_3$ | $CH_3$ | $CH_3$ | N | |
| H | $CH_3$ | H | $C(O)CH_2Cl$ | $CH_3$ | $OCH_3$ | N | |
| H | $CH_3$ | H | $C(O)CH_2Cl$ | $OCH_3$ | $OCH_3$ | N | |
| H | $CH_3$ | H | $C(O)CH_2Cl$ | $OCH_3$ | Cl | CH | |
| H | $CH_3$ | H | $C(O)CH_2CH(CH_3)CN$ | $CH_3$ | $CH_3$ | CH | |
| $CH_3$ | $CH_3$ | H | $C(O)CH_2CH(CH_3)CN$ | $CH_3$ | $OCH_3$ | CH | |
| H | $CH_3$ | H | $C(O)CH_2N(CH_3)_2$ | $OCH_3$ | $OCH_3$ | CH | |
| H | $CH_3$ | H | $C(O)CH_2N(CH_3)_2$ | $CH_3$ | $CH_3$ | N | |
| H | $CH_3$ | H | $C(O)CH_2CH=CH_2$ | $CH_3$ | $OCH_3$ | N | |
| H | $CH_3$ | H | $C(O)CH_2CH=CH_2$ | $OCH_3$ | $OCH_3$ | N | |
| H | $CH_3$ | H | $C(O)CH_2C\equiv CH$ | $OCH_3$ | Cl | CH | |
| H | $CH_3$ | H | $CO_2CH_3$ | $CH_3$ | $CH_3$ | CH | |
| H | $CH_3$ | H | $CO_2CH_3$ | $CH_3$ | $OCH_3$ | CH | |
| H | $CH_3$ | H | $CO_2CH_3$ | $OCH_3$ | $OCH_3$ | CH | |
| H | $CH_3$ | H | $CO_2CH_3$ | $CH_3$ | $CH_3$ | N | |
| H | $CH_3$ | H | $CO_2CH_3$ | $CH_3$ | $OCH_3$ | N | |
| H | $CH_3$ | H | $CO_2CH_3$ | $OCH_3$ | $OCH_3$ | N | |
| H | $CH_3$ | H | $CO_2CH_3$ | $OCH_3$ | Cl | CH | |
| H | $CH_3$ | H | $CO_2CH_2CH_3$ | $CH_3$ | $CH_3$ | CH | |
| H | $CH_3$ | H | $CO_2CH_2CH_3$ | $CH_3$ | $OCH_3$ | CH | |
| H | $CH_3$ | H | $CO_2CH_2CH_3$ | $OCH_3$ | $OCH_3$ | CH | |
| H | $CH_3$ | H | $CO_2CH_2CH_3$ | $CH_3$ | $CH_3$ | N | |
| H | $CH_3$ | H | $CO_2CH_2CH_3$ | $CH_3$ | $OCH_3$ | N | |
| H | $CH_3$ | H | $CO_2CH_2CH_3$ | $OCH_3$ | $OCH_3$ | N | |
| H | $CH_3$ | H | $CO_2CH_2CH_3$ | $OCH_3$ | Cl | CH | |
| H | $CH_3$ | H | $CO_2CH_2CF_3$ | $CH_3$ | $CH_3$ | CH | |
| H | $CH_3$ | H | $CO_2CH_2CF_3$ | $CH_3$ | $OCH_3$ | CH | |
| H | $CH_3$ | H | $CO_2CH_2CF_3$ | $OCH_3$ | $OCH_3$ | CH | |
| H | $CH_3$ | H | $CO_2CH_2CF_3$ | $CH_3$ | $CH_3$ | N | |
| H | $CH_3$ | H | $CO_2CF_3$ | $OCH_3$ | $OCH_3$ | N | |
| H | $CH_3$ | H | $CO_2CF_3$ | $OCH_3$ | Cl | CH | |
| H | $CH_3$ | H | $CO_2CF_3$ | $CH_3$ | $CH_3$ | CH | |
| H | $CH_3$ | H | $CO_2CH_2C\equiv CH$ | $CH_3$ | $OCH_3$ | CH | |
| H | $CH_3$ | H | $CO_2CH_2C\equiv CH$ | $OCH_3$ | $OCH_3$ | CH | |
| H | $CH_3$ | H | $CO_2CH_2C\equiv CH$ | $CH_3$ | $CH_3$ | N | |
| H | $CH_3$ | H | $CO_2CH_2C\equiv CH$ | $CH_3$ | $OCH_3$ | N | |
| H | $CH_3$ | H | $CO_2CH_2C\equiv CH$ | $OCH_3$ | $OCH_3$ | N | |
| H | $CH_3$ | H | $CO_2CH_2CH=CH_2$ | $OCH_3$ | Cl | CH | |
| H | $CH_3$ | H | $CO_2CH_2CH=CH_2$ | $CH_3$ | $CH_3$ | CH | |
| H | $CH_3$ | H | $CO_2CH_2CH=CH_2$ | $CH_3$ | $OCH_3$ | CH | |
| H | $CH_3$ | H | $CO_2CH_2CH=CH_2$ | $OCH_3$ | $OCH_3$ | CH | |
| H | $CH_3$ | H | $CO_2CH_2CH=CH_2$ | $CH_3$ | $CH_3$ | N | |
| H | $CH_3$ | H | $CO_2CH_2CH=CH_2$ | $CH_3$ | $OCH_3$ | N | |
| H | $CH_3$ | $CH_3$ | $CO_2CH_3$ | $OCH_3$ | $OCH_3$ | N | |
| H | $CH_3$ | H | $CO_2CF_3$ | $OCH_3$ | Cl | CH | |
| H | $CH_3$ | H | $CO_2CF_3$ | $CH_3$ | $CH_3$ | CH | |
| H | $CH_3$ | H | $CO_2CF_3$ | $CH_3$ | $OCH_3$ | CH | |
| H | $CH_3$ | H | $CO_2CF_3$ | $OCH_3$ | $OCH_3$ | CH | |
| H | $CH_3$ | H | $CO_2CH_2CH_2Cl$ | $CH_3$ | $CH_3$ | N | |
| H | $CH_3$ | H | $CO_2CH_2CH_2Cl$ | $CH_3$ | $OCH_3$ | N | |
| H | $CH_3$ | H | $CO_2CH_2CH_2Cl$ | $OCH_3$ | $OCH_3$ | N | |
| H | $CH_3$ | H | $CO_2CH_2CH_2P(O)(CH_3)_2$ | $OCH_3$ | Cl | CH | |
| H | $CH_3$ | H | $CO_2CH_2CH_2P(O)(CH_3)_2$ | $CH_3$ | $CH_3$ | CH | |
| $CH_3$ | $CH_3$ | H | $CO_2C(CH_3)_3$ | $CH_3$ | $OCH_3$ | CH | |
| H | $CH_3$ | H | $CO_2C(CH_3)_3$ | $OCH_3$ | $OCH_3$ | CH | |
| H | $CH_3$ | H | $CO_2CH_2(CH_2)_4CH_3$ | $CH_3$ | $CH_3$ | N | |
| H | $CH_3$ | H | $CO_2CH_2(CH_2)_4CH_3$ | $CH_3$ | $OCH_3$ | N | |
| H | $CH_3$ | H | $CO_2CH_2OCH_3$ | $OCH_3$ | $OCH_3$ | N | |
| H | $CH_3$ | H | $CO_2CH_2OCH_3$ | $OCH_3$ | Cl | CH | |
| H | $CH_3$ | H | $(C(O))_2OCH_3$ | $CH_3$ | $CH_3$ | CH | |
| H | $CH_3$ | H | $(C(O))_2OCH_3$ | $CH_3$ | $OCH_3$ | CH | |
| H | $CH_3$ | H | $(C(O))_2OCH_3$ | $OCH_3$ | $OCH_3$ | CH | |
| H | $CH_3$ | H | $(C(O))_2OCH_3$ | $CH_3$ | $CH_3$ | N | |
| H | $CH_3$ | H | $(C(O))_2OCH_3$ | $CH_3$ | $OCH_3$ | N | |
| H | $CH_3$ | H | $(C(O))_2OCH_3$ | $OCH_3$ | $OCH_3$ | N | |
| H | $CH_3$ | H | $(C(O))_2OCH_3$ | $OCH_3$ | Cl | CH | |
| H | $CH_3$ | H | $(CO)_2CH_3$ | $CH_3$ | $CH_3$ | CH | |
| H | $CH_3$ | H | $(CO)_2CH_3$ | $CH_3$ | $OCH_3$ | CH | |
| H | $CH_3$ | H | $(CO)_2CH_3$ | $OCH_3$ | $OCH_3$ | CH | |
| H | $CH_3$ | H | $(CO)_2CH_3$ | $CH_3$ | $CH_3$ | N | |
| H | $CH_3$ | H | $(CO)_2CH_3$ | $CH_3$ | $OCH_3$ | N | |
| H | $CH_3$ | H | $(CO)_2CH_3$ | $OCH_3$ | $OCH_3$ | N | |
| H | $CH_3$ | H | $(CO)_2CH_3$ | $OCH_3$ | Cl | CH | |
| H | $CH_3$ | H | $C(O)N(CH_3)_2$ | $CH_3$ | $CH_3$ | CH | |
| H | $CH_3$ | H | $C(O)N(CH_3)_2$ | $CH_3$ | $OCH_3$ | CH | |
| H | $CH_3$ | H | $C(O)N(CH_3)_2$ | $OCH_3$ | $OCH_3$ | CH | |
| H | $CH_3$ | H | $C(O)N(CH_3)_2$ | $CH_3$ | $CH_3$ | N | |
| H | $CH_3$ | H | $C(O)N(CH_3)_2$ | $OCH_3$ | $OCH_3$ | N | |
| H | $CH_3$ | H | $C(O)N(CH_3)_2$ | $OCH_3$ | Cl | CH | |
| H | $CH_3$ | H | $C(O)N(CH_2CH_3)_2$ | $CH_3$ | $CH_3$ | CH | |

TABLE IIa-continued

General Structure IIa

| R | R₁ | R₂ | R₃ | X | Y | Z | m.p. (°C.) |
|---|---|---|---|---|---|---|---|
| H | CH₃ | H | C(O)N(CH₂CH₃)₂ | CH₃ | OCH₃ | CH | |
| H | CH₃ | H | C(O)N(CH₂CH₃)₂ | OCH₃ | OCH₃ | CH | |
| H | CH₃ | H | C(O)N(CH₂CH₃)₂ | CH₃ | CH₃ | N | |
| H | CH₃ | H | C(O)N(CH₂CH₃)₂ | CH₃ | OCH₃ | N | |
| H | CH₃ | H | C(O)N(CH₂CH₃)₂ | OCH₃ | OCH₃ | N | |
| H | CH₃ | H | C(O)N(CH₃)CH₂CH₃ | OCH₃ | Cl | CH | |
| H | CH₃ | H | C(O)N(CH₃)CH₂CH₃ | CH₃ | CH₃ | CH | |
| H | CH₃ | H | C(O)N(CH₃)CH₂CH₃ | CH₃ | OCH₃ | CH | |
| H | CH₃ | H | C(O)N(CH₃)CH₂CH₃ | OCH₃ | OCH₃ | CH | |
| H | CH₃ | H | C(O)N(CH₃)CH₂CH₃ | CH₃ | CH₃ | N | |
| H | CH₃ | H | C(O)N(CF₃)CH₃ | CH₃ | OCH₃ | N | |
| H | CH₃ | CH₃ | C(O)N(CF₃)CH₃ | OCH₃ | OCH₃ | N | |
| H | CH₃ | H | C(O)N(CF₃)CH₃ | OCH₃ | Cl | CH | |
| H | CH₃ | H | C(O)N(CH₃)OCH₃ | CH₃ | CH₃ | CH | |
| H | CH₃ | H | C(O)N(CH₃)OCH₃ | CH₃ | OCH₃ | CH | |
| H | CH₃ | H | C(O)N(CH₃)OCH₃ | OCH₃ | OCH₃ | CH | |
| H | CH₃ | H | C(O)N(CH₃)OCH₃ | CH₃ | CH₃ | N | |
| H | CH₃ | H | C(O)N(CH=CH₂)CH₃ | CH₃ | OCH₃ | N | |
| H | CH₃ | H | C(O)N(CH=CH₂)CH₃ | OCH₃ | OCH₃ | N | |
| H | CH₃ | H | C(O)N(CH=CH₂)CH₃ | OCH₃ | Cl | CH | |
| H | CH₃ | H | C(O)N(CH=CH₂)CH₃ | CH₃ | CH₃ | CH | |
| CH₃ | CH₃ | H | C(O)N(CH=CH₂)CH₃ | CH₃ | OCH₃ | CH | |
| H | CH₃ | H | C(O)N(CH₃)Ph | OCH₃ | OCH₃ | CH | |
| H | CH₃ | H | C(O)N(CH₃)Ph | CH₃ | CH₃ | N | |
| H | CH₃ | H | C(O)N(CH₃)Ph | CH₃ | OCH₃ | N | |
| H | CH₃ | H | C(O)N(OCH₃)₂ | OCH₃ | OCH₃ | N | |
| H | CH₃ | H | C(O)N(OCH₃)₂ | OCH₃ | Cl | CH | |
| H | CH₃ | H | CS₂CH₃ | CH₃ | CH₃ | CH | |
| H | CH₃ | H | CS₂CH₃ | CH₃ | OCH₃ | CH | |
| H | CH₃ | H | CS₂CH₃ | OCH₃ | OCH₃ | CH | |
| H | CH₃ | H | CS₂CH₃ | CH₃ | CH₃ | N | |
| H | ᵒCH₃ | H | CS₂CH₃ | CH₃ | OCH₃ | N | |
| H | CH₃ | H | CS₂CH₃ | OCH₃ | OCH₃ | N | |
| H | CH₃ | H | CS₂CH₃ | OCH₃ | Cl | CH | |
| H | CH₃ | H | CS₂CH₂CH₃ | CH₃ | CH₃ | CH | |
| H | CH₃ | H | CS₂CH₂CH₃ | CH₃ | OCH₃ | CH | |
| H | CH₃ | H | CS₂CH₂CH₃ | OCH₃ | OCH₃ | CH | |
| H | CH₃ | H | CS₂CH₂CH₃ | CH₃ | CH₃ | N | |
| H | CH₃ | H | CS₂CH₂CH₃ | CH₃ | OCH₃ | N | |
| H | CH₃ | H | CS₂CH₂CH=CH₂ | OCH₃ | OCH₃ | N | |
| H | CH₃ | H | CS₂CH₂CH=CH₂ | OCH₃ | Cl | CH | |
| H | CH₃ | H | CS₂CH₂CH=CH₂ | CH₃ | CH₃ | CH | |
| H | CH₃ | H | NH₂ | CH₃ | CH₃ | CH | |
| H | CH₃ | H | NH₂ | CH₃ | OCH₃ | CH | |
| H | CH₃ | H | NH₂ | OCH₃ | OCH₃ | CH | |
| H | CH₃ | H | NH₂ | CH₃ | CH₃ | N | |
| H | CH₃ | H | NH₂ | CH₃ | OCH₃ | N | |
| H | CH₃ | H | NH₂ | OCH₃ | OCH₃ | N | |
| H | CH₃ | H | NH₂ | OCH₃ | Cl | CH | |
| H | CH₃ | H | N(CH₃)₂ | CH₃ | CH₃ | CH | |
| H | CH₃ | H | N(CH₃)₂ | CH₃ | OCH₃ | CH | |
| H | CH₃ | H | N(CH₃)₂ | OCH₃ | OCH₃ | CH | |
| H | CH₃ | H | N(CH₃)₂ | CH₃ | CH₃ | N | |
| H | CH₃ | H | N(CH₃)₂ | CH₃ | OCH₃ | N | |
| H | CH₃ | CH₃ | N(CH₃)₂ | OCH₃ | OCH₃ | N | |
| H | CH₃ | H | N(CH₃)₂ | OCH₃ | Cl | CH | |
| H | CH₃ | H | N(CH₃)(CH₂CH₃) | CH₃ | CH₃ | CH | |
| H | CH₃ | H | N(CH₃)(CH₂CH₃) | CH₃ | OCH₃ | CH | |
| H | CH₃ | H | N(CH₃)(CH₂CH₃) | OCH₃ | OCH₃ | CH | |
| H | CH₃ | H | N(CH₃)OCH₃ | CH₃ | CH₃ | N | |
| H | CH₃ | H | N(CH₃)OCH₃ | CH₃ | OCH₃ | N | |
| H | CH₃ | H | N(CH₃)OCH₃ | OCH₃ | OCH₃ | N | |
| H | CH₃ | H | N(CH₃)CH=CH₂ | OCH₃ | Cl | CH | |
| H | CH₃ | H | N(CH₃)CH=CH₂ | CH₃ | CH₃ | CH | |
| CH₃ | CH₃ | H | N(CH₃)CH=CH₂ | CH₃ | OCH₃ | CH | |
| H | CH₃ | H | N(CH₃)CH=CH₂ | OCH₃ | OCH₃ | CH | |
| H | CH₃ | H | N(CH₂CH₃)₂ | CH₃ | CH₃ | N | |
| H | CH₃ | H | N(CH₂CH₃)₂ | CH₃ | OCH₃ | N | |
| H | CH₃ | H | N(CH₂CH₃)₂ | OCH₃ | OCH₃ | N | |
| H | CH₃ | H | N(CH₂CH₃)₂ | OCH₃ | Cl | CH | |
| H | CH₃ | H | OH | CH₃ | CH₃ | CH | |
| H | CH₃ | H | OH | CH₃ | OCH₃ | CH | |
| H | CH₃ | H | OH | OCH₃ | OCH₃ | CH | |
| H | CH₃ | H | OH | CH₃ | CH₃ | N | |
| H | CH₃ | H | OH | CH₃ | OCH₃ | N | |
| H | CH₃ | H | OH | OCH₃ | OCH₃ | N | |
| H | CH₃ | H | OH | OCH₃ | Cl | CH | |
| H | CH₃ | H | CN | CH₃ | CH₃ | CH | |
| H | CH₃ | H | CN | CH₃ | OCH₃ | CH | |
| H | CH₃ | H | CN | OCH₃ | OCH₃ | CH | |

TABLE IIa-continued

General Structure IIa

| R | R$_1$ | R$_2$ | R$_3$ | X | Y | Z | m.p. (°C.) |
|---|---|---|---|---|---|---|---|
| H | CH$_3$ | H | CN | CH$_3$ | CH$_3$ | N | |
| H | CH$_3$ | H | CN | CH$_3$ | OCH$_3$ | N | |
| H | CH$_3$ | H | CN | OCH$_3$ | OCH$_3$ | N | |
| H | CH$_3$ | H | CN | OCH$_3$ | Cl | CH | |
| H | CH$_3$ | H | P(O)(CH$_3$)$_2$ | CH$_3$ | CH$_3$ | CH | |
| H | CH$_3$ | H | P(O)(CH$_3$)$_2$ | CH$_3$ | OCH$_3$ | CH | |
| H | CH$_3$ | H | P(O)(CH$_3$)$_2$ | OCH$_3$ | OCH$_3$ | CH | |
| H | CH$_3$ | H | P(O)(CH$_3$)$_2$ | CH$_3$ | CH$_3$ | N | |
| H | CH$_3$ | H | P(O)(CH$_3$)$_2$ | OCH$_3$ | OCH$_3$ | N | |
| H | CH$_3$ | H | P(O)(OCH$_3$)$_2$ | OCH$_3$ | Cl | CH | |
| H | CH$_3$ | H | P(O)(OCH$_3$)$_2$ | CH$_3$ | CH$_3$ | CH | |
| H | CH$_3$ | H | P(O)(OCH$_3$)$_2$ | CH$_3$ | OCH$_3$ | CH | |
| H | CH$_3$ | H | P(O)(OCH$_3$)$_2$ | OCH$_3$ | OCH$_3$ | CH | |
| H | CH$_3$ | H | P(O)(OCH$_3$)SCH$_3$ | CH$_3$ | CH$_3$ | N | |
| H | CH$_3$ | H | P(O)(OCH$_3$)SCH$_3$ | CH$_3$ | OCH$_3$ | N | |
| H | CH$_3$ | H | P(O)(OCH$_3$)SCH$_3$ | OCH$_3$ | OCH$_3$ | N | |
| H | CH$_3$ | H | P(O)(OCH$_3$)SCH$_3$ | OCH$_3$ | Cl | CH | |
| H | CH$_3$ | H | P(O)(OCH$_3$)SCH$_2$CH$_2$CH$_3$ | CH$_3$ | CH$_3$ | CH | |
| H | CH$_3$ | H | P(O)(OCH$_3$)SCH$_2$CH$_2$CH$_3$ | CH$_3$ | OCH$_3$ | CH | |
| H | CH$_3$ | H | P(O)(OCH$_3$)SCH$_2$CH$_2$CH$_3$ | OCH$_3$ | OCH$_3$ | CH | |
| H | CH$_3$ | H | P(O)(OCH$_3$)SCH$_2$CH$_2$CH$_3$ | CH$_3$ | CH$_3$ | N | |
| H | CH$_3$ | H | P(O)(OCH$_3$)SCH$_2$CH$_2$CH$_3$ | CH$_3$ | OCH$_3$ | N | |
| H | CH$_3$ | CH$_3$ | OH | OCH$_3$ | OCH$_3$ | N | |
| H | CH$_3$ | H | P(S)(CH$_3$)$_2$ | OCH$_3$ | Cl | CH | |
| H | CH$_3$ | H | P(S)(CH$_3$)$_2$ | CH$_3$ | CH$_3$ | CH | |
| H | CH$_3$ | H | P(S)(CH$_3$)$_2$ | CH$_3$ | OCH$_3$ | CH | |
| H | CH$_3$ | H | P(S)(CH$_3$)$_2$ | OCH$_3$ | OCH$_3$ | CH | |
| H | CH$_3$ | H | P(S)(CH$_3$)$_2$ | CH$_3$ | CH$_3$ | N | |
| H | CH$_3$ | H | P(S)(CH$_3$)$_2$ | CH$_3$ | OCH$_3$ | N | |
| H | CH$_3$ | H | P(S)(CH$_3$)$_2$ | OCH$_3$ | OCH$_3$ | N | |
| H | CH$_3$ | H | P(S)(OCH$_3$)$_2$ | OCH$_3$ | Cl | CH | |
| H | CH$_3$ | H | P(S)(OCH$_3$)$_2$ | CH$_3$ | CH$_3$ | CH | |
| CH$_3$ | CH$_3$ | H | P(S)(OCH$_3$)$_2$ | CH$_3$ | OCH$_3$ | CH | |
| H | CH$_3$ | H | P(S)(OCH$_3$)$_2$ | OCH$_3$ | OCH$_3$ | CH | |
| H | CH$_3$ | H | P(S)(OCH$_3$)$_2$ | CH$_3$ | CH$_3$ | N | |
| H | CH$_3$ | H | P(S)(OCH$_3$)$_2$ | CH$_3$ | OCH$_3$ | N | |
| H | CH$_3$ | H | P(S)(OCH$_3$)SCH$_3$ | OCH$_3$ | OCH$_3$ | N | |
| H | CH$_3$ | H | P(S)(OCH$_3$)SCH$_3$ | OCH$_3$ | Cl | CH | |
| H | CH$_3$ | H | NO$_2$ | CH$_3$ | CH$_3$ | CH | |
| H | CH$_3$ | H | NO$_2$ | CH$_3$ | OCH$_3$ | CH | |
| H | CH$_3$ | H | NO$_2$ | OCH$_3$ | OCH$_3$ | CH | |
| H | CH$_3$ | H | NO$_2$ | CH$_3$ | CH$_3$ | N | |
| H | CH$_3$ | H | NO$_2$ | CH$_3$ | OCH$_3$ | N | |
| H | CH$_3$ | H | NO$_2$ | OCH$_3$ | OCH$_3$ | N | |
| H | CH$_3$ | H | CH$_2$C(O)CH(CH$_2$)(CH$_2$)(CH$_2$) | CH$_3$ | CH$_3$ | N | |
| H | CH$_3$ | H | CH$_2$C(O)CH(CH$_2$)(CH$_2$)(CH$_2$) | CH$_3$ | OCH$_3$ | N | |
| H | CH$_3$ | H | CH$_2$C(O)CH(CH$_2$)(CH$_2$)(CH$_2$) | OCH$_3$ | OCH$_3$ | N | |
| H | CH$_3$ | H | CH$_2$C(O)CH(CH$_2$)(CH$_2$)(CH$_2$) | OCH$_3$ | Cl | CH | |
| H | CH$_3$ | H | CH$_2$C(O)CH(CH$_2$)(CH$_2$)(CH$_2$) | CH$_3$ | CH$_3$ | CH | |
| H | CH$_3$ | H | CH$_2$C(O)CH(CH$_2$)(CH$_2$)(CH$_2$) | CH$_3$ | OCH$_3$ | CH | |
| H | CH$_3$ | H | CH$_2$C(O)Ph | OCH$_3$ | OCH$_3$ | CH | |
| H | CH$_3$ | H | CH$_2$C(O)Ph | CH$_3$ | CH$_3$ | N | |
| H | CH$_3$ | H | CH$_2$C(O)Ph | CH$_3$ | OCH$_3$ | N | |
| H | CH$_3$ | CH$_3$ | CH$_2$C(O)Ph | OCH$_3$ | OCH$_3$ | N | |
| H | CH$_3$ | H | CH$_2$C(O)Ph | OCH$_3$ | Cl | CH | |
| H | CH$_3$ | H | CH$_2$C(O)Ph | CH$_3$ | CH$_3$ | CH | |

TABLE IIa-continued

General Structure IIa

| R | $R_1$ | $R_2$ | $R_3$ | X | Y | Z | m.p. (°C.) |
|---|---|---|---|---|---|---|---|
| H | $CH_3$ | H | $CH_2C(O)Ph$ | $CH_3$ | $OCH_3$ | CH | |
| H | $CH_3$ | H | $CH(CH)_3C(O)CH_3$ | $OCH_3$ | $OCH_3$ | CH | |
| H | $CH_3$ | H | $CH(CH)_3C(O)CH_3$ | $CH_3$ | $CH_3$ | N | |
| H | $CH_3$ | H | $CH(CH)_3C(O)CH_3$ | $CH_3$ | $OCH_3$ | N | |
| H | $CH_3$ | H | $CH(CH)_3C(O)CH_3$ | $OCH_3$ | $OCH_3$ | N | |
| H | $CH_3$ | H | $CH_2CF_2-C(O)CH_3$ | $OCH_3$ | Cl | CH | |
| H | $CH_3$ | H | $CH_2CF_2-C(O)CH_3$ | $CH_3$ | $CH_3$ | CH | |
| $CH_3$ | $CH_3$ | H | $CH_2CF_2-C(O)CH_3$ | $CH_3$ | $OCH_3$ | CH | |
| H | $CH_3$ | H | $CH_2CF_2-C(O)CH_3$ | $OCH_3$ | $OCH_3$ | CH | |
| H | $CH_3$ | H | $CH_2C(O)CH_2OCH_3$ | $CH_3$ | $CH_3$ | N | |
| H | $CH_3$ | H | $CH_2C(O)CH_2OCH_3$ | $CH_3$ | $OCH_3$ | N | |
| H | $CH_3$ | H | $CH_2C(O)CH_2OCH_3$ | $OCH_3$ | $OCH_3$ | N | |
| H | $CH_3$ | H | $CH_2C(O)CH_2OCH_3$ | $OCH_3$ | Cl | CH | |
| H | $CH_3$ | H | $CH_2CO_2CH_3$ | $CH_3$ | $CH_3$ | CH | |
| H | $CH_3$ | H | $CH_2CO_2CH_3$ | $CH_3$ | $OCH_3$ | CH | |
| H | $CH_3$ | H | $CH_2CO_2CH_3$ | $OCH_3$ | $OCH_3$ | CH | |
| H | $CH_3$ | H | $CH_2CO_2CH_3$ | $CH_3$ | $CH_3$ | N | |
| H | $CH_3$ | H | $CH_2CO_2CH_3$ | $CH_3$ | $OCH_3$ | N | |
| H | $CH_3$ | H | $CH_2CO_2CH_3$ | $OCH_3$ | $OCH_3$ | N | |
| H | $CH_3$ | H | $CH_2CO_2CH_3$ | $OCH_3$ | Cl | CH | |
| H | $CH_3$ | H | $CH_2CO_2CH_2CH_3$ | $CH_3$ | $CH_3$ | CH | |
| H | $CH_3$ | H | $CH_2CO_2CH_2CH_3$ | $CH_3$ | $OCH_3$ | CH | |
| H | $CH_3$ | H | $CH_2CO_2CH_3$ | $OCH_3$ | $OCH_3$ | CH | |
| H | $CH_3$ | H | $CH_2CO_2CH_2CH_3$ | $CH_3$ | $CH_3$ | N | |
| H | $CH_3$ | H | $CH_2CO_2CH_2CH_3$ | $CH_3$ | $OCH_3$ | N | |
| H | $CH_3$ | H | $CH_2CO_2CH_2CH_3$ | $OCH_3$ | $OCH_3$ | N | |
| H | $CH_3$ | H | $CH_2CO_2CH_2CH_3$ | $OCH_3$ | Cl | CH | |
| H | $CH_3$ | H | $CH_2CH_2CO_2CH_3$ | $CH_3$ | $CH_3$ | CH | |
| H | $CH_3$ | H | $CH_2CH_2CO_2CH_3$ | $CH_3$ | $OCH_3$ | CH | |
| H | $CH_3$ | H | $CH_2CH_2CO_2CH_3$ | $OCH_3$ | $OCH_3$ | CH | |
| H | $CH_3$ | H | $CH_2CH_2CO_2CH_3$ | $CH_3$ | $CH_3$ | N | |
| H | $CH_3$ | H | $CH_2CH_2CO_2CH_3$ | $OCH_3$ | $OCH_3$ | N | |
| H | $CH_3$ | H | $CH_2CH_2CO_2CH_3$ | $OCH_3$ | Cl | CH | |
| H | $CH_3$ | H | $CH_2-CO_2CH_2CH=CH_2$ | $CH_3$ | $CH_3$ | CH | |
| H | $CH_3$ | H | $CH_2-CO_2CH_2CH=CH_2$ | $CH_3$ | $OCH_3$ | CH | |
| H | $CH_3$ | H | $CH_2-CO_2CH_2CH=CH_2$ | $OCH_3$ | $OCH_3$ | CH | |
| H | $CH_3$ | H | $CH_2-CO_2CH_2CH=CH_2$ | $CH_3$ | $CH_3$ | N | |
| H | $CH_3$ | H | $CH_2-CO_2CH_2CH=CH_2$ | $CH_3$ | $OCH_3$ | N | |
| H | $CH_3$ | H | $CH_2-CO_2CH_2CH=CH_2$ | $OCH_3$ | $OCH_3$ | N | |
| H | $CH_3$ | H | $CH_2-CO_2CH_2CH=CH_2$ | $OCH_3$ | Cl | CH | |
| H | $CH_3$ | H | $CH_2(CH_2)_4CO_2CH_3$ | $CH_3$ | $CH_3$ | CH | |
| H | $CH_3$ | H | $CH_2(CH_2)_4CO_2CH_3$ | $CH_3$ | $OCH_3$ | CH | |
| H | $CH_3$ | H | $CH_2(CH_2)_4CO_2CH_3$ | $OCH_3$ | $OCH_3$ | CH | |
| H | $CH_3$ | H | $CH_2(CH_2)_4CO_2CH_3$ | $CH_3$ | $CH_3$ | N | |
| H | $CH_3$ | H | $CH_2(CH_2)_4CO_2CH_3$ | $CH_3$ | $OCH_3$ | N | |
| H | $CH_3$ | $CH_3$ | $CH_2(CH_2)_4CO_2CH_3$ | $OCH_3$ | $OCH_3$ | N | |
| H | $CH_3$ | H | $CH_2(CH_2)_4CO_2CH_3$ | $OCH_3$ | Cl | CH | |
| H | $CH_3$ | H | $CH_2CO_2CH_2C\equiv CH$ | $CH_3$ | $CH_3$ | CH | |
| H | $CH_3$ | H | $CH_2CO_2CH_2C\equiv CH$ | $CH_3$ | $OCH_3$ | CH | |
| H | $CH_3$ | H | $CH_2CO_2CH_2C\equiv CH$ | $OCH_3$ | $OCH_3$ | CH | |
| H | $CH_3$ | H | $CH_2CO_2CH_2C\equiv CH$ | $CH_3$ | $CH_3$ | N | |
| H | $CH_3$ | H | $CH_2CO_2CH_2C\equiv CH$ | $CH_3$ | $OCH_3$ | N | |
| H | $CH_3$ | H | $CH_2CO_2CH_2C\equiv CH$ | $OCH_3$ | $OCH_3$ | N | |
| H | $CH_3$ | H | $CH_2CO_2CH_2C\equiv CH$ | $OCH_3$ | Cl | CH | |
| H | $CH_3$ | H | $CH_2CO_2CF_3$ | $CH_3$ | $CH_3$ | CH | |
| $CH_3$ | $CH_3$ | H | $CH_2CO_2CF_3$ | $CH_3$ | $OCH_3$ | CH | |
| H | $CH_3$ | H | $CH_2CO_2CF_3$ | $OCH_3$ | $OCH_3$ | CH | |
| H | $CH_3$ | H | $CH_2CO_2CF_3$ | $CH_3$ | $CH_3$ | N | |
| H | $CH_3$ | H | $CH_2CO_2CF_3$ | $CH_3$ | $OCH_3$ | N | |
| H | $CH_3$ | H | $CH_2CO_2CF_3$ | $OCH_3$ | $OCH_3$ | N | |
| H | $CH_3$ | H | $CH_2CO_2CF_3$ | $OCH_3$ | Cl | CH | |
| H | $CH_3$ | H | $CH_2C(O)N(CH_3)_2$ | $CH_3$ | $CH_3$ | CH | |
| H | $CH_3$ | H | $CH_2C(O)N(CH_3)_2$ | $CH_3$ | $OCH_3$ | CH | |
| H | $CH_3$ | H | $CH_2C(O)N(CH_3)_2$ | $OCH_3$ | $OCH_3$ | CH | |
| H | $CH_3$ | H | $CH_2C(O)N(CH_3)_2$ | $CH_3$ | $CH_3$ | N | |
| H | $CH_3$ | H | $CH_2C(O)N(CH_3)_2$ | $CH_3$ | $OCH_3$ | N | |
| H | $CH_3$ | H | $CH_2C(O)N(CH_3)_2$ | $OCH_3$ | $OCH_3$ | N | |
| H | $CH_3$ | H | $CH_2C(O)N(CH_3)_2$ | $OCH_3$ | Cl | CH | |
| H | $CH_3$ | H | $SeCH_3$ | $CH_3$ | $CH_3$ | CH | |
| H | $CH_3$ | H | $SeCH_3$ | $CH_3$ | $OCH_3$ | CH | |
| H | $CH_3$ | H | $SeCH_3$ | $OCH_3$ | $OCH_3$ | CH | |
| H | $CH_3$ | H | $SeCH_3$ | $CH_3$ | $CH_3$ | N | |
| H | $CH_3$ | H | $SeCH_3$ | $CH_3$ | $OCH_3$ | N | |
| H | $CH_3$ | H | $SeCH_3$ | $OCH_3$ | $OCH_3$ | N | |
| H | $CH_3$ | H | $SeCH_3$ | $OCH_3$ | Cl | CH | |
| H | $CH_3$ | H | $CH_2Ph$ | $CH_3$ | $CH_3$ | CH | |
| H | $CH_3$ | H | $CH_2Ph$ | $CH_3$ | $OCH_3$ | CH | |
| H | $CH_3$ | H | $CH_2Ph$ | $OCH_3$ | $OCH_3$ | CH | |
| H | $CH_3$ | H | $CH_2Ph$ | $CH_3$ | $CH_3$ | N | |
| H | $CH_3$ | H | $CH_2Ph$ | $OCH_3$ | $OCH_3$ | N | |

TABLE IIa-continued

General Structure IIa

| R | R₁ | R₂ | R₃ | X | Y | Z | m.p. (°C.) |
|---|----|----|----|----|---|---|---|
| H | CH₃ | H | CH₂Ph | OCH₃ | Cl | CH | |
| H | CH₃ | H | CH₂—(1,3-dioxolan-2-yl) | CH₃ | CH₃ | CH | |
| H | CH₃ | H | CH₂—(1,3-dioxolan-2-yl) | CH₃ | OCH₃ | CH | |
| H | CH₃ | H | CH₂—(1,3-dioxolan-2-yl) | OCH₃ | OCH₃ | CH | |
| H | CH₃ | H | CH₂—(1,3-dioxolan-2-yl) | CH₃ | CH₃ | N | |
| H | CH₃ | H | CH₂—(1,3-dioxolan-2-yl) | CH₃ | OCH₃ | N | |
| H | CH₃ | H | CH₂—(1,3-dioxolan-2-yl) | OCH₃ | OCH₃ | N | |
| H | CH₃ | H | CH₂—OTHP | OCH₃ | Cl | CH | |
| H | CH₃ | H | CH₂—OTHP | CH₃ | CH₃ | CH | |
| H | CH₃ | H | CH₂—OTHP | CH₃ | OCH₃ | CH | |
| H | CH₃ | H | CH₂—OTHP | OCH₃ | OCH₃ | CH | |
| H | CH₃ | H | CH₂—OTHP | CH₃ | CH₃ | N | |
| H | CH₃ | H | CH₂—OTHP | CH₃ | OCH₃ | N | |
| H | CH₃ | CH₃ | CH₂—OTHP | OCH₃ | OCH₃ | N | |
| H | CH₃ | H | Si(CH₃)₃ | CH₃ | CH₃ | CH | |
| H | CH₃ | H | Si(CH₃)₃ | CH₃ | OCH₃ | CH | |
| H | CH₃ | H | Si(CH₃)₃ | OCH₃ | OCH₃ | CH | |
| H | CH₃ | H | Si(CH₃)₃ | CH₃ | CH₃ | N | |
| H | CH₃ | H | Si(CH₃)₃ | CH₃ | OCH₃ | N | |
| H | CH₃ | H | Si(CH₃)₃ | OCH₃ | OCH₃ | N | |
| H | CH₃ | H | Si(CH₃)₃ | OCH₃ | Cl | CH | |
| H | CH₃ | H | Si(CH₃)₂Ph | CH₃ | CH₃ | CH | |
| H | CH₃ | H | Si(CH₃)₂Ph | CH₃ | OCH₃ | CH | |
| H | CH₃ | H | Si(CH₃)₂Ph | OCH₃ | OCH₃ | CH | |
| H | CH₃ | H | Si(CH₃)₂Ph | CH₃ | CH₃ | N | |
| H | CH₃ | H | Si(CH₃)₂Ph | CH₃ | OCH₃ | N | |
| H | CH₃ | H | Si(CH₃)₂Ph | OCH₃ | OCH₃ | N | |
| H | CH₃ | H | Si(CH₃)₂Ph | OCH₃ | Cl | CH | |
| H | CH₃ | H | Si(CH₃)₂CH₂CH₃ | CH₃ | CH₃ | CH | |
| H | CH₃ | H | Si(CH₃)₂CH₂CH₃ | CH₃ | OCH₃ | CH | |
| H | CH₃ | H | Si(CH₃)₂CH₃ | OCH₃ | OCH₃ | CH | |
| H | CH₃ | H | Si(CH₃)₂CH₂CH₃ | CH₃ | CH₃ | N | |
| H | CH₃ | H | Si(CH₃)₂CH₂CH₃ | OCH₃ | OCH₃ | N | |
| H | CH₃ | H | Si(CH₃)₂CH₂CH₃ | OCH₃ | Cl | CH | |
| H | CH₃ | H | A-HET | CH₃ | CH₃ | CH | |
| H | CH₃ | H | A-HET | CH₃ | OCH₃ | CH | |
| H | CH₃ | H | A-HET | OCH₃ | OCH₃ | CH | |
| H | CH₃ | H | A-HET | CH₃ | CH₃ | N | |
| H | CH₃ | H | A-HET | CH₃ | OCH₃ | N | |
| H | CH₃ | H | A-HET | OCH₃ | OCH₃ | N | |
| H | CH₃ | H | A-HET | OCH₃ | Cl | CH | |
| H | CH₃ | H | B-HET | CH₃ | CH₃ | CH | |
| H | CH₃ | H | B-HET | CH₃ | OCH₃ | CH | |
| H | CH₃ | H | B-HET | OCH₃ | OCH₃ | CH | |
| H | CH₃ | H | B-HET | CH₃ | OCH₃ | N | |
| H | CH₃ | CH₃ | B-HET | OCH₃ | OCH₃ | N | |
| H | CH₃ | H | B-HET | OCH₃ | Cl | CH | |
| H | CH₃ | H | C-HET | CH₃ | CH₃ | CH | |
| H | CH₃ | H | C-HET | CH₃ | OCH₃ | CH | |
| H | CH₃ | H | C-HET | OCH₃ | OCH₃ | CH | |
| H | CH₃ | H | C-HET | CH₃ | CH₃ | N | |
| H | CH₃ | H | C-HET | CH₃ | OCH₃ | N | |
| H | CH₃ | H | C-HET | OCH₃ | OCH₃ | N | |
| H | CH₃ | H | C-HET | OCH₃ | Cl | CH | |
| H | CH₃ | H | D-HET | CH₃ | CH₃ | CH | |
| CH₃ | CH₃ | H | D-HET | CH₃ | OCH₃ | CH | |
| H | CH₃ | H | D-HET | OCH₃ | OCH₃ | CH | |
| H | CH₃ | H | D-HET | CH₃ | CH₃ | N | |
| H | CH₃ | H | D-HET | CH₃ | OCH₃ | N | |
| H | CH₃ | H | D-HET | OCH₃ | OCH₃ | N | |
| H | CH₃ | H | D-HET | OCH₃ | Cl | CH | |
| H | CH₃ | H | C(O)A-HET | CH₃ | CH₃ | CH | |
| H | CH₃ | H | C(O)A-HET | CH₃ | OCH₃ | CH | |
| H | CH₃ | H | C(O)A-HET | OCH₃ | OCH₃ | CH | |
| H | CH₃ | H | C(O)A-HET | CH₃ | CH₃ | N | |
| H | CH₃ | H | C(O)A-HET | CH₃ | OCH₃ | N | |
| H | CH₃ | H | C(O)A-HET | OCH₃ | OCH₃ | N | |
| H | CH₃ | H | C(O)A-HET | OCH₃ | Cl | CH | |
| H | CH₃ | H | C(O)B-HET | CH₃ | CH₃ | CH | |
| H | CH₃ | H | C(O)B-HET | CH₃ | OCH₃ | CH | |
| H | CH₃ | H | C(O)B-HET | OCH₃ | OCH₃ | CH | |
| H | CH₃ | H | C(O)B-HET | CH₃ | CH₃ | N | |
| H | CH₃ | H | C(O)B-HET | CH₃ | OCH₃ | N | |
| H | CH₃ | H | C(O)B-HET | OCH₃ | OCH₃ | N | |
| H | CH₃ | H | C(O)B-HET | OCH₃ | Cl | CH | |
| H | CH₃ | H | C(O)C-HET | CH₃ | CH₃ | CH | |
| H | CH₃ | H | C(O)C-HET | CH₃ | OCH₃ | CH | |
| H | CH₃ | H | C(O)C-HET | OCH₃ | OCH₃ | CH | |
| H | CH₃ | H | C(O)C-HET | CH₃ | CH₃ | N | |

TABLE IIa-continued

General Structure IIa

| R | R₁ | R₂ | R₃ | X | Y | Z | m.p. (°C.) |
|---|---|---|---|---|---|---|---|
| H | CH₃ | H | C(O)C-HET | OCH₃ | OCH₃ | N | |
| H | CH₃ | H | C(O)C-HET | OCH₃ | Cl | CH | |
| H | CH₃ | H | C(O)C-HET | CH₃ | CH₃ | CH | |
| H | CH₃ | H | C(O)D-HET | CH₃ | OCH₃ | CH | |
| H | CH₃ | H | C(O)D-HET | OCH₃ | OCH₃ | CH | |
| H | CH₃ | H | C(O)D-HET | CH₃ | CH₃ | N | |
| H | CH₃ | H | C(O)D-HET | CH₃ | OCH₃ | N | |
| H | CH₃ | H | C(O)D-HET | OCH₃ | OCH₃ | N | |
| H | CH₃ | H | C(O)D-HET | OCH₃ | Cl | CH | | wherein

A-HET is 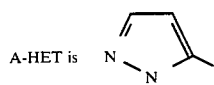

B-HET is 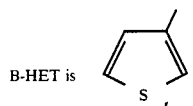

C-HET is 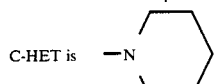

D-HET is 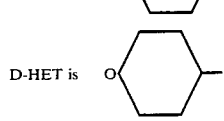

TABLE III

General Structure III

| A | R | R₁ | R₂ | R₃ | X | Y | Z | m.p. (°C.) |
|---|---|---|---|---|---|---|---|---|
| A-1 | H | CH₃ | H | CH₂F | OCH₂CH₃ | OCH₃ | CH | |
| A-1 | H | CH₃ | H | CH₂F | OCH₂CH₃ | NHCH₃ | N | |
| A-1 | H | CH₃ | H | CH₂F | OCF₂H | CH₃ | CH | |
| A-1 | H | CH₃ | H | CH₂F | SCH₃ | CH₃ | N | |
| A-1 | H | CH₃ | H | CH(CF₃)₂ | O-cyclopropyl | OCH₃ | N | |
| A-1 | H | CH₃ | H | CH(CF₃)₂ | CH₂OCH₃ | CH₃ | CH | |
| A-1 | H | CH₃ | H | Si(CH₃)₃ | H | OCH₃ | CH | |
| A-1 | H | CH₃ | H | Si(CH₃)₃ | OCH₃ | OCH₂CH=CH₂ | CH | |
| A-1 | H | CH₃ | H | CH₂F | OCH₃ | CN | CH | |
| A-1 | H | CH₃ | H | CH₂F | OCH₃ | CH(OCH₃)₂ | CH | |

| | | | | | X₁ | Y₁ | | |
| A-2 | H | CH₃ | H | CH₂—CH=CH₂ | CH₃ | CH₂ | | |
| A-2 | H | CH₃ | H | CH₂—CH=CH₂ | CH₃ | O | | |
| A-2 | H | CH₃ | H | CH₂—C≡CH | OCH₃ | CH₂ | | |
| A-2 | H | CH₃ | H | CH₂F | OCF₂H | CH₂ | | |
| A-3 | H | CH₃ | H | CH₂CH₂Cl | CH₃ | | | |
| A-3 | H | CH₃ | H | CH₂P(O)(CH₃)₂ | OCH₃ | | | |
| A-3 | H | CH₃ | H | CH₂(CH₂)₆CH₃ | OCH₂CH₃ | | | |
| A-3 | H | CH₃ | H | CH₂CH=CF₂ | OCF₂H | | | |

| | | | | | | Y₃ | | |
| A-4 | H | CH₃ | H | CH₂—C(O)(CH₃)epoxide | CH₃ | H | | |
| A-4 | H | CH₃ | H | CH₂—C(O)(CH₃)epoxide | OCH₃ | H | | |
| A-4 | H | CH₃ | H | CH₂SO₂CH₃ | OCF₂H | CH₃ | | |
| A-4 | H | CH₃ | H | CH₂SO₂CH₃ | OCF₂H | H | | |
| A-4 | H | CH₃ | H | SCH₃ | OCH₂CH₃ | H | | |
| A-4 | H | CH₃ | H | CH₂Si(CH₃)₃ | CH₃ | H | | |
| A-4 | H | CH₃ | H | CH₂C(O)CH₃ | OCH₃ | CH₃ | | |

| | | | | | X₂ | Y₂ | | |
| A-5 | H | CH₃ | H | CH₂C(O)CH₃ | CH₃ | OCH₃ | | |
| A-5 | H | CH₃ | H | CH₂C(O)CH₃ | CH₂CH₃ | OCH₃ | | |
| A-5 | H | CH₃ | H | CH₂C(O)OCH₃ | CH₂CF₃ | SCH₃ | | |
| A-5 | H | CH₃ | H | CH₂C(O)OCH₃ | CH₃ | CH₃ | | |

TABLE III-continued

General Structure III

| A | R | R₁ | R₂ | R₃ | | | Z | m.p. (°C.) |
|---|---|---|---|---|---|---|---|---|
| A-5 | H | CH₃ | H | CH₂C(O)OCH₃ | CH₃ | CH₂CH₃ | | |
| A-5 | H | CH₃ | H | CH₂(CH₂)₂CF₃ | CH₃ | SCH₃ | | |
| | | | | | X₃ | | | |
| A-6 | H | CH₃ | H | CH₂CHF₂ | CH₃ | | | |
| A-6 | H | CH₃ | H | C(O)N(CH₃)₂ | CH₃ | | | |
| A-6 | H | CH₃ | H | C(O)OCH₃ | OCH₃ | | | |
| A-6 | H | CH₃ | H | CH₂SCH₃ | OCH₃ | | | |
| A-6 | H | CH₃ | H | CH₂—C(CH₂)(CH₂)(CH₂) | CH₃ | | | |

TABLE IIIa

General Structure IIIa

| A | R | R₁ | R₂ | R₃ | | | Z | m.p. (°C.) |
|---|---|---|---|---|---|---|---|---|
| | | | | | X | Y | | |
| A-1 | H | CH₃ | H | CH₂F | OCH₂CH₃ | OCH₃ | CH | |
| A-1 | H | CH₃ | H | CH₂F | OCH₂CH₃ | NHCH₃ | N | |
| A-1 | H | CH₃ | H | CH₂F | OCF₂H | CH₃ | CH | |
| A-1 | H | CH₃ | H | CH₂F | SCH₃ | CH₃ | N | |
| A-1 | H | CH₃ | H | CH(CF₃)₂ | O—▷ | OCH₃ | N | |
| A-1 | H | CH₂CH₃ | H | CH(CF₃)₂ | CH₂OCH₃ | CH₃ | CH | |
| A-1 | H | CH₃ | H | Si(CH₃)₃ | H | OCH₃ | CH | |
| A-1 | H | CH₃ | H | Si(CH₃)₃ | SCH₃ | CH₃ | CH | |
| A-1 | H | CH₃ | H | Si(CH₃)₃ | OCH₃ | OCH₂CH=CH₂ | CH | |
| | | | | | X₁ | Y₁ | | |
| A-2 | H | CH₃ | H | CH₂—CH=CH₂ | CH₃ | CH₂ | | |
| A-2 | H | CH₃ | H | CH₂—CH=CH₂ | CH₃ | O | | |
| A-2 | H | CH₃ | H | CH₂—C≡CH | OCH₃ | CH₂ | | |
| A-2 | H | CH₃ | H | CH₂F | OCF₂H | CH₂ | | |
| A-3 | H | CH₃ | H | CH₂CH₂Cl | CH₃ | | | |
| A-3 | H | CH₃ | H | CH₂P(O)(CH₃)₂ | OCH₃ | | | |
| A-3 | H | CH₃ | H | CH₂(CH₂)₆CH₃ | OCH₂CH₃ | | | |
| A-3 | H | CH₃ | H | CH₂CH=CF₂ | OCF₂H | | | |
| | | | | | | Y₃ | | |
| A-4 | H | CH₃ | H | CH₂—C(O)(CH₃) (epoxide) | CH₃ | H | | |
| A-4 | H | CH₃ | H | CH₂—C(O)(CH₃) (epoxide) | OCH₃ | H | | |
| A-4 | H | CH₃ | H | CH₂SO₂CH₃ | OCF₂H | CH₃ | | |
| A-4 | H | CH₃ | H | CH₂SO₂CH₃ | OCF₂H | H | | |
| A-4 | H | CH₃ | H | SCH₃ | OCH₂CH₃ | H | | |
| A-4 | H | CH₃ | H | CH₂Si(CH₃)₃ | CH₃ | H | | |
| A-4 | H | CH₃ | H | CH₂C(O)CH₃ | OCH₃ | CH₃ | | |
| | | | | | X₂ | Y₂ | | |
| A-5 | H | CH₃ | H | CH₂C(O)CH₃ | CH₃ | OCH₃ | | |
| A-5 | H | CH₃ | H | CH₂C(O)CH₃ | CH₂CH₃ | OCH₃ | | |
| A-5 | H | CH₃ | H | CH₂C(O)OCH₃ | CH₂CF₃ | SCH₃ | | |
| A-5 | H | CH₃ | H | CH₂C(O)OCH₃ | CH₃ | CH₃ | | |
| A-5 | H | CH₃ | H | CH₂C(O)OCH₃ | CH₃ | CH₂CH₃ | | |
| A-5 | H | CH₃ | H | CH₂(CH₂)₂CF₃ | CH₃ | SCH₃ | | |
| | | | | | X₃ | | | |
| A-6 | H | CH₃ | H | CH₂CHF₂ | CH₃ | | | |
| A-6 | H | CH₃ | H | C(O)N(CH₃)₂ | CH₃ | | | |
| A-6 | H | CH₃ | H | C(O)OCH₃ | OCH₃ | | | |
| A-6 | H | CH₃ | H | CH₂SCH₃ | OCH₃ | | | |
| A-6 | H | CH₃ | H | CH₂—C(CH₂)(CH₂)(CH₂) | CH₃ | | | |

TABLE IV

General Structure IV

| A | R | R₁ | R₂ | R₃ | | | Z | m.p. (°C.) |
|---|---|---|---|---|---|---|---|---|
| | | | | | X | Y | | |
| A-1 | H | CH₃ | H | CH₂F | OCH₂CH₃ | OCH₃ | CH | |
| A-1 | H | CH₃ | H | CH₂F | OCH₂CH₃ | NHCH₃ | N | |

TABLE IV-continued

General Structure IV

| A | R | R₁ | R₂ | R₃ | X | Y | Z | m.p. (°C.) |
|---|---|---|---|---|---|---|---|---|
| A-1 | H | CH₃ | H | CH₂F | OCF₂H | CH₃ | CH | |
| A-1 | H | CH₃ | H | CH₂F | SCH₃ | CH₃ | N | |
| A-1 | H | CH₃ | H | CH(CF₃)₂ | O—◁ | OCH₃ | N | |
| A-1 | H | CH₃ | H | CH(CF₃)₂ | CH₂OCH₃ | CH₃ | CH | |
| A-1 | H | CH₃ | H | Si(CH₃)₃ | H | OCH₃ | CH | |
| A-1 | H | CH₃ | H | Si(CH₃)₃ | OCH₃ | OCH₂CH=CH₂ | CH | |
| A-1 | H | CH₃ | H | CH₂F | OCH₃ | CN | CH | |
| A-1 | H | CH₃ | H | CH₂F | OCH₃ | CH(OCH₃)₂ | CH | |

| A | R | R₁ | R₂ | R₃ | X₁ | Y₁ | | |
|---|---|---|---|---|---|---|---|---|
| A-2 | H | CH₃ | H | CH₂—CH=CH₂ | CH₃ | CH₂ | | |
| A-2 | H | CH₃ | CH₃ | CH₂—CH=CH₂ | CH₃ | O | | |
| A-2 | H | CH₃ | H | CH₂—C≡CH | OCH₃ | CH₂ | | |
| A-2 | H | CH₃ | H | CH₂F | OCF₂H | CH₂ | | |
| A-3 | H | CH₃ | H | CH₂CH₂Cl | CH₃ | | | |
| A-3 | H | CH₃ | H | CH₂P(O)(CH₃)₂ | OCH₃ | | | |
| A-3 | H | CH₃ | H | CH₂(CH₂)₆CH₃ | OCH₂CH₃ | | | |
| A-3 | H | CH₂CH₂CH₃ | H | CH₂CH=CF₂ | OCF₂H | | | |

| A | R | R₁ | R₂ | R₃ | X | Y₃ | | |
|---|---|---|---|---|---|---|---|---|
| A-4 | H | CH₃ | H | CH₂—C(O)(CH₃)—CH₃ (epoxide) | CH₃ | H | | |
| A-4 | H | CH₃ | H | CH₂—C(O)(CH₃)—CH₃ (epoxide) | OCH₃ | H | | |
| A-4 | H | CH₃ | H | CH₂SO₂CH₃ | OCF₂H | CH₃ | | |
| A-4 | H | CH₃ | H | CH₂SO₂CH₃ | OCF₂H | H | | |
| A-4 | H | CH₃ | H | SCH₃ | OCH₂CH₃ | H | | |
| A-4 | H | CH₃ | H | CH₂Si(CH₃)₃ | CH₃ | H | | |
| A-4 | H | CH₃ | H | CH₂C(O)CH₃ | OCH₃ | CH₃ | | |

| A | R | R₁ | R₂ | R₃ | X₂ | Y₂ | | |
|---|---|---|---|---|---|---|---|---|
| A-5 | H | CH₃ | H | CH₂C(O)CH₃ | CH₃ | OCH₃ | | |
| A-5 | H | CH₃ | H | CH₂C(O)CH₃ | CH₂CH₃ | OCH₃ | | |
| A-5 | H | CH₃ | H | CH₂C(O)OCH₃ | CH₂CF₃ | SCH₃ | | |
| A-5 | H | CH₃ | H | CH₂C(O)OCH₃ | CH₃ | CH₃ | | |
| A-5 | H | CH₃ | H | CH₂C(O)OCH₃ | CH₃ | CH₂CH₃ | | |
| A-5 | H | CH₃ | H | CH₂(CH₂)₂CF₃ | CH₃ | SCH₃ | | |

| A | R | R₁ | R₂ | R₃ | X₃ | | | |
|---|---|---|---|---|---|---|---|---|
| A-6 | H | CH₃ | H | CH₂CHF₂ | CH₃ | | | |
| A-6 | H | CH₃ | H | C(O)N(CH₃)₂ | CH₃ | | | |
| A-6 | H | CH₃ | H | C(O)OCH₃ | OCH₃ | | | |
| A-6 | H | CH₃ | H | CH₂SCH₃ | OCH₃ | | | |
| A-6 | H | CH₃ | H | CH₂—C(CH₂)(CH₂) (cyclopropyl) | CH₃ | | | |

TABLE IVa

General Structure IVa

| A | R | R₁ | R₂ | R₃ | X | Y | Z | m.p. (°C.) |
|---|---|---|---|---|---|---|---|---|
| A-1 | H | CH₃ | H | CH₂F | OCH₂CH₃ | OCH₃ | CH | |
| A-1 | H | CH₃ | H | CH₂F | OCH₂CH₃ | NHCH₃ | N | |
| A-1 | H | CH₃ | H | CH₂F | OCF₂H | CH₃ | CH | |
| A-1 | H | CH₃ | H | CH₂F | SCH₃ | CH₃ | N | |
| A-1 | H | CH₃ | H | CH(CF₃)₂ | O—◁ | OCH₃ | N | |
| A-1 | H | CH₃ | H | CH(CF₃)₂ | CH₂OCH₃ | CH₃ | CH | |
| A-1 | H | CH₃ | H | Si(CH₃)₃ | H | OCH₃ | CH | |
| A-1 | H | CH₃ | H | Si(CH₃)₃ | OCH₃ | OCH₂CH=CH₂ | CH | |
| A-1 | H | CH₃ | H | CH₂F | OCH₃ | CN | CH | |
| A-1 | H | CH₃ | H | CH₂F | OCH₃ | CH(OCH₃)₂ | CH | |

| A | R | R₁ | R₂ | R₃ | X₁ | Y₁ | | |
|---|---|---|---|---|---|---|---|---|
| A-2 | H | CH₃ | H | CH₂—CH=CH₂ | CH₃ | CH₂ | | |
| A-2 | H | CH₃ | H | CH₂—CH=CH₂ | CH₃ | O | | |

TABLE IVa-continued

General Structure IVa

| A | R | R₁ | R₂ | R₃ | | Z | m.p. (°C.) |
|---|---|---|---|---|---|---|---|
| A-2 | H | CH₃ | H | CH₂—C≡CH | OCH₃ | CH₂ | |
| A-2 | H | CH₃ | H | CH₂F | OCF₂H | CH₂ | |
| A-3 | H | CH₃ | H | CH₂CH₂Cl | CH₃ | | |
| A-3 | H | CH₃ | H | CH₂P(O)(CH₃)₂ | OCH₃ | | |
| A-3 | H | CH₃ | H | CH₂(CH₂)₆CH₃ | OCH₂CH₃ | | |
| A-3 | H | CH₃ | H | CH₂CH=CF₂ | OCF₂H | | |

| | | | | | | Y₃ | |
| A-4 | H | CH₃ | H | CH₂—C(O)(CH₃) (epoxide) | CH₃ | H | |
| A-4 | H | CH₃ | H | CH₂—C(O)(CH₃) (epoxide) | OCH₃ | H | |
| A-4 | H | CH₃ | H | CH₂SO₂CH₃ | OCF₂H | CH₃ | |
| A-4 | H | CH₃ | H | CH₂SO₂CH₃ | OCF₂H | H | |
| A-4 | H | CH₃ | H | SCH₃ | OCH₂CH₃ | H | |
| A-4 | H | CH₃ | H | CH₂Si(CH₃)₃ | CH₃ | H | |
| A-4 | H | CH₃ | H | CH₂C(O)CH₃ | OCH₃ | CH₃ | |

| | | | | | X₂ | Y₂ | |
| A-5 | H | CH₃ | H | CH₂C(O)CH₃ | CH₃ | OCH₃ | |
| A-5 | H | CH₃ | H | CH₂C(O)CH₃ | CH₂CH₃ | OCH₃ | |
| A-5 | H | CH₃ | H | CH₂C(O)OCH₃ | CH₂CF₃ | SCH₃ | |
| A-5 | H | CH₃ | H | CH₂C(O)OCH₃ | CH₃ | CH₃ | |
| A-5 | H | CH₃ | H | CH₂C(O)OCH₃ | CH₃ | CH₂CH₃ | |
| A-5 | H | CH₃ | H | CH₂(CH₂)₂CF₃ | CH₃ | SCH₃ | |

| | | | | | X₃ | | |
| A-6 | H | CH₃ | H | CH₂CHF₂ | CH₃ | | |
| A-6 | H | CH₃ | H | C(O)N(CH₃)₂ | CH₃ | | |
| A-6 | H | CH₃ | H | C(O)OCH₃ | OCH₃ | | |
| A-6 | H | CH₃ | H | CH₂SCH₃ | OCH₃ | | |
| A-6 | H | CH₃ | H | CH₂—C(cyclopropyl) | CH₃ | | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE V

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5 line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A Evans, "Weed Control Handbook", 5th Ed., Blackwell Scientific Publications, Oxford, 1968, pp. 101–103.

In the following examples, all parts are by weight unless otherwise indicated.

EXAMPLE 3

Wettable Powder

N-[(4,6-dimethoxypyrimidin-2-yl)aminocarbonyl]-5-(2-fluoroethyl)-2,5,6,7-tetrahydro-2-methyl-pyrazolo[3,4-e][1,2]thiazine-3-sulfonamide, 4,4-dioxide: 80%
sodium alkylnaphthalenesulfonate: 2%
sodium ligninsulfonate: 2%
synthetic amorphous silica: 3%
kaolinite: 13%.

The ingredients are blended, hammer-milled until all the solids are essentially under 50 microns, reblended, and packaged.

EXAMPLE 4

Wettable Powder 5-acetyl-2,5,6,7-tetrahydro-N-[(4-methoxy-6-methyl-1,3,5-triazin-2-yl)aminocarbonyl]-2-methyl-pyrazolo[3,4-e]thiazine-3-sulfonamide, 4,4-dioxide: 50%
sodium alkylnaphthalenesulfonate: 2%
low viscosity methyl cellulose: 2%
diatomaceous earth: 46%

The ingredients are blended, coarsely hammer-milled and then air-milled to produce particles essentially all below 10 microns in diameter. The product is reblended before packaging.

EXAMPLE 5

Granule

Wettable Powder of Example 4: 5%
attapulgite granules: 95% (U.S.S. 20–40 mesh; 0.84–0.42 mm).

A slurry of wettable powder containing 25% solids is sprayed on the surface of attapulgite granules while tumbling in a double-cone blender. The granules are dried and packaged.

EXAMPLE 6

Extruded Pellet 5-butyl-N-[(4,6-dimethoxypyrimidin-2-yl)aminocarbonyl]-2,5,6,7-tetrahydro-2-methylpyrazolo[3,4-e][1,2]thiazine-3-sulfonamide, 4,4-dioxide: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 7

Oil Suspension

N-[(4,6-dimethoxypyrimidin-2-yl)aminocarbonyl]-5-(2l-fluoroethyl)-2,5,6,7-tetrahydro-2-methyl-pyrazolo[3,4-e][1,2]thiazine-3-sulfonamide, 4,4dioxide: 25%
polyoxyethylene sorbitol hexaoleate: 5%
highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 8

Wettable Powder 5-acetyl-2,5,6,7-tetrahydro-N-[(4-methoxy-6-methyl-1,3,5-triazin-2-yl)aminocarbonyl]-2-methyl-pyrazolo[3,4-e]thiazine-3-sulfonamide, 4,4-dioxide: 20%
sodium alkylnaphthalenesulfonate: 4%
sodium ligninsulfonate: 4%
low viscosity methyl cellulose: 3%
attapulgite: 69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 9

Low Strength Granule 5-butyl-N-[(4,6-dimethoxypyrimidin-2-yl)aminocarbonyl]-2,5,6,7-tetrahydro-2-methylpyrazolo[3,4-e][1,2]thiazine-3-sulfonamide, 4,4-dioxide: 1%
N,N-dimethylformamide: 9%
attapulgite granules (U.S.S. 20–40sieve): 90%

The active ingredient is dissolved in the solvent and the solution is sprayed upon dedusted granules in a double cone blender. After spraying of the solution has been completed, the blender is allowed to run for a short period and then the granules are packaged.

EXAMPLE 10

Aqueous Suspension 5-butyl-N-[(4,6-dimethoxypyrimidin-2-yl)aminocarbonyl]2,5,6,7-tetrahydro-2-methylpyrazolo[3,4-e][1,2]thiazine-3-sulfonamide, 4,4-dioxide: 40%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 11

Solution

N-[(4,6-dimethoxypyrimidin-2-yl)aminocarbonyl]-5-(2-fluoroethyl)-2,5,6,7-tetrahydro-2-methyl-pyrazolo[3,4-e][1,2]thiazine-3-sulfonamide, 4,4-dioxide: 5%
water: 95%

The salt is added directly to the water with stirring to produce the solution, which may then be packaged for use.

EXAMPLE 12

Low Strength Granule 5-acetyl-2,5,6,7-tetrahydro-N-[(4-methoxy-6-methyl-1,3,5-triazin-2-yl)aminocarbonyl]-2-methyl-pyrazolo[3,4-e]thiazine-3-sulfonamide, 4,4-dioxide: 0.1%
attapulgite granules (U.S.S. 20–40 mesh): 99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 13

Granule 5-acetyl-2,5,6,7-tetrahydro-N-[(4-methoxy-6-methyl-1,3,5-triazin-2-yl)aminocarbonyl]-2-methyl-pyrazolo[3,4-e]thiazine-3-sulfonamide, 4,4-dioxide: 80%
wetting agent: 1%
crude ligninsulfonate salt (containing 5–20% of the natural sugars): 10%
attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 14

High Strength Concentrate 5-butyl-N-[(4,6-dimethoxypyrimidin-2-yl)aminocarbonyl]-2,5,6,7-tetrahydro-2-methylpyrazolo[3,4-e][1,2]thiazine-3-sulfonamide, 4,4-dioxide: 99%
silica aerogel: 0.5%
synthetic amorphous silica: 0.5%

The ingredients are blended and ground in a hammer-mill to produce a material essentially all passing a U.S.S. No. 50 screen (0.3 mm opening). The concentrate may be formulated further if necessary.

EXAMPLE 15

Wettable Powder

N-[(4,6-dimethoxypyrimidin-2-yl)aminocarbonyl]-5-(2-fluoroethyl)-2,5,6,7-tetrahydro-2-methyl-pyrazolo[3,4-e][1,2]thiazine-3-sulfonamide, 4,4-dioxide: 90%
dioctyl sodium sulfosuccinate: 0.1%
synthetic fine silica: 9.9%

The ingredients are blended and ground in a hammer-mill to produce particles essentially all below 100 microns. The material is sifted through a U.S.S. No. 50 screen and then packaged.

EXAMPLE 16

Wettable Powder 5-acetyl-2,5,6,7-tetrahydro-N-[(4-methoxy-6-methyl-1,3,5-triazin-2-yl)aminocarbonyl]-2-methyl-pyrazolo[3,4-e]thiazine-3-sulfonamide, 4,4-dioxide: 40%
sodium ligninsulfonate: 20%
montmorillonite clay: 40%

The ingredients are thoroughly blended, coarsely hammer-milled and then air-milled to produce particles essentially all below 10 microns in size. The material is reblended and then packaged.

EXAMPLE 17

Oil Suspension 5-butyl-N-[(4,6-dimethoxypyrimidin-2-yl)aminocarbonyl]-2,5,6,7-tetrahydro-2-methylpyrazolo[3,4-e][1,2]thiazine-3-sulfonamide, 4,4-dioxide: 35%
blend of polyalcohol carboxylic esters and oil soluble petroleum sulfonates: 6%
xylene: 59%

The ingredients are combined and ground together in a sand mill to produce particles essentially all below 5 microns. The product can be used directly, extended with oils, or emulsified in water.

EXAMPLE 18

Dust

N-[(4,6-dimethoxypyrimidin-2-yl)aminocarbonyl]-5-(2-fluoroethyl)-2,5,6,7-tetrahydro-2-methyl-pyrazolo[3,4-e][1,2]thiazine-3-sulfonamide, 4,4-dioxide: 10%
attapulgite: 10%
Pyrophyllite: 80%

The active ingredient is blended with attapulgite and then passed through a hammer-mill to produce particles substantially all below 200 microns. The ground concentrate is then blended with powdered pyrophyllite until homogeneous.

Utility

The compounds of the present invention are active preemergent or postemergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highways and railroad structures. Some of the compounds have utility for selective weed control in crops. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foiliage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of the invention may be used in combination with any other commercial herbicide; examples of which are those of the triazine, triazole, uracil, urea, amide, diphenylether, carbamate and bipyridylium types.

What is claimed is:

1. A compound of the formula:

$$\underset{\underset{R}{|}}{LSO_2NHCN}-A$$
$$\overset{O}{\|}$$

wherein
L is

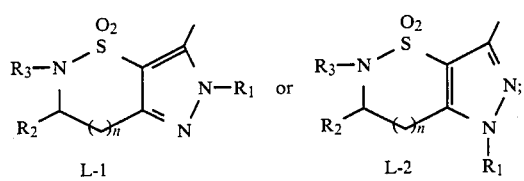

L-1    L-2

R is H or CH$_3$;
R$_1$ is H, C$_1$-C$_3$ alkyl, CH$_2$CH=CH$_2$, CH$_2$C≡CH, CH$_2$CF$_3$, CHF$_2$, C(O)CH$_3$, SO$_2$CH$_3$, SO$_2$N(CH$_3$)$_2$, CO$_2$CH$_3$, phenyl or phenyl substituted with NO$_2$, CH$_3$, OCH$_3$, Cl, Br or F;
R$_2$ is H or CH$_3$;
R$_3$ is R$_4$, SR$_4$, SO$_2$R$_4$, OR$_4$, C(O)R$_4$, C(O)OR$_4$, (C(O))$_2$OR$_4$, (CO)$_2$R$_4$, C(O)NR$_5$R$_6$, C(O)NRA, C(S)SR$_4$, NR$_5$R$_6$, OH, CN, P(O)R$_7$R$_8$, P(S)R$_7$R$_8$, Si(CH$_3$)$_2$R$_9$, J or C(O)J;
R$_4$ is C$_1$-C$_{10}$ alkyl, C$_2$-C$_{10}$ alkoxyalkyl, C$_2$-C$_{10}$ alkenyl, C$_2$-C$_{10}$ epoxyalkyl, C$_2$-C$_{10}$ alkynyl, C$_3$-C$_6$ cycloalkyl, C$_4$-C$_7$ cycloalkylalkyl or

when R$_4$ is C$_3$-C$_6$ cycloalkyl or C$_4$-C$_7$ cycloalkylalkyl it may optionally be substituted by C$_1$-C$_4$ alkyl, 1 to 3 atoms of Cl or F or 1 Br; when R$_4$ is C$_1$-C$_{10}$ alkyl, C$_2$-C$_{10}$ alkenyl or C$_2$-C$_{10}$ alkynyl it may optionally be substituted by one or more halogens and/or by (R$_{11}$)$_p$, provided that when p is 2, 1 the values of R$_{11}$ may be identical or different;
p is 1 or 2;
R$_5$ is H or C$_1$-C$_4$ alkyl;
R$_6$ is H, C$_1$-C$_{10}$ alkyl, C$_1$-C$_{10}$ haloalkyl, C$_2$-C$_{10}$ alkenyl, C$_2$-C$_{10}$ alkynyl, C$_3$-C$_6$ cycloalkyl or

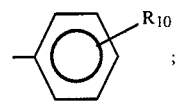

R$_7$ and R$_8$ are independently C$_1$-C$_4$ alkyl, C$_1$-C$_4$ alkoxy or C$_1$-C$_4$ alkylthio;
R$_9$ is C$_1$-C$_{10}$ alkyl, benzyl or

R$_{10}$ is H, F, Cl, Br, CH$_3$, OCH$_3$, NO$_2$, CN, SCH$_3$, SO$_2$CH$_3$ or CF$_3$;
R$_{11}$ is OR$_6$, OC(O)R$_6$, P+R$_9$R$_{13}$R$_{14}$, P+(C$_6$H$_5$)$_3$, OC(O)NR$_5$R$_6$, OSO$_2$R$_6$, OP(O)R$_7$R$_8$, P(O)R$_7$R$_8$, OP(S)R$_7$R$_8$, P(S)R$_7$R$_8$, OSi(CH$_3$)$_2$R$_9$, Si(CH$_3$)$_2$R$_9$, SR$_6$, SOR$_6$, SO$_2$R$_6$, SCN, CN, SP(O)R$_7$R$_8$, SP(S)R$_7$R$_8$, N+R$_5$R$_6$R$_9$, NR$_5$R$_6$, NR$_5$C(O)R$_6$, NR$_5$C(O)OR$_6$, NR$_5$C(O)NR$_5$R$_6$, NR$_5$SO$_2$R$_6$, NR$_5$P(O)R$_7$R$_8$, NR$_5$P(S)R$_7$R$_8$, NO$_2$, C(O)R$_6$, C(O)OR$_6$, C(O)NR$_5$R$_6$, SeR$_6$, naphthyl, J,

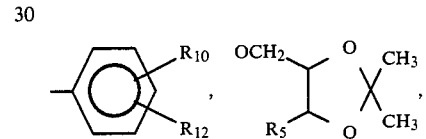

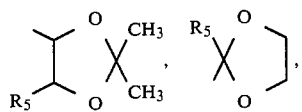

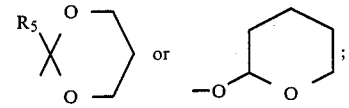

R$_{12}$ is H, F, Cl, Br, CH$_3$,

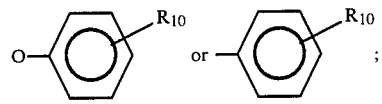

R$_{13}$ and R$_{14}$ are independently C$_1$-C$_3$ alkyl;
J is a 5- or 6-membered aromatic heterocycle, a 5- or 6-membered dihydroaromatic heterocycle or a 5- or 6-membered tetrahydroaromatic heterocycle which contains 1-4 heteroatoms selected from 0-1 oxygen atoms, 0-1 sulfur atoms and/or 0-4 nitrogen atoms and these heterocycles may optionally be substituted by 1-4 CH$_3$, 1-2 OCH$_3$, SCH$_3$, Cl, N(CH$_3$)$_2$ or CN groups or J is a 5- or 6-membered lactone, lactam or cycloalkanone which may optionally be substituted by 1-4 CH$_3$ groups;
A is

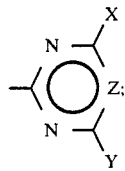
A-1

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, or $C_1$-$C_3$ alkylamino, di($C_1$-$C_3$ alkyl)amino or $C_3$-$C_5$ cycloalkyl;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_hd 4$ alkenyloxy, $C_3$-$C_4$ alkynyloxy, $C_2$-$C_5$ alkylthioalkyl, $C_2$-$C_5$ *l alkylsulfinylalkyl*, $C_2$-$C_5$ alkylsulfonylalkyl, $C_1$-$C_4$ haloalkyl, $C_2$-$C_4$ alkynyl, azido, cyano,

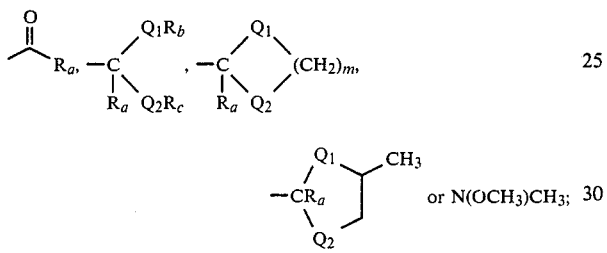

or N(OCH$_3$)CH$_3$;

m is 2 or 3;
$Q_1$ and $Q_2$ are independently O or S;
$R_a$ is H or $C_1$-$C_3$ alkyl;
$R_b$ and $R_c$ are independently $C_1$-$C_3$ alkyl; and
Z is CH;
provided that
1. when X is halogen, then Y is OCH$_3$, OC$_2$H$_5$, NHCH$_3$, N(CH$_3$)$_2$ or OCF$_2$H;
2. when $R_3$ is $R_4$, then $R_4$ is other than $C_1$-$C_3$ alkyl or CF$_2$H;
3. the total number of carbon atoms in $R_3$ does not exceed 13; and
4. when $R_6$ is H, then $R_{11}$ is other than SOR$_6$, SO$_2$R$_6$, OSO$_2$R$_6$ or NR$_5$CO$_2$R$_6$.

2. Compounds of claim 1 wherein
X is CH$_3$, OCH$_3$, OCH$_2$CH$_3$, Cl, F, Br, OCF$_2$H, CH$_2$F, CF$_3$ or cyclopropyl;
X is H, $C_1$-$C_3$ alkyl, OCH$_3$, OC$_2$H$_5$, CH$_2$OCH$_3$, NH$_2$, NHCH$_3$, N(OCH$_3$)CH$_3$, N(CH$_3$)$_2$, C$_2$H$_5$, CF$_3$, SCH$_3$, OCH$_2$CH=CH$_2$, OCH$_2$C≡CH, OCH$_2$CF$_3$, CN, N$_3$, OCH$_2$CH$_2$OCH$_3$, CH$_2$SCH$_3$,

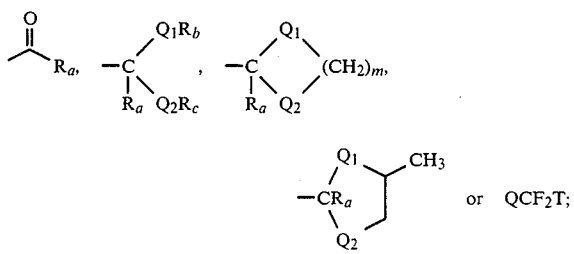

or QCF$_2$T;

Q is O or S; and
T is H, CHClF, CHBrF or CHFCF$_3$.

3. Compounds of claim 2 wherein $R_3$ is $C_4$-$C_6$ alkyl, $C_1$-$C_6$ alkylcarbonyl, $C_1$-$C_6$ alkoxycarbonyl, $C_1$-$C_6$ alkyl substituted by 1-3 atoms of F, Cl or 1 Br, or by 1 or 2 groups selected from $C_1$-$C_2$ alkoxy, CN, $C_1$-$C_2$ alkoxycarbonyl, $C_1$-$C_2$ alkylcarbonyl, OH, $C_1$-$C_2$ alkylthio $C_1$-$C_2$ alkylsulfonyl, $C_1$-$C_2$ alkylsulfonyloxy or $C_1$-$C_2$ alkylcarbonyloxy, $C_3$-$C_4$ alkenyl, $C_3$-$C_4$ haloalkenyl, $C_3$-$C_4$ alkynyl, $C_4$ alkynyl substituted by 1 atom of F or Cl, phenyl or phenyl substituted with Cl, CF$_3$, NO$_2$, CN or SO$_2$CH$_3$.

4. Compounds of claim 3 wherein $R_1$ is H, $C_1$-$C_3$ alkyl, allyl, propargyl, CH$_2$CF$_3$ or CHF$_2$.

5. Compounds of claim 4 wherein R is H, Y or CH$_3$, C$_2$H$_5$, OCH$_3$, CH$_2$OCH$_3$, OCF$_2$H or CH(OCH$_3$)$_2$, and Z is CH or N.

6. Compounds of claim 5 wherein Z is CH; and $R_3$ is $C_4$ alkyl, $C_1$-$C_4$ alkyl substituted by 1-3 atoms of F or Cl or 1 Br, $C_1$-$C_3$ alkyl substituted with $C_1$-$C_2$ alkoxy, $C_1$-$C_2$ alkylthio, $C_1$-$C_2$ alkylsulfonyl or CN, $C_3$-$C_4$ alkenyl, $C_3$-$C_4$ haloalkenyl, $C_3$-$C_4$ alkynyl, $C_1$-$C_3$ alkoxycarbonyl or $C_1$-$C_3$ alkylcarbonyl.

7. The compound of claim 1 which is N-[(4,6-dimethoxypyrimidin-2-yl)aminocarbonyl]-5-(2-fluoroethyl)-2,5,6,7-tetrahydro-2-methylpyrazolo[b 3,4-e][1,2]thiazine-3-sulfonamide, 4,4-dioxide.

8. The compound of claim 1 which is 5-butyl-N-[(4,6-dimethoxypyrimidin-2-yl)aminocarbonyl]-2,5,6,7-tetrahydro-2-methylpyrazolo[3,4-e][1,2]thiazine-3-sulfonamide, 4,4-dioxide.

9. A composition suitable for controlling the growth of undesired vegetation which comprises an effective amount of a compound of claim 1 and at least one of the following: surfactant, solid or liquid diluent.

10. A composition suitable for controlling the growth of undesired vegetation which comprises an effective amount of a compound of claim 2 and at least one of the following: surfactant, solid or liquid diluent.

11. A composition suitable for controlling the growth of undesired vegetation which comprises an effective amount of a compound of claim 3 and at least one of the following: surfactant, solid or liquid diluent.

12. A composition suitable for controlling the growth of undesired vegetation which comprises an effective amount of a compound of claim 4 and at least one of the following: surfactant, solid or liquid diluent.

13. A composition suitable for controlling the growth of undesired vegetation which comprises an effective amount of a compound of claim 5 and at least one of the following: surfactant, solid or liquid diluent.

14. A composition suitable for controlling the growth of undesired vegetation which comprises an effective amount of a compound of claim 6 and at least one of the following: surfactant, solid or liquid diluent.

15. A composition suitable for controlling the growth of undesired vegetation which comprises an effective amount of the compound of claim 7 and at least one of the following: surfactant, solid or liquid diluent.

16. A composition suitable for controlling the growth of undesired vegetation which comprises an effective amount of the compound of claim 8 and at least one of the following: surfactant, solid or liquid diluent.

17. A method for controlling the growth of undesired vegetation which comprises applying to the locus to be protected an effective amount of a compound of claim 1.

18. A method for controlling the growth of undesired vegetation which comprises applying to the locus to be protected an effective amount of a compound of claim 2.

19. A method for controlling the growth of undesired vegetation which comprises applying to the locus to be protected an effective amount of a compound of claim 3.

20. A method for controlling the growth of undesired vegetation which comprises applying to the locus to be protected an effective amount of a compound of claim 4.

21. A method for controlling the growth of undesired vegetation which comprises applying to the locus to be protected an effective amount of a compound of claim 5.

22. A method for controlling the growth of undesired vegetation which comprises applying to the locus to be protected an effective amount of a compound of claim 6.

23. A method for controlling the growth of undesired vegetation which comprises applying to the locus to be protected an effective amount of the compound of claim 7.

24. A method for controlling the growth of undesired vegetation which comprises applying to the locus to be protected an effective amount of the compound of claim 8.

* * * * *